(12) United States Patent
Link et al.

(10) Patent No.: US 11,187,702 B2
(45) Date of Patent: Nov. 30, 2021

(54) ENZYME QUANTIFICATION

(71) Applicant: Bio-Rad Laboratories, Inc., Hercules, CA (US)

(72) Inventors: Darren R. Link, Lexington, MA (US); Michael L. Samuels, Windham, NH (US)

(73) Assignee: Bio-Rad Laboratories, Inc., Hercules, CA (US)

(*) Notice: Subject to any disclaimer, the term of this patent is extended or adjusted under 35 U.S.C. 154(b) by 0 days.

(21) Appl. No.: 17/081,220

(22) Filed: Oct. 27, 2020

(65) Prior Publication Data

US 2021/0088519 A1 Mar. 25, 2021

Related U.S. Application Data

(63) Continuation of application No. 16/733,132, filed on Jan. 2, 2020, which is a continuation of application
(Continued)

(51) Int. Cl.
*G01N 33/573* (2006.01)
*B01F 5/06* (2006.01)
(Continued)

(52) U.S. Cl.
CPC ......... *G01N 33/573* (2013.01); *B01F 3/0807* (2013.01); *B01F 5/0646* (2013.01); *B01F 5/0653* (2013.01); *B01F 13/0062* (2013.01); *B01J 19/0046* (2013.01); *B01L 3/502761* (2013.01); *C12Q 1/25* (2013.01); *C12Q 1/6804* (2013.01); *C12Q 1/6818* (2013.01);
(Continued)

(58) Field of Classification Search
None
See application file for complete search history.

(56) References Cited

U.S. PATENT DOCUMENTS 2,097,692 A 11/1937 Fiegel
2,164,172 A 6/1939 Dalton
(Continued)

FOREIGN PATENT DOCUMENTS

AT 140025 T 7/1996
AT 140880 T 8/1996
(Continued)

OTHER PUBLICATIONS

Abate, 2011, Synthesis of monidisperse microparticles from non-Newtonian polymer solutions with microfluidic devices, Adv Mat 23(15): 1757-1760.
(Continued)

*Primary Examiner* — Rebecca M Giere
(74) *Attorney, Agent, or Firm* — Brown Rudnick LLP; Thomas C. Meyers

(57) ABSTRACT

The invention generally relates to methods for quantifying an amount of enzyme molecules. Systems and methods of the invention are provided for measuring an amount of target by forming a plurality of fluid partitions, a subset of which include the target, performing an enzyme-catalyzed reaction in the subset, and detecting the number of partitions in the subset. The amount of target can be determined based on the detected number.

10 Claims, 43 Drawing Sheets

Related U.S. Application Data

No. 13/487,030, filed on Jun. 1, 2012, now Pat. No. 10,533,998, which is a continuation-in-part of application No. 10/389,130, filed on Mar. 14, 2003, now Pat. No. 7,041,481, said application No. 16/733,132 is a continuation of application No. 12/504,764, filed on Jul. 17, 2009, now abandoned.

(60) Provisional application No. 61/081,930, filed on Jul. 18, 2008.

(51) Int. Cl.

| | | |
|---|---|---|
| B01J 19/00 | (2006.01) | |
| B01F 13/00 | (2006.01) | |
| B01L 3/00 | (2006.01) | |
| B01F 3/08 | (2006.01) | |
| C40B 40/04 | (2006.01) | |
| C40B 50/08 | (2006.01) | |
| C40B 60/10 | (2006.01) | |
| G01N 33/50 | (2006.01) | |
| C12Q 1/6851 | (2018.01) | |
| C12Q 1/25 | (2006.01) | |
| C12Q 1/6804 | (2018.01) | |
| C12Q 1/6818 | (2018.01) | |
| C12Q 1/6827 | (2018.01) | |
| G01N 33/542 | (2006.01) | |
| G01N 33/58 | (2006.01) | |
| B01L 7/00 | (2006.01) | |
| G01N 21/64 | (2006.01) | |

(52) U.S. Cl.
CPC ......... *C12Q 1/6827* (2013.01); *C12Q 1/6851* (2013.01); *C40B 40/04* (2013.01); *C40B 50/08* (2013.01); *C40B 60/10* (2013.01); *G01N 33/5008* (2013.01); *G01N 33/542* (2013.01); *G01N 33/582* (2013.01); *B01J 2219/0059* (2013.01); *B01J 2219/0065* (2013.01); *B01J 2219/0072* (2013.01); *B01J 2219/0074* (2013.01); *B01J 2219/00286* (2013.01); *B01J 2219/00351* (2013.01); *B01J 2219/00418* (2013.01); *B01J 2219/00479* (2013.01); *B01J 2219/00576* (2013.01); *B01J 2219/00585* (2013.01); *B01J 2219/00592* (2013.01); *B01J 2219/00599* (2013.01); *B01J 2219/00657* (2013.01); *B01J 2219/00664* (2013.01); *B01J 2219/00702* (2013.01); *B01J 2219/00722* (2013.01); *B01J 2219/00743* (2013.01); *B01L 7/52* (2013.01); *B01L 2200/027* (2013.01); *B01L 2300/0636* (2013.01); *B01L 2300/0645* (2013.01); *B01L 2300/0654* (2013.01); *B01L 2300/0681* (2013.01); *B01L 2300/0864* (2013.01); *B01L 2300/0867* (2013.01); *B01L 2400/0415* (2013.01); *B01L 2400/0487* (2013.01); *G01N 21/6428* (2013.01); *G01N 21/6445* (2013.01); *G01N 2500/00* (2013.01)

(56) References Cited

U.S. PATENT DOCUMENTS

| | | |
|---|---|---|
| 2,636,855 A | 4/1953 | Schwartz |
| 2,656,508 A | 10/1953 | Coulter |
| 2,692,800 A | 10/1954 | Nichols et al. |
| 2,797,149 A | 6/1957 | Skeggs |
| 2,879,141 A | 3/1959 | Skeggs |
| 2,971,700 A | 2/1961 | Peeps |
| 3,479,141 A | 11/1969 | Smythe et al. |
| 3,608,821 A | 9/1971 | Simm et al. |
| 3,621,059 A | 11/1971 | Bartlett |
| 3,698,635 A | 10/1972 | Sickles |
| 3,784,471 A | 1/1974 | Kaiser |
| 3,816,331 A | 6/1974 | Brown, Jr. et al. |
| 3,828,085 A | 8/1974 | Price et al. |
| 3,930,061 A | 12/1975 | Scharfenberger |
| 3,960,187 A | 6/1976 | Stock et al. |
| 3,980,541 A | 9/1976 | Aine |
| 3,982,541 A | 9/1976 | L'Esperance, Jr. |
| 4,014,469 A | 3/1977 | Sato |
| 4,022,575 A | 5/1977 | Hansen et al. |
| 4,034,966 A | 7/1977 | Suh et al. |
| 4,059,552 A | 11/1977 | Zweigle et al. |
| 4,091,042 A | 5/1978 | Alexanderson et al. |
| 4,117,550 A | 9/1978 | Folland et al. |
| 4,130,394 A | 12/1978 | Negersmith |
| 4,210,809 A | 7/1980 | Pelavin |
| 4,253,846 A | 3/1981 | Smythe et al. |
| 4,266,721 A | 5/1981 | Sickles |
| 4,279,345 A | 7/1981 | Mired |
| 4,297,345 A | 10/1981 | Howarth |
| 4,315,754 A | 2/1982 | Ruzicka et al. |
| 4,378,957 A | 4/1983 | Malkin et al. |
| 4,383,767 A | 5/1983 | Jido |
| 4,439,980 A | 4/1984 | Biblarz et al. |
| 4,508,265 A | 4/1985 | Jido |
| 4,533,634 A | 8/1985 | Maldonado et al. |
| 4,566,908 A | 1/1986 | Nakatani et al. |
| 4,585,209 A | 4/1986 | Aine et al. |
| 4,618,476 A | 10/1986 | Columbus |
| 4,675,285 A | 6/1987 | Clark et al. |
| 4,676,274 A | 6/1987 | Brown |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,767,515 A | 8/1988 | Scott et al. |
| 4,767,929 A | 8/1988 | Valentine |
| 4,779,805 A | 10/1988 | Jackson et al. |
| 4,795,330 A | 1/1989 | Noakes et al. |
| 4,801,086 A | 1/1989 | Noakes |
| 4,801,529 A | 1/1989 | Perlman |
| 4,829,996 A | 5/1989 | Noakes et al. |
| 4,853,336 A | 8/1989 | Saros et al. |
| 4,856,363 A | 8/1989 | LaRocca et al. |
| 4,859,363 A | 8/1989 | Davis et al. |
| 4,865,444 A | 9/1989 | Green et al. |
| 4,883,750 A | 11/1989 | Whiteley et al. |
| 4,908,112 A | 3/1990 | Pace |
| 4,931,225 A | 6/1990 | Cheng |
| 4,941,959 A | 7/1990 | Scott |
| 4,962,885 A | 10/1990 | Coffee |
| 4,963,498 A | 10/1990 | Hillman et al. |
| 4,981,580 A | 1/1991 | Auer |
| 4,996,004 A | 2/1991 | Bucheler et al. |
| 5,055,390 A | 10/1991 | Weaver et al. |
| 5,091,652 A | 2/1992 | Mathies et al. |
| 5,096,615 A | 3/1992 | Prescott et al. |
| 5,104,813 A | 4/1992 | Besemer et al. |
| 5,122,360 A | 6/1992 | Harris et al. |
| 5,149,625 A | 9/1992 | Church et al. |
| 5,180,662 A | 1/1993 | Sitkovsky |
| 5,185,099 A | 2/1993 | Delpuech et al. |
| 5,188,290 A | 2/1993 | Gebauer et al. |
| 5,188,291 A | 2/1993 | Cross |
| 5,192,659 A | 3/1993 | Simons |
| 5,204,112 A | 4/1993 | Hope et al. |
| 5,207,973 A | 5/1993 | Harris et al. |
| 5,241,159 A | 8/1993 | Chatteriee et al. |
| 5,260,466 A | 11/1993 | McGibbon |
| 5,262,027 A | 11/1993 | Scott |
| 5,270,163 A | 12/1993 | Gold et al. |
| 5,296,375 A | 3/1994 | Kricka et al. |
| 5,304,487 A | 4/1994 | Wilding et al. |
| 5,310,653 A | 5/1994 | Hanausek-Walaszek et al. |
| 5,313,009 A | 5/1994 | Guenkel et al. |
| 5,333,675 A | 8/1994 | Mullis et al. |
| 5,344,489 A | 9/1994 | Matijevic et al. |
| 5,344,594 A | 9/1994 | Sheridon |

(56) References Cited

U.S. PATENT DOCUMENTS

| | | |
|---|---|---|
| 5,354,670 A | 10/1994 | Nickoloff et al. |
| 5,376,252 A | 12/1994 | Ekstrom et al. |
| 5,378,957 A | 1/1995 | Kelly |
| 5,397,605 A | 3/1995 | Barbieri et al. |
| 5,399,461 A | 3/1995 | Van et al. |
| 5,399,491 A | 3/1995 | Kacian et al. |
| 5,403,617 A | 4/1995 | Haaland |
| 5,413,924 A | 5/1995 | Kosak et al. |
| 5,417,235 A | 5/1995 | Wise et al. |
| 5,427,946 A | 6/1995 | Kricka et al. |
| 5,445,934 A | 8/1995 | Fodor et al. |
| 5,452,878 A | 9/1995 | Gravesen et al. |
| 5,452,955 A | 9/1995 | Lundstrom |
| 5,454,472 A | 10/1995 | Benecke et al. |
| 5,460,945 A | 10/1995 | Springer et al. |
| 5,468,613 A | 11/1995 | Erlich et al. |
| 5,475,096 A | 12/1995 | Gold et al. |
| 5,475,610 A | 12/1995 | Atwood et al. |
| 5,480,614 A | 1/1996 | Kamahori |
| 5,486,335 A | 1/1996 | Wilding et al. |
| 5,498,392 A | 3/1996 | Wilding et al. |
| 5,498,523 A | 3/1996 | Tabor et al. |
| 5,500,415 A | 3/1996 | Dollat et al. |
| 5,503,851 A | 4/1996 | Mank et al. |
| 5,512,131 A | 4/1996 | Kumar et al. |
| 5,516,635 A | 5/1996 | Ekins et al. |
| 5,518,709 A | 5/1996 | Sutton et al. |
| 5,523,162 A | 6/1996 | Franz et al. |
| 5,587,128 A | 12/1996 | Wilding et al. |
| 5,589,136 A | 12/1996 | Northrup et al. |
| 5,602,756 A | 2/1997 | Atwood et al. |
| 5,604,097 A | 2/1997 | Brenner |
| 5,610,016 A | 3/1997 | Sato et al. |
| 5,612,188 A | 3/1997 | Shuler et al. |
| 5,616,478 A | 4/1997 | Chetverin et al. |
| 5,617,997 A | 4/1997 | Kobayashi et al. |
| 5,635,358 A | 6/1997 | Wilding et al. |
| 5,636,400 A | 6/1997 | Young |
| 5,641,658 A | 6/1997 | Adams et al. |
| 5,643,729 A | 7/1997 | Taniguchi et al. |
| 5,655,517 A | 8/1997 | Coffee |
| 5,656,155 A | 8/1997 | Norcross et al. |
| 5,656,493 A | 8/1997 | Mullis et al. |
| 5,661,222 A | 8/1997 | Hare |
| 5,662,874 A | 9/1997 | David |
| 5,670,325 A | 9/1997 | Lapidus et al. |
| 5,681,600 A | 10/1997 | Antinone et al. |
| 5,695,934 A | 12/1997 | Brenner |
| 5,726,026 A | 3/1998 | Wilding et al. |
| 5,726,404 A | 3/1998 | Brody |
| 5,733,526 A | 3/1998 | Trevino et al. |
| 5,739,036 A | 4/1998 | Parris |
| 5,744,366 A | 4/1998 | Kricka et al. |
| 5,750,988 A | 5/1998 | Apffel et al. |
| 5,762,775 A | 6/1998 | DePaoli |
| 5,779,868 A | 7/1998 | Parce et al. |
| 5,783,431 A | 7/1998 | Peterson et al. |
| 5,789,206 A | 8/1998 | Tavtigian et al. |
| 5,813,988 A | 9/1998 | Alfano et al. |
| 5,840,506 A | 11/1998 | Giordano |
| 5,846,719 A | 12/1998 | Brenner et al. |
| 5,849,491 A | 12/1998 | Radomski et al. |
| 5,851,769 A | 12/1998 | Gray et al. |
| 5,858,187 A | 1/1999 | Ramsey et al. |
| 5,858,655 A | 1/1999 | Arnold |
| 5,858,670 A | 1/1999 | Lam et al. |
| 5,863,722 A | 1/1999 | Brenner |
| 5,868,322 A | 2/1999 | Loucks |
| 5,872,010 A | 2/1999 | Karger et al. |
| 5,876,771 A | 3/1999 | Sizer et al. |
| 5,880,071 A | 3/1999 | Parce et al. |
| 5,882,680 A | 3/1999 | Suzuki et al. |
| 5,882,856 A | 3/1999 | Shuber |
| 5,884,846 A | 3/1999 | Fan |
| 5,887,755 A | 3/1999 | Hood, III |
| 5,888,746 A | 3/1999 | Fabiti et al. |
| 5,888,778 A | 3/1999 | Shuber |
| 5,904,933 A | 5/1999 | Riess et al. |
| 5,921,678 A | 7/1999 | Desai et al. |
| 5,927,852 A | 7/1999 | Serafin |
| 5,928,870 A | 7/1999 | Lapidus et al. |
| 5,932,100 A | 8/1999 | Yager et al. |
| 5,935,331 A | 8/1999 | Naka et al. |
| 5,942,056 A | 8/1999 | Singh |
| 5,942,443 A | 8/1999 | Parce et al. |
| 5,958,203 A | 9/1999 | Parce et al. |
| 5,972,187 A | 10/1999 | Parce et al. |
| 5,980,936 A | 11/1999 | Krafft et al. |
| 5,989,815 A | 11/1999 | Skolnick et al. |
| 5,989,892 A | 11/1999 | Nishimaki et al. |
| 5,995,341 A | 11/1999 | Tanaka et al. |
| 5,997,636 A | 12/1999 | Gamarnik et al. |
| 6,008,003 A | 12/1999 | Haak-Frendscho et al. |
| 6,023,540 A | 2/2000 | Walt et al. |
| 6,028,066 A | 2/2000 | Unger |
| 6,042,709 A | 3/2000 | Parce et al. |
| 6,045,755 A | 4/2000 | Lebl et al. |
| 6,046,056 A | 4/2000 | Parce et al. |
| 6,048,551 A | 4/2000 | Hilfinger et al. |
| 6,048,690 A | 4/2000 | Heller et al. |
| 6,068,199 A | 5/2000 | Coffee |
| 6,074,879 A | 6/2000 | Zelmanovic et al. |
| 6,080,295 A | 6/2000 | Parce et al. |
| 6,081,612 A | 6/2000 | Gutkowicz-Krusin et al. |
| 6,086,740 A | 7/2000 | Kennedy |
| 6,096,495 A | 8/2000 | Kasai et al. |
| 6,103,537 A | 8/2000 | Ullman et al. |
| 6,105,571 A | 8/2000 | Coffee |
| 6,105,877 A | 8/2000 | Coffee |
| 6,107,059 A | 8/2000 | Hart |
| 6,116,516 A | 9/2000 | Ganan-Calvo |
| 6,118,849 A | 9/2000 | Tanimori et al. |
| 6,119,953 A | 9/2000 | Ganan-Calvo et al. |
| 6,120,666 A | 9/2000 | Jacobson et al. |
| 6,124,388 A | 9/2000 | Takai et al. |
| 6,124,439 A | 9/2000 | Friedman et al. |
| 6,130,052 A | 10/2000 | Van Baren et al. |
| 6,130,098 A | 10/2000 | Handique et al. |
| 6,137,214 A | 10/2000 | Raina |
| 6,138,077 A | 10/2000 | Brenner |
| 6,139,303 A | 10/2000 | Reed et al. |
| 6,140,053 A | 10/2000 | Koster |
| 6,143,496 A | 11/2000 | Brown et al. |
| 6,146,828 A | 11/2000 | Lapidus et al. |
| 6,149,789 A | 11/2000 | Benecke et al. |
| 6,150,180 A | 11/2000 | Parce et al. |
| 6,150,516 A | 11/2000 | Brenner et al. |
| 6,155,710 A | 12/2000 | Nakajima et al. |
| 6,162,421 A | 12/2000 | Ordino et al. |
| 6,165,778 A | 12/2000 | Kedar |
| 6,171,796 B1 | 1/2001 | An et al. |
| 6,171,850 B1 | 1/2001 | Nagle et al. |
| 6,172,214 B1 | 1/2001 | Brenner |
| 6,172,218 B1 | 1/2001 | Brenner |
| 6,174,160 B1 | 1/2001 | Lee et al. |
| 6,174,469 B1 | 1/2001 | Gañan-Calvo |
| 6,177,479 B1 | 1/2001 | Nakajima |
| 6,180,372 B1 | 1/2001 | Franzen |
| 6,184,012 B1 | 2/2001 | Neri et al. |
| 6,187,214 B1 | 2/2001 | Ganan-Calvo |
| 6,189,803 B1 | 2/2001 | Ganan-Calvo |
| 6,196,525 B1 | 3/2001 | Ganan-Calvo |
| 6,197,335 B1 | 3/2001 | Sherman |
| 6,197,835 B1 | 3/2001 | Ganan-Calvo |
| 6,203,993 B1 | 3/2001 | Shuber et al. |
| 6,207,372 B1 | 3/2001 | Shuber |
| 6,207,397 B1 | 3/2001 | Lynch et al. |
| 6,208,749 B1 | 3/2001 | Gutkowicz-Krusin et al. |
| 6,210,396 B1 | 4/2001 | MacDonald et al. |
| 6,210,891 B1 | 4/2001 | Nyren et al. |
| 6,210,896 B1 | 4/2001 | Chan |
| 6,214,558 B1 | 4/2001 | Shuber et al. |
| 6,221,654 B1 | 4/2001 | Quake et al. |
| 6,227,466 B1 | 5/2001 | Hartman et al. |

(56) References Cited

U.S. PATENT DOCUMENTS

| | | |
|---|---|---|
| 6,234,402 B1 | 5/2001 | Ganan-Calvo |
| 6,235,383 B1 | 5/2001 | Hong et al. |
| 6,235,475 B1 | 5/2001 | Brenner et al. |
| 6,241,159 B1 | 6/2001 | Ganan-Calvo et al. |
| 6,243,373 B1 | 6/2001 | Turock |
| 6,248,378 B1 | 6/2001 | Ganan-Calvo |
| 6,251,661 B1 | 6/2001 | Urabe et al. |
| 6,252,129 B1 | 6/2001 | Coffee |
| 6,258,568 B1 | 7/2001 | Nyren |
| 6,258,858 B1 | 7/2001 | Nakajima et al. |
| 6,261,661 B1 | 7/2001 | Ohno et al. |
| 6,261,797 B1 | 7/2001 | Sorge et al. |
| 6,263,222 B1 | 7/2001 | Diab et al. |
| 6,266,459 B1 | 7/2001 | Walt et al. |
| 6,267,353 B1 | 7/2001 | Friedline et al. |
| 6,267,858 B1 | 7/2001 | Parce et al. |
| 6,268,152 B1 | 7/2001 | Fodor et al. |
| 6,268,165 B1 | 7/2001 | O'Brien |
| 6,268,222 B1 | 7/2001 | Chandler et al. |
| 6,274,320 B1 | 8/2001 | Rothberg et al. |
| 6,274,337 B1 | 8/2001 | Parce et al. |
| 6,280,948 B1 | 8/2001 | Guilfoyle et al. |
| 6,292,756 B1 | 9/2001 | Lievois et al. |
| 6,294,344 B1 | 9/2001 | O'Brien |
| 6,296,020 B1 | 10/2001 | McNeely et al. |
| 6,296,673 B1 | 10/2001 | Santarsiero et al. |
| 6,299,145 B1 | 10/2001 | Ganan-Calvo |
| 6,301,055 B1 | 10/2001 | Legrand et al. |
| 6,306,659 B1 | 10/2001 | Parce et al. |
| 6,307,957 B1 | 10/2001 | Gutkowicz-Krusin et al. |
| 6,309,842 B1 * | 10/2001 | Dower .................. G01N 33/532 435/5 |
| 6,310,354 B1 | 10/2001 | Hanninen et al. |
| 6,310,653 B1 | 10/2001 | Malcolm, Jr. et al. |
| 6,316,208 B1 | 11/2001 | Roberts et al. |
| 6,316,213 B1 | 11/2001 | O'Brien |
| 6,318,640 B1 | 11/2001 | Coffee |
| 6,324,417 B1 | 11/2001 | Cotton |
| 6,326,145 B1 | 12/2001 | Whitcombe et al. |
| 6,336,463 B1 | 1/2002 | Ohta |
| 6,344,325 B1 | 2/2002 | Quake et al. |
| 6,352,828 B1 | 3/2002 | Brenner |
| 6,355,193 B1 | 3/2002 | Stott |
| 6,355,198 B1 | 3/2002 | Kim et al. |
| 6,357,670 B2 | 3/2002 | Ganan-Calvo |
| 6,386,463 B1 | 5/2002 | Ganan-Calvo |
| 6,391,559 B1 | 5/2002 | Brown et al. |
| 6,394,429 B2 | 5/2002 | Ganan-Calvo |
| 6,399,339 B1 | 6/2002 | Wolberg et al. |
| 6,399,389 B1 | 6/2002 | Parce et al. |
| 6,403,373 B1 | 6/2002 | Scanlan et al. |
| 6,405,936 B1 | 6/2002 | Ganan-Calvo |
| 6,408,878 B2 | 6/2002 | Unger et al. |
| 6,409,832 B2 | 6/2002 | Weigl et al. |
| 6,429,025 B1 | 8/2002 | Parce et al. |
| 6,429,148 B1 | 8/2002 | Chu et al. |
| 6,432,143 B2 | 8/2002 | Kubiak et al. |
| 6,432,148 B1 | 8/2002 | Ganan-Calvo |
| 6,432,630 B1 | 8/2002 | Blankenstein |
| 6,439,103 B1 | 8/2002 | Miller |
| 6,440,706 B1 | 8/2002 | Vogelstein et al. |
| 6,440,760 B1 | 8/2002 | Cho et al. |
| 6,450,139 B1 | 9/2002 | Watanabe |
| 6,450,189 B1 | 9/2002 | Ganan-Calvo |
| 6,454,193 B1 | 9/2002 | Busick et al. |
| 6,464,336 B1 | 10/2002 | Sharma |
| 6,464,886 B2 | 10/2002 | Ganan-Calvo |
| 6,469,094 B1 | 10/2002 | Keoshkerian et al. |
| 6,475,441 B1 | 11/2002 | Parce et al. |
| 6,481,648 B1 | 11/2002 | Zimmermann |
| 6,489,103 B1 | 12/2002 | Griffiths et al. |
| 6,503,933 B1 | 1/2003 | Moloney et al. |
| 6,506,609 B1 | 1/2003 | Wada et al. |
| 6,508,988 B1 | 1/2003 | Van Dam et al. |
| 6,511,803 B1 | 1/2003 | Church et al. |
| 6,520,425 B1 | 2/2003 | Reneker |
| 6,524,456 B1 | 2/2003 | Ramsey et al. |
| 6,530,944 B2 | 3/2003 | West et al. |
| 6,540,395 B2 | 4/2003 | Muhlbauer et al. |
| 6,540,895 B1 | 4/2003 | Spence et al. |
| 6,551,836 B1 | 4/2003 | Chow et al. |
| 6,553,944 B1 | 4/2003 | Allen et al. |
| 6,553,960 B1 | 4/2003 | Yoshikawa et al. |
| 6,554,202 B2 | 4/2003 | Ganan-Calvo |
| 6,557,334 B2 | 5/2003 | Jager |
| 6,557,834 B2 | 5/2003 | Ganan-Calvo |
| 6,558,944 B1 | 5/2003 | Parce et al. |
| 6,558,960 B1 | 5/2003 | Parce et al. |
| 6,560,030 B2 | 5/2003 | Legrand et al. |
| 6,565,010 B2 | 5/2003 | Anderson et al. |
| 6,569,631 B1 | 5/2003 | Pantoliano et al. |
| 6,576,420 B1 | 6/2003 | Carson et al. |
| 6,591,852 B1 | 7/2003 | McNeely et al. |
| 6,592,321 B2 | 7/2003 | Bonker et al. |
| 6,592,821 B1 | 7/2003 | Wada et al. |
| 6,601,613 B2 | 8/2003 | McNeely et al. |
| 6,608,726 B2 | 8/2003 | Legrand et al. |
| 6,610,499 B1 | 8/2003 | Fulwyler et al. |
| 6,614,598 B1 | 9/2003 | Quake et al. |
| 6,627,603 B1 | 9/2003 | Bibette et al. |
| 6,630,006 B2 | 10/2003 | Santarsiero et al. |
| 6,630,353 B1 | 10/2003 | Parce et al. |
| 6,632,619 B1 | 10/2003 | Harrison et al. |
| 6,637,463 B1 | 10/2003 | Lei et al. |
| 6,638,749 B1 | 10/2003 | Beckman et al. |
| 6,645,432 B1 | 11/2003 | Anderson et al. |
| 6,646,253 B1 | 11/2003 | Rohwer et al. |
| 6,653,626 B2 | 11/2003 | Fischer et al. |
| 6,656,267 B2 | 12/2003 | Newman |
| 6,659,370 B1 | 12/2003 | Inoue |
| 6,660,252 B2 | 12/2003 | Matathia et al. |
| 6,670,142 B2 | 12/2003 | Lau et al. |
| 6,679,441 B1 | 1/2004 | Borra et al. |
| 6,680,178 B2 | 1/2004 | Harris et al. |
| 6,682,890 B2 | 1/2004 | Mack et al. |
| 6,717,136 B2 | 4/2004 | Andersson et al. |
| 6,729,561 B2 | 5/2004 | Hirae et al. |
| 6,738,502 B1 | 5/2004 | Coleman et al. |
| 6,739,036 B2 | 5/2004 | Koike et al. |
| 6,744,046 B2 | 6/2004 | Valaskovic et al. |
| 6,752,922 B2 | 6/2004 | Huang et al. |
| 6,753,147 B2 | 6/2004 | Vogelstein et al. |
| 6,766,817 B2 | 7/2004 | da Silva |
| 6,767,194 B2 | 7/2004 | Jeon et al. |
| 6,767,704 B2 | 7/2004 | Waldman et al. |
| 6,790,328 B2 | 9/2004 | Jacobson et al. |
| 6,793,753 B2 | 9/2004 | Unger et al. |
| 6,797,056 B2 | 9/2004 | David |
| 6,800,849 B2 | 10/2004 | Staats |
| 6,806,058 B2 | 10/2004 | Jesperson et al. |
| 6,808,382 B2 | 10/2004 | Lanfranchi |
| 6,808,882 B2 | 10/2004 | Griffiths et al. |
| 6,814,980 B2 | 11/2004 | Levy et al. |
| 6,818,395 B1 | 11/2004 | Quake et al. |
| 6,832,787 B1 | 12/2004 | Renzi |
| 6,833,242 B2 | 12/2004 | Quake et al. |
| 6,841,350 B2 | 1/2005 | Ogden et al. |
| 6,844,377 B1 | 1/2005 | Auweter et al. |
| 6,872,250 B2 | 3/2005 | David et al. |
| 6,890,487 B1 | 5/2005 | Sklar et al. |
| 6,897,018 B1 | 5/2005 | Yuan et al. |
| 6,905,844 B2 | 6/2005 | Kim |
| 6,918,404 B2 | 7/2005 | Dias da Silva |
| 6,926,313 B1 | 8/2005 | Renzi |
| 6,935,768 B2 | 8/2005 | Lowe et al. |
| 6,936,417 B2 | 8/2005 | Ortoft |
| 6,942,978 B1 | 9/2005 | O'Brien |
| 6,949,342 B2 | 9/2005 | Golub et al. |
| 6,960,437 B2 | 11/2005 | Enzelberger et al. |
| 6,964,847 B1 | 11/2005 | Englert |
| 6,974,667 B2 | 12/2005 | Horne et al. |
| 6,998,232 B1 | 2/2006 | Feinstein et al. |
| 7,022,472 B2 | 4/2006 | Robbins et al. |
| 7,041,481 B2 | 5/2006 | Anderson et al. |

(56) References Cited

U.S. PATENT DOCUMENTS

| | | |
|---|---|---|
| 7,049,072 B2 | 5/2006 | Seshi |
| 7,056,674 B2 | 6/2006 | Baker et al. |
| 7,057,026 B2 | 6/2006 | Barnes et al. |
| 7,066,586 B2 | 6/2006 | da Silva |
| 7,068,874 B2 | 6/2006 | Wang et al. |
| 7,078,180 B2 | 7/2006 | Genetta |
| 7,081,192 B1 | 7/2006 | Wang et al. |
| 7,081,340 B2 | 7/2006 | Baker et al. |
| 7,090,983 B1 | 8/2006 | Muramatsu et al. |
| 7,115,230 B2 | 10/2006 | Sundararajan |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,153,700 B1 | 12/2006 | Pardee et al. |
| 7,156,917 B2 | 1/2007 | Moriyama et al. |
| 7,163,801 B2 | 1/2007 | Reed |
| 7,169,560 B2 | 1/2007 | Lapidus et al. |
| 7,171,311 B2 | 1/2007 | Dai et al. |
| 7,198,899 B2 | 4/2007 | Schleyer et al. |
| 7,204,431 B2 | 4/2007 | Li et al. |
| 7,229,760 B2 | 6/2007 | Zohlnhofer et al. |
| 7,229,770 B1 | 6/2007 | Price et al. |
| 7,252,943 B2 | 8/2007 | Griffiths et al. |
| 7,267,938 B2 | 9/2007 | Anderson et al. |
| 7,268,167 B2 | 9/2007 | Higuchi et al. |
| 7,282,337 B1 | 10/2007 | Harris |
| 7,291,462 B2 | 11/2007 | O'Brien et al. |
| 7,294,503 B2 | 11/2007 | Quake et al. |
| 7,300,765 B2 | 11/2007 | Patel |
| 7,308,364 B2 | 12/2007 | Shaughnessy et al. |
| 7,314,721 B2 | 1/2008 | Gure et al. |
| 7,316,906 B2 | 1/2008 | Chiorazzi et al. |
| 7,323,305 B2 | 1/2008 | Leamon et al. |
| 7,323,309 B2 | 1/2008 | Mirkin et al. |
| 7,326,529 B2 | 2/2008 | Ali et al. |
| 7,332,280 B2 | 2/2008 | Levy et al. |
| 7,332,590 B2 | 2/2008 | Nacht et al. |
| 7,341,211 B2 | 3/2008 | Ganan Calvo et al. |
| 7,348,142 B2 | 3/2008 | Wang |
| 7,358,231 B1 | 4/2008 | McCaffey et al. |
| 7,361,474 B2 | 4/2008 | Siegler |
| 7,364,862 B2 | 4/2008 | Ali et al. |
| 7,368,255 B2 | 5/2008 | Bae et al. |
| 7,378,233 B2 | 5/2008 | Sidransky et al. |
| 7,378,280 B2 | 5/2008 | Quake et al. |
| 7,390,463 B2 | 6/2008 | He et al. |
| 7,393,634 B1 | 7/2008 | Ahuja et al. |
| 7,393,665 B2 | 7/2008 | Brenner |
| 7,405,002 B2 | 7/2008 | Ting et al. |
| 7,416,851 B2 | 8/2008 | Davi et al. |
| 7,429,467 B2 | 9/2008 | Holliger et al. |
| 7,432,064 B2 | 10/2008 | Salceda et al. |
| 7,442,507 B2 | 10/2008 | Polsky et al. |
| 7,449,303 B2 | 11/2008 | Coignet |
| 7,468,271 B2 | 12/2008 | Golovchenko et al. |
| 7,473,530 B2 | 1/2009 | Huttemann |
| 7,473,531 B1 | 1/2009 | Domon et al. |
| 7,476,506 B2 | 1/2009 | Schleyer et al. |
| 7,479,370 B2 | 1/2009 | Coignet |
| 7,479,371 B2 | 1/2009 | Ando et al. |
| 7,479,376 B2 | 1/2009 | Waldman et al. |
| 7,482,129 B2 | 1/2009 | Soyupak et al. |
| 7,501,244 B2 | 3/2009 | Reinhard et al. |
| 7,504,214 B2 | 3/2009 | Erlander et al. |
| 7,507,532 B2 | 3/2009 | Chang et al. |
| 7,507,541 B2 | 3/2009 | Raitano et al. |
| 7,510,707 B2 | 3/2009 | Platica et al. |
| 7,510,842 B2 | 3/2009 | Podust et al. |
| 7,514,209 B2 | 4/2009 | Dai et al. |
| 7,514,210 B2 | 4/2009 | Holliger et al. |
| 7,524,633 B2 | 4/2009 | Sidransky |
| 7,527,933 B2 | 5/2009 | Sahin et al. |
| 7,537,897 B2 | 5/2009 | Brenner et al. |
| 7,541,383 B2 | 6/2009 | Fu et al. |
| 7,544,473 B2 | 6/2009 | Brenner |
| 7,556,776 B2 | 7/2009 | Fraden et al. |
| 7,582,446 B2 | 9/2009 | Griffiths et al. |
| 7,595,195 B2 | 9/2009 | Lee et al. |
| 7,604,938 B2 | 10/2009 | Takahashi et al. |
| 7,622,081 B2 | 11/2009 | Chou et al. |
| 7,632,562 B2 | 12/2009 | Nair et al. |
| 7,635,562 B2 | 12/2009 | Harris et al. |
| 7,638,276 B2 | 12/2009 | Griffiths et al. |
| 7,655,435 B2 | 2/2010 | Holliger et al. |
| 7,655,470 B2 | 2/2010 | Ismagilov et al. |
| 7,666,593 B2 | 2/2010 | Lapidus |
| 7,691,576 B2 | 4/2010 | Holliger et al. |
| 7,698,287 B2 | 4/2010 | Becker et al. |
| 7,708,949 B2 | 5/2010 | Stone et al. |
| 7,718,578 B2 | 5/2010 | Griffiths et al. |
| 7,736,890 B2 | 6/2010 | Sia et al. |
| 7,741,130 B2 | 6/2010 | Lee, Jr. et al. |
| RE41,780 E | 9/2010 | Anderson et al. |
| 7,814,175 B1 | 10/2010 | Chang et al. |
| 7,824,889 B2 | 11/2010 | Vogelstein et al. |
| 7,888,017 B2 | 2/2011 | Quake et al. |
| 7,897,044 B2 | 3/2011 | Hoyos et al. |
| 7,897,341 B2 | 3/2011 | Griffiths et al. |
| 7,901,939 B2 | 3/2011 | Ismagliov et al. |
| 7,915,015 B2 | 3/2011 | Vogelstein et al. |
| 7,968,287 B2 | 6/2011 | Griffiths et al. |
| 7,990,525 B2 | 8/2011 | Kanda |
| 8,012,382 B2 | 9/2011 | Kim et al. |
| 8,067,159 B2 | 11/2011 | Brown et al. |
| 8,153,402 B2 | 4/2012 | Holliger et al. |
| 8,252,539 B2 | 8/2012 | Quake et al. |
| 8,257,925 B2 | 9/2012 | Brown et al. |
| 8,278,071 B2 | 10/2012 | Brown et al. |
| 8,278,711 B2 | 10/2012 | Rao et al. |
| 8,318,434 B2 | 11/2012 | Cuppens |
| 8,337,778 B2 | 12/2012 | Stone et al. |
| 8,436,993 B2 | 5/2013 | Kaduchak et al. |
| 8,462,269 B2 | 6/2013 | Cheng et al. |
| 8,528,589 B2 | 9/2013 | Miller et al. |
| 8,535,889 B2 | 9/2013 | Larson et al. |
| 8,592,221 B2 | 11/2013 | Fraden et al. |
| 8,673,595 B2 | 3/2014 | Nakamura et al. |
| 8,715,934 B2 | 5/2014 | Diehl et al. |
| 8,765,485 B2 | 7/2014 | Link et al. |
| 8,772,046 B2 | 7/2014 | Fraden et al. |
| 8,841,071 B2 | 9/2014 | Link |
| 8,857,462 B2 | 10/2014 | Miller et al. |
| 8,871,444 B2 | 10/2014 | Griffiths et al. |
| 9,029,083 B2 | 5/2015 | Griffiths et al. |
| 9,029,085 B2 | 5/2015 | Agresti et al. |
| 9,080,056 B2 | 7/2015 | Glennon et al. |
| 9,176,031 B2 | 11/2015 | Watson |
| 9,186,643 B2 | 11/2015 | Griffiths et al. |
| 9,273,308 B2 | 3/2016 | Link et al. |
| 9,273,349 B2 | 3/2016 | Nguyen et al. |
| 9,328,344 B2 | 5/2016 | Link et al. |
| 9,364,803 B2 | 6/2016 | Yurkovetsky et al. |
| 9,399,797 B2 | 7/2016 | Hutchison et al. |
| 9,410,151 B2 | 8/2016 | Link et al. |
| 9,448,172 B2 | 9/2016 | Griffiths et al. |
| 9,816,121 B2 | 11/2017 | Agresti et al. |
| 9,839,890 B2 | 12/2017 | Griffiths et al. |
| 9,857,202 B2 | 1/2018 | Seki |
| 9,919,277 B2 | 3/2018 | Griffiths et al. |
| 9,925,501 B2 | 3/2018 | Griffiths et al. |
| 9,944,977 B2 | 4/2018 | Link et al. |
| 10,144,950 B2 | 12/2018 | Nolan |
| 10,151,698 B2 | 12/2018 | Griffiths et al. |
| 10,357,772 B2 | 7/2019 | Fraden et al. |
| 10,526,605 B2 | 1/2020 | Liu et al. |
| 10,584,332 B2 | 3/2020 | Samuels et al. |
| 10,596,541 B2 | 3/2020 | Weitz et al. |
| 10,612,081 B2 | 4/2020 | Hutchison et al. |
| 10,633,652 B2 | 4/2020 | Link et al. |
| 10,639,597 B2 | 5/2020 | Link et al. |
| 10,639,598 B2 | 5/2020 | Griffiths et al. |
| 10,675,626 B2 | 6/2020 | Fraden et al. |
| 2001/0010338 A1 | 8/2001 | Ganan-Calvo |
| 2001/0020011 A1 | 9/2001 | Mathiowitz et al. |

(56) References Cited

U.S. PATENT DOCUMENTS

| | | |
|---|---|---|
| 2001/0023078 A1 | 9/2001 | Bawendi et al. |
| 2001/0029983 A1 | 10/2001 | Unger et al. |
| 2001/0032053 A1 | 10/2001 | Hielscher et al. |
| 2001/0034025 A1 | 10/2001 | Modlin et al. |
| 2001/0034031 A1 | 10/2001 | Short et al. |
| 2001/0041343 A1 | 11/2001 | Pankowsky |
| 2001/0041344 A1 | 11/2001 | Sepetov et al. |
| 2001/0041357 A1 | 11/2001 | Fouillet et al. |
| 2001/0042793 A1 | 11/2001 | Ganan-Calvo |
| 2001/0048900 A1 | 12/2001 | Bardell et al. |
| 2001/0050881 A1 | 12/2001 | Depaoli et al. |
| 2002/0004532 A1 | 1/2002 | Matathia et al. |
| 2002/0005354 A1 | 1/2002 | Spence et al. |
| 2002/0008028 A1 | 1/2002 | Jacobson et al. |
| 2002/0012971 A1 | 1/2002 | Mehta |
| 2002/0015997 A1 | 2/2002 | Lafferty |
| 2002/0022038 A1 | 2/2002 | Biatry et al. |
| 2002/0022261 A1 | 2/2002 | Anderson et al. |
| 2002/0033422 A1 | 3/2002 | Ganan-Calvo |
| 2002/0034737 A1 | 3/2002 | Drmanac |
| 2002/0036018 A1 | 3/2002 | McNeely et al. |
| 2002/0036139 A1 | 3/2002 | Becker et al. |
| 2002/0041378 A1 | 4/2002 | Peltie et al. |
| 2002/0058332 A1 | 5/2002 | Quake et al. |
| 2002/0065609 A1 | 5/2002 | Ashby |
| 2002/0067800 A1 | 6/2002 | Newman et al. |
| 2002/0084417 A1 | 7/2002 | Khalil et al. |
| 2002/0085961 A1 | 7/2002 | Morin et al. |
| 2002/0090720 A1 | 7/2002 | Mutz et al. |
| 2002/0106667 A1 | 8/2002 | Yamamoto et al. |
| 2002/0119455 A1 | 8/2002 | Chan |
| 2002/0119459 A1 | 8/2002 | Griffiths |
| 2002/0127591 A1 | 9/2002 | Wada et al. |
| 2002/0142344 A1 | 10/2002 | Akeson et al. |
| 2002/0143437 A1 | 10/2002 | Handique et al. |
| 2002/0155080 A1 | 10/2002 | Glenn et al. |
| 2002/0158027 A1 | 10/2002 | Moon et al. |
| 2002/0164271 A1 | 11/2002 | Ho |
| 2002/0164629 A1 | 11/2002 | Quake et al. |
| 2002/0166582 A1 | 11/2002 | O'Connor et al. |
| 2002/0179849 A1 | 12/2002 | Maher et al. |
| 2003/0008308 A1 | 1/2003 | Enzelberger et al. |
| 2003/0012586 A1 | 1/2003 | Iwata et al. |
| 2003/0015425 A1 | 1/2003 | Bohm et al. |
| 2003/0017305 A1 | 1/2003 | Roitman et al. |
| 2003/0017579 A1 | 1/2003 | Corn et al. |
| 2003/0039169 A1 | 2/2003 | Ehrfeld et al. |
| 2003/0040620 A1 | 2/2003 | Langmore et al. |
| 2003/0059764 A1 | 3/2003 | Ravkin et al. |
| 2003/0061687 A1 | 4/2003 | Hansen et al. |
| 2003/0064414 A1 | 4/2003 | Benecky et al. |
| 2003/0082795 A1 | 5/2003 | Shuler et al. |
| 2003/0083276 A1 | 5/2003 | Li et al. |
| 2003/0104372 A1 | 6/2003 | Ahmadian et al. |
| 2003/0108900 A1 | 6/2003 | Oliphant et al. |
| 2003/0124586 A1 | 7/2003 | Griffiths et al. |
| 2003/0143599 A1 | 7/2003 | Makarov et al. |
| 2003/0144260 A1 | 7/2003 | Gilon |
| 2003/0148273 A1 | 8/2003 | Dong et al. |
| 2003/0148544 A1 | 8/2003 | Nie et al. |
| 2003/0181574 A1 | 9/2003 | Adam et al. |
| 2003/0183525 A1 | 10/2003 | Elrod et al. |
| 2003/0207295 A1 | 11/2003 | Gunderson et al. |
| 2003/0219754 A1 | 11/2003 | Oleksy et al. |
| 2003/0224509 A1 | 12/2003 | Moon et al. |
| 2003/0229376 A1 | 12/2003 | Sandhu |
| 2003/0230486 A1 | 12/2003 | Chien et al. |
| 2003/0232356 A1 | 12/2003 | Dooley et al. |
| 2004/0005582 A1 | 1/2004 | Shipwash |
| 2004/0005594 A1 | 1/2004 | Holliger et al. |
| 2004/0018525 A1 | 1/2004 | Wirtz et al. |
| 2004/0027915 A1 | 2/2004 | Lowe et al. |
| 2004/0030255 A1 | 2/2004 | Alfano et al. |
| 2004/0031688 A1 | 2/2004 | Shenderov |
| 2004/0037739 A1 | 2/2004 | McNeely et al. |
| 2004/0037813 A1 | 2/2004 | Simpson et al. |
| 2004/0041093 A1 | 3/2004 | Schultz et al. |
| 2004/0050946 A1 | 3/2004 | Wang et al. |
| 2004/0053247 A1 | 3/2004 | Cordon-Cardo et al. |
| 2004/0057906 A1 | 3/2004 | Hsu et al. |
| 2004/0058450 A1 | 3/2004 | Pamula et al. |
| 2004/0068019 A1 | 4/2004 | Higuchi et al. |
| 2004/0071781 A1 | 4/2004 | Chattopadhyay et al. |
| 2004/0079881 A1 | 4/2004 | Fischer et al. |
| 2004/0086892 A1 | 5/2004 | Crothers et al. |
| 2004/0091923 A1 | 5/2004 | Reyes et al. |
| 2004/0092824 A1 | 5/2004 | Stamnes et al. |
| 2004/0096515 A1 | 5/2004 | Bausch et al. |
| 2004/0101822 A1 | 5/2004 | Wiesner et al. |
| 2004/0134854 A1 | 7/2004 | Higuchi et al. |
| 2004/0136497 A1 | 7/2004 | Meldrum et al. |
| 2004/0142329 A1 | 7/2004 | Erikson et al. |
| 2004/0146866 A1 | 7/2004 | Fu |
| 2004/0146921 A1 | 7/2004 | Eveleigh et al. |
| 2004/0159633 A1 | 8/2004 | Whitesides et al. |
| 2004/0180346 A1 | 9/2004 | Anderson et al. |
| 2004/0181131 A1 | 9/2004 | Maynard et al. |
| 2004/0181343 A1 | 9/2004 | Wigstrom et al. |
| 2004/0182712 A1 | 9/2004 | Basol |
| 2004/0185484 A1 | 9/2004 | Costa et al. |
| 2004/0188254 A1 | 9/2004 | Spaid |
| 2004/0209299 A1 | 10/2004 | Pinter et al. |
| 2004/0224325 A1 | 11/2004 | Knapp et al. |
| 2004/0224419 A1 | 11/2004 | Zheng et al. |
| 2004/0229349 A1 | 11/2004 | Daridon |
| 2004/0241693 A1 | 12/2004 | Ricoul et al. |
| 2004/0253731 A1 | 12/2004 | Holliger et al. |
| 2004/0258203 A1 | 12/2004 | Yamano et al. |
| 2004/0259083 A1 | 12/2004 | Oshima |
| 2005/0000970 A1 | 1/2005 | Kimbara et al. |
| 2005/0003380 A1 | 1/2005 | Cohen et al. |
| 2005/0008592 A1 | 1/2005 | Gardel et al. |
| 2005/0019776 A1 | 1/2005 | Callow et al. |
| 2005/0032238 A1 | 2/2005 | Karp et al. |
| 2005/0032240 A1 | 2/2005 | Lee et al. |
| 2005/0037392 A1 | 2/2005 | Griffiths et al. |
| 2005/0037397 A1 | 2/2005 | Mirkin et al. |
| 2005/0042639 A1 | 2/2005 | Knapp et al. |
| 2005/0042648 A1 | 2/2005 | Griffiths et al. |
| 2005/0048467 A1 | 3/2005 | Sastry et al. |
| 2005/0064460 A1 | 3/2005 | Holliger et al. |
| 2005/0069920 A1 | 3/2005 | Griffiths et al. |
| 2005/0079501 A1 | 4/2005 | Koike et al. |
| 2005/0079510 A1 | 4/2005 | Berka et al. |
| 2005/0084923 A1 | 4/2005 | Mueller et al. |
| 2005/0087122 A1 | 4/2005 | Ismagliov et al. |
| 2005/0095611 A1 | 5/2005 | Chan et al. |
| 2005/0100895 A1 | 5/2005 | Waldman et al. |
| 2005/0103690 A1 | 5/2005 | Kawano et al. |
| 2005/0123937 A1 | 6/2005 | Thorp et al. |
| 2005/0129582 A1 | 6/2005 | Breidford et al. |
| 2005/0130173 A1 | 6/2005 | Leamon et al. |
| 2005/0152908 A1 | 7/2005 | Liew et al. |
| 2005/0161669 A1 | 7/2005 | Jovanovich et al. |
| 2005/0164239 A1 | 7/2005 | Griffiths et al. |
| 2005/0169797 A1 | 8/2005 | Oshima |
| 2005/0170373 A1 | 8/2005 | Monforte |
| 2005/0170431 A1 | 8/2005 | Ibrahim et al. |
| 2005/0172476 A1 | 8/2005 | Stone et al. |
| 2005/0183995 A1 | 8/2005 | Deshpande et al. |
| 2005/0202429 A1 | 9/2005 | Trau et al. |
| 2005/0202489 A1 | 9/2005 | Cho et al. |
| 2005/0207940 A1 | 9/2005 | Butler et al. |
| 2005/0208495 A1 | 9/2005 | Joseph et al. |
| 2005/0208529 A1 | 9/2005 | Winther et al. |
| 2005/0214173 A1 | 9/2005 | Facer et al. |
| 2005/0221339 A1 | 10/2005 | Griffiths et al. |
| 2005/0221341 A1 | 10/2005 | Shimkets et al. |
| 2005/0226742 A1 | 10/2005 | Unger et al. |
| 2005/0227264 A1 | 10/2005 | Nobile et al. |
| 2005/0248066 A1 | 11/2005 | Esteban |
| 2005/0251049 A1 | 11/2005 | Cane et al. |
| 2005/0260566 A1 | 11/2005 | Fischer et al. |
| 2005/0272159 A1 | 12/2005 | Ismagilov et al. |

(56) References Cited

U.S. PATENT DOCUMENTS

| | | |
|---|---|---|
| 2005/0287572 A1 | 12/2005 | Mathies et al. |
| 2006/0003347 A1 | 1/2006 | Griffiths et al. |
| 2006/0003429 A1 | 1/2006 | Frost et al. |
| 2006/0003439 A1 | 1/2006 | Ismagilov et al. |
| 2006/0008824 A1 | 1/2006 | Ronaghi et al. |
| 2006/0035386 A1 | 2/2006 | Hattori et al. |
| 2006/0036348 A1 | 2/2006 | Handique et al. |
| 2006/0040197 A1 | 2/2006 | Kabai |
| 2006/0040297 A1 | 2/2006 | Leamon et al. |
| 2006/0046257 A1 | 3/2006 | Pollock et al. |
| 2006/0051329 A1 | 3/2006 | Lee et al. |
| 2006/0068398 A1 | 3/2006 | McMillan |
| 2006/0078475 A1 | 4/2006 | Tai et al. |
| 2006/0078888 A1 | 4/2006 | Griffiths et al. |
| 2006/0078893 A1 | 4/2006 | Griffiths et al. |
| 2006/0094119 A1 | 5/2006 | Ismagilov et al. |
| 2006/0096923 A1 | 5/2006 | Wagler et al. |
| 2006/0100788 A1 | 5/2006 | Carrino et al. |
| 2006/0105170 A1 | 5/2006 | Dobson et al. |
| 2006/0108012 A1 | 5/2006 | Barrow et al. |
| 2006/0110759 A1 | 5/2006 | Paris et al. |
| 2006/0115821 A1 | 6/2006 | Einstein et al. |
| 2006/0147909 A1 | 7/2006 | Rarbach et al. |
| 2006/0153924 A1 | 7/2006 | Griffiths et al. |
| 2006/0154298 A1 | 7/2006 | Griffiths et al. |
| 2006/0160762 A1 | 7/2006 | Zetter et al. |
| 2006/0163385 A1 | 7/2006 | Link et al. |
| 2006/0169800 A1 | 8/2006 | Resell et al. |
| 2006/0177832 A1 | 8/2006 | Brenner |
| 2006/0195269 A1 | 8/2006 | Yeatman et al. |
| 2006/0223127 A1 | 10/2006 | Yip et al. |
| 2006/0234254 A1 | 10/2006 | An et al. |
| 2006/0234259 A1 | 10/2006 | Rubin et al. |
| 2006/0234264 A1 | 10/2006 | Hardenbol |
| 2006/0245971 A1 | 11/2006 | Burns et al. |
| 2006/0246431 A1 | 11/2006 | Balachandran |
| 2006/0247532 A1 | 11/2006 | Ramanujam et al. |
| 2006/0252057 A1 | 11/2006 | Raponi et al. |
| 2006/0257893 A1 | 11/2006 | Takahashi et al. |
| 2006/0258841 A1 | 11/2006 | Michl et al. |
| 2006/0263888 A1 | 11/2006 | Fritz et al. |
| 2006/0269558 A1 | 11/2006 | Murphy et al. |
| 2006/0269934 A1 | 11/2006 | Woudenberg et al. |
| 2006/0269971 A1 | 11/2006 | Diamandis |
| 2006/0281089 A1 | 12/2006 | Gibson et al. |
| 2006/0281098 A1 | 12/2006 | Miao et al. |
| 2006/0286570 A1 | 12/2006 | Rowlen et al. |
| 2007/0003442 A1 | 1/2007 | Link et al. |
| 2007/0009914 A1 | 1/2007 | Wallace et al. |
| 2007/0009954 A1 | 1/2007 | Wang et al. |
| 2007/0016078 A1 | 1/2007 | Hoyt et al. |
| 2007/0020617 A1 | 1/2007 | Trnovsky et al. |
| 2007/0026439 A1 | 2/2007 | Faulstich et al. |
| 2007/0031829 A1 | 2/2007 | Yasuno et al. |
| 2007/0039866 A1 | 2/2007 | Schroeder et al. |
| 2007/0042400 A1 | 2/2007 | Choi et al. |
| 2007/0042419 A1 | 2/2007 | Barany et al. |
| 2007/0045117 A1 | 3/2007 | Pamula et al. |
| 2007/0048744 A1 | 3/2007 | Lapidus |
| 2007/0053896 A1 | 3/2007 | Ahmed et al. |
| 2007/0054119 A1 | 3/2007 | Garstecki et al. |
| 2007/0056853 A1 | 3/2007 | Aizenberg et al. |
| 2007/0065823 A1 | 3/2007 | Dressman et al. |
| 2007/0077572 A1 | 4/2007 | Tawfik et al. |
| 2007/0077579 A1 | 4/2007 | Griffiths et al. |
| 2007/0092914 A1 | 4/2007 | Griffiths et al. |
| 2007/0111303 A1 | 5/2007 | Inoue et al. |
| 2007/0120899 A1 | 5/2007 | Ohnishi et al. |
| 2007/0123430 A1 | 5/2007 | Pasquier et al. |
| 2007/0141593 A1 | 6/2007 | Lee et al. |
| 2007/0142720 A1 | 6/2007 | Ridder et al. |
| 2007/0154889 A1 | 7/2007 | Wang |
| 2007/0156037 A1 | 7/2007 | Pilon et al. |
| 2007/0166705 A1 | 7/2007 | Milton et al. |
| 2007/0172873 A1 | 7/2007 | Brenner et al. |
| 2007/0184439 A1 | 8/2007 | Guilford et al. |
| 2007/0184489 A1 | 8/2007 | Griffiths et al. |
| 2007/0195127 A1 | 8/2007 | Ahn et al. |
| 2007/0202525 A1 | 8/2007 | Quake et al. |
| 2007/0213410 A1 | 9/2007 | Hastwell et al. |
| 2007/0241068 A1 | 10/2007 | Pamula et al. |
| 2007/0242105 A1 | 10/2007 | Srinivasan et al. |
| 2007/0243634 A1 | 10/2007 | Pamula et al. |
| 2007/0259351 A1 | 11/2007 | Chinitz et al. |
| 2007/0259368 A1 | 11/2007 | An et al. |
| 2007/0259374 A1 | 11/2007 | Griffiths et al. |
| 2007/0269804 A1 | 11/2007 | Liew et al. |
| 2007/0275415 A1 | 11/2007 | Srinivasan et al. |
| 2007/0292869 A1 | 12/2007 | Becker et al. |
| 2008/0003142 A1 | 1/2008 | Link et al. |
| 2008/0003571 A1 | 1/2008 | McKernan et al. |
| 2008/0004436 A1 | 1/2008 | Tawfik et al. |
| 2008/0009005 A1 | 1/2008 | Kruk |
| 2008/0014589 A1 | 1/2008 | Link et al. |
| 2008/0014590 A1 | 1/2008 | Dahary et al. |
| 2008/0020940 A1 | 1/2008 | Stedronsky et al. |
| 2008/0021330 A1 | 1/2008 | Hwang et al. |
| 2008/0023330 A1 | 1/2008 | Viovy et al. |
| 2008/0032413 A1 | 2/2008 | Kim et al. |
| 2008/0038754 A1 | 2/2008 | Farias-Eisner et al. |
| 2008/0044828 A1 | 2/2008 | Kwok |
| 2008/0050378 A1 | 2/2008 | Nakamura et al. |
| 2008/0050723 A1 | 2/2008 | Belacel et al. |
| 2008/0053205 A1 | 3/2008 | Pollack et al. |
| 2008/0057514 A1 | 3/2008 | Goldenring |
| 2008/0058432 A1 | 3/2008 | Wang et al. |
| 2008/0063227 A1 | 3/2008 | Rohrseitz |
| 2008/0064047 A1 | 3/2008 | Zetter et al. |
| 2008/0081330 A1 | 4/2008 | Kahvejian |
| 2008/0081333 A1 | 4/2008 | Mori et al. |
| 2008/0092973 A1 | 4/2008 | Lai |
| 2008/0113340 A1 | 5/2008 | Schlegel |
| 2008/0118462 A1 | 5/2008 | Alani et al. |
| 2008/0124726 A1 | 5/2008 | Monforte |
| 2008/0138806 A1 | 6/2008 | Chow et al. |
| 2008/0166772 A1 | 7/2008 | Hollinger et al. |
| 2008/0166793 A1 | 7/2008 | Beer et al. |
| 2008/0171078 A1 | 7/2008 | Gray |
| 2008/0176211 A1 | 7/2008 | Spence et al. |
| 2008/0176236 A1 | 7/2008 | Tsao et al. |
| 2008/0181850 A1 | 7/2008 | Thaxton et al. |
| 2008/0206756 A1 | 8/2008 | Lee et al. |
| 2008/0213377 A1 | 9/2008 | Bhatia et al. |
| 2008/0216563 A1 | 9/2008 | Reed et al. |
| 2008/0220986 A1 | 9/2008 | Gormley et al. |
| 2008/0222741 A1 | 9/2008 | Chinnaiyan |
| 2008/0234138 A1 | 9/2008 | Shaughnessy et al. |
| 2008/0234139 A1 | 9/2008 | Shaughnessy et al. |
| 2008/0241830 A1 | 10/2008 | Vogelstein et al. |
| 2008/0261295 A1 | 10/2008 | Butler et al. |
| 2008/0268473 A1 | 10/2008 | Moses et al. |
| 2008/0269157 A1 | 10/2008 | Srivastava et al. |
| 2008/0274513 A1 | 11/2008 | Shenderov et al. |
| 2008/0274908 A1 | 11/2008 | Chang |
| 2008/0280285 A1 | 11/2008 | Chen et al. |
| 2008/0280302 A1 | 11/2008 | Kebebew |
| 2008/0286199 A1 | 11/2008 | Livingston et al. |
| 2008/0286801 A1 | 11/2008 | Arjol et al. |
| 2008/0286811 A1 | 11/2008 | Moses et al. |
| 2008/0293578 A1 | 11/2008 | Shaugnessy et al. |
| 2008/0299565 A1 | 12/2008 | Schneider et al. |
| 2008/0305482 A1 | 12/2008 | Brentano et al. |
| 2008/0311570 A1 | 12/2008 | Lai |
| 2008/0311604 A1 | 12/2008 | Elting et al. |
| 2009/0004687 A1 | 1/2009 | Mansfield et al. |
| 2009/0005254 A1 | 1/2009 | Griffiths et al. |
| 2009/0009855 A1 | 1/2009 | Nakatsuka et al. |
| 2009/0012187 A1 | 1/2009 | Chu et al. |
| 2009/0017463 A1 | 1/2009 | Bhowmick |
| 2009/0021728 A1 | 1/2009 | Heinz et al. |
| 2009/0023137 A1 | 1/2009 | Van Der Zee et al. |
| 2009/0026082 A1 | 1/2009 | Rothberg et al. |
| 2009/0029372 A1 | 1/2009 | Wewer |
| 2009/0035770 A1 | 2/2009 | Mathies et al. |

(56) References Cited

U.S. PATENT DOCUMENTS

| | | |
|---|---|---|
| 2009/0042737 A1 | 2/2009 | Katz et al. |
| 2009/0053700 A1 | 2/2009 | Griffiths et al. |
| 2009/0053732 A1 | 2/2009 | Vermesh et al. |
| 2009/0060797 A1 | 3/2009 | Mathies et al. |
| 2009/0062144 A1 | 3/2009 | Guo |
| 2009/0068170 A1 | 3/2009 | Weitz et al. |
| 2009/0069194 A1 | 3/2009 | Ramakrishnan |
| 2009/0075265 A1 | 3/2009 | Budiman et al. |
| 2009/0075307 A1 | 3/2009 | Fischer et al. |
| 2009/0075311 A1 | 3/2009 | Karl |
| 2009/0081237 A1 | 3/2009 | D'Andrea et al. |
| 2009/0081685 A1 | 3/2009 | Beyer et al. |
| 2009/0087849 A1 | 4/2009 | Malinowski et al. |
| 2009/0092973 A1 | 4/2009 | Erlander et al. |
| 2009/0098542 A1 | 4/2009 | Budiman et al. |
| 2009/0098543 A1 | 4/2009 | Budiman et al. |
| 2009/0098555 A1 | 4/2009 | Roth et al. |
| 2009/0105959 A1 | 4/2009 | Braverman et al. |
| 2009/0118128 A1 | 5/2009 | Liu et al. |
| 2009/0124569 A1 | 5/2009 | Bergan et al. |
| 2009/0124789 A1 | 5/2009 | Koshida et al. |
| 2009/0127454 A1 | 5/2009 | Ritchie et al. |
| 2009/0127589 A1 | 5/2009 | Rothberg et al. |
| 2009/0131353 A1 | 5/2009 | Insel et al. |
| 2009/0131543 A1 | 5/2009 | Weitz et al. |
| 2009/0134027 A1 | 5/2009 | Jary |
| 2009/0134331 A1 | 5/2009 | Miyamae et al. |
| 2009/0169482 A1 | 7/2009 | Zheng et al. |
| 2009/0191565 A1 | 7/2009 | Lapidus et al. |
| 2009/0197248 A1 | 8/2009 | Griffiths et al. |
| 2009/0197772 A1 | 8/2009 | Griffiths et al. |
| 2009/0215633 A1 | 8/2009 | Van Eijk et al. |
| 2009/0226971 A1 | 9/2009 | Beer et al. |
| 2009/0226972 A1 | 9/2009 | Beer et al. |
| 2009/0233802 A1 | 9/2009 | Bignell et al. |
| 2009/0246788 A1 | 10/2009 | Albert et al. |
| 2009/0317798 A1 | 12/2009 | Heid et al. |
| 2009/0325217 A1 | 12/2009 | Luscher |
| 2009/0325236 A1 | 12/2009 | Griffiths et al. |
| 2010/0003687 A1 | 1/2010 | Simen et al. |
| 2010/0009353 A1 | 1/2010 | Barnes et al. |
| 2010/0015617 A1 | 1/2010 | Toyama |
| 2010/0021984 A1 | 1/2010 | Edd et al. |
| 2010/0022414 A1 | 1/2010 | Link et al. |
| 2010/0035252 A1 | 2/2010 | Rothberg et al. |
| 2010/0055677 A1 | 3/2010 | Colston, Jr. et al. |
| 2010/0075436 A1 | 3/2010 | Urdea et al. |
| 2010/0105112 A1 | 4/2010 | Holtze et al. |
| 2010/0111768 A1 | 5/2010 | Banerjee et al. |
| 2010/0124759 A1 | 5/2010 | Wang et al. |
| 2010/0130369 A1 | 5/2010 | Shenderov et al. |
| 2010/0136544 A1 | 6/2010 | Agresti et al. |
| 2010/0137143 A1 | 6/2010 | Rothberg et al. |
| 2010/0137163 A1 | 6/2010 | Link et al. |
| 2010/0159592 A1 | 6/2010 | Holliger et al. |
| 2010/0172803 A1 | 7/2010 | Stone et al. |
| 2010/0173293 A1 | 7/2010 | Woudenberg et al. |
| 2010/0173394 A1 | 7/2010 | Colston, Jr. et al. |
| 2010/0183504 A1 | 7/2010 | Chen |
| 2010/0184069 A1 | 7/2010 | Fernando et al. |
| 2010/0188073 A1 | 7/2010 | Rothberg et al. |
| 2010/0197507 A1 | 8/2010 | Rothberg et al. |
| 2010/0210479 A1 | 8/2010 | Griffiths et al. |
| 2010/0213628 A1 | 8/2010 | Bausch et al. |
| 2010/0233026 A1 | 9/2010 | Ismagliov et al. |
| 2010/0233083 A1 | 9/2010 | Dias et al. |
| 2010/0240101 A1 | 9/2010 | Lieberman et al. |
| 2010/0273173 A1 | 10/2010 | Hirai et al. |
| 2010/0282617 A1 | 11/2010 | Rothberg et al. |
| 2010/0285975 A1 | 11/2010 | Mathies et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0000560 A1 | 1/2011 | Miller et al. |
| 2011/0024455 A1 | 2/2011 | Bethuy et al. |
| 2011/0033854 A1 | 2/2011 | Drmanac et al. |
| 2011/0045462 A1 | 2/2011 | Fu et al. |
| 2011/0053151 A1 | 3/2011 | Hansen et al. |
| 2011/0053798 A1 | 3/2011 | Hindson et al. |
| 2011/0059435 A1 | 3/2011 | Vogelstein et al. |
| 2011/0059556 A1 | 3/2011 | Strey et al. |
| 2011/0104725 A1 | 5/2011 | Pamula et al. |
| 2011/0104816 A1 | 5/2011 | Pollack et al. |
| 2011/0111981 A1 | 5/2011 | Love et al. |
| 2011/0142734 A1 | 6/2011 | Ismagliov et al. |
| 2011/0151444 A1 | 6/2011 | Albers et al. |
| 2011/0159499 A1 | 6/2011 | Hindson et al. |
| 2011/0174622 A1 | 7/2011 | Ismagilov et al. |
| 2011/0176966 A1 | 7/2011 | Ismagilov et al. |
| 2011/0177494 A1 | 7/2011 | Ismagilov et al. |
| 2011/0177586 A1 | 7/2011 | Ismagilov et al. |
| 2011/0177609 A1 | 7/2011 | Ismagilov et al. |
| 2011/0188717 A1 | 8/2011 | Baudry et al. |
| 2011/0190146 A1 | 8/2011 | Boehm et al. |
| 2011/0218123 A1 | 9/2011 | Weitz et al. |
| 2011/0223314 A1 | 9/2011 | Zhang et al. |
| 2011/0244455 A1 | 10/2011 | Larson et al. |
| 2011/0250597 A1 | 10/2011 | Larson et al. |
| 2011/0257031 A1 | 10/2011 | Bodeau et al. |
| 2011/0267457 A1 | 11/2011 | Weitz et al. |
| 2011/0274706 A1 | 11/2011 | Nelson et al. |
| 2011/0275063 A1 | 11/2011 | Weitz et al. |
| 2011/0311978 A1 | 12/2011 | Makarewicz, Jr. et al. |
| 2012/0010085 A1 | 1/2012 | Rava et al. |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0021919 A1 | 1/2012 | Scholl et al. |
| 2012/0021930 A1 | 1/2012 | Schoen et al. |
| 2012/0088691 A1 | 4/2012 | Chen et al. |
| 2012/0122714 A1 | 5/2012 | Samuels et al. |
| 2012/0164652 A1 | 6/2012 | Clemens et al. |
| 2012/0165219 A1 | 6/2012 | Van Der Zaag et al. |
| 2012/0167142 A1 | 6/2012 | Hey |
| 2012/0171667 A1 | 7/2012 | Shoemaker et al. |
| 2012/0190032 A1 | 7/2012 | Ness et al. |
| 2012/0220494 A1 | 8/2012 | Samuels et al. |
| 2012/0231972 A1 | 9/2012 | Golyshin et al. |
| 2012/0244043 A1 | 9/2012 | Leblanc et al. |
| 2012/0252012 A1 | 10/2012 | Armougom et al. |
| 2012/0253689 A1 | 10/2012 | Rogan |
| 2012/0258516 A1 | 10/2012 | Schultz et al. |
| 2012/0288857 A1 | 11/2012 | Livak |
| 2012/0302448 A1 | 11/2012 | Hutchison et al. |
| 2012/0322058 A1 | 12/2012 | Regan et al. |
| 2013/0099018 A1 | 4/2013 | Miller et al. |
| 2013/0109577 A1 | 5/2013 | Korlach et al. |
| 2013/0123339 A1 | 5/2013 | Heyes et al. |
| 2013/0143745 A1 | 6/2013 | Christen et al. |
| 2013/0157870 A1 | 6/2013 | Pushkarev et al. |
| 2013/0157872 A1 | 6/2013 | Griffiths et al. |
| 2013/0178368 A1 | 7/2013 | Griffiths et al. |
| 2013/0178378 A1 | 7/2013 | Hatch et al. |
| 2013/0203606 A1 | 8/2013 | Pollack et al. |
| 2013/0217071 A1 | 8/2013 | Montesclaros et al. |
| 2013/0217601 A1 | 8/2013 | Griffiths et al. |
| 2013/0224751 A1 | 8/2013 | Olson et al. |
| 2013/0225418 A1 | 8/2013 | Watson |
| 2013/0225623 A1 | 8/2013 | Buxbaum et al. |
| 2013/0244906 A1 | 9/2013 | Collins |
| 2013/0274117 A1 | 10/2013 | Church et al. |
| 2013/0288254 A1 | 10/2013 | Pollack et al. |
| 2013/0295567 A1 | 11/2013 | Link et al. |
| 2013/0295568 A1 | 11/2013 | Link |
| 2013/0296535 A1 | 11/2013 | Church et al. |
| 2014/0065631 A1 | 3/2014 | Froehlich et al. |
| 2014/0235452 A1 | 8/2014 | Rothberg et al. |
| 2014/0256568 A1 | 9/2014 | Link |
| 2014/0256585 A1 | 9/2014 | McCoy |
| 2014/0274786 A1 | 9/2014 | McCoy et al. |
| 2014/0323317 A1 | 10/2014 | Link et al. |

(56) References Cited

U.S. PATENT DOCUMENTS

| | | |
|---|---|---|
| 2014/0329239 A1 | 11/2014 | Larson et al. |
| 2015/0018236 A1 | 1/2015 | Green et al. |
| 2015/0038356 A1 | 2/2015 | Karlin-Neumann et al. |
| 2015/0126400 A1 | 5/2015 | Watson et al. |
| 2015/0184256 A1 | 7/2015 | Samuels et al. |
| 2015/0197790 A1 | 7/2015 | Tzonev |
| 2015/0247191 A1 | 9/2015 | Zhang et al. |
| 2015/0336072 A1 | 11/2015 | Weitz et al. |
| 2016/0060621 A1 | 3/2016 | Agresti et al. |
| 2016/0289670 A1 | 10/2016 | Samuels et al. |
| 2016/0304954 A1 | 10/2016 | Lin et al. |
| 2017/0304785 A1 | 10/2017 | Link et al. |
| 2018/0057863 A1 | 3/2018 | Larson et al. |
| 2018/0057868 A1 | 3/2018 | Walder et al. |
| 2018/0223348 A1 | 8/2018 | Link et al. |
| 2018/0272294 A1 | 9/2018 | Griffiths et al. |
| 2018/0272296 A1 | 9/2018 | Link et al. |
| 2018/0272299 A1 | 9/2018 | Griffiths et al. |
| 2018/0304222 A1 | 10/2018 | Weitz et al. |
| 2018/0353913 A1 | 12/2018 | Link et al. |
| 2018/0355350 A1 | 12/2018 | Link et al. |
| 2018/0361346 A1 | 12/2018 | Griffiths et al. |
| 2018/0363050 A1 | 12/2018 | Hutchison et al. |
| 2019/0024261 A1 | 1/2019 | Griffiths et al. |
| 2019/0107489 A1 | 4/2019 | Griffiths et al. |
| 2019/0134581 A1 | 5/2019 | Yurkovetsky et al. |
| 2019/0316119 A1 | 10/2019 | Samuels et al. |

FOREIGN PATENT DOCUMENTS

| | | |
|---|---|---|
| AT | 155711 T | 8/1997 |
| AT | 167816 T | 7/1998 |
| AU | 4032078 A | 4/1980 |
| AU | 6415380 A | 5/1981 |
| AU | 1045983 A | 6/1984 |
| AU | 2177292 A | 1/1993 |
| AU | 4222393 A | 11/1993 |
| AU | 4222593 A | 11/1993 |
| AU | 4222693 A | 11/1993 |
| AU | 4222793 A | 11/1993 |
| AU | 4223593 A | 11/1993 |
| AU | 677197 B2 | 4/1997 |
| AU | 677781 B2 | 5/1997 |
| AU | 680195 B2 | 7/1997 |
| AU | 2935197 A | 1/1998 |
| AU | 3499097 A | 1/1998 |
| AU | 3501297 A | 1/1998 |
| AU | 1276099 A | 6/1999 |
| AU | 4955799 A | 12/1999 |
| AU | 3961100 A | 10/2000 |
| AU | 4910300 A | 11/2000 |
| AU | 747464 B2 | 5/2002 |
| AU | 768399 B2 | 12/2003 |
| AU | 2004225691 B2 | 6/2010 |
| AU | 2010224352 A1 | 10/2010 |
| BR | 8200642 A | 12/1982 |
| BR | 9710052 A | 1/2000 |
| CA | 1093344 A1 | 1/1981 |
| CA | 2258481 A1 | 1/1998 |
| CA | 2520548 A1 | 10/2004 |
| CH | 563 087 A5 | 6/1975 |
| CH | 563807 A5 | 7/1975 |
| DE | 2100685 A1 | 7/1972 |
| DE | 3042915 A1 | 9/1981 |
| DE | 43 08 839 C2 | 4/1997 |
| DE | 69126763 T2 | 2/1998 |
| DE | 199 61 257 A1 | 7/2001 |
| DE | 100 15 109 A1 | 10/2001 |
| DE | 100 41 823 A1 | 3/2002 |
| EP | 0047130 B1 | 2/1985 |
| EP | 0402995 A2 | 12/1990 |
| EP | 0249007 A3 | 3/1991 |
| EP | 0418635 A1 | 3/1991 |
| EP | 0476178 A1 | 3/1992 |
| EP | 0546174 A1 | 6/1993 |
| EP | 0618001 | 10/1994 |
| EP | 620432 A1 | 10/1994 |
| EP | 0637996 A1 | 2/1995 |
| EP | 0637997 A1 | 2/1995 |
| EP | 0718038 A2 | 6/1996 |
| EP | 0540281 B1 | 7/1996 |
| EP | 0528580 B1 | 12/1996 |
| EP | 0486351 B1 | 7/1997 |
| EP | 0895120 | 2/1999 |
| EP | 1362634 A1 | 11/2003 |
| EP | 1447127 A1 | 8/2004 |
| EP | 1462517 A1 | 9/2004 |
| EP | 04782399.2 | 5/2006 |
| EP | 1741482 | 1/2007 |
| EP | 2017910 A1 | 1/2009 |
| EP | 2127736 | 12/2009 |
| EP | 2047910 B1 | 1/2012 |
| EP | 13165665.4 | 11/2013 |
| EP | 13165667.0 | 11/2013 |
| EP | 2363205 A3 | 6/2014 |
| EP | 2534267 B1 | 4/2018 |
| ES | 2 095 413 T3 | 2/1997 |
| FR | 2 404 834 A1 | 4/1979 |
| FR | 2 451 579 A1 | 10/1980 |
| FR | 2 469 714 A1 | 5/1981 |
| FR | 2 470 385 A1 | 5/1981 |
| FR | 2 650 657 A1 | 2/1991 |
| FR | 2 669 028 A1 | 5/1992 |
| FR | 2 703 263 A1 | 10/1994 |
| GB | 1148543 | 4/1969 |
| GB | 1 446 998 | 8/1976 |
| GB | 2 005 224 | 4/1979 |
| GB | 2 047 880 | 12/1980 |
| GB | 2 062 225 | 5/1981 |
| GB | 2 064 114 | 6/1981 |
| GB | 2097692 A | 11/1982 |
| GB | 2 210 532 | 6/1989 |
| IE | 922432 A1 | 2/1993 |
| JP | S5372016 A | 6/1978 |
| JP | S5455495 A | 5/1979 |
| JP | 55125472 | 9/1980 |
| JP | S5636053 A | 4/1981 |
| JP | 56-124052 | 9/1981 |
| JP | 59-49832 A | 3/1984 |
| JP | 59-102163 | 6/1984 |
| JP | H0665609 A | 3/1994 |
| JP | 6-265447 A | 9/1994 |
| JP | 7-489 A | 1/1995 |
| JP | 8-153669 | 6/1996 |
| JP | 10-217477 | 8/1998 |
| JP | 3-232525 | 10/1998 |
| JP | 2000-271475 | 10/2000 |
| JP | 2001-301154 A | 10/2001 |
| JP | 2001-517353 A | 10/2001 |
| JP | 2002-085961 A | 3/2002 |
| JP | 2003-501257 A | 1/2003 |
| JP | 2003-502656 A | 1/2003 |
| JP | 2003-149136 A | 5/2003 |
| JP | 2003-222633 A | 8/2003 |
| JP | 2005-037346 A | 2/2005 |
| JP | 2005-192944 A | 7/2005 |
| JP | 2007-190364 A | 8/2007 |
| JP | 2009-265751 A | 11/2009 |
| JP | 2010-198393 A | 9/2010 |
| JP | 2012-204765 A | 10/2012 |
| JP | 2013-143959 A | 7/2013 |
| JP | 2016063824 A | 4/2016 |
| NZ | 264353 A | 5/1996 |
| WO | 84/02000 | 5/1984 |
| WO | 90/15807 A1 | 12/1990 |
| WO | 91/05058 A1 | 4/1991 |
| WO | 91/07772 | 5/1991 |
| WO | 91/16966 A1 | 11/1991 |
| WO | 92/03734 | 3/1992 |
| WO | 92/21746 | 12/1992 |
| WO | 93/03151 | 2/1993 |
| WO | 93/08278 | 4/1993 |
| WO | 93/22053 | 11/1993 |
| WO | 93/22054 | 11/1993 |

(56) References Cited

FOREIGN PATENT DOCUMENTS

| | | |
|---|---|---|
| WO | 93/22055 | 11/1993 |
| WO | 93/22058 | 11/1993 |
| WO | 93/22421 | 11/1993 |
| WO | 94/16332 | 7/1994 |
| WO | 94/23738 | 10/1994 |
| WO | 94/24314 | 10/1994 |
| WO | 94/26766 | 11/1994 |
| WO | 98/00705 | 1/1995 |
| WO | 95/11922 | 5/1995 |
| WO | 95/19922 | 7/1995 |
| WO | 95/24929 | 9/1995 |
| WO | 95/33447 | 12/1995 |
| WO | 96/34112 | 10/1996 |
| WO | 96/38730 | 12/1996 |
| WO | 96/40057 A2 | 12/1996 |
| WO | 96/40062 | 12/1996 |
| WO | 96/40723 | 12/1996 |
| WO | 97/00125 | 1/1997 |
| WO | 97/00442 | 1/1997 |
| WO | 97/04297 | 2/1997 |
| WO | 97/04748 | 2/1997 |
| WO | 97/23140 | 7/1997 |
| WO | 97/28556 | 8/1997 |
| WO | 97/38318 A1 | 10/1997 |
| WO | 97/39814 | 10/1997 |
| WO | 97/40141 | 10/1997 |
| WO | 97/45644 | 12/1997 |
| WO | 97/47763 A1 | 12/1997 |
| WO | 98/00231 | 1/1998 |
| WO | 98/02237 | 1/1998 |
| WO | 98/10267 | 3/1998 |
| WO | 98/13502 | 4/1998 |
| WO | 98/22625 A1 | 5/1998 |
| WO | 98/23733 | 6/1998 |
| WO | 98/31700 | 7/1998 |
| WO | 98/33001 | 7/1998 |
| WO | 98/34120 | 8/1998 |
| WO | 98/37186 | 8/1998 |
| WO | 98/41869 | 9/1998 |
| WO | 98/52691 | 11/1998 |
| WO | 98/58085 | 12/1998 |
| WO | 99/02671 | 1/1999 |
| WO | 99/22858 | 5/1999 |
| WO | 99/28020 | 6/1999 |
| WO | 99/28507 A1 | 6/1999 |
| WO | 99/31019 | 6/1999 |
| WO | 99/42539 A1 | 8/1999 |
| WO | 99/54730 | 10/1999 |
| WO | 99/61888 | 12/1999 |
| WO | 00/04139 A1 | 1/2000 |
| WO | 00/47322 | 2/2000 |
| WO | 00/52455 | 2/2000 |
| WO | 00/37924 A1 | 6/2000 |
| WO | 00/40712 | 6/2000 |
| WO | 00/54735 | 9/2000 |
| WO | 00/61275 | 10/2000 |
| WO | 00/70080 | 11/2000 |
| WO | 00/76673 | 12/2000 |
| WO | 00/078455 A1 | 12/2000 |
| WO | 01/12327 | 2/2001 |
| WO | 01/14589 | 3/2001 |
| WO | 01/18244 | 3/2001 |
| WO | 01/64332 | 9/2001 |
| WO | 01/68257 | 9/2001 |
| WO | 01/69289 | 9/2001 |
| WO | 01/72431 | 10/2001 |
| WO | 01/80283 | 10/2001 |
| WO | 01/089787 A2 | 11/2001 |
| WO | 01/89788 A2 | 11/2001 |
| WO | 01/94635 A2 | 12/2001 |
| WO | 02/16017 | 2/2002 |
| WO | 02/18949 | 3/2002 |
| WO | 02/22869 | 3/2002 |
| WO | 02/23163 A1 | 3/2002 |
| WO | 02/27660 A2 | 4/2002 |
| WO | 02/31203 | 4/2002 |
| WO | 2002/036815 A2 | 5/2002 |
| WO | 02/47665 | 8/2002 |
| WO | 02/060275 | 8/2002 |
| WO | 02/060591 A1 | 8/2002 |
| WO | 02/066992 A1 | 8/2002 |
| WO | 02/068104 A1 | 9/2002 |
| WO | 02/078845 | 10/2002 |
| WO | 02/103011 | 12/2002 |
| WO | 02/103363 | 12/2002 |
| WO | 03/011443 | 2/2003 |
| WO | 03/026798 A1 | 4/2003 |
| WO | 03/037302 | 5/2003 |
| WO | 03/044187 | 5/2003 |
| WO | 03/078659 | 9/2003 |
| WO | 2003/003015 | 10/2003 |
| WO | 03/099843 | 12/2003 |
| WO | 2004/002627 | 1/2004 |
| WO | 2004/018497 A2 | 3/2004 |
| WO | 2004/024917 | 3/2004 |
| WO | 2004/026453 A2 | 4/2004 |
| WO | 2004/037374 A2 | 5/2004 |
| WO | 2004/038363 | 5/2004 |
| WO | 04/071638 A2 | 8/2004 |
| WO | 2004/069849 A2 | 8/2004 |
| WO | 2004/074504 | 9/2004 |
| WO | 2004/083443 A1 | 9/2004 |
| WO | 2004/087308 | 10/2004 |
| WO | 2004/088314 | 10/2004 |
| WO | 2004/091763 | 10/2004 |
| WO | 2004/102204 | 11/2004 |
| WO | 2004/103565 | 12/2004 |
| WO | 2005/000970 | 1/2005 |
| WO | 2005/002730 | 1/2005 |
| WO | 2005/003375 A2 | 1/2005 |
| WO | 2005/11867 A2 | 2/2005 |
| WO | 05/021151 | 3/2005 |
| WO | 2005/023427 A1 | 3/2005 |
| WO | 2005/041884 A2 | 5/2005 |
| WO | 05/049787 A2 | 6/2005 |
| WO | 2005/103106 | 11/2005 |
| WO | 2005/118138 | 12/2005 |
| WO | 2005/118867 A2 | 12/2005 |
| WO | 2006/002641 | 1/2006 |
| WO | 2006/009657 | 1/2006 |
| WO | 2006/027757 | 3/2006 |
| WO | 2006/027757 A2 | 3/2006 |
| WO | 2006/038035 A2 | 4/2006 |
| WO | 2006/040551 | 4/2006 |
| WO | 2006/040554 | 4/2006 |
| WO | 2006/042303 A2 | 4/2006 |
| WO | 2006/076810 A1 | 7/2006 |
| WO | 2006/078841 | 7/2006 |
| WO | 2006/096571 | 9/2006 |
| WO | 2006/101851 | 9/2006 |
| WO | 2007/012638 A1 | 2/2007 |
| WO | 2007/021343 | 2/2007 |
| WO | 2007/030501 | 3/2007 |
| WO | 2007026884 A1 | 3/2007 |
| WO | 2007/081385 | 7/2007 |
| WO | 2007/081387 A1 | 7/2007 |
| WO | 2007/089541 | 8/2007 |
| WO | 2007/092473 A2 | 8/2007 |
| WO | 2007/114794 A1 | 10/2007 |
| WO | 2007/123744 A2 | 11/2007 |
| WO | 2007/133710 | 11/2007 |
| WO | 2007/138178 | 12/2007 |
| WO | 2007/140015 A2 | 12/2007 |
| WO | 2008/021123 | 2/2008 |
| WO | 2008/052138 A2 | 5/2008 |
| WO | 2008/063227 | 5/2008 |
| WO | 2008/097559 | 8/2008 |
| WO | 2008/115626 A2 | 9/2008 |
| WO | 2008/121342 | 10/2008 |
| WO | 2008/130623 | 10/2008 |
| WO | 2008/134153 A1 | 11/2008 |
| WO | 2009/015296 A1 | 1/2009 |
| WO | 2009/029229 | 3/2009 |
| WO | 2009/049889 A1 | 4/2009 |

(56) References Cited

FOREIGN PATENT DOCUMENTS

| WO | 2009/059430 | A1 | 5/2009 |
|---|---|---|---|
| WO | 2009/085929 | A1 | 7/2009 |
| WO | 2009/094623 | A2 | 7/2009 |
| WO | 2009/117485 | A2 | 9/2009 |
| WO | 2009/137415 | A2 | 11/2009 |
| WO | 2009/137606 | A1 | 11/2009 |
| WO | 2010/009365 | A1 | 1/2010 |
| WO | 2010/056728 | A1 | 5/2010 |
| WO | 2010/040006 | | 8/2010 |
| WO | 2010/115154 | A1 | 10/2010 |
| WO | 2010/151776 | | 12/2010 |
| WO | 2011/042564 | | 4/2011 |
| WO | 2011/079176 | | 6/2011 |
| WO | 2011/100604 | A2 | 8/2011 |
| WO | 2012/022976 | A1 | 2/2012 |
| WO | 2012/036679 | A1 | 3/2012 |
| WO | 2012/045012 | A2 | 4/2012 |
| WO | 2012/047297 | A2 | 4/2012 |
| WO | 2012/048341 | A1 | 4/2012 |
| WO | 2012/083225 | A2 | 6/2012 |
| WO | 2012/142213 | A2 | 10/2012 |
| WO | 2012/167142 | A2 | 12/2012 |
| WO | 2013/14356 | A2 | 1/2013 |
| WO | 2013/120089 | A1 | 8/2013 |
| WO | 2013/165748 | A1 | 11/2013 |
| WO | 2014/026031 | A1 | 2/2014 |
| WO | 2014/065756 | A1 | 5/2014 |
| WO | 2014/165559 | A2 | 10/2014 |
| WO | 2014/204939 | A2 | 12/2014 |
| WO | 2015/013681 | A1 | 1/2015 |
| WO | 2015/164212 | A1 | 10/2015 |
| WO | 2015/200541 | A1 | 12/2015 |
| WO | 2015/200893 | A2 | 12/2015 |
| WO | 2017/100350 | A1 | 6/2017 |
| WO | 2017/117358 | A1 | 7/2017 |

OTHER PUBLICATIONS

Adang, 2001, The contribution of combinatorial chemistry to lead generation: an interim analysis, Curr Med Chem 8:985-998.
Affholter 1999, Engineering a Revolution, Chemistry in Britain 48-51.
Agrawal, 1990, Site-specific functionalization of oligodeoxynucleotides for non-radioactive labelling, Tetrahedron Let 31:1543-1546.
Aharoni, 2005, High-Throughput screens and selections of enzyme-encoding genes, Curr Opin Chem Biol, 9(2):210-6.
Ahn, 2006, Dielectrophoretic manipulation of drops for high-speed microluidic sorting devices, Applied Phys Lett 88:024104.
Akasheh, 2004, Development of piezoelectric micromachined ultrasonic transducers, Sensors and Actuators A Physical, 111:275-287.
Allen, 2000, High throughput fluorescence polarization: a homogeneous alternative to radioligand binding for cell surface receptors J Biomol Screen. 5(2):63-69.
Ammar, 2003, UV/Vis absorption and fluorescence spectroscopic study of novel symmetrical biscoumarin dyes, Dyes and Pigments 57:259-265.
Amstutz, 2001, In vitro display technologies: novel developments and applications. Curr Opin Biotech 12:400-405.
Anarbaev, 1998, Klenow fragment and DNA polymerase alpha-primase fromserva calf thymus in water-in-oil microemulsions, Biochim Biophy Acta 1384:315-324.
Anderson, 1983, Preparation of a cell-free protein-synthesizing system from wheat germ, Methods Enz 101:635-644.
Anderson, 1993, Restriction endonucleases and modification methylases, Curr Op Struct Biol 3:24-30.
Ando, 1999, PLGA microspheres containing plasmid DNA: preservation of supercoiled DNA via cryopreparation and carbohydrate stabilization, J Pharm Sci 88(1):126-130.
Angell, 1983, Silicon micromechanical devices, Scientific Am 248:44-55.

Anhuf, 2003, Determination of SMN1 and SMN2 copy number using TaqMan technology, Hum Mutat 22(1):74-78.
Anna, 2003, Formation of dispersions using flow focusing in microchannels, Appl Phys Lett82(3):364-366.
Armstrong, 1996, Multiple-Component condensation strategies for combinatorial library synthesis, Acc Chem Res 29(3):123-131.
Ashkin, 1987, Optical trapping and manipulation of single cells using infrared laser beams, Nature 330:769-771.
Ashkin, 1987, Optical trapping and manipulation of viruses and bacteria, Science 235(4795):1517-20.
Auroux, 2002, Micro Total Analysis Systems 2: Analytical standard operations and applications, Anal Chern 74(12):2637-2652.
Baccarani, 1977, *Escherichia coli* dihydrofolate reductase: isolation and characterization of two isozymes, Biochemistry 16(16):3566-72.
Bagwe, 2001, Improved drug delivery using microemulsions: rationale, recent progress, and new horizons, Crit Rev Ther Drug Carr Sys 18(1):77-140.
Baker, 2010, Clever PCR: more genotyping, smaller volumes, Nat Meth 7:351-356.
Ballantyne, 1973, Selective area metallization by electron-beam controlled direct metallic deposition, J Vac Sci Tech 10:1094.
Barany, 1991, Genetic disease detection and DNA amplification using cloned thermostable ligase, PNAS 88(1):189-93.
Barany, 1991, The ligase chain reaction in a PCR World, PCR Meth App 1(1):5-16.
Baret, 2009, Fluorescence-activated droplet sorting (FADS): efficient microfluidic cell sorting based on enzymatic activity, Lab Chip 9:1850-1858.
Baret, 2009, Kinetic aspects of emulsion stabilization by surfactants: a microfluidic analysis, Langmuir 25:6088-6093.
Baroud, 2004, Multiphase flows in microfluidics, Physique 5:547-555.
Bauer, 1999, Advances in cell separation: recent developments in counterflow centrifugal elutriation and continuous flow cell separation, J Chromot 722:55-69.
Beebe, 2000, Functional hydrogel structures for autonomous flow control inside microfluidic channels, Nature 404:588-590.
Beer, 2007, On-chip, real-time, single-copy polymerase chain reaction in picoliter droplets, Anal Chem 79(22):8471-8475.
Beer, 2008, On-chip single-copy real-time reverse transcription PCR in isolated picoliter droplets, Anal Chem 80(6): 1854-1858.
Bein, 1999, Efficient assays for combinatorial methods for the eiscovery of catalysts, Agnew Chern Int Ed 38:3:323-26.
Benichou, 2002, Double emulsions stabilized by new molecular recognition hybrids of natural polymers, Polym Adv Tech 13:1019-1031.
Benner, 1994, Expanding the genetic lexicon, Trends Biotech 12:158-63.
Benning, 2000, The binding of substrate analogs to phosphotriesterase. J Biol Chem 275:30556-30560.
Berman, 1987, An agarose gel electrophoresis assay for the detection of DNA-binding activities in yeast cell extracts, Meth Enz 155:528-37.
Bernath, 2004, In Vitro Compartmentalization by double emulsions: sorting and gene enrichment by FACS Anal Biochem 325:151-157.
Bernath, 2005, Directed evolution of protein inhibitors of DNA-nucleases by in vitro comparlnentalization (IVC) and nano-droplet delivery, J Mol Biol 345(5):1015-26.
Betlach, 1976, A restriction endonuclease analysis of the bacterial plasmid controlling the EcoRI restriction and modification of DNA, Fed Proc 35:2037-2043.
Bibette, 1999, Emulsions: basic principles, Rep Prog Phys 62:969-1033.
Bico, 2002, Rise of liquids and bubbles in angular capillary tubes, J Colloid & Interface Sc 247:162-166.
Bico, 2002, Self-Propelling Slugs, J Fluid Meeh 467:101-127.
Binder, 2009, Mismatch and G-stack modulated probe signals on SNP microarrays, PLoS One, 4(11):e7862.
Binladen, 2007, The use of coded PCR primers enables high-throughput sequencing of multiple homolog amplification products by 454 parallel sequencing, PLoSOne 2(2):e197.

(56) References Cited

OTHER PUBLICATIONS

Blanchet, 1993, Laser Ablation and the Production of Polymer Films, Science, 262(5134)719-721.
Boder, 1997, Yeast surface display for screening combinatorial polypeptide libraries, Nat Biotech 15(6):553-7.
Bosque, 2009, Induction of HIV-1 latency and reactivation in primary memory CD4+ T cells, Blood, 113(1):58-65.
Cooper, 2000, The Central Role of Enzymes as Biological Catalysts, The Cell: A Molecular Approach, 2nd Edition, pp. 1-6.
Cormack, 1996, FACS-optimized mutants of the green fluorescent protein (GFP), Gene 173(1 ):33-38.
Cortesi, 2002, Production of lipospheres as carriers for bioactive compounds, Biomateials, 23(11): 2283-2294.
Courrier, 2004, Reverse water-in-fluorocarbon emulsions and microemulsions obtained with a fluorinated surfactant, Colloids and Surfaces A: Physicochem. Eng. Aspects 244:141-148.
Craig, 1995, Fluorescence-based enzymatic assay by capillary electrophoresis laser-induced fluoresence detection for the determination of a few alpha-galactosidase molecules, Anal Biochem. 226:147.
Creagh, 1993, Structural and catalytic properties of enzymes in reverse micelles, Enzyme Microb Technol 15(5):383-92.
Crosland-Taylor, 1953, A Device for Counting Small Particles suspended in a Fluid through a Tube, Nature 171:37-38.
Crowley, 1973, Electrical breakdown of bimolecular lipid membranes as an electromechanical instability, Biophys J. 13(7):711-724.
Cull, 1992, Screening for receptor ligands using large libraries of peptides linked to the C terminus of the lac repressor, PNAS 89:1865-9.
Curran, 1998, Strategy-level separations in organic synthesis: from planning to practice. Angew Chern Int Ed, 37:1174-11-96.
Czarnik, 1997, Encoding methods for combinatorial chemistry, Curr Opin Chem Biol 1:60-66.
Dankwardt, 1995, Combinatorial synthesis of small-molecule libraries using 3-amino-5-hydroxybenzoic acid, 1:113-120.
David, 1974, Protein iodination with solid-state lactoperoxidase, Biochemistry 13:1014-1021.
Davis, 1987, Multiple emulsions as targetable delivery systems, Meth Enzymol 149:51-64.
Davis, 2006, Deterministic hydrodynamics: Taking blood apart, PNAS 103:14779-14784.
De Gans, 2004, Inkjet printing of polymers: state of the art and future developments, Advanced materials, 16: 203-213.
De Wildt, 2002, Isolation of receptor-ligand pairs by capture of long-lived multivalent interaction complexes, Proceedings of the National Academy of Sciences of the United States, 99, 8530-8535.
DelRaso, 1993, In vitro methodologies for enhanced toxicity testing, Toxicol. Lett. 68:91-99.
Deng, 2008, Design and analysis of mismatch probes for long oligonucleotide microarrays, BMC Genomics; 9:491, 13 pages.
Dickinson, 1992, Interfacial interactions and the stability of oil-in-water emulsions, Pure Appl Chem 64(11):1721-1724.
Dickinson, 1994, Emulsions and droplet size control, Wedlock, D.J., Ed., in Controlled Particle Droplet and Bubble Formulation, ButterWorth-Heine-mann, 191-257.
DiMatteo, 2008, Genetic conversion of an SMN2 gene to SMN1: A novel approach to the treatment of spinal muscular atrophy, Exp Cell Res. 314(4):878-886.
Ding, 2001, Scheduling of microfluidic operations for reconfigurable two-dimensional electrowetting arrays, IEEE Trans CADICS 20(12):1463-1468.
Ding, 2003, Direct molecular haplotyping of long-range genomic DNA with M1-PCR, Proc. Natl. Acad. Sci. USA, 100(33):7449-7453.
Dinsmore, 2002, Colioidosomes: Selectively Permeable Capsules Composed of Colloidal Particles, Science 298(5595):1006-1009.
Dittrich, 2005, A new embedded process for compartmentalized cell-free protein expression and on-line detection in microfluidic devices, Chembiochem 6(5):811-814.
Doi, 1999, STABLE: protein-DNA fusion system for screening of combinatorial protein libraries in vitro, FEBS Lett., 457: 227-230.
Doi, 2004, In vitro selection of restriction endonucleases by in vitro compartmentilization, Nucleic Acids Res, 32(12): e95.
Doman, 2002, Molecular docking and high-throughput screening for novel inhibitors of protein tyrosine phosphatase-1B, J Med Chem, 45: 2213-2221.
Domling, 2000, Multicomponent Reactions with Isocyanides, Angew Chem Int Ed 39(18):3168-3210.
Domling, 2002, Recent advances in isocyanide-based multicomponent chemistry, Curr Opin Chem Biol, 6(3):306-13.
Dorfman, 2005, Contamination-free continuous flow microfluidic polymerase chain reaction for quantitative and clinical applications, Anal Chem 77:3700-3704.
Dove, 2002, Research News Briefs, Nature Biotechnology 20:1213, 1 page.
Dower, 1988, High efficiency transformation of $E.\ coli$ by high voltage electroporation, Nucleic Acids Res 16:6127-6145.
Dressman, 2003, Transforming single DNA molecules into fluorescent magnetic particles for detection and enumeration of genetic variations, PNAS 100:8817-22.
Dreyfus, 2003, Ordered and disordered patterns in two phase flows in microchannels, Phys Rev Lett 90(14):144505-1-144505-4.
Drmanac, 1992, Sequencing by hybridization: towards an automated sequencing of one million M13 clones arrayed on membranes, Elctrophoresis 13:566-573.
Du, 2009, SlipChip, Lab Chip, 9, 2286-2292.
Dubertret, 2002, In vivo imaging of quantum dots encapsulated in phospholipid micelles, Science, 298: 1759-1762.
Duffy, 1998, Rapid Protyping of Microfluidic Systems and Polydimethylsiloxane, Anal Chem 70:474-480.
Duggleby, 1995, Analysis of Enzyme Progress Curves by Nonlinear Regression, Pt D. Academic Press 249:61-90.
Dumas, 1989, Purification and properties of the phosphotriesterase from Psuedomonas diminuta, J Biol Chem 264:19659-19665.
Eckert, 1991, DNA polymerase fidelity and the polymerase chain reaction, Genome Res 1:17-24.
Ecole Polytech Federate de Lausanne, 2014, Tracing water channels in cell surface receptors, PhysOrg News (2 pages).
Edel, 2002, Microfluidic Routes to the Controlled Production of Nanopaticles, Chemical Communications, 1136-1137.
Edris, 2001, Encapsulation of orange oil in a spray dried double emulsion, Nahrung/Food, 45(2):133-137.
Effenhauser, 1993, Glass chips for high-speed capillary electrophoresis separations with submicrometer plate heights, Anal Chem 65:2637-2642.
Eggers, 1999, Coalescence of Liquid Drops, J Fluid Meeh 401:293-310.
Ehrig, 1995, Green-fluorescent protein mutants with altered fluorescence excitation spectra, Febs Lett, 367(2):163-66.
Eigen, 1980, Hypercycles and compartments: compartments assists—but does not replace—hypercyclic organization of early genetic information, J Theor Biol, 85:407-11.
Kumaresan, 2008, High-throughput single copy DNA amplification and cell analysis in engineered nanoliter droplets, Anal Chem, 80:3522-3529.
Lage, 2003, Whole genome analysis of genetic alterations in small DNA samples using hyperbranched strand displacement amplification and array-CGH, Genome Res 13:294-307.
Laird, 2013, Rapid Quantification of the Latent Reservoir for HIV-1 Using a Viral Outgrowth Assay, Plos Pathogens 9(5):e1003398.
Lamprecht, 2004, pH-sensitive microsphere delivery increases oral bioavailability of calcitonin, J Control Rel 98(1):1-9.
Lancet, 1993, Probability model for molecular recognition in biological receptor repertoirs, PNAS 90(8):3715-9.
Landergren, 1988, A ligase mediated gene detection technique, Science 241(4869):1077-80.
Lasheras, 1998, Breakup and atomization of a round waterjet by a high speed annular air jet, J Fluid Mech 357:351-379.
Laufer, 1996, Introduction to Optics and Lasers in Engineering, Cambridge University Press, Cambridge UK:156-162.
Leamon, 2003, A massively parallel pictoterplate based platform for discrete picoliter-scale PCR, Electrophoresis 24:3769-3777.

(56) References Cited

OTHER PUBLICATIONS

Leary, 2000, Application of advanced cytometric and molecular technologies to minimal residual disease monitoring, Proc SPIE 3913:36-44.
Lee, 2000, Circulating flows inside a drop under time-periodic non-uniform electric fields, Phys Fuilds 12(8):1899-1910.
Lee, 2001, Preparation of silica particles encapsulating retinol using O/W/O multiple emulsions, J Coll Interface Sci 240(1):83-89.
Lee, 2002, Effective formation of silicone-in-fluorocarbon-in-water double emulsions, J Disp Sci Tech 23(4):491-497.
Lee, 2002, Investigating the target recognition of DNA cytosine-5 methyltransferase Hhal by library selection using in vitro compartmentalisation (IVC), Nucleic Acids Res 30:4937-4944.
Lee, 2004, Special issue on biomedical applications for MEMS and microfluidics, Proc IEEE 92(1):3-5.
Lemof, 2003, An AC magnetohydrodynamic microfluidic switch for Micro Total Analysis Systems, Biomed Microdev 5(I):55-60.
Leng 2009, Microfluidic crystalizaiton,Lab Chip 9:24-23.
Leng, 2010, Agarose droplet microfluidics for highly parallel and efficient single molecule emulsion PCR, Lab Chip 10:2841-2843.
Lesley, 1991, Use of in vitro protein synthesis from PCR-generated templates to study interaction of *E coli* transcription factors with core RNA polymerase, J Biol Chem 266(4):2632-8.
Lesley, 1995, Preparation and use of *E. coli* S-30 extracts, Methods Mol Biol 37:265-78.
Leung, 1989, A method for random mutagenesis of a defined DNA segment using a modified polymerase chain reaction, Technique 1:11-15.
Li, 1995, Single-step procedure for labeling DNA strand breaks with fllourescein- or BODIPY-conjugated deoxynucleotides, Cytometry 20:172-180.
Li, 1997, Transport, manipulation, and reaction of biological cells on-chip using electrokinetic effects, Anal Chem 69(8):1564-1568.
Li, 2005, Multiplexed detection of pathogen DNA with DNA-based fluorescence nanobarcodes, Nat Biotech 23(7):885-889.
Li, 2006, Nanoliter microfluidic hybrid method for simultaneous screening and optimization validated with crystallization of membrane proteins, PNAS 103:19243-19248.
Li, 2018, Microfluidic fabrication of microparticles for biomedical applications, Chem Soc Rev 47(15):5646-5683.
Liao, 1986, Isolation of a thermostable enzyme variant by cloning and selection in a thermophile, PNAS 83:576-80.
Lim, 1980, Microencapsulated islets as bioartificial endocrine pancreas, Science 210(4472):908-10.
Lin, 2007, Self-assembled combinatorial encoding nanoarrays for multiplexed biosensing, Nano Lett 7(2):507-512.
Link, 2004, Geometrically mediated breakup of drops in microfluidic devices, Phys Rev Lettv92(5):054503-1-4.
Link, 2006, Electric control droplets in microfluidic devices, Angew Chem Int Ed 45:2556-2560.
Lipinski, 2001, Experimental and computational approaches to estimate solubility and permeability in drug discovery, , Adv Drug Deliv Rev 46:3-26.
Lipkin, 1988, Biomarkers of increased susceptibility to gastreointestinal cancer: new application to studies of cancer prevention in human subjects, Cancer Res 48:235-245.
Liu, 2000, Passive mixing in a three-dimensional serpentine microchannel, J MEMS 9(2):190-197.
Liu, 2002, Fabrication and characterization of hydrogel-based microvalves, Mecoelectromech. Syst.11:45-53.
Lizardi, 1998, Mutation detection and single-molecule counting using isothermal rolling-circle amplification. Nat Genet 19(3):225-32.
Lo, 2007, Digital PCR for the molecular detection of fetal chromosomal aneuploidy, PNAS 104(32):13116-13121.
Loakes, 1994, 5-Nitroindole as a universal base analogue, Nucleic Acids Res 22:4039-4043.
Loakes, 1997, Stability and structure of DNA oligonucleotides containing non-specific base analogues, J Mol Biol 270:426-435.

Lodish, 2000, Structure of Nucleic Acids, Section 4.1 , Molecular Cell Biology, 4th edition, New York, 1-3.
Loeker, 2003, FTIR analysis of water in supercritical carbon dioxide microemulsions using monofunctional perfluoropolyether surfanctants, Colloids and Surfaces A: Phys Eng Asp 214:143-150.
Loo, 2004, Nanoshell Enabled Photonics-Based Imaging and Therapy of Cancer, Technology in Cancer Research & Treatment 3(1):33-40.
Lopez-Herrera, 1995, The electrospraying of viscous and non-viscous semi-insulating liquids: scaling laws, Bull Am Phys Soc 40 (12):2041.
Lopez-Herrera, 1999, One-dimensional simulation of the breakup of capillary jets of conducting liquids application to EHD spraying, Aerosol Set 30(7):895-912.
Lopez-Herrera, 2003, Coaxial jets generated from electrified Taylor cones, Aerosol Sci 34:535-552.
Lorenceau, 2005, Generation of polymerosomes from double-emulsions, Langmuir21(20):9183-9186.
Lorenz, 1991, Isolation and expression of a cDNA encoding Renilla reniformis luciferase, PNAS 88(10):4438-42.
Loscertales, 2002, Micro/nano encapsulation via electrified coaxial liquid jets, Science 295(5560):1695-1698.
Lowe, 2002, Perfluorochemical respiratory gas carriers: benefits to cell culture systems, J Fluorine Chern 118:19-26.
Lu, 2007, Robust fluorescein-doped silica nanoparticles via dense-liquid treatment, Colloids and Surfaces A Phys Eng Asp 303(3):207-210.
Elghanian, 1997, Selective colorimetric detection of polynucleotides based on the distance-dependent optical properties of gold nanoparticles, Science, 277(5329):1078-1080.
Ellington, 1990, In vitro selection of RNA molecules that bind specific ligands, Nature, 346:818-822.
Ellman, 1991, Biosynthetic method for introducing unnatural amino acids site-specifically into proteins, Methods Enzymol, 202:301-36.
Endo, 1996, Autocatalytic decomposition of cobalt complexes as an indicator system for the determination of trace amounts of cobalt and effectors, Analyst 121:391-394.
Endo, 1998, Kinetic determination of trace cobalt by visual autocatalytic indication, Talanta 47:349-353.
Engl, 2005, Droplet Traffic at a Simple Junction at Low Capillary Numbers Physical Review Letters, vol. 95, 208304, 1 page.
Eow, 2002, Electrocoalesce-separators for the separation of aqueous drops from a flowing dielectric viscous liquid, Separation and Purification Tech 29:63-77.
Eow, 2002, Electrostatic and hydrodynamic separation of aqueous drops in a flowing viscous oil, Chemical Eng Proc 41:649-657.
Eow, 2002, Electrostatic enhancement of coalescence of water droplets in oil: a review of the technology, Chemical Engineeing Journal 85:357-368.
Eow, 2003, Motion, deformation and break-up of aqueous drops in oils under high electric field strengths, Chemical Eng Proc 42:259-272.
Eow, 2003, The behavior of a liquid-liquid interface and drop-interface coalescence under the influence of an electric field, Colloids and Surfaces A: Physiochern. Eng. Aspects 215:101-123.
Eriksson, 2013, Comparative analysis of measures of viral reservoirs in HIV-1 eradication studies, PLoS Pathogens 9(2):e1003174, 17 pages.
Faca, 2008, A mouse to human search for plasma proteome changes associated with pancreatic tumor development, PLoS Med 5(6):el23:0953-0967.
Fahy, 1991, Self-sustained sequence replication (3SR): an isothermal transcription-based amplification system alternative to PCR, PCR Methods Appl 1:25-33.
Fan, 1994, Micromachining of capillary electrophoresis injectors and separators on glass chips and evaluation of flow at capillary intersections, Anal Chem 66:177-184.
Fan, 2007, Detection of Aneuploidy with Digital PCR, available at https://arxiv.org/ftp/arxiv/papers /0705/0705.1 030.pdf, 16 pages.
Fastrez, 1997, In vivo versus in vitro screening or selection for catalytic activity in enzymes and abzymes, Mol Biotechnol 7(1):37-55.

(56) References Cited

OTHER PUBLICATIONS

Fettinger, 1993, Stacked modules for micro flow systems in chemical analysis: concept and studies using an enlarged model, Sens Actuat B. 17:19-25.
Fiedler, 1998, Dielectrophoretic sorting of particles and cells in a microsystem, Anal Chem 70(9):1909-1915.
Field, 1988, Purification of a RAS-responsive adenylyl cyclase complex from Saccharomyces cervisiae by use of an epitope addition method. Mol Cell Biol, 8: 2159-2165.
Fields, 1989, A novel genetic system to detect protein-protein interactions, Nature 340(6230):245-6.
Filella, 1994, TAG-72, CA 19.9 and CEA as tumor markers in gastric cancer, Acta Oncol. 33(7):747-751.
Finch, 1993, Encapsulation and controlled release, Spec Publ R Soc Chem, 138:35, 12 pages.
Fingas, 1997, Studies of Water-In-Oil Emulsions: Stability Studies, Environment Canada, Proceedings of the Twentieth Arctic Marine Oilspill Program Technical Seminer, 1-20.
Fire, 1995, Rolling replication of short DNA circles, PNAS 92(10):4641-5.
Firestine, 2000, Using an AraC-based three hybrid system to detect biocatalysts in vivo, Nat Biotechnol 18: 544-547.
Fisher, 2004, Cell Encapsulation on a Microfluidic Platform, The Eighth International Conference on Miniaturised Systems for Chemistry and Life Scieces, MicroTAS, Malmo, Sweden.
Fletcher, 2002, Micro reactors: principles and applications in organic synthesis, Tetrahedron 58:4735-4757.
Fluri, 1996, Integrated capillary electrophoresis devices with an efficient postcolumn reactor in planar quartz and glass chips. Anal Chem 68:4285-4290.
Fornusek, 1986, Polymeric microspheres as diagnostic tools for cell surface marker tracing, Crit Rev Ther Drug Carrier Syst, 2:137-74.
Fowler, 2002, Enhancement of Mixing By Droplet-Based Microfluidics, Int Conf MEMS 97-100.
Frenz, 2008, Reliable microfluidicon-chip incubation of droplets in delay-lines, Lab on a Chip 9:1344-1348.
Fu, 1999, A microfabricated fluorescence-activated cell sorter, Nature Biotechnology, 17(11):1109-1111.
Fu, 2002, An Integrated Microfabricated Cell Sorter, Anal. Chem., 74: 2451-2457.
Fulton, 1997, Advanced multiplexed analysis with the FlowMetrix system, Clin Chern 43:1749-1756.
Fulwyler, 1965, Electronic Separation of Biological Cells by Volume, Science 150(3698):910-911.
Galan, 2010, A 454 multiplex sequencing method for rapid and reliable genotyping of highly polymorphic genes in large-scale studies , BMC Genomics 11 (296):1-15.
Gallarate, 1999, On the stability of ascorbic acid in emulsified systems for topical and cosmetic use, Int J Pharm 188(2):233-241.
Ganan-Calvo, 1998, Generation of Steady Liquid Microthreads and Micron-Sized Monodisperse Sprays and Gas Streams, Phys Rev Lett 80(2):285-288.
Ganan-Calvo, 2001, Perfectly Monodisperse Microbubbling by Capillary Flow Focusing, Phys Rev Lett 87(27):274501-1-4.
Garcia-Ruiz, 1994, Investigation on protein crystal growth by the gel acupuncture method, Acta, Cryst., D50, 99. pp. 484-490.
Garcia-Ruiz, 2001, A super-saturation wave of protein crystallization, J. Crystal Growth, 232:149-155.
Garstecki, 2004, Formation of monodisperse bubbles in a microfluidic flow-focusing device, Appl Phys Lett 85(13):2649-2651.
Gasperlin, 1994, The structure elucidation of semisolid w/o emulsion systems containing silicone surfactant, Intl J Pharm, 107:51-6.
Gasperlin, 2000, Viscosity prediction of lipophillic semisolid emulsion systems by neural network modeling, Intl J Pharm, 196:37-50.
Gelderblom, 2008, Viral complemnation allows HIV-1 replication without integration, Retrovirology 5:60.
Georgiou, 1997, Display of heterologous proteins on the surface of microorganisms: from the screenign of combinational libraires to live recombinant vaccines Nat Biotechnol 15(1), 29-34.
Georgiou, 2000, Analysis of large libraries of protein mutants using flow cytometry, Adv Protein Chem, 55: 293-315.
Gerdts, 2004, A Synthetic Reaction NetWork: Chemical Amplification Using Nonequilibrium Autocatalytic Reactions Coupled in Time, J. Am. Chem. Soc 126:6327-6331.
Ghadessy, 2001, Directed Evolution of Polymerase Function by Compartmentalized Self-Replication, PNSAS 98(8):4552-4557.
Joo, 1999, Laboratory evolution of peroxide-mediated cytochrome P450 hydroxylaion, Nature 399:670.
Joos, 1997, Covalent attachment of hybridizable oligonucleotides to glass supports, Analytical Biochemistry 247:96-101.
Joyce, 1994, In vitro Evolution of Nucleic Acids, Curr. Opp. Structural Biol, 4: 331-336.
Kadir, 1990, Haem binding to horse spleen ferritin, Febs Lett, 276: 81-4.
Kallen, 1966, The mechanism of the condensation of formaldehyde with tetrahydrofolic acid, J. Biol. Chem., 241:5851-63.
Kambara, 1988, Optimization of Parameters in a DNA Sequenator Using Fluorescence Detection, Nature Biotechnology 6:816-821.
Kamensky, 1965, Spectrophotometer: new instrument for ultrarapid cell analysis, Science 150(3696):630-631.
Kanouni, 2002, Preparation of a stable double emulsion (W1/0/W2): role of the interfacial films on the stability of the system, Adv. Collid. Interf. Sci., 99(3): 229-254.
Karapatis, 1998, Direct rapid tooling:a review of current research, Rapid Prototyping Journal, 4(2):77-89.
Katanaev, 1995, Viral Q beta RNA as a high expression vector for mRNA translation in a cell-free system, Febs Lett, 359:89-92.
Katsura, 2001, Indirect micromanipulation of single molecules in water-in-oil emulsion, Electrophoresis, 22:289-93.
Kawakatsu, 1997, Regular-sized cell creation in microchannel emulsification by visual microprocessing method, Journal of the American Oil Chemists Society, 74:317-21.
Keana, 1990, New reagents for photoaffinity labeling: synthesis and photolysis of functionalized perfluorophenyl azides, J. Org. Chem. 55(11):3640-3647.
Keefe, 2001, Functional proteins from a random-sequence library, Nature, 410: 715-718.
Keij, 1994, High-speed photodamage cell sorting: An evaluation of the ZAPPER prototype, Methods in cell biology, 42:371-358.
Kelly, 2005, Detection of Vascular Adhesion Molecule-1 Expression Using a Novel Multimodal Nanoparticle, Circulation Research 96:327-336.
Kelly, 2007, Miniaturizing chemistry and biology in microdroplets, Chem Commun 18:1773-1788.
Kerker, 1983, Elastic and inelastic light scattering in flow cytometry, Cytometry, 4:1-10.
Khandjian, 1986, UV crosslinking of RNA to nylon membrane enhances hybridization signals, Mol. Bio. Rep. 11:107-115.
Kheir, 2012, Oxygen gas-filled microparticles provide intravenous oxygen delivery, Sci Trans Med 4(140):140ra88.
Kim, 2003, Type II quantum dots: CdTe/CdSe (core/shell) and CdSe/ZnTe (core/shell) heterostructures, J. Am Chem Soc. 125:11466-11467.
Kim, 2004, Comparative study on sustained release of human growth hormone from semi-crystalline poly(L-lactic acid) and amorphous poly(D,L-lactic-co-glycolic acid) microspheres: morphological effect on protein release, Journal of Controlled Release, 98(1):115-125.
Kircher, 2010, High-throughput DNA sequencing-concepts and limitations, Bioessays 32(6):524-536.
Kiss, 2008, High-throughput quantitative polymerase chain reaction in picoliter droplets, Anal. Chem 80:8975-8981.
Kitagawa, 1995, Manipulation of a single cell with microcapillary tubing based on its electrophoretic mobility, Electrophoresis 16:1364-1368.
Klug, 1994, All you wanted to know about selex, Molecular Biology Reports, 20:97-107.
Klug, 1995, Gene Regulatory Proteins and Their Interaction with DNA, Ann NY Acad Sci, 758: 143-60.
Klug, 1995, Protein motifs 5. Zinc fingers, FASEB J 9(8):597-604.
Knaak, 1995, Development of partition coefficients, Vmax and Km values, and allometric relationships, Toxicol Lett. 79(I-3):87-98.

(56) References Cited

OTHER PUBLICATIONS

Knight, 1998, Hydrodynamic Focusing on a Silicon Chip: Mixing Nanoliters in Microseconds, Physical Review Lett 80(17):3863-3866.
Koeller, 2001, Enzymes for chemical synthesis, Nature 409:232-240.
Kohler, 1975, Continuous cultures of fused cells secreting antibody of predefined specificity, Nature, 256:495-7.
Kojima, 2005, PCR amplification from single DNA molecules on magnetic beads in emulsion: application for high-throughput screening of transcription factor targets Nucleic Acids Res. 33:e150, 9 pages.
Kolb, 1995, Cotranslational folding of proteins, Biochem Cell Biol, 73:1217-20.
Komatsu, 2001, Roles of cytochromes P450 1A2, 2A6, and 2C8 in 5-fluorouracil formation ram tegafur, an anticancer prodrug, in human liver microsomes. Drug Met. Disp., 28:1457-1463.
Kopp, 1998, Chemical amplification: continuous flow PCR on a chip, Science, 280:1046-48.
Koster, 2008, Drop-based microfluidic devices for encapsulation of single cells, Lab on a Chip 8:1110-1115.
Kowalczykowski, 1994, Biochemistry of homologous recombination in *Escherichia coli*, Microbiol Rev 58(3):401-65.
Kozbor, 1984, A human hybrid myeloma for production of human monoclonal antibodies, J. Immunol., 133:3001-3005.
Krafft, 1991, Synthesis and preliminary data on the biocompatibility and emulsifying properties of perfluoroalkylated phosphoramidates as injectable surfactants, Eur. J. Med. Chem., 26:545-550.
Krafft, 2001, Fluorocarbons and fluorinated amphiphiles in drug delivery and biomedical research, Adv Rev Drug Disc 47:209-228.
Krafft, 2003, Emulsions and microemulsions with a fluorocarbon phase, Colloid and Interface Science 8(3):251-258.
Kralj, 2005, Surfactant-enhanced liquid-liquid extraction in microfluidic channels with inline electric-field enhanced coalescence. Lab Chip 5:531-535.
Kricka, 1996, Micromachining: a new direction for clinical analyzers, Pure and Applied Chemistry 68(10):1831-1836.
Kricka, 2003, Microchip PCR, Anal Bioanal Chem 377(5):820-825.
Kritikou, 2005, It's cheaper in the Picolab, Nature 6:668.
Krumdiek, 1980, Solid-phase synthesis of pteroylpolyglutamates, Methods Enzymol, 524-29.
Kruth, 2003, Lasers and materials in selective laser sintering, Assembly Automation, 23(4):357-371.
Kumagai, 1994, Ablation of polymer films by a femtosecond high-peak-power Ti:sapphire laser at 798 nm, Applied Physics Letters, 65(14): 1850-1852.
Kumar, 1989, Activity and kinetic characteristics of glutathione reductase in vitro in reverse micellar waterpool, Biochem Biophys Acta, 996(1-2):1-6.
Luft, 20001, Detection of integrated papillomavirus sequences by ligation-mediaated PCR (DIPS-PCR) and molecular characterization in cervical cancer cells, In J Cancer 92:9-17.
Luisi, 1987, Activity and conformation of enzymes in reverse micellar solutions, Meth Enzymol 136:188-216.
Lund, 1988, Assesment of methods for covalent binding of nucleic acids to magnetic beads, Dynabeads, and the characteristics of the bound nucleic acids in hybridization reactions, Nucleic Acids Res 16(22):10861-10880.
Lunderberg, 1995, Solid-phase technology: magnetic beads to improve nucleic acid detection and analysis, Biotech Ann Rev 1:373-401.
Lundstrom, 2002, Breakthrough in cancer therapy: Encapsulation of drugs and viruses, Curr Drug Disc 19-23.
Lyne, 2002, Structure-based virtual screening: an overview, Drug Disc Tod 7(20):1047-1055.
Ma, 1993, In vitro protein engineering using synthetic tRNA(Ala) with different anticodons, Biochemistry 32(31):7939-45.
Mackenzie, 1985, IABS Symposium on Reduction of Animal Usage in the Development and Control of Biological Products, London, UK, 16 pages.
Mackenzie, 1986, The application of flow microfluorimetry to biomedical research and diagnosis: a review, Dev Biol Stand 64:181-193.
Maclean, 1999, Glossary of terms used in combinatorial chemistry, Pure Appl. Chem. 71(12):2349-2365.
Magdassi, 1984, Multiple Emulsions: HLB Shift Caused by Emulsifier Migration to External Interface, J. Colloid Interface Sci 97:374-379.
Mahajan, 1998, Bcl-2 and Bax Interactions in Mitochondria Probed with Green Florescent Protein and Fluorescence Resonance Energy Transfer, Nat. Biotechnol. 16(6): 547-552.
Mahjoob, 2008, Rapid microfluidic thermal cycler for polymerase chain reaction nucleic acid amplification. Int J HeatMass Transfer;51:2109-22.
Manafi, 2000, New developments in chromogenic and fluorogenic culture media, 2000, International Journal of Food Microbiology, 60, 205-218.
Manley, 1983, In vitro transcription: whole cell extract, Methods Enzymol, 101:568-82.
Manz, 1991, Micromachining of monocrystalline silicon and glass for chemical analysis systems A look into next century's technology or just a fashionable craze, Trends in Analytical Chemistry 10(5):144-149.
Mao, 1991, Substrate effects on the enzymatic activity of alphachymotrypsin in reverse micelles, Biochem Biophys Res Commun, 178(3): 1105-12.
Mao, 1992, Kinetic behaviour of alpha-chymotrypsin in reverse micelles: a stopped-flow study, Eur J Biochem 208(1):165-70.
Mardis, 2008, The impact of next-generation sequencing technology on genetics, Trends Genet 24:133-141.
Margulies, 2005, Genome sequencing in microfabricated high-density picolitre reactors, Nature 437(7057):376-380.
Marks, 1992, Bypassing immunization: building high affinity human antibodies by chain shuffling, BioTechnol 10:779-783.
Marques, 1996, Porous Flow within Concentric Cylinders, Bull Am Phys Soc Div Fluid Dyn 41:1768, 1 page.
Maruno, 1991, Fluorine containing optical adhesives for optical communications systems, J. Appl. Polymer. Sci. 42:2141-2148.
Mason, 1997, Shear Rupturing of Droplets in Complex Fluids, Langmuir, 13(17):4600-4613.
Mastrobattista, 2005, High-throughput screening of enzyme libraries: in vitro evolution of a beta-galactosidase by fluorescence-activated sorting of double emulsions, Chem. Biol. 12(12): 1291-1300.
Masui, 1998, Probing of DNA-Binding Sites of Escherichia Coli RecA Protein Utilizing 1-anilinonaphthalene-8-Sulfonic Acid, Biochem 37(35):12133-12143.
Matayoshi, 1990, Novel fluorogenic substrates for assaying retroviral proteases by resonance energy transfer, Science 247:954.
Matsubara, 2003, Detection of Single Nucleotide Substitution by Competitive Allele-Specific Short Oligonucleotide Hybridization (CASSOH) With Ummunochromatographic Strip, Human Mutation 22:166-172.
Mattheakis, 1994, An in vitro polysome display system for identifying ligands from very large peptide libraries, PNAS 91:9022-6.
Mayr, 2008, The Future of High-Throughput Screening, JBiomol Screen 13:443-448.
Mazutis, 2009, Droplet-Based Microfluidic Systems for High-Throughput Single DNA Molecule Isothermal Amplification and Analysis, Anal Chem 81(12):4813-4821.
Mazutis, 2009, Multi-step microfluidic droplet processing: kinetic analysis of an in vitro translated enzyme, Lab Chip 9:2902-2908.
McDonald, 2000, Fabrication of microfluidic systems in poly(dimethylsiloxane), Electrophoresis 21(1):27-40.
McDonald, 2002, Poly(dimethylsiloxane) as a material for fabricating microfluidic devices, Account Chem. Res. 35:491-499.
Melton, 1984, Efficient in vitro synthesis of biologically active RNA and RNA hybridization probes from plasmids containing a bacteriophage SP6 promoter, Nucl. Acids Res. 12(18):7035-7056.
Mendel, 1995, Site-Directed Mutagenesis with an Expanded Genetic Code, Annu Rev Biophys Biomol Struct, 24:435-62.

(56) References Cited

OTHER PUBLICATIONS

Mendieta, 1996, Complementary sequence correlations with applications to reflectometry studies, Instrumentation and Development 3(6):37-46.
Metzker, 2010, Sequencing Technologies—the next generation, Nature Reviews, vol. 11, pp. 31-46.
Meylan, 1995, Atom/fragment contribution method for estimating octanol-water partition coefficients, J Pharm Sci. 84(1):83-92.
Michalatos-Beloin, 1996, Molecular haplotyping of genetic markers 10 kb apart by allele-specific long-range PCR, Nucleic Acids Research, 24:4841-4843.
Miele, 1983, Autocatalytic replication of a recombinant RNA, J Mol Biol, 171:281-95.
Milstein, 1983, Hybrid hybridomas and their use in immunohistochemistry, Nature 305:537-540.
Mindlin, 1936, A force at a point of a semi-infinite solid, Physics, 7:195-202.
Minshuil, 1999, Protein evolution by molecular breeding, Curr Opin Chem Biol 3(3): 284-90.
Miroux, 1996, Over-production of proteins in *Escherichia coli*: mutant hosts that allow synthesis of some membrane proteins and globular proteins at high levels, J of Mol Biol 260(3):289-98.
Miyawaki, 1997, Fluorescent Indicators for Ca2+ Based on Green Fluorescent Proteins and Calmodulin, Nature, 388:882-887.
Mize, 1989, Dual-enzyme cascade-an amplified method for the detection of alkaline phosphatase, Anal Biochem 179(2): 229-35.
Mock, 1985, A fluorometric assay for the biotin-avidin interaction based on displacement of the fluorescent probe 2-anilinonaphthalene-6-sulfonic acid, Anal Biochem, 151:178-81.
Moldavan, 1934, Photo-electric technique for the counting of microscopical cells, Science 80:188-189.
Monie, 2005, A Novel Assay Allows Genotyping of the Latent Reservoir for Human Imnunodeficiency Virus Type 1 in the Resting CD4+ T Cells of Viremic Patients, Journal of Virology, 79(8):5185-5202.
Trolier-Mckinstry, 2004, Thin Film Piezoelectric for MEMS, Journal of Electroceramics 12:7-17.
Tsuchiya, 2007, On-chip polymerase chain reaction microdevice employing a magnetic droplet-manipulation system, Sens Actuators B 130:583-588.
Tuzel, 2006, Region Covariance: A Fast Descriptor for Detection and Classification, European Conference on Computer Vision (ECCV), 14 pages.
Umbanhowar, 2000, Monodisperse Emulsion Generation via Drop Break Off in a Coflowing Stream, Langmuir 16(2):347-351.
Unger, 2000, Monolithic microfabricated valves and pumps by multylayersoft lithography, Science 288(5463): 113-116.
Utada, 2005, Monodisperse double emulsions generated from a microcapillary device, Science, 308:537-541.
Vainshtein, 1996, Peptide rescue of an N-terminal truncation of the stoffel fragment of Taq DNA polymerase, Protein Science, 5:1785-92.
Van der Sluis, 2013, Dendritic Cell-induced Activation of Latent HIV-1 Provirus in Actively Proliferating Primary T Lymphocytes, PLOS Pathog 9(3): 16 pages.
Van Dilla, 1968, The fluorescent cell photometer: a new method for the rapid measurement of biological cells stained with fluorescent dyes, Annual Report of the Los Alamos Scientific Laboratory of the University of California (Los Alamos, NM), Biological and Medical Research Groupp (H-4) of the Health Division, Compiled by D. G. Ott, pp. 100-105.
Van Dilla, 1969, Cell Microfluorometry: A Method for Rapid Fluorescence Measurement, Science 163(3872):1213-1214.
Vanhooke, 1996, Three-dimensional structure of the zinc-containing phosphotrieesterase with the bound substrate analog diethy 4-methylbenzylphosphonate, Biochemistry 35:6020-6025.
Varga, 1991, Mechanism of allergic cross-reactions-I. Multispecific binding of ligands to a mouse monoclonal anti-DNP IgE antibody Mol Immunol 28(6), 641-54.

Vary, 1987, A homogeneous nucleic acid hybridization assay based on strand displacement, Nucl Acids Res 15(17):6883-6897.
Venkateswaran, 1992, Production of Anti-Fibroblast Growth Factor Receptor Monoclonal Antibodies by In Vitro Immunization, Hybirdoma, 11(6):729-739.
Verhoeyen, 1988, Reshaping human antibodies: grafting an antilysozyme activity, Science, 239:1534-1536.
Vogelstein, 1999, Digital PCR, PNAS 96(16):9236-9241.
Voss, 1993, Kinetic measurements of molecular interactions by spectrofluorometry, J Mol Recognit, 6:51-58.
Wahler, 2001, Novel methods for biocatalyst screening. Curr Opin Chem Biol, 5: 152-158.
Walde, 1988, Structure and activity of trypsin in reverse micelles, Eur J Biochem, 173(2):401-9.
Walde, 1993, Spectroscopic and kinetic studies of lipases solubilized in reverse micelles, Biochemistry, 32(15):4029-34.
Walde, 1994, Oparin's reactions revisited: enzymatic synthesis of poly(adenylic acid) in micelles and self-reproducing vesicles. J Am Chem Soc, 116: 7541-7547.
Walker, 1992, Isothermal in vitro amplification of DNA by a restriction enzyme/DNA polymerase system, PNAS 89(1):392-6.
Walker, 1992, Strand displacement amplification-an isothermal, in vitro DNA amplification technique, Nucleic Acid Res, 20(7):1691-6.
Wang, 1989, Quantitation of mRNA by the polymerase chain reaction. Proc natl Acad Sci USA 86(24), 9717-21.
Wang, 1990, Design and synthesis of new fluorogenic HIV protease substrates based on resonance energy transfer, Tetrahedron Lett., 31:6493.
Wang, 2002, Preparation of Titania Particles Utilizing the Insoluble Phase Interface in a MicroChannel Reactor, Chemical Communications 14:1462-1463.
Wang, 2008, DEP actuated nanoliter droplet dispensing using feedback control, Lab on a Chip 9:901-909.
Wang, 2010, Quantifying EGFR Alterations in the Lung Cancer Genome with Nanofluidic Digital PCR Arrays, Clinical Chemistry 56:4.
Warburton, 1993, Microcapsules for Multiple Emulsions, Encapsulation and Controlled Release, Spec Publ R Soc Chem, 35-51.
Wasserman, 1989, Structure and reactivity of allyl-siloxane monolayers formed by reaction of allcyltrichlorosilanes on silicon substrates, Langmuir 5:1074-1087.
Weaver, 2010, Taking qPCR to a higher level: Analysis of CNV reveals the power of high throughput qPCR to enhance quantitative resolution, Methods 50, 271-276.
Weil, 1979, Selective and accurate initiation of transcription at the Ad2 major late promotor in a soluble system dependent on purified RNA polymerase II and DNA, Cell, 18(2):469-84.
Werle, 1994, Convenient single-step, one tube purification of PCR products for direct sequencing, Nucl Acids Res 22(20):4354-4355.
Wetmur, 2005, Molecular haplotyping by linking emulsion PCR: analysis of paraoxonase 1 haplotypes and phenotypes. Nucleic Acids Res 33(8):2615-2619.
White, 2009, Digital PCR provides sensitive and absolute calibration for high throughput sequencing, BMC Genomics 10:116.
Wick, 1996, Enzyme-containing liposomes can endogenously produce membrane-constituting lipids, Chem Biol 3(4):277-85.
Wiggins, 2004, Foundations of chaotic mixing, Philos Transact A Math Phys Eng Sci 362(1818):937-70.
Williams, 1979, Methotrexate, a high-affinity pseudosubstrate of dihydrofolate reductase, Biochemistry, 18(12):2567-73.
Williams, 2006, Amplification of complex gene libraries by emulsion PCR, Nature Methods 3(7):545-550.
Wilson, 1999, In vitro selection of functional nucleic acids, Ann. Rev. Biochem. 68: 611-647.
Wittrup, 2001, Protein engineering by cell-surface display. Curr Opin Biotechnology, 12: 395-399.
Wittwer, 1989, Automated polymerase chain reaction in capillary tubes with hot air, Nucleic Acids Res., 17(11) 4353-4357.
Wittwer, 1990, Minimizing the Time Required for DNA Amplification by Efficient Heat Transfer to Small Samples, Anal. Biochem., 186, 328-331.

(56) References Cited

OTHER PUBLICATIONS

Wolff, 2003, Integrating advanced functionality in a microfabricated high-throughput fluorescent-activated cell sorter, Lab Chip, 3(1): 22-27.
Woolley, 1994, Ultra-high-speed DNA fragment separations using microfabricated capillary array electrophoresis chips, Proc. Natl. Acad. Sci. USA, 91, 11348-11352.
Woolley, 1996, Functional Integration of PCR Amplification and Capillary Electrophoresis in a Microfabricated DNA Analysis Device, Anal. Chem. 68, 4081-4086.
Wronski, 2002, Two-color, fluorescence-based microplate assay for apoptosis detection. Biotechniques, 32:666-668.
Wu, 1989, The ligation amplification reaction (LAR)-amplification of specific DNA sequences using sequential rounds of template-dependent ligation, Genomics 4(4):560-9.
Wyatt, 1991, Synthesis and purification of large amounts of RNA oligonucleotides, Biotechniques 11(6):764-9.
Xia, 1998, Soft Lithography, Angew. Chem. Int. Ed. 37:550-575.
Soumillion, 2001, Novel concepts for the selection of catalytic activity. Curr Op Biotech 12:387-394.
Spiro, 2000, A bead-based method for multiplexed identification and quantitation of DNA sequences using flow cytometry, Appl Env Micro 66:4258-4265.
Sproat, 1987, The synthesis of protected 5'-mercapto-2',5'-dideoxyribonucleoside-3'-0-phosphorainidites, uses of 5'-mercapto-oligodeoxyribonucleotides. Nucleic Acids Res 15:4837-4848.
Squires, 2005, Microfluidics: fluid physics at the nanoliter scale, Rev Mod Phys 77:977-1026.
Stauber, 1993, Rapid generation of monoclonal antibody-secreting hybridomas against African horse sickness virus by in vitro immunization and the fusion/cloning technique, J Immunol Meth 161(2):157-168.
Stemmer, 1994, DNA shuffling by random fragmentation and reassembly: in vitro recombination for molecular evolution. PNAS 91(22):10747-51.
Stemmer, 1994, Rapid evolution of a protein in vitro by DNA shuffling, Nature 370(6488):389-91.
Stober, 1998, Controlled growth of monodisperse silica spheres in the micron size range, J Colloid Interface Sci 26(1):62-69.
Stofko, 1992, A single step purification for recombinant proteins, Febs Lett 302:274-278.
Stone, 2004, Engineering flows in small devices: microfluidics toward a lab-on-a-chip, Ann Rev Fluid Mech 36:381-441.
Strizhkov, 2000, PCR amplification on a microarray of gel-immobilized oligonucleotides: Detection of bacterial toxin-and drug-resistant genes and their mutations, BioTechniques 29(4):844-857.
Strommenger, 2003, Multiplex PCR assay for simultaneous detection of nine clinicly relevant antibiotic resistance genes in S aureus, J Clin Microb 41 (9):4089-4094.
Stroock, 2002, Chaotic mixer for microchannels, Science 295(5555):647-651.
Studer, 1997, Fluorous synthesis: a fluorous-phase strategy for improving separation efficiency in organic synthesis, Science 275:823-826.
Sugiura, 2001, Interfacial tension driven monodispersed droplet formation from mtcrofabricated channel array, Langmuir 17:5562-5566.
Sugiura, 2002, Effect of channel structure on microchannel emuisification, Langmuir 18:5708-5712.
Sundberg, 1995, Spatially-addressable immobilisation of macromolecules on solid supports, J Am Chem Soc 117:12050-12057.
Sung, 2005, Chip-based microfluidic devices coupled with electrospray ionization-mass spectrometry, Electrophoresis 26:1783-1791.
Sutcliffe, 1986, Dynamics of UV laser ablation of organic polymer surfaces, J Appl Phys 60(9):3315-3322.
Suzuki, 1996, Random mutagenesis of thermus aquaticus DNA polmerase I: concordance of immutable sites in vivo with the crystal structure, PNAS 93:96701-9675.
Syed, 2009, Next-generation sequencing library preparation: simultaneous fragmentation and tagging using in vitro transposition, Nat Meth 6:1-2.
Takayama, 1999, Patterning cells and their environmnets using multiple laminar fluid flows in cappillary networks, PNAS 96:5545-5548.
Takeuchi, 2005, An axisymmetric flow-focusing microfluidic device, Adv Mater 17(8): 1067-1072.
Taly, 2007, Droplets as microreactors for high-throughput biology, Chembiochem 8(3):263-272.
Tan, 2003, Controlled fission of droplet emulsions in bifurcating microfluidic channels, 12th Int Conf SSAM 28-31.
Tan, 2003, Microfluidic liposome generation from monodisperse droplet emulsion, Summer Bioeng Conf, Florida, 2 pages.
Tan, 2003, Monodisperse droplet emulsions in co-flow microfluidic channels, Micro TAS, 2 pages.
Tan, 2004, Design of microluidic channel geometries for the control of droplet volume, chemical concentration, and sorting, Lab Chip 4(4):292-298.
Tang, 2009, A multi-color fast-switching microfluidic droplet dye laser, Lab Chip 9:2767-2771.
Taniguchi, 2002, Chemical reactions in microdroplets by electrostatic manipulation of droplets in liquid media, Lab Chip 2:19-23.
Tawfik, 1998, Man-made cell-like compartments for molecular evolution, Nat Biotech 7(16):652-56.
Taylor, 1934, The formation of emulsions in definable field of flow, Proc R Soc London A 146(858):501-523.
Taylor, 1991, Characterization of chemisorbed monolayers by surface potential measurments, J Phys D Appl Phys 24:1443.
Tencza, 2000, Development of a fluorescence polarization-based diagnostic assay for equine infectious anemia virus, J Clin Microbiol 38(5):1854-185.
Terray, 2002, Fabrication of linear colloidal structures for microfluidic applications, Applied Phys Lett 81(9):1555-1557.
Terray, 2002, Microfluidic control using colloidal devices, Science 296(5574):1841-1844.
Tewhey, 2009, Microdroplet based PCR environment for large scale targeted sequence, Nat Biotech 27(11):1025-1031.
Theberge, 2010, Microdroplets in microfluidics: an evolving platform for discoveries in chemistry and biology, Angew Chem Int Ed 49(34):5846-5868.
Thompson, 1983, Introduction to Lithography, ACS Symp Ser 219:1-13.
Thorsen, 2001, Dynamic pattern formation in a vesicle-generating microfluidic device, Phys Rev Lett 86(18):4163-4166.
Thorsen, 2002, Microfluidic large-scale integration, Science 298:580-584.
Thorsen, 2003, Microfluidic technologies for highthroughput screening applications, California Institute of Technology.
Tice, 2003, Formation of droplets and mixing in multiphase microfluidics at low values of the reynolds and the capillary numbers, Langmuir 19:9127-9133.
Tice, 2004, Effects of viscosity on droplet formation and mixing in microfluidic channels, Analytica Chimica Acta 507:73-77.
Titomanlio, 1990, Capillary experiments of flow induced crystallization of HDPE, AlChe J 36(1):13-18.
Tleugabulova, 2004, Evaluating formation and growth mechanisms of silica particles using fluorescence anisotropy decay analysis, Langmuir 20(14):5924-5932.
Tokatlidis, 1995, Nascent chains: folding and chaperone infraction during elongation on ribosomes, Philos Trans R Soc Lend B Biol Sci, 348:89-95.
Tokeshi, 2002, Continuous-flow chemical processing on a microchip by combining microunit operations and a multiphase flow network, Anal Chem 74(7):1565-1571.
Tokumitsu, 1999, Preparation of gadopentetic acid-loaded chitosan microparticles for gadolinium neutron-capture therapy of cancer by a novel emulsion-droplet coalescence technique, Chem Pharm Bull 47(6):838-842.
Tonelli et al., 2002, Perfluoropolyether functional oligomers: unusual reactivity in organic chemistry, Journal of fluorine Chemistry, 118; 107-121.

(56) References Cited

OTHER PUBLICATIONS

Montigiani, 1996, Alanine substitutions in calmodulin-binding peptides result in unexpected affinity enhancement, J Mol Biol, 258:6-13.
Moore, 1995, Exploration by lamp light, Nature, 374:766-7.
Morrison, 1984, Chimeric human antibody molecules: mouse antigen-binding domains with human constant region domains, PNAS 81:6851-6855.
Moudrianakis, 1965, Base sequence determination in nucelic acids with the electron microscope 3. Chemistry and microscopy of guanine-labeled DNA, PNAS 53:564-71.
Mueth, 1996, Origin of stratification in creaming emulsions, Physical Review Letters 77(3):578-581.
Mulbry, 1989, Parathion hydrolase specified by the Flavobacterium opd gene: relationshio between the gene and protein. J Bacteriol, 171: 6740-6746.
Mulder, 1993, Characterization of two human monoclonal antibodies reactive with HLA-B12 and HLA-B60, respectively, raised by in vitro secondary immunization of peripheral blood lymphocytes, Hum. Immunol 36(3):186-192.
Munson, 1980, Ligand: a versatile computerized approach for characterization of ligand-binding systems, Analytical Biochemistry, 107:220-239.
Nakano, 1994, High speed polymerase chain reaction in constant flow, Biosci Biotech and Biochem, 58:349-52.
Nakano, 2003, Single-molecule PCR using water-in-oil emulsion, J Biotech, 102:117-124.
Nakano, 2005, Single-molecule reverse transcription polymerase chain reaction using water-in-oil emulsion, J Biosci Bioeng 99:293-295.
Nametkin, 1992, Cell-free translation in reversed micelles, FEB Letters, 309(3):330-32.
Narang, 1979, Improved phosphotriester method for the synthesis of gene fragments, Methods Enzymol, 68:90-98.
Neiman, 2011, Decoding a substantial set of samples in parallel by massive sequencing, PLoS ONE 6(3):1-7.
Nelson, 1989, Bifunctional oligonucleotide probes synthesized using a novel CPG support are able to detect single base pair mutations, Nucl Acids Res 17(18): 7187-7194.
Nemoto, 1997, In vitro virus: bonding of mRNA bearing puromycin at the 3 terminal end to the C-terminal end of its encoded protein on the ribosome in vitro, Federation of European Biochemical Societies, 414:405-8.
Ness, 2000, Molecular Breeding: the natural approach to protein design. Adv Protein Chem, 55: 261-292.
Ng, 2003, Protein crystallization by capillary counter-diffusion for applied crystallographic structure determination, J. Struct. Biol, 142:218-231.
Ng, 2006, Factors affecting flow karyotype resolution, Cytometry, Part A 69A: 1028-1036.
Nguyen, 2006, Optical detection for droplet size control in microfluidic droplet-based analysis systems, Sensors and Actuators B 117(2):431-436.
Nihant, 1994, Polylactide Microparticles Prepared by Double Emulsion/Evaporation Technique. I. Effect of Primary Emulsion Stability, Pharmaceutical Research, 11(10):1479-1484.
Nisisako, 2002, Droplet formation in a microchannel network, Lab Chip 2:24-26.
Nisisako, 2002, Formation of droplets using branch channels in a microfluidic circuit, Proceedings of the SICE Annual Conference. International Session Papers 1262-1264.
Nisisako, 2005, Controlled formulation of monodisperse double emulsions in a multiple-phase microluidic system, Sot Matter, 1:23-27.
Nisisako, 2008, Microstructured Devices for Preparing Controlled Multiple Emulsions. Chern. Eng. Technol 31(8):1091-1098.
Nof, 2002, Drug-releasing scaffolds fabricated from drug-loaded microspheres, J. Biomed Mater Res 59:349-356.
Norman, 1980, Flow Cytometry, Med. Phys., 7(6):609-615.
Nygren, 1982, Conjugation of horseradish peroxidase to Fab fragments with different homobifunctional and heterobifunctional cross-linking reagents. A comparative study, J. Histochem. and Cytochem. 30:407-412.
Oberholzer, 1995, Enzymatic RNA replication in self-reproducing vesicles: an approach to a minimal cell, Biochem Biophys Res Commun 207(1):250-7.
Oberholzer, 1995, Polymerase chain reaction in liposomes, Chem. Biol. 2(10):677-82.
Obukowicz, 1988, Secretion and export of IGF-1 in *Escerichia coli* strain JM101, Mol Gen Genet, 215:19-25.
Ogura, 1955, Catalase activity at high concentrations of hydrogen peroxide, Archs Biochem Biophys, 57:288-300.
Oh, 2002, Distribution of Macropores in Silica Particles Prepared by Using Multiple Emulsions, Journal of Colloid and Interface Science, 254(1): 79-86.
Oh, 2005, World-to-chip microfluidic interface with built-in valves for multichamber chip-based PCR assays, Lab Chip, 5, 845-850.
Okuno, 2003, Recent Advances in Optical Switches Using Silica-based PLC Technology, NTT Technical Review 1(7):20-30.
Okushima, 2004, Controlled production of monodisperse double emulsions by two-step droplet breakup in microfluidic devices, Langmuir 20(23): 9905-8.
Olsen, 2000, Function-based isolation of novel enzymes from a large library, Nat Bioteoltnol 13(10):1071-4.
Omburo, 1992, Characterization of the zinc binding site of bacterial phosphotriesterase, J of Biological Chem, 267:13278-83.
Oroskar, 1996, Detection of immobilized amplicons by ELISA-like techniques, Clin. Chem. 42:1547-1555.
Ostermeier, 1999, A combinatorial approach to hybrid enzymes independent of DNA homology, Nat Biotechnol, 17(12):1205-9.
Ott, 1967, Biological and medical research annual report, Los Alamos Scientific Laboratory, 14 pages.
Ouelette, 2003, A new wave of microfluidic devices, Indust Physicist pp. 14-17.
Pabit, 2002, Laminar-Flow Fluid Mixer for Fast Fluorescence Kinetics Studies, Biophys J 83:2872-2878.
Paddison, 2002, Stable suppression of gene expression by RNAi in mammalian cells, PNAS 99(3):1443-1448.
Pain, 1981, Preparation of protein A-peroxidase mono conjugate using a heterobifunctional reagent, and its use in enzyme immunoassays, J Immunol Methods, 40:219-30.
Pannacci, 2008, Equilibrium and Nonequilibrium States in Microluidic Double Emulsions Physical Review Letters, 101(16):164502.
Park, 2001, Model of Formation of Monodispersed Colloids, J. Phys. Chem. B 105:11630-11635.
Park, 2003, Cylindrical compact thermal-cycling device for continuous-flow polymeras chain reaction, Anal Chem, ACS, 75:6029-33.
Parker, 2000, Development of high throughput screening assays using fluorescence polarization: nuclear receptor-ligand-binding and kinase/phosphatase assays, J Biomol Screen, 5(2): 77-88.
Pasternak, 2013, Cell-associated HIV RNA: a dynmic biomarker of viral persistence, Retrovirology 10:41.
Bougueleret, 1984, Characterization of the gene coding for the EcoRV restriction and modification system of *E coli*, Nucleic Acids Res 12(8)13659-76.
Branebjerg, 1996, Fast mixing by lamination, MEMS Proc 9th Ann 9:441-446.
Braslavsky, 2003, Sequence information can be obtained from single DNA molecules, PNAS 100(7):3960-3964.
Breslauer, 2006, Microfluidics based systems biology, Mol Bio Syst 2:97-112.
Bringer, 2004, Microfluidic systems for chemical kinetics that rely on chaotic mixing in droplets, Phil Trans A Math Phys Eng Sci 362:1-18.
Brown, 1979, Chemical synthesis and cloning of a tyrosine tRNA gene, Methods Enzymol 68:109-151.
Bru, 1991, Product inhibition of alpha-chymotrypsin in reverse micelles. Eur J Biochem 199(1):95-103.
Bru, 1993, Catalytic activity of elastase in reverse micelles, Biochem Mol Bio Int, 31(4):685-92.
Brummelkamp, 2002, A system for stable expression of short interfering RNAs in mammalian cells, Science 296(5567):550-3.

(56) References Cited

OTHER PUBLICATIONS

Buican, 1987, Automated single-cell manipulation and sorting by light trapping, Appl Optics 26(24):5311-5316.
Burbaum, 1998, Miniaturization technologies in HTS, Drug Disc Today 3:313-322.
Burns, 1996, Microfabricated structures for integrated DNA analysis, PNAS 93:5556-5561.
Burns, 1998, An integrated nanoliter DNA analysis device, Science 282:484-487.
Burns, 2002, The intensification of rapid reactions in multiphase systems using slug flow in capillaries, Lab on a Chip 1:10-15.
Byrnes, 1982, Sensitive fluorogenic substrates for the detection of trypsin-like proteases and pancreatic elastase, Anal Biochem 126:447.
Cahill, 1991, Polymerase chain reaction and Q beta replicase amplification, Clin Chem 37(9):1482-5.
Caldwell, 1991, Limits of diffusion in the hydrolysis of substrates by the phosphodiesterase from Pseudomonas diminuta, Biochem 30:7438-7444.
Calvert, 2001, Inkjet printing for materials and devices, Chem Mater 13:3299-3305.
Caruccio, 2009, Nextura technology for Ngs DNA library preparation: simulaneous fragmentation and tagging by in vitro transposition, Epibio Newsletter.
Caruthers, 1985, Gene synthesis machines: DNA chemistry and its uses, Science 230:281-285.
Cavalli, 2010, Nanosponge formulations as oxygen delivery systems, Int J Pharmaceutics 402:254-257.
Chakrabarti, 1994, Production of RNA by a polymerase protein encapsulated within phospholipid vesicles, J Mol Evol 39(6):555-9.
Chamberlain, 1973, Characterization of T7-specific ribonucleic acid polymerase. 1. General properties of the enzymatic reaction and the template specificity of the enzyme, J Biol Chem 248:2235-44.
Chan, 2003, Size-Controlled Growth of CdSe Nanocrystals in Microfluidic Reactors, Nano Lett 3(2):199-201.
Chan, 2008, New trends in immunoassays, Adv Biochem Engin/Biotech 109:123-154.
Chang, 1987, Recycling of NAD(P) by multienzyme systems immobilized by microencapsulation in artifical cells, Methods Enzymol, 136(67):67-82.
Chang, 2008, Controlled double emulsification utilizing 3D PDMS microchannels, Journal of Micromechanics and Microengineering 18:1-8.
Chao, 2004, Control of Concentration and vol. Gradients in Microfluidic Droplet Arrays for Protein Crystallization Screening, 26th Annual International Conference of the IEEE Engineering in Medicine and Biology Society, San Francisco, California Sep. 1-5.
Chao, 2004, Droplet Arrays in Microfluidic Channels for Combinatorial Screening Assays, Hilton Head: A Solid State Sensor, Actuator and Microsystems Workshop, Hilton Head Island, South Carolina, Jun. 6-10.
Chapman, 1994, In vitro selection of catalytic RNAs, Curr. op. Struct. Biol., 4:618-22.
Chayen, 1999, Crystallization with oils: a new dimension in macromolecular crystal growth Journal of Crystal Growth, 196:434-441.
Chen, 2001, Capturing a Photoexcited Molecular Structure Through Time-Domain X-ray Absorption Fine Structure, Science 292(5515):262-264.
Chen, 2003, Microfluidic Switch for Embryo and Cell Sorting The 12th International Conference on Solid State Sensors, Actuators, and Microsystems, Boston, MA, Transducers, 1: 659-662.
Chen-Goodspeed, 2001, Enhancement, relaxation, and reversal of the stereoselectivity for phosphotriesterase by rational evolution of active site residues, Biochemistry, 40: 1332-1339.
Chen-Goodspeed, 2001, Structural Determinants of the substrate and stereochemical specificity of phosphotriesterase, Biochemistry, 40(5):1325-31.
Cheng, 2003, Electro flow focusing inmicrofluidic devices, Microfluidics Poster, presented at DBAS, Frontiers in Nanoscience, 1 page.
Cheng, 2006, Nanotechnologies for biomolecular detection and medical diagnostics, Current Opinion in Chemical Biology, 10:11-19.
Chetverin, 1995, Replicable RNA vectors: prospects for cell-free gene amplification, expression, and cloning, Prog Nucleic Acid Res Mol Biol, 51:225-70.
Chiang, 1993, Expression and purification of general transcription factors by FLAG epitope-tagging and peptide elution, Pept Res, 6:62-64.
Chiba, 1997, Controlled protein delivery from biodegradable tyrosino-containing poly(anhydride-co-imide) microspheres, Biomaterials, 18(13):893-901.
Chiou, 2001, A closed-cycle capillary polymerase chain reaction machine, Analytical Chemistry, American Chamical Society, 73:2018-21.
Chiu, 1999, Chemical transformations in individual ultrasmall biomimetic containers, Science, 283:1892-1895.
Chou, 1998, A microfabricated device for sizing and sorting DNA molecules 96:11-13.
Clackson, 1994, In vitro selection from protein and peptide libraries, Trends Biotechnol, 12:173-84.
Clausell-Tormos, 2008, Droplet-based microfluidic platforms for the encapsulation and screening of Mammalian cells and multicellular organisms, Chem Biol 15(5):427-437.
Cohen, 1991, Controlled delivery systems for proteins based on poly(lactic/glycolic acid) microspheres, Pharm Res, 8(6):713-720.
Collins, 2003, Optimization of Shear Driven Droplet Generation in a Microluidic Device, ASME International Mechanical Engineering Congress and R&D Expo, Washington, 4 pages.
Collins, 2004, Microfluidic flow transducer based on the measurements of electical admittance, Lab on a Chip, 4:7-10.
Compton, 1991, Nucleic acid sequence-based amplification, Nature, 350(6313):91-2.
Cook, 2007, Use and misuse of receiver operating characteristic curve in risk prediction, Circulation 115(7):928-35.
Patel, 2003, Formation of Fluorinated Nonionic Surfactant Microemulsions in Hydrfuorocarbon 134a, Journal of Colloid and Interface Science, 258, 345-353.
Pedersen, 1998, A method for directed evolution and functional cloning of enzymes, PNAS 95(18):10523-8.
Pekin, 2011, Quantitative and sensitive detection of rare mutations using droplet-based microfluidics, Lab on a Chip 11(13):2156-2166.
Pelham, 1976, An efficient mRNA-dependent translation system from reticulocyte lysates, Eur J Biochem 67:247-56.
Pelletier, 1999, An in vivo library-versus-library selection of optimized protein-protein interactions, Nature Biotechnology, 17:683-90.
Peng, 1998, Controlled Production of Emulsions Using a Crossflow Membrane, Particle & Particle Systems Characterization 15:21-25.
Pepe, 2004, Limitations of the odds ratio in gauging the performance of a diagnostic, prognostic, or screening marker, American Journal of Epidemiology 159(9):882-890.
Perelson, 1979, Theorectical studies of clonal selection: minimal antibody repertoire size and relaibility of self-non-self discrimination J Theor Biol 81(4):645-70.
Perez-Gilabert, 1992, Application of active-phase plot to the kinetic analysis of lipoxygenase in reverse micelles, Biochemistry J. 288:1011-1015.
Petrounia, 2000, Designed evolution of enzymatic properties, Curr Opin Biotechnol, 11:325-330.
Pirrung, 1996, A General Method for the Spatially Defined Immobilization of Biomolecules on Glass Surfaces Using Caged Biotin, Bioconjug Chem 7: 317-321.
Ploem, 1993, in Fluorescent and Luminescent Probes for Biological Activity Mason, T. G. Ed., Academic Press, Landon, pp. 1-11.
Pluckthun, 2000, In vitro selection and evolution of proteins, Adv Protein Chem, 55: 367-403.
Pollack, 1986, Selective chemical catalysis by an antibody, Science 234(4783):1570-3.
Pollack, 2002, Electrowetting-based actuation of droplets for integrated microfluidics, Lab Chip 2:96-101.

(56) References Cited

OTHER PUBLICATIONS

Pons, 2009, Synthesis of Near-Infrared-Emitting, Water-Soluble CdTeSe/CdZnS Core/Shell Quantum Dots, Chemistry of Materials 21(8):1418-1424.
Posner, 1996, Engineering specificity for folate into dihydrofolate reductase from *Escherichia coli*, Biochemistry, 35:1653-63.
Priest, 2006, Generation of Monodisperse Gel Emulsions in a Microfluidic Device, Applied Physics Letters, 88:024106, 3 pages.
Qi, 1998, Acid Beta-Glucosidase: Intrinsic Fluorescence and Conformational Changes Induced by Phospholipids and Saposin C, Biochem., 37(33): 11544-11554.
Raghuraman, 1994, Emulston Liquid Membranes for Wastewater Treatment: Equilibrium Models for Some Typical Metal-Extractant Systems,Environ. Sci Technol 28:1090-1098.
Ralhan, 2008, Discovery and Verification of Head-and-neck Cancer Biomarkers by Differential Protein Expression Analysis Using iTRAQ Labeling, Multidimensional Liquid Chromatography, and Tandem Mass Spectrometry, Mol Cell Proteomics 7(6):1162-1173.
Ramanan, 2016, Algae-bacteria interactions, Biotech ADv 34:14-29.
Ramsey, 1999, The burgeoning power of the shrinking laboratory, Nat Biotechnol 17(11):1061-2.
Ramstrom, 2002, Drug discovery by dynamic combinatorial libraries, Nat Rev Drug Discov 1:26-36.
Rasmussen, 2013, Comparison of HDAC inhibitors in clinical development, Human Vacc Immunother 9(5):993-1001.
Raushel, 2000, Phosphotriesterase: an enzyme in search of its natural substrate, Adv Enzymol Relat Areas Mol Biol, 74: 51-93.
Rech, 1990, Introduction of a yeast artificial chromosome vector into Sarrachomyeces cervesia by electroporation, Nucleic Acids Res 18:1313.
Reyes, 2002, Micro Total Analysis Systems. 1. Introduction, Theory and Technology, Anal Chem 74(12):2623-2636.
Riechmann, 1988, Reshaping human antibodies for therapy, Nature, 332:323-327.
Riess, 2002, Fluorous micro- and nanophases with a biomedical perspective, Tetrahedron 58(20):4113-4131.
Roach, 2005, Controlling nonspecific protein adsorption in a plug-based microfluidic system by controlling inteifacial chemistry using fluorous-phase surfactants, Anal Chem 77:785-796.
Roberts, 1969, Termination factor for RNA synthesis, Nature, 224:1168-74.
Roberts, 1975, Simian virus 40 DNA directs synthesis of authentic viral polypeptides in a linked transcription-translation cell-free system 72(5):1922-1926.
Roberts, 1997, RNA-peptide fusion for the in vitro selection of peptides and proteins, PNAS 94:12297-302.
Roberts, 1999, In vitro selection of nucleic acids and proteins: What are we learning, Curr Opin Struct Biol 9(4): 521-9.
Roberts, 1999, Totally in vitro protein selection using mRNA-protein fusions and ribosome display. Curr Opin Chem Biol 3(3), 268-73.
Roche, 2011, 454 Sequencing System Guidelines for Amplicon Experimental Design, 50 pages.
Rodriguez-Antona, 2000, Quantitative RT-PCR measurement of human cytochrome P-450s: application to drug induction studies Arch. Biochem. Biophys., 376:109-116.
Rogers, 2005, Closing bacterial genoimc sequence gaps with adaptor-PCR, BioTechniques 39(1):1-3.
Rolland, 1985, Fluorescence Polarization Assay by Flow Cytometry, J. Immunol. Meth., 76(1): 1-10.
Rosenberg, 1975, Inhibition of Human Factor IX by Human Antithrombin, J Biol Chem, 250: 4755-64.
Rosenberry, 1975, Acetylcholinesterase, Adv Enzymol Relat Areas Mol Biol, 43: 103-218.
Rotman, 1961, Measurement of activities of single molecules of beta-galactosidase, PNAS, 47:1981-91.
Rouzioux, 2013, How to best measure HIV reservoirs, Curr Op HIV AIDS 8(3):170-175.
Russon et al., Single-nucleotide polymorphism analysis by allele-specific extension of fluorescently labeled nucleotides in a microfluidic flow-through device, Electrophoresis, 24:158-61 (2003).
Saarela, 2006, Re-usable multi-inlet PDMS fluidic connector, Sensors Actuators B 114(1):552-57.
Sadtler, 1996, Achieving stable, reverse water-in-fluorocarbon emulsions, Angew Chern Int Ed 35(17):1976-1978.
Sadtler, 1999, Reverse water-ln-fluorocarbon emulsions as a drug delivery system: an in vitro study, Colloids & Surfaces A: Phys Eng Asp 147:309-315.
Saiki, 1988, Primer directed enzymatic amplification of DNA with a thermostable DNA polymerase, Science 239(4839):487-91.
Sakamoto, 2005, Rapid and simple quantification of bacterial cells by using a microfluidic device, Appl Env Microb 71:2.
Hermankova, 2003, Analysis of human immunodeficiency virus type 1 gene expression in lately infected reseting CD4 T lymphocytes in vivo, J Virology 77(13):7383-7392.
Herzer, 2001, DNA Purification, in Molecular Biology Problem Solver: A Laboratory Guide, Edited by Alan S. Gerstein, Ch.1.
Heyries, 2011, Megapixel digital PCR, Nat. Methods 8, 649-651.
Hildebrand, 1949, Liquid-Liquid Solubility of Perfluoromethylcyclohexane with Benzene, Carbon Tetrachloride, Chlorobenzene, Chloroform and Toluene, J. Am Chern Soc, 71:22-25.
Hindson, 2011, High-Throughput Droplet Digital PCR System for Absolute Quantitation of DNA Copy Number, Anal. Chem., 83, 8604-8610.
Hjelmfelt, 1993, Pattern-Recognition in Coupled Chemical Kinetic Systems, Science, 260(5106):335-337.
Ho, 1989, Site-directed mutageneiss by overlap extension using the polymerase chain reaction, Gene, 77(1):51-9.
Hochuli, 1987, New metal chelate adsorbent selective for proteins and peptides containing neighbouring histidine residues, J Chromatogr 411: 177-84.
Holmes, 1995, Reagents for Combinatorial Organic Synthesis: Development of a New O-Nitrobenzyl Photolabile Linder for Solid Phase Synthesis, J. OrgChem., 60: 2318-2319.
Holtze, 2008, Biocompatible surfactants for water-in-fluorocarbon emulsions, Lab Chip, 8, 1632-1639.
Hong, 1999, Stereochemical constraints on the substrate specificity of phosphodiesterase, Biochemistry, 38:1159-1165.
Hoogenboom, 1997, Designing and optimizing library selection strategies for generating high-affinity antibodies, Trends Biotechnol, 15:62-70.
Hopfinger, 1996, Explosive Breakup of a Liquid Jet by a Swirling Coaxial Jet, Physics of Fluids 8(7):1696-1700.
Hopman, 1998, Rapid synthesis of biotin-, digoxigenin-, trinitrophenyl-, and fluorochrome-labeled tyramides and their application for In situ hybridization using CARD amplification, J of Histochem and Cytochem, 46(6):771-77.
Horton, 1989, Engineering hybrid genes without the use of restriction enzymes: gene splicing by overlap extension, Gene 77(1):61-8 (.
Hosokawa, 1999, Handling of Picoliter Liquid Samples in a Poly(dimethylsiloxane)-Based Microfluidic Device, Analytical Chemistry, 71(20):4781-4785.
Hsieh, 2009, Rapid label-free DNA analysis in picoliter microfluidic droplets using FREI probes, Microfluidics and nanofluidics 6(3):391-401.
Hsu, 1999, et al.. Comparison of process parameters for microencapsulation of plasmid DNA in poly(D, L-lactic-co-glycolic acid microspheres, J Drug Target, 7:313-23.
Hua, 2010, Multiplexed Real-Time Polymerase Chain Reaction on a Digital Microfluidic Platform, Analytical Chemistry 82(6):2310-2316.
Huang, 1991, Kinetic assay of fluorescein mono-beta-D-galactosidase hydrolysis by beta-galactosidase: a front-face measurement for strongly absorbing fluorogenic substrates, Biochemistry, 30:8530-4.
Huang, 1992, A sensitive competitive ELISA for 2,4-dinitrophenol using 3,6-fluorescein diphosphate as a fluorogenic substrate, J Immunol Meth, 149:261.

(56) References Cited

OTHER PUBLICATIONS

Huang, 2004, Continuous particle separation through deterministic lateral displacement, Science 304(5673):987-990.
Huang, 2007, Identification of 8 foodborne pathogens by multicolor combinational probe coding technology in a single real-time PCR, Clin Chem., 53(10):1741-8.
Hubert, 2003, Data Concordance from a Comparison between Filter Binding and Fluorescence Polarization Assay Formats for Identification of RUOCK-II Inhibitors, J biomol Screen 8(4):399-409.
Huebner, 2007, Quantitative detection of protein expression in single cells using droplet microfluidics, Chem Com 12:1218-1220.
Hug, 2003, Measurement of the No. of molecules of a single mRNA species in a complex mRNA preparation. J Theor Biol; 221(4):615-24.
Hung, 2004, Controlled Droplet Fusion in Microfluidic Devices, MicroTAS 2004, Sep. 26-30, Malmo, Sweden.
Hung, 2004, Optimization of Droplet Generation by controlling PDMS Surface Hydrophobicity, 2004 ASME International Mechanical Engineering Congress and RD&D Expo, Nov. 13-19, Anaheim, CA, 47-48.
Hutchison, 2005, Cell-free cloning using Phi29 polymerase, PNAS 102(48):17332-17336.
Ibrahim, 2003, High-speed cell sorting: fundamentals and recent advances, Curr Opin Biotchnol, 14(1):5-12.
Ikeda, 2000, Bioactivation of tegafur to 5-fluorouracil is catalyzed by cytochrome P-450 2A6 in human liver microsomes in vitro, Clin Cancer Res 6(11):4409-4415.
Illumina, 2010, Genomic Sequencing, data Sheet, 6 pages.
Inai, 1993, Immunohistochemical detection of an enamel protein-related epitope in rat bone at an early stage of osteogenesis, Histochemistry 99(5):335-362.
Invitrogen, 2008, Specification sheet for Dynabeads® Oligo (dT)25, http://www.invitrogen.com, 2 pages.
Ismagilov, 2003, Integrated Microfluidic Systems, Angew. Chernm. Int. Ed 42:4130-4132.
Jakobovits, 1993, Analysis of homozygous mutant chimeric mice:deletion of the immunoglobulin heavy-chain joining region blocks B-cell development and antibody production, PNAS USA 90:2551-255.
Jakobovits, 1993, Germ-line transmission and expression of a human-derived yeast artificial chromosome, Nature 362:255-258.
Janda, 1997, Chemical selection for catalysis in combinatorial antibody libraries, Science, 275:945-948.
Jang, 2003, Controllable delivery of non-viral DNA from porous scaffold, J Controlled Release 86(1):157-168.
Jarvie, 2007, Amplicon Sequencing, Roche Dx Application Note No. 5 (16 pages).
Jermutus, 1998, et al., Recent advances in producing and selecting functional proteins by using cell-free translation, Curr Opin Biotechnol 9(5): 534-48.
Jo, 2003, Encapsulation of Bovine Serum Albumin in Temperature-Programmed Shell-in-Shell Structures, Macromol. Rapid Comm 24:957-962.
Joerger, 1995, Analyte detection with DNA-labeled antibodies and polymerase chain reaction, Clin. Chem. 41(9):1371-7.
Johannsson, 1988, Amplification by Second Enzymes, In ELISA and Other Solid Phase Immunoassays, Kemeny et al (ed.), Chapter 4, pp. 85-106 John Wiley.
Johannsson, 1991, Heterogeneous Enzyme Immunoassays, In Principles and Practice of Immunoassay, pp. 295-325 Stockton Press.
Johnson, 1993, Human antibody engineering: Current Opinion in Structural Biology, 3:564-571.
Johnson, 2002, Protein tyrosine phosphatase 1B inhibitors for diabetes, Nature Review Drug Discovery 1, 696-709.
Jones, 1986, Replacing the complementarity-determining regions in a human antibody with those from a mouse, Nature, 321:522-525.
Jones, 1997, Quenched BODIPY dye-labeled casein substrates for the assay of protease activity by direct fluorescence measurement, Anal Biochem, 251:144-152.
Jones, 1999, Glowing jellyfish, luminescence and a molecule called coelenterazine. Trends Biotechnol. 17(12):477-81.
Sano, 1992, Immuno-PCR: very sensitive antigen-detection by means of sepcific Ab-DNA conjugates, Science 258(5079):120-122.
Santalucia, 1998, A unified view of polymer, dumbbell, and oligonucleotide DNA nearest-neighbor thermodynamics, PNAS 95(4):1460-5.
Santra, 2006, Fluorescence lifetime measurements to determine the core-shell nanostructure of FITC-doped silica nanoparticles, J Luminescence 117(1):75-82.
Sawada, 1996, Synthesis and surfactant properties of novel fluoroalkylated amphiphilic oligomers, Chem Commun 2:179-190.
Schatz, 1996, Screening of peptide libraries linked to lac repressor, Meth Enzymol 267:171-91.
Schneegass, 2001, Miniaturized flow-through PCR with different template types in a silicone chip thermocycler, Lab on a Chip 1:42-9.
Schopman, 2012, Selective packaging of cellular miRNAs in HIV-1 particles, Virus Res 169(2):438-47.
Schubert, 2002, Designer Capsules, Nat Med 8:1362.
Schweitzer, 2000, Immunoassays with rolling circle DNA amplification, PNAS 97(18):10113-10119.
Schweitzer, 2001, Combining nucleic acid amplification and detection. Curr Opin Biotechnol 12(1):21-7.
Scott, 1948, The solubility of fluorocarbons, J Am Chem Soc 70:4090-4093.
Sedlak, 2013, Viral diagnostics in the era of digital polymerase chain reaction, Diag Microb Inf Dis 75(1):1-4.
Seethala, 1997, Homogeneous fluorescence polarization assay for Src-Family tyrosine kinases, Anal Biochem 253(2):210-218.
Seiler, 1993, Planar glass chips for capillary electrophoresis: repetitive sample injection, quantitation, and separation efficiency. Anal Chem 65(10):1481-1488.
Selwyn, 1965, A simple test for inactivation of an enzyme during assay, Biochim Biophys Acta 105:193-195.
Seo, 2007, Microfluidic consecutive flow-focusing droplet generators, Soft Matter 3:986-992.
Seong, 2002, Efficient mixing and reactions within microfluidic channels using microbead-supported catalysts, J Am Chem Soc 124(45):13360-1.
Seong, 2002, Fabrication of microchambers defined by photopolymerized hydrogels and weirs within microfluidic systems, Anal Chem 74(14):3372-3377.
Sepp, 2002, Microbead display by in vitro compartmentalisation: selection for binding using flow cytometry, FEBS Letters 532:455-58.
Serpersu, 1985, Reversible and irreversible modification of erythrocyte membrane permeability by electric field, Biochim Biophys Acta 812(3):779-785.
Shapiro, 1983, Multistation multiparameter flow cytometry: a critical review and rationale, Cytometry 3: 227-243.
Shastry, 2006, Directing droplets using microstructured surfaces, Langmuir 22:6161-6167.
Shen, 2006, Eigengene-based linear discriminant model for tumor classification using gene expression microarray data, Bioinformatics 22(21):2635-2642.
Shestopalov, 2004, Multi-step synthesis of nanoparticles performed on millisecond time scale in a microfluidic droplet-based system, Royal Soc Chem 4:316-321.
Shim, 2007, Using microfluidics to decouple nucleation and growth of protein crystals, Cryst Growth Des 7(11):2192-2194.
Shimizu, 1995, Encapsulation of biologically active proteins in a multiple emulsion, Biosci Biotech Biochem 59(3):492-496.
Shtern, 1996, Hysteresis in swirling jets, J Fluid Meeh 309:1-44.
Sia, 2003, Microfluidic devices fabricated in poly(dimethylsiloxane) for biological studies, Electrophoresis 24(21):3563-3576.
Siemering, 1996, Mutations that suppress the thermosensitivity of green fluorescent protein, Curr Biol 6:1653-1663.
Silva-Cunha, 1998, W/O/W multiple emulsions of insulin containing a protease inhibitor and an absorption enhancer: biological activity after oral administration to normal and diabetic rats, Int J Pharm 169:33-44.

(56) References Cited

OTHER PUBLICATIONS

Sims, 2000, Immunopolymerase chain reaction using real-time polymerase chain reaction for detection, Anal. Biochem. 281(2):230-2.
Sista, 2007, Development of a Digital Microfluidic Lab-on-a-Chip for Automated Immunoassay with Magnetically Responsive Beads, Doctoral Thesis, Florida State University, 128 pages.
Sista, 2008, Development of a digital microfluidic platform for point care testing, Lab on a Chip 8:2091-2104.
Siwy, 2003, Electro-responsive asymmetric nanopores in polyimide with stable ion-current signal, Appl Phys A: Mat Sci Proc 76:781-785.
Slappendel, 1994, Normal cations and abnormal membrane lipids in the red blood cells of dogs with familial stomatocytosis hypertrophic gastritis, Blood 84:904-909.
Slob, 1997, Structural identifiability of PBPK models: practical consequences for modeling strategies and study designs, Crit Rev Toxicol. 27(3):261-72.
Smith, 1985, The synthesis of oligonucleotides containing an aliphatic amino group at the 5' terminus: synthesis of fluorescent DNA primers for use in DNA sequence analysis, Nucl Acid Res 13:2399-2412.
Smith, 1986, Fluorescence detection in automated DNA sequence analysis, Nature 321:674-679.
Smith, 1989, Absolute displacement measurements using modulation of the spectrum of white light in a Michelson Interferometer, Applied Optics, 28(16):3339-3342.
Smith, 1992, Direct mechanical measurements of the elasticity of single DNA molecules by using magnetic beads, Science 258(5085):1122-1126.
Smith, 2010, Highly-multiplexed barcode sequencing: an efficient method for parallel analysis of pooled samples, Nucleic Acids Res 38(13):e142.
Smyth, 2000, Markers of apoptosis: methods for elucidating the mechanism of apoptotic cell death from the nervous system, Biotechniques 32:648-665.
Sohn, 2000, Capacitance cytometry: Measuring biological cells one by one, PNAS 97(20):10687-10690.
Sola, 2014, Fabrication of a microfluidic cell made of thiolene for microarray applications, 18th Int Conf Miniaturized Systems for Chem and Life Sciences, MicroTAS, San Antonio, TX 1719-1721.
Somasundaram, 1999, Gain studies of Rhodamine 6G dye doped polymer laser, J Photochem Photobiol 125(1-3):93-98.
Song, 2002, Experimental test of scaling of mixing by chaotic advection in droplets moving through microfluidic channels, App Phy Lett 83(22):4664-4666.
Song, 2003, A microfluidic system for controlling reaction networks in time, Angew Chern Int Ed 42(7):768-772.
Song, 2003, Millisecond kinetics on a microluidic chip using nanoliters of reagents, J Am Chem Soc 125:14613-14619.
Song, 2006, Reactions in droplets in microfluidic channels, Angew chem Int ed 45(44):7336-7356.
Soni, 2007, Progress toward ultrafast DNA sequencing using solid-state nanopores, Clin Chem 53:1996-2001.
Xia, 1998, Soft Lithography, Ann. Rev. Mat. Sci. 28:153-184.
Xiao, 2007, Rapid DNA mapping by fluorescent single molecule detection, Nucleic Acids Research 35:1-12.
Xing, 2011, Novel structurally related compounds reactivate latent HIV-1 in a bcl-2-transduced primary CD4+ T cell model without inducing global T cell activation, Journal of Antimicrobial Chemotherapy, 67(2):398-403.
Xu, 2005, Generation of monodisperse particles by using microfluidics: control over size, shape, and composition, Angew. Chem. Int. Ed. 44:724-728.
Xu, 2009, Design of 240, 000 orthogonal 25mer DNA barcode probes, PNAS, 106(7) p. 2289-2294.
Yamagishi, 1990, Mutational analysis of structure-activity relationships in human tumor necrosis factor-alpha, Protein Eng, 3:713-9.

Yamaguchi, 2002, Insulin-loaded biodegradable PLGA microcapsules: initial burst release controlled by hydrophilic additives, Journal of Controlled Release, 81(3): 235-249.
Yelamos, 1995, Targeting of non-Ig sequences in place of the V segment by somatic hypermutation. Nature 376(6537):225-9.
Yershov, 1996, DNA analysis and diagnostics on oligonucleotide microchips, PNAS 93(10):4913-4918.
Yonezawa, 2003, DNA display for in vitro selection of diverse peptide libraries, Nucleic Acids Research, 31(19): e118, 5 pages.
Yu, 1997, Specific inhibition of PCR by non-extendable oligonucleotides using a 5' to 3' exonuclease-deficient DNA polymerase, Biotechniques 23(4):714-6, 718-20.
Yu, 2001, Responsive biomimetic hydrogel valve for microfluidics. Appl. Phys. Lett 78:2589-2591.
Yu, 2002, Environmental Carcinogenic Polycyclic Aromatic Hydrocarbons: Photochemisrty and Phototoxicity, J Environ Scie Health C Environ Carcinog Exotoxicol Rev, 20(2), 1-43.
Yu, 2007, Quantum dot and silica nanoparticle doped polymer optical fibers, Optics Express 15(16):9989-9994.
Zaccolo, 1996, An approach to random mutagenesis of DNA using mixtures of triphosphate derivatives of nucleoside analogues. J Mol Biol 255(4):589-603.
Zakrzewski, 1980, Preparation of tritiated dihydrofolic acid of high specific activity, Methods Enzymol, 529-533.
Zaug, 1986, The intervening sequence RNA of Tetrahymena is an enzyme, Science 231(4737):470-5.
Zaug, 1986, The Tetrahymena intervening sequence ribonucleic acid enzyme is a phosphotransferase and an acid phosphatase, Biochemistry 25(16):4478-82.
Zaug, 1986, The Tetrahymena ribozyme acts like an RNA restriction endonuclease, Nature 324(6096):429-33.
Zhang, 1993, Substrate specificity of the protein tyrosine phosphatases, PNAS 90: 4446-4450.
Zhang, 1999, A Simple Statistical Parameter for Use in Evaluation and Validation of High Throughput Screening Assays, Journal of Biomolecular Screening, 4(2): 67-73.
Zhao, 1998, Molecular evolution by staggered extension process (StEP) in vitro recombination. Nat Biotechnol 16(3):258-61.
Zhao, 2002, Control and Applications of Immiscible Liquids in Microchannels, J. Am. Chem. Soc, vol. 124:5284-5285.
Zheng, 2003, Screening of Protein Crystallization Conditions on a Microfluidic Chip Using Nanoliter-Size Droplets, J Am Chem Soc 125(37):11170-11171.
Zheng, 2004, A Droplet-Based, Composite PDMS/Glass Capillary Microfluidic System for Evaluating Protein Crystallization Conditions by Microbatch and Vapor-Diffusion Methods with On-Chip X-Ray Diffraction, Angew. Chem., 116:1-4.
Zheng, 2004, Formation of Droplets of Alternating Composition in Microfluidic Channels and Applications to Indexing of Concentrations in Droplet-Based /Assays, Anal. Chem.,76: 4977-4982.
Zheng, 2005, A Microiuidic Approach for Screening Submicroliter vols. against Multiple Reagents by Using Performed Arrays of Nanoliter Plugs in a Three-Phase Liquid/Liquid/Gas Flow, Angew. Chem. Int. Ed., 44(17):2520-2523.
Zhong, 2011, Multiplex digital PCR: breaking the one target per color barrier of quantitative PCR, Lab on a Chip 11(13):2167-2174.
Zimmermann, 1974, Dielectric Breakdown of Cell Membranes, Biophys J 14(11):881-889.
Zimmermann, 1992, Microscale Production of Hybridomas by Hypo-Osmolar Electrofusion, Hum. Antibod. Hybridomas, 3(1): 14-18.
Zimmermann, 2008, Digital PCR: a powerful new tool for noninvasive prenatal diagnosis?, Prenat Diagn 28, 1087-1093.
Zubay, 1973, In vitro synthesis of protein in microbial systems, Annu Rev Genet, 7: 267-87.
Zubay, 1980, The isolation and properties of CAP, the catabolite gene activator, Methods Enzymol, 65: 856-77.
Zuckermann, 1987, Efficient Methods for Attachment of Thiol-Specific Probes to the 3-end of Synthetic Oligodeoxyribonucleotides, Nucleic Acids Res 15:5305-5321.
Gibbs, 1989, Detection of single DNA base differences by competitive oligonucleotide priming, Nucleic Acids Res 17(7): 2437-48.

(56) References Cited

OTHER PUBLICATIONS

Gilliland, 1990, Analysis of cytokine mRNA and DNA: Detection and quantitation by competitive polymerase chain reaction, PNAS, 87(7):2725-9.
Giusti, 1993, Synthesis and characterization of 5' fluorescent dye labeled oligonucleotides, Genome Res 2:223-227.
Glass, 1995, Development of primer sets designed for use with the PCR to amlify conserved genes from filamentous ascomycetes, Applied and Environmental Microbiology, vol. 6, pp. 1323-1330.
Gold, 1995, Diversity of Oligonucleotide Functions Annu Rev Biochem, 64: 763-97.
Gong, 2015, Simple method to prepare oligonucleotide conjugated antibodies and its applicaiotn in multiplex protein detection in single cells, Bioconjugate Chm 27(1):271-225.
Goodall, 1998, Operation of mixed-culture immobilized cell reactors for the metabolism of meta- and para-nitrobenzoate by Comamonas Sp. JS46 and Comamonas Sp. JS47, Biotech Bioeng 59 (1):21-27.
Gordon, 1999, Solid phase synthesis—designer linkers for combinatorial chemistry: a review, J. Chem. Technol. Biotechnol., 74(9):835-851.
Grasland-Mongrain, 2003, Droplet coalescence in microfluidic devices, 30 pages, From internet: http://www.eleves.ens.fr/home/grasland/rapports/stage4pdf.
Gray, 1987, High speed crhomosome sorting, Science 238(4825):323-329.
Green, 1992, Selection of a Ribozyme That Functions as a Superior Template in a Self Copying Reaction, Science, 258: 1910-5.
Gregoriadis, 1976, Enzyme entrapment in liposomes, Methods Enzymol 44:218-227.
Giffiths, 2000, Man-made enzymes-from design to in vitro compartmentalisation, Curr Opin Biotechnol 11:338-353.
Giffilhs, 2003, Directed evolution of an extremely fast phosphotriesterase by in vitro compartmentalization, EMBO J, 22:24-25.
Giffiths, 2006, Miniaturising the laboratory in emulsion droplets, Trend Biotech 24(9):395-402.
Grinwood, 2004, The DNA sequence and biology of human chromosome 19, Nature 428:529-535.
Grothues, 1993, PCR amplification of megabase DNA with tagged random primers (T-PCR), Nucl. Acids Res vol. 21(5):1321-1322.
Grund, 2010, Analysis of biomarker dataHogs, odds, ratios and ROC curves, Curr Opin HIV AIDS 5(6):473-479.
Guatelli, 1990, Isothermal, in vitro amplification of nucleic acids by a multienzyme reaction modeled after retroviral replication, PNAS, 87(5):1874-8.
Guixe, 1998, Ligand-Induced Conformational Transitions in Escherichia Coli Phosphofructokinase 2: Evidence for an Allosteric Site for MgATP2n, Biochem., 37: 13269-12375.
Gupta, 1991, A general method for the synthesis of 3'-sulfhydryl and phosphate group containing oligonucleotides, Nucl Acids Res 19 (11): 3019-3026.
Haber, 1993, Activity and spectroscopic properties of bovine liver catalase in sodium bis(2-ethylhexyl) sulfosuccinate/isooctane reverse micelles, Eur J Biochem 217(2): 567-73.
Habig, 1981, Assays for differentiation of glutathione S-transferases, Methods in Enzymology, 77: 398-405.
Hadd, 1997, Microchip Device for Performing Enzyme Assays, Anal. Chem 69(17): 3407-3412.
Haeberle, 2007, Microfluidic platforms for lab-on-a-chip applications, Lab on a Chip 7:1081-1220.
Hagar, 1992, The effect of endotoxemia on concanavalin A induced alterations in cytoplasmic free calcium in rat spleen cells as determined with Fluo-3, Cell Calcium 13:123-130.
Hai, 2004, Investigation on the release of fluorescent markers from the w/o/w emulsions by fluorescence-activated cell sorter, J Control Release, 96(3): 393-402.
Haies, 1981, Morphometric study of rat lung cells. I. Numerical and dimensional characteristics of parenchymal cell population. Am. Rev Respir Dis 123:533-54.
Hall, 2003, The EBG system of E. coli: origin and evolution of a novel beta-galactosidase for the metabolism of lactose, Genetica 118(2-3):143-56.
Hamady, 2008, Error-correcting barcoded primers for pyrosequencing hundreds of samples in multiplex. Nature Nethods vol. 5, No. 3, p. 235-237.
Han, 2001, Quantum-dot-tagged Microbeads for Multiplexed Optical Coding of Biomolecules, Nat Biotech 19(7):631-635.
Handen, 2002, High-throughput screening- challenges for the future, Drug Discov World, 47-50.
Handique, 2001, On-Chip Thermopneumatic Pressure for Discrete Drop Pumping, Analytical Chemistry, 73:1831-1838.
Hanes, 1997, In vitro selection and evolution of functional proteins by using ribosome display, PNAS 94:4937-42.
Hanes, 1998, Degradation of porous poly(anhydide-co-imide) microspheres and implication for controlled macromolecule delivery, Biomaterials, 19(1-3): 163-172.
Hansen, 2002, A robust and scalable microfluidic metering method that allows protein crystal growth by free interface diffusion, PNAS 99(26):16531-16536.
Harada, 1993, Monoclonal antibody G6K12 specific for membrane-associated differentiation marker of human stratified squamous epithelia and squamous cell carcinoma, J. Oral Pathol. Med 22(4):145-152.
Harder, 1994, Characterization and kinetic analysis of the intracellular domain of human protein tyrosine phosphatase beta (HPTP beta) using synthetic phosphopeptides, Biochem J 298 (Pt 2): 395-401.
Harries, 2006, A Numerical Model for Segmented Flow in a Microreactor, Int J of Heat and Mass Transfer, 46:3313-3322.
Harris, 2008, Single-molecule DNA sequencing of a viral genome, Science 320(5872):106-109.
Harrison, 1993, Micromachining a miniaturized capillary electrophoresis-based chemical analysis system on a chip, Science 261(5123):895-897.
Hasina, 2003, Plasminogen activator inhibitor-2: a molecular biomarker for head and neck cancer progression, Cancer Research 63:555-559.
Haynes, 2012, Digital PCR: A Technology Primer, Principles of Digital PCR and Measurement Issues: The certification of Cytomegalovirus Standard Reference Material (SRM 2366) as a model for future SRMs, National Institute of Standards and Tecnology, San Diego, CA, 4 pages.
Hayward, 2006, Dewetting Instability during the Formation of Polymersomes from BloceCopolymer-Stabilized Double Emulsions, Langmuir, 22(10): 4457-4461.
He, 2005, Selective encapsulation of single cells and subcellular organelles into picoliter- and femtoliter-volume droplets. Anal Chem 77(6):1539-1544.
Head, 2014, Library construction for next generation sequencing, Biotech Rap Disp 56(2):61.
Heim, 1996, Engineering Green Fluorescent Protein for Improved Brightness, Longer Wavelengths and Fluorescence Response Energy Transfer, Carr Biol, 6(2): 178-182.
Hellman, 2009, Differential tissue-specific protein markers of vaginal carcinoma, Br J Cancer, 100(8): 1303-131.
Henrich, 2012, Low-level detection and quantitation of cellular HIV-1 DNA and 2-ILTR circles using droplet dPCR, J Virol Meth 186(1-2):68-72.
Hergenrother, 2000, Small-Molecule Microarrays: Covalent Attachment and Screening of Alcohol-Containing Small Molecules on Glass Slides, J Am. Chem. Soc, 122: 7849-7850.
Chiu, 2008, Noninvasive prenatal diagnosis of chromosomal aneuploidy by massively paralel genomic seuqencing of DNA in maternal plasma, PNAS 105(51):20458-20463.
Eijk-Van Os, 2011, Multiplex ligation-dependent probe amplification (MLPA(R)) for the detection of copy number variation in genomic sequences, Meth Mol Biol 688:97-126.
Gruner, 2015, Stabilisers for water-in-fluorinated-oil dispersions, Gurr Op Coll Int Sci 20:183-191.
Guo, 2010, Simultaneous detection of trisomies 13, 18, and 21 with multiplex ligation dependent probe amplification-based real-time PCR, Clin Chem 56(9):1451-1459.

(56) References Cited

OTHER PUBLICATIONS

Meng, 2015, Self-assembling amphiphilic poly(propargyl methacrylate) grafted DNA copolymers into multi-strand helices, Soft Matter 11(28):5610-5613.
Salomon, 2019, Droplet-based single cell RNAseq tools: a practical guide, Lab on a Chip 19:1706-1727.
Shendure, 2008, Next-generation DNA sequencing, Nature Biotechnology, 26(10):1135-1145.

* cited by examiner

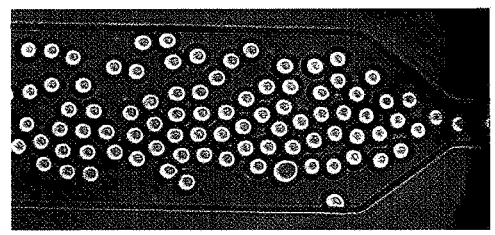
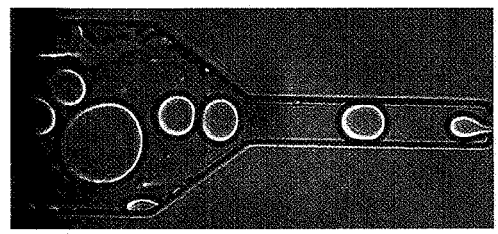
Figure 5

Fluorescence Measured Per Molecule

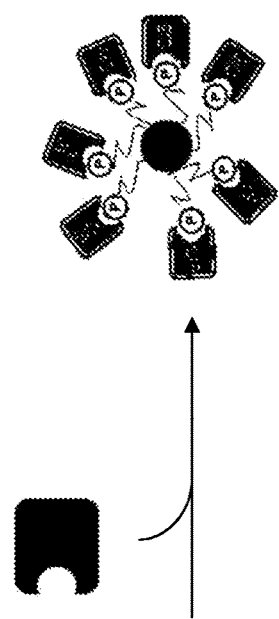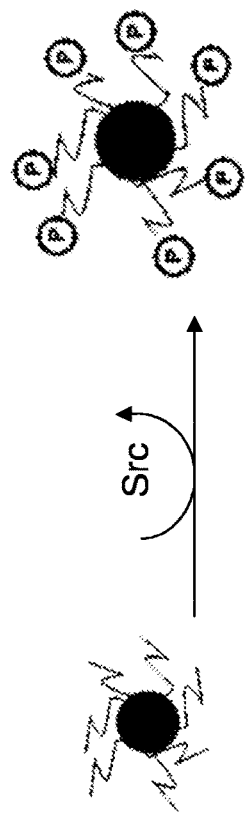
Figure 16A
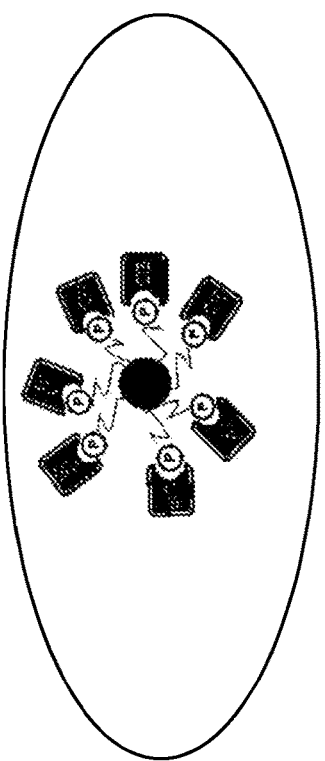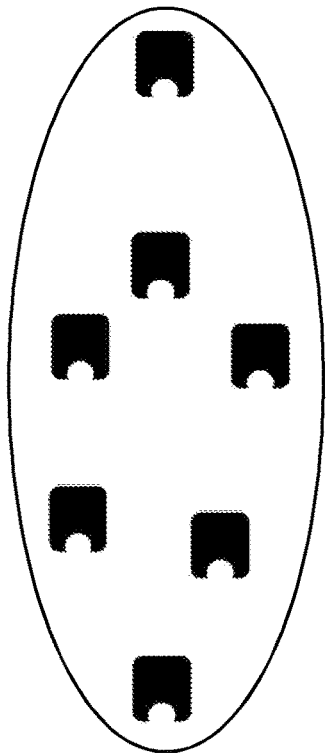
Figure 16B

ENZYME QUANTIFICATION

FIELD OF INVENTION

The present invention generally relates to droplet libraries and to systems and methods for the formation of libraries of droplets. The present invention also relates to methods utilizing these droplet libraries in various biological, chemical, or diagnostic assays.

BACKGROUND

The manipulation of fluids to form fluid streams of desired configuration, discontinuous fluid streams, droplets, particles, dispersions, etc., for purposes of fluid delivery, product manufacture, analysis, and the like, is a relatively well-studied art. Microfluidic systems have been described in a variety of contexts, typically in the context of miniaturized laboratory (e.g., clinical) analysis. Other uses have been described as well. For example, International Patent Application Publication Nos. WO 01/89788; WO 2006/040551; WO 2006/040554; WO 2004/002627; WO 2008/063227; WO 2004/091763; WO 2005/021151; WO 2006/096571; WO 2007/089541; WO 2007/081385 and WO 2008/063227.

Precision manipulation of streams of fluids with microfluidic devices is revolutionizing many fluid-based technologies. Networks of small channels are a flexible platform for the precision manipulation of small amounts of fluids. However, virtually all microfluidic devices are based on flows of streams of fluids; this sets a limit on the smallest volume of reagent that can effectively be used because of the contaminating effects of diffusion and surface adsorption. As the dimensions of small volumes shrink, diffusion becomes the dominant mechanism for mixing, leading to dispersion of reactants; moreover, surface adsorption of reactants, while small, can be highly detrimental when the concentrations are low and volumes are small. As a result, current microfluidic technologies cannot be reliably used for applications involving minute quantities of reagent; for example, bioassays on single cells or library searches involving single beads are not easily performed. An alternate approach that overcomes these limitations is the use of aqueous droplets in an immiscible carrier fluid; these provide a well-defined, encapsulated microenvironment that eliminates cross contamination or changes in concentration due to diffusion or surface interactions. Droplets provide the ideal microcapsule that can isolate reactive materials, cells, or small particles for further manipulation and study. However, essentially all enabling technology for microfluidic systems developed thus far has focused on single phase fluid flow and there are few equivalent active means to manipulate droplets requiring the development of droplet handling technology. While significant advances have been made in dynamics at the macro- or microfluidic scale, improved techniques and the results of these techniques are still needed. For example, as the scale of these reactors shrinks, contamination effects due to surface adsorption and diffusion limit the smallest quantities that can be used. Confinement of reagents in droplets in an immiscible carrier fluid overcomes these limitations, but demands new fluid-handling technology.

The present invention overcomes the current limitations in the field by providing precise, well-defined, droplet libraries which can be utilized alone, or within microfluidic channels and devices, to perform various biological and chemical assays efficiently and effectively, especially at high speeds.

SUMMARY

This invention provides methods to identify and quantify the presence, type, and amount of reactants and products of chemical reactions. The invention takes advantage of the ability to form discrete droplets that contain the components of a chemical reaction. Because measurements can be performed on individual droplets and collections of individual droplet, it is possible to identify and quantify chemical reaction components in the droplets according to methods described herein. Methods of the invention are useful to detect and/or quantify any component of a chemical reaction. In one preferred embodiment, enzyme molecules are quantified based on their activity inside individual droplets. In order to identify and quantitate enzyme activity, droplets are identified as "negative" and/or "positive" droplets for the reaction catalyzed by the target enzyme, and the number of enzyme molecules within positive droplets (e.g., based on the quantized signal strength) is determined. Digital counting of enzyme molecules provides an extremely wide dynamic range of detection, with a lower limit of detection dependent on the number of molecules available to count and the total number of droplets read (e.g. 1 in $10^7$, in one hour using a droplet flow rate of $10^7$ per hour) and the upper limit for single molecule counting determined by the number of droplets but also includes a further range where multiple or average numbers of molecules are present in droplets.

In general, the invention involves incorporating components of a chemical reaction in a droplet and allowing the chemical reaction to occur in the droplet. One or more of the components of the reaction is detectably labeled (e.g., with a reporter molecule) such that label is detectable as a result of the reaction (e.g., release of a reporter). Detection and quantification of the label allows detection and quantification of the reaction components. The reporter moiety may be any detectable moiety that can be used as an indicator of reaction components (e.g., enzyme activity). Any reporter system known in the art may be used with methods of the invention. In certain embodiments, the reporter moiety is a fluorescent moiety.

In a preferred embodiment, a reporter is attached to one or more substrate(s) of a chemical reaction in a droplet, which label is released upon enzymatic catalysis. The number of droplets containing quantified enzyme molecules are then determined based upon the presence and/or signal strength of the reporter. Reporter (and therefore enzyme) can be quantified based upon these measurements as well. Methods of the invention involve forming a sample droplet. Any technique known in the art for forming sample droplets may be used with methods of the invention. An exemplary method involves flowing a stream of sample fluid so that the sample stream intersects one or more opposing streams of flowing carrier fluid. The carrier fluid is immiscible with the sample fluid. Intersection of the sample fluid with the two opposing streams of flowing carrier fluid results in partitioning of the sample fluid into individual sample droplets. The carrier fluid may be any fluid that is immiscible with the sample fluid. An exemplary carrier fluid is oil, which may in some cases be fluorinated. In certain embodiments, the carrier fluid includes a surfactant, such as a fluorosurfactant.

In some aspects, the invention provides methods for digital distribution assays that allow, for example, for detection of a physiological condition in a human. Detectable physiological conditions include conditions associated with aggregation of proteins or other targets. Methods include forming fluid partitions that include components of a detectable chemical reaction and conducting the reaction. A distribution of at least one of the components is determined based on detecting the detectable reaction. A statistically expected distribution can be computed and compared to the determined distribution or comparisons of distributions from known or typical samples. Based on these comparisons, the presence and/or the severity of the potential condition can be determined. In certain embodiments, the condition involves protein aggregation. The protein can be a protein from a sample from a patient. In some embodiments, methods assay for Alzheimer's disease, Parkinson's disease, Huntington's disease, Type II diabeties mellitus, prion-associated diseases, or other conditions.

Another droplet formation method includes merging at least two droplets, in which each droplet includes different material. Another droplet formation method includes forming a droplet from a sample, and contacting the droplet with a fluid stream, in which a portion of the fluid stream integrates with the droplet to form a droplet. An electric field may be applied to the droplet and the fluid stream. The electric field assists in rupturing the interface separating the two fluids. In particular embodiments, the electric field is a high-frequency electric field.

Methods of the invention may be conducted in microfluidic channels. As such, in certain embodiments, methods of the invention may further involve flowing the droplet channels and under microfluidic control.

BRIEF DESCRIPTION OF THE DRAWINGS

Non-limiting embodiments of the present invention will be described by way of example with reference to the accompanying drawings, which are schematic and are not intended to be drawn to scale. In the drawings, each identical or nearly identical component illustrated is typically represented by a single numeral. For the purposes of clarity, not every component is labeled in every drawing, nor is every component of each embodiment of the invention shown where illustration is not necessary to allow those of ordinary skill in the art to understand the invention. In the drawings:

FIG. 5 Panel A is a photograph showing droplets containing Ammonium Carboxylate Salt of Krytox 157 FSH 2 Wt % in FC 3283 without PEG amine salt. Panel B is a photograph showing droplets containing PEG 600 Diammonium Carboxylate Salt of Krytox 157 FSH at 4.0% by volume.

FIGS. 16A and 16B illustrate localized florescence as another mode for readout.

DETAILED DESCRIPTION

Droplet Libraries

Figure 1:
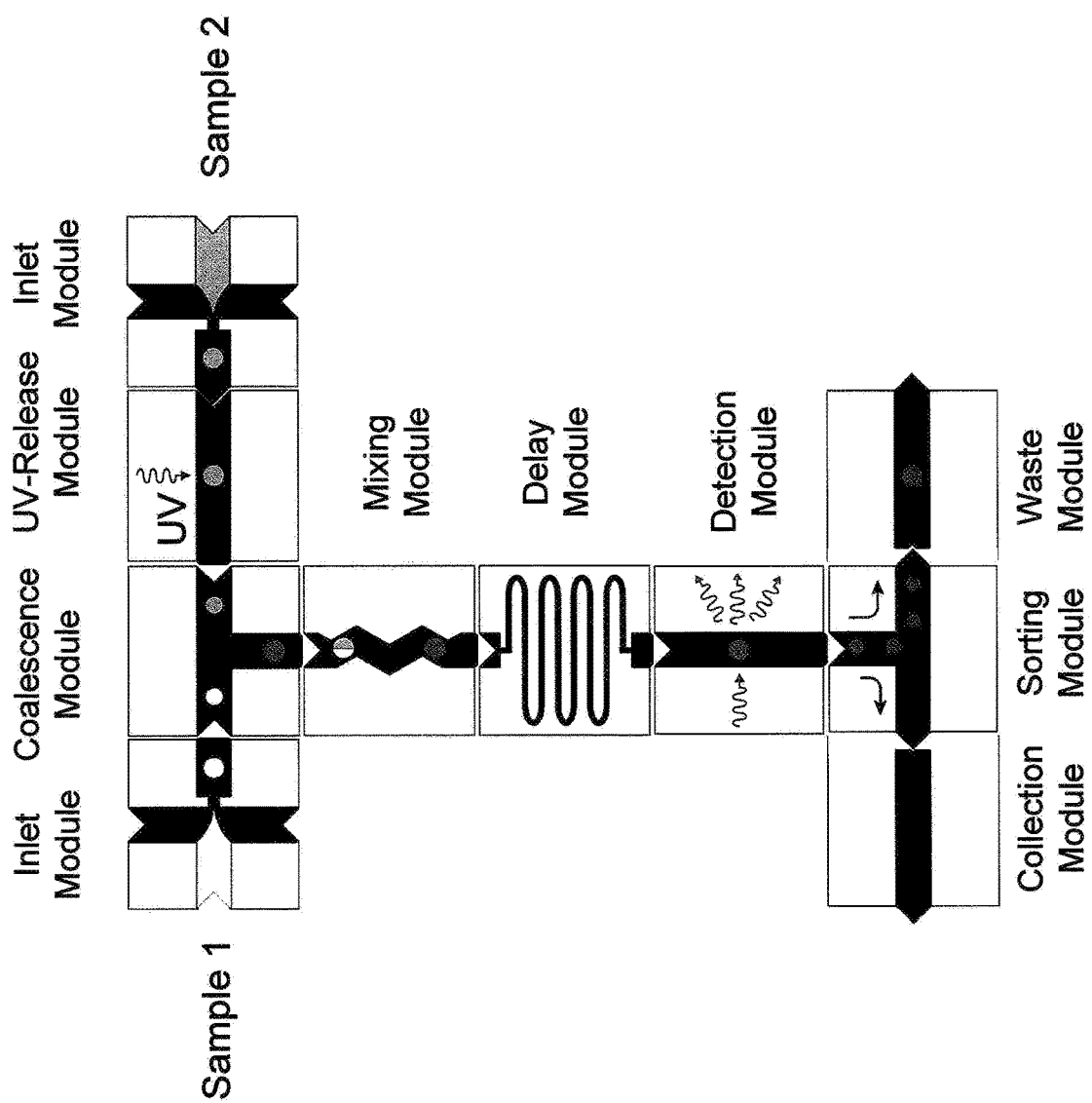
FIG. 1 is an schematic illustrating the interacting modules of a microfluidic device of the present invention.

Droplet libraries are useful to perform large numbers of assays while consuming only limited amounts of reagents. A "droplet," as used herein, is an isolated portion of a first fluid that completely surrounded by a second fluid. In some cases, the droplets may be spherical or substantially spherical; however, in other cases, the droplets may be non-spherical, for example, the droplets may have the appearance of "blobs" or other irregular shapes, for instance, depending on the external environment. As used herein, a first entity is "surrounded" by a second entity if a closed loop can be drawn or idealized around the first entity through only the second entity.

In general, a droplet library is made up of a number of library elements that are pooled together in a single collection. Libraries may vary in complexity from a single library element to $10^{15}$ library elements or more. Each library element is one or more given components at a fixed concentration. The element may be, but is not limited to, cells, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

A cell library element can include, but is not limited to, hybridomas, B-cells, primary cells, cultured cell lines, cancer cells, stem cells, or any other cell type. Cellular library elements are prepared by encapsulating a number of cells from one to tens of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops" Lab Chip, 8(8):1262-1264, 2008. The discreet nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

A bead based library element contains one or more beads, of a given type and may also contain other reagents, such as antibodies, enzymes or other proteins. In the case where all library elements contain different types of beads, but the same surrounding media, the library elements can all be prepared from a single starting fluid or have a variety of starting fluids. In the case of cellular libraries prepared in mass from a collection of variants, such as genomically modified, yeast or bacteria cells, the library elements will be prepared from a variety of starting fluids.

Often it is desirable to have exactly one cell per droplet with only a few droplets containing more than one cell when starting with a plurality of cells or yeast or bacteria, engineered to produce variants on a protein. In some cases, variations from Poisson statistics can be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, small molecules, DNA, primers, antibodies. The droplets range in size from roughly 0.5 micron to 500 micron in diameter, which corresponds to about 1 pico liter to 1 nano liter. However, droplets can be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the droplet library provided by the instant invention are uniform in size. That is, the diameter of any droplet within the library will vary less than 5%, 4%, 3%, 2%, 1% or 0.5% when compared to the diameter of other droplets within the same library. The uniform size of the droplets in the library is critical to maintain the stability and integrity of the droplets and is also essential for the subsequent use of the droplets within the library for the various biological and chemical assays described herein.

The droplets comprised within the emulsion libraries of the present invention are contained within an immiscible fluorocarbon oil comprising at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays described herein. Fluids (e.g., aqueous fluids, immiscible oils, etc.) and other surfactants that can be utilized in the droplet libraries of the present invention are described in greater detail herein.

The droplet libraries of the present invention are very stable and are capable of long-term storage. The droplet libraries are determined to be stable if the droplets comprised within the libraries maintain their structural integrity, that is the droplets do not rupture and elements do not diffuse from the droplets. The droplets libraries are also determined to be stable if the droplets comprised within the libraries do not coalesce spontaneously (without additional energy input, such as electrical fields described in detail herein). Stability can be measured at any temperature. For example, the droplets are very stable and are capable of long-term storage at any temperature; for example, e.g., −70° C., 0° C., 4° C., 37° C., room temperature, 75° C. and 95° C. Specifically, the droplet libraries of the present invention are stable for at least 30 days. More preferably, the droplets are stable for at least 60 days. Most preferably, the droplets are stable for at least 90 days.

The present invention provides an emulsion library comprising a plurality of aqueous droplets within an immiscible fluorocarbon oil comprising at least one fluorosurfactant, wherein each droplet is uniform in size and comprises the same aqueous fluid and comprises a different library element. The present invention also provides a method for forming the emulsion library comprising providing a single aqueous fluid comprising different library elements, encapsulating each library element into an aqueous droplet within an immiscible fluorocarbon oil comprising at least one fluorosurfactant, wherein each droplet is uniform in size and comprises the same aqueous fluid and comprises a different library element, and pooling the aqueous droplets within an immiscible fluorocarbon oil comprising at least one fluorosurfactant, thereby forming an emulsion library.

For example, in one type of emulsion library, all different types of elements (e.g., cells or beads), are pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In one example, the cells can comprise cancer cells of a tissue biopsy, and each cell type is encapsulated to be screened for genomic data or against different drug therapies. Another example is that $10^{11}$ or $10^{15}$ different type of bacteria; each having a different plasmid spliced therein, are encapsulated. One example is a bacterial library where each library element grows into a clonal population that secretes a variant on an enzyme.

In another example, the emulsion library comprises a plurality of aqueous droplets within an immiscible fluorocarbon oil, wherein a single molecule is encapsulated, such that there is a single molecule contained within a droplet for every 20-60 droplets produced (e.g., 20, 25, 30, 35, 40, 45, 50, 55, 60 droplets, or any integer in between). Single molecules are encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 μm droplets were made at 10 kHz per second. Formation of these libraries rely on limiting dilutions.

The present invention also provides an emulsion library comprising at least a first aqueous droplet and at least a second aqueous droplet within a fluorocarbon oil comprising at least one fluorosurfactant, wherein the at least first and the at least second droplets are uniform in size and comprise a different aqueous fluid and a different library element. The present invention also provides a method for forming the emulsion library comprising providing at least a first aqueous fluid comprising at least a first library of elements, providing at least a second aqueous fluid comprising at least a second library of elements, encapsulating each element of said at least first library into at least a first aqueous droplet within an immiscible fluorocarbon oil comprising at least one fluorosurfactant, encapsulating each element of said at least second library into at least a second aqueous droplet within an immiscible fluorocarbon oil comprising at least one fluorosurfactant, wherein the at least first and the at least second droplets are uniform in size and comprise a different aqueous fluid and a different library element, and pooling the at least first aqueous droplet and the at least second aqueous droplet within an immiscible fluorocarbon oil comprising at least one fluorosurfactant thereby forming an emulsion library.

Figure 2:
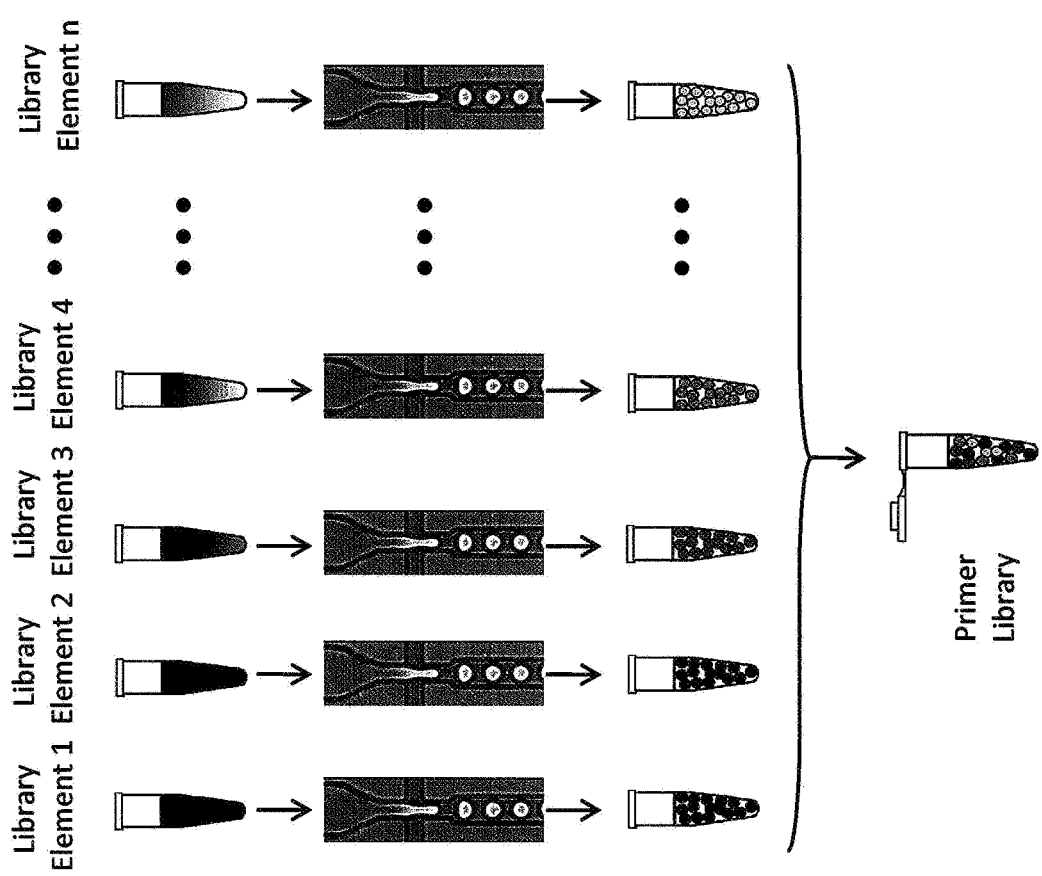
FIG. 2 is a schematic illustrating a one emulsion library.

For example, in one type of emulsion library, there are library elements that have different particles, i.e., cells or beads in a different medium and are encapsulated prior to pooling. As exemplified in FIG. 2, a specified number of library of elements, i.e., n number of different cells or beads, are contained within different mediums. Each of the library elements are separately emulsified and pooled, at which point each of the n number of pooled different library elements are combined and pooled into a single pool. The resultant pool contains a plurality of water-in-oil emulsion droplets each containing a different type of particle.

In some embodiments, the droplets formed will either contain a single library element or will not contain anything, i.e., be empty. In other embodiments, the droplets formed will contain multiple copies of a library element. The contents of the beads follow a Poisson distribution, where there is a discrete probability distribution that expresses the probability of a number of events occurring in a fixed period of time if these events occur with a known average rate and independently of the time since the last event. The oils and surfactants used to create the libraries prevents the exchange of the contents of the library between droplets.

Examples of assays that utilize these emulsion libraries are ELISA assays. The present invention provides another emulsion library comprising a plurality of aqueous droplets within an immiscible fluorocarbon oil comprising at least one fluorosurfactant, wherein each droplet is uniform in size and comprises at least a first antibody, and a single element linked to at least a second antibody, wherein said first and second antibodies are different. In one example, each library element comprises a different bead, wherein each bead is attached to a number of antibodies and the bead is encapsulated within a droplet that contains a different antibody in solution. These antibodies can then be allowed to form "ELISA sandwiches," which can be washed and prepared for a ELISA assay. Further, these contents of the droplets can be altered to be specific for the antibody contained therein to maximize the results of the assay. A specific example of an ELSA assay is shown in Example 5 and in FIG. 3.

Figure 4:
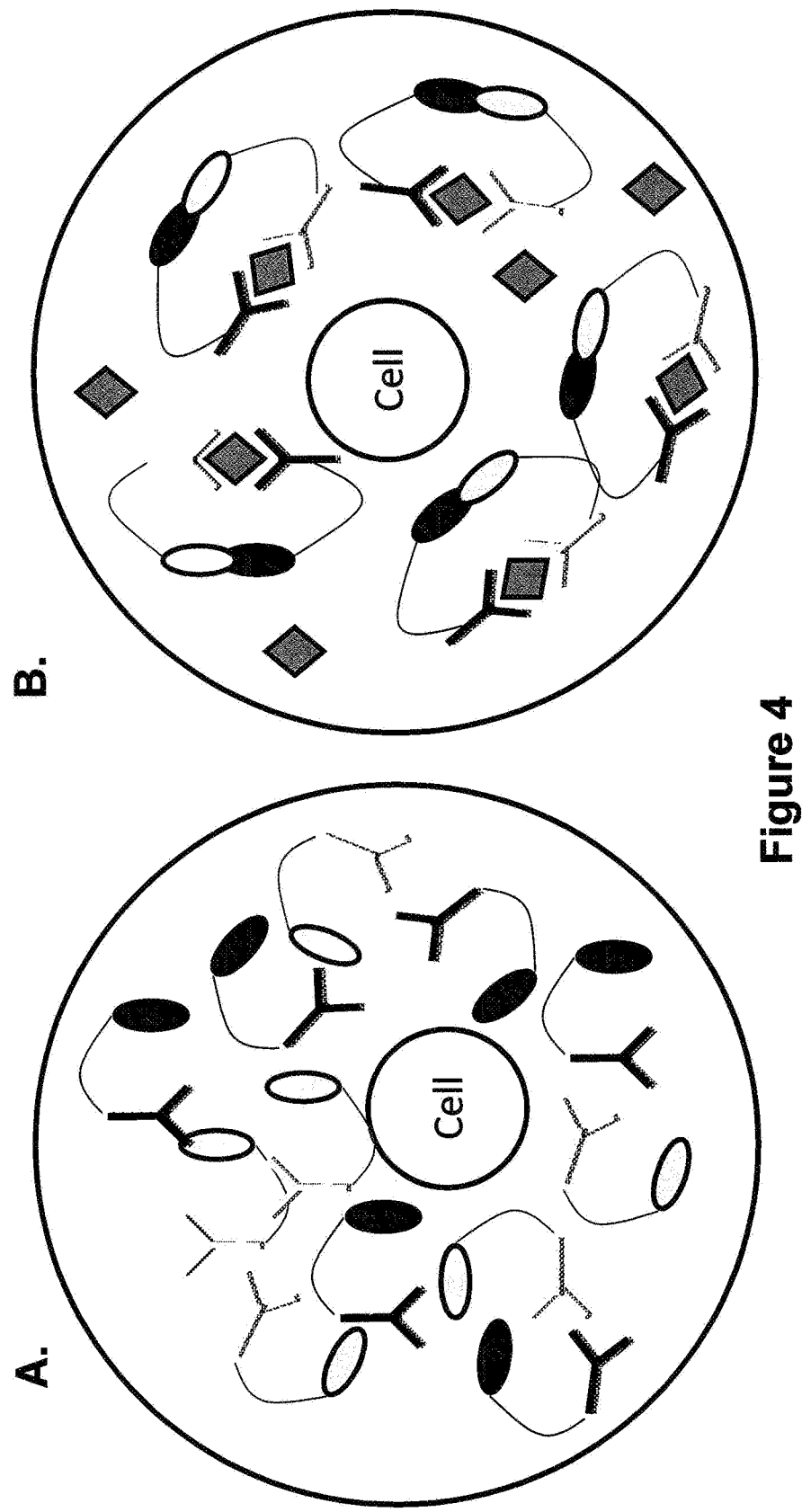
FIG. 4 Panel A is a schematic illustrating that the cell in the Protein-Fragment Complementation Assay is not secreting any antigen hence the fluorogenic substrate is not converted into a fluorescent product. Panel B is a schematic showing the conversion to a fluorescent product.

The present invention also provides another emulsion library comprising a plurality of aqueous droplets within an immiscible fluorocarbon oil comprising at least one fluorosurfactant, wherein each droplet is uniform in size and comprises at least a first element linked to at least a first antibody, and at least a second element linked to at least a second antibody, wherein said first and second antibodies are different. In one example of a Protein-Fragment Complementation Assay (PCA), library droplets are prepared to contain a mixture of two different antibodies. Wherein the two antibodies bind with strong affinity to different epitopes of the antigen molecule that is to be detected. Detection is achieved by tethering protein fragments to the each of the antibodies such that when held in proximity the two fragments create an active enzyme capable of turning over a fluorogenic substrate, only in the presence of the antigen. For example, as shown in FIG. 4 Panel A, the cell is not secreting any antigen hence the fluorogenic substrate is not converted into a fluorescent product. By contrast, in Panel B, the cell is secreting the antigen. Hence when the antibodies bind to it the two protein fragments are held in close enough proximity to form an active enzyme. The intensity of the fluorescence signal generated from these sandwiches is indicative of the antigen concentration in the droplet.

In another example, of the emulsion library, the library begins with a certain number of library elements, which may contain proteins, enzymes, small molecules and PCR primers, among other reagents. However, there is no Poisson distribution in these droplet libraries, Rather, each library is added to a droplet in a specific concentration. In these droplet libraries, there are a large number of the reagent contained within the droplets. With small molecule chemical compounds, each library element can be the same small molecule chemical compound at different concentrations or be completely different small molecule chemical compound per element. When encapsulating PCR primers there are any number of a single type of primer pairs contained within each droplet.

Labels can be used for identification of the library elements of the various types of droplet libraries. Libraries can be labeled for unique identification of each library element by any means known in the art. The label can be an optical label, an enzymatic label or a radioactive label. The label can be any detectable label, e.g., a protein, a DNA tag, a dye, a quantum dot or a radio frequency identification tag, or combinations thereof. Preferably the label is an optical label. The label can be detected by any means known in the art. Preferably, the label is detected by fluorescence polarization, fluorescence intensity, fluorescence lifetime, fluorescence energy transfer, pH, ionic content, temperature or combinations thereof. Various labels and means for detection are described in greater detail herein.

Specifically, after a label is added to each of the various library elements, the elements are then encapsulated and each of the droplets contains a unique label so that the library elements may be identified. In one example, by using various combinations of labels and detection methods, it is possible to use two different colors with different intensities or to use a single color at a different intensity and different florescence anisotropy.

Optical labels are also utilized in quality control in order to ensure that the droplet libraries are well controlled, and that equal number of each library elements are contained within uniform volumes in each droplet library. After 120 minutes of mixing, using 8-labels in a 96-member library, the average number of droplets is 13,883 for each of the library elements. As Table 1 shows below, there is very little variation between the number of droplets for each library element, i.e., between −0.8% to +1.1%. The slight variation in the number of droplets allows the pooled droplet libraries to be used in any number of assays.

TABLE 1

| Element | G1 | G2 | G3 | G4 | G5 | G6 | G7 | G8 |
| --- | --- | --- | --- | --- | --- | --- | --- | --- |
| # drops | 13913 | 13898 | 14036 | 13898 | 13834 | 13927 | 13788 | 13769 |
| % variation | +0.2% | 0% | +1.1% | 0% | −0.4% | +0.3% | −0.7% | −0.8% |

In some quality control examples, 384-member libraries were prepared with eight optical labels; typically 5 to 20 micro-liters of each library element are emulsified into approximately 10 picoliter volume droplets so there are about 1 million droplets of each library element and 384 million droplets in the library.

The eight optical labels are a dye at concentrations that increase by a factor of c (where c ranges from about 1.2 to 1.4) from one optical label to the next so that the nth optical label has $(c)(n-1)$ the dye concentration of the lowest concentration. Optical labels are used with concentrations between 10 nM and 1 uM. Typically, the range of optical label concentrations for one series of labels is 1 order of magnitude (e.g., 10 nM to 100 nM with a multiplier of 1.43 for each increasing label concentration). A larger range of droplet label concentrations can also be used. Further, multiplexed two-color labels can be used as well.

Plates are prepared with 384 separate library elements in separate wells of the 384-well plates; 8 of which have optical labels. The library elements are made into droplets, collected in a vial, (also known as a creaming tower) and the collection is mixed on the mixer for several hours. The mixer works by flipping the vial over about once every 30 seconds and then allowing the droplets to rise. Multiple plates can be emulsified and pooled or collected sequentially into the same vial.

A small fraction of the droplets are taken out of the vial to verify 1) that the droplets are present in the correct predetermined ratio and 2) that the droplets are of uniform size. Typically, 1,000 to 10,000 droplets of each library element (0.384 to 3.84 million QC-droplets) are removed from the vial through a PEEK line in the center opening in the vial cap by positive displacement with a drive oil infused through the side opening in vial cap. The PEEK line takes the droplets into a port on a microfluidic chip at a rate of several thousand droplets/second; for 10 picoliter droplets at a rate of 3000 droplets/s corresponds to a typical infusion rate of roughly 110 micro-liters/hr. Once on chip the droplets are spaced out by adding oil before they are imaged and pass one droplet at a time through a laser excitation spot. Maximum fluorescence intensity data from individual droplets is collected for all of the QC-droplets and histograms are built to show the number of droplets within a given fluorescence intensity range. As expected, if eight of the library elements have optical labels, then there are eight peaks in the histograms. The increasing concentration factor c=1.38 results in uniformly separated peaks across one decade when plotted on a log scale. The relative number of droplets in each peak is used as a quality metric to validate that the libraries were prepared with the expected relative representation. In this example, the percent variation is determined to be only 2.7% demonstrating that all library elements have uniform representation.

Image analysis can be utilized to determine and monitor osmotic pressure within the droplets. Osmotic pressure (e.g., two member library prepared with a small difference in buffer concentration) can effect droplets. Specifically, droplets with a lower salt concentration shrink over time and droplets with higher salt concentration grow over time, until uniform salt concentrations are achieved. Thus it.

Image analysis can also be utilizes for quality control of the library reformatting process. After the various library elements are generated, pooled and mixed, optical labels can be used to verify uniform representation of all library elements. Additionally, image analysis is used to verify uniform volume for all droplets.

Further, image analysis can be used for shelf life testing by quantifying the materials performance. Droplets are stored in vials under a variety of conditions to test droplets stability against droplet-droplet coalescence events. Conditions tested include temperature, vibration, presence of air in vials, surfactant type, and surfactant concentration. A Quality Score of percent coalescence is calculated by image analysis. Shelf-life for the droplet libraries of the present invention exceed 90 days.

Microfluidic Systems

Reagents can be reformatted as droplet libraries utilizing automated devices. Specifically, the library elements can be placed onto plates containing any number of wells, i.e. 96, 384, etc. The plates can then be placed in an Automated Droplet Library Production machine (or other such automated device known in the art), which forms the droplets and puts them into a vial or other such container, containing the ready to use droplet library. In general, the process aspirates each of the library elements from the well plates through tubing connected to a microfluidic device (described in greater detail herein) which can be used to form the droplets. The tubing that aspirates the library elements can be rinsed at a wash station and then the process can be repeated for the next library element.

A collection vial can be used to contain the droplets made using the Automated Droplet Library Production. In one example, the collection vial has two holes, a first hole in the center of the vial cap and a second hole part way to the edge of the vial cap. The vial is first filled with oil through the second hole to purge air out first hole, the emulsion is then introduced to the vial through the first hole, typically this is done sequentially one library element at a time at low volume fraction, and oil is displaced and goes out through the second hole. The collected droplets can be stored in the vial for periods of time in excess of 3 months. To remove the emulsion for use or to make smaller aliquots, oil is introduced through the second opening to displace the emulsion and drive out the first opening.

The droplet libraries of the present invention are preferably formed by utilizing microfluidic devices and are preferably utilized to perform various biological and chemical assays on microfluidic devices, as described in detail herein. The present invention also provides embedded microfluidic nozzles. In order to create a monodisperse (<1.5% polydispersity) emulsion directly from a library well, a nozzle can be formed directly into the fitting used to connect the storage well/reservoir (e.g. syringe) to a syringe tip (e.g. capillary tubing). Examples of suitable nozzles to create the droplet libraries of the instant invention are described in WO 2007/081385 and WO 2008/063227.

Since the flow is three dimensional, under this design surface wetting effects are minimized. The nozzle can be made from one or two oil lines providing constant flow of oil into the nozzle, a connection to the capillary tubing, and a connection to the storage well/reservoir (e.g. syringe). The high resolution part of the nozzle can be made out of a small bore tubing or a small, simple part molded or stamped from an appropriate material (TEFLON, plastic, metal, etc). If necessary, the nozzle itself could be formed into the tip of the ferrule using post mold processing such as laser ablation or drilling.

This nozzle design eliminates the surface wetting issues surrounding the quasi-2D flow associated with typical microfluidic nozzles made using soft lithography or other standard microfluidic chip manufacturing techniques. This is because the nozzle design is fully 3-dimensional, resulting is a complete isolation of the nozzle section from the continuous aqueous phase. This same design can also be used for generation of emulsions required for immediate use, where the aqueous line would be attached directly to a syringe and the outlet of the nozzle would be used to transport the emulsion to the point of use (e.g. into a microfluidic PCR chip, delay line, etc).

In another embodiment, the present invention provides compositions and methods to directly emulsify library elements from standard library storage geometries (e.g. 96 well plates, etc). In order to create a monodisperse emulsion from fluids contained in a library well plate, this invention would include microfluidic based nozzles manufactured simultaneously with an appropriately designed fluidic interconnect or well.

Specifically, the microfluidic devices and methods described herein are based on the creation and electrical manipulation of aqueous phase droplets (e.g., droplet libraries) completely encapsulated by an inert immiscible oil stream. This combination enables precise droplet generation, highly efficient, electrically addressable droplet coalescence, and controllable, electrically addressable single droplet sorting. The microfluidic devices include one or more channels and modules. A schematic illustrating one example of interacting modules of a microfluidic substrate is shown in FIG. 1. The integration of these modules is an essential enabling technology for a droplet based, high-throughput microfluidic reactor system and provides an ideal system for utilizing the droplet libraries provided herein for numerous biological, chemical, or diagnostic applications.

Substrates

The microfluidic device of the present invention includes one or more analysis units. An "analysis unit" is a microsubstrate, e.g., a microchip. The terms microsubstrate, substrate, microchip, and chip are used interchangeably herein. The analysis unit includes at least one inlet channel, at least one main channel and at least one inlet module. The analysis unit can further include at least one coalescence module, at least one detection module and one or more sorting modules. The sorting module can be in fluid communication with branch channels which are in fluid communication with one or more outlet modules (collection module or waste module). For sorting applications, at least one detection module cooperates with at least one sorting module to divert flow via a detector-originated signal. It shall be appreciated that the "modules" and "channels" are in fluid communication with each other and therefore may overlap; i.e., there may be no clear boundary where a module or channel begins or ends. A plurality of analysis units of the invention may be combined in one device. The dimensions of the substrate are those of typical microchips, ranging between about 0.5 cm to about 15 cm per side and about 1 micron to about 1 cm in thickness. The analysis unit and specific modules are described in further detail in WO 2006/040551; WO 2006/040554; WO 2004/002627; WO 2004/091763; WO 2005/021151; WO 2006/096571; WO 2007/089541; WO 2007/081385 and WO 2008/063227. A variety of materials and methods can be used to form any of the described components of the systems and devices of the invention. For example, various components of the invention can be formed from solid materials, in which the channels can be formed via molding, micromachining, film deposition processes such as spin coating and chemical vapor deposition, laser fabrication, photolithographic techniques, etching methods including wet chemical or plasma processes, and the like. See, for example, Angell, et al., Scientific American, 248:44-55, 1983. At least a portion of the fluidic system can be formed of silicone by molding a silicone chip. Technologies for precise and efficient formation of various fluidic systems and devices of the invention from silicone are known. Various components of the systems and devices of the invention can also be formed of a polymer, for example, an elastomeric polymer such as polydimethylsiloxane ("PDMS"), polytetrafluoroethylene ("PTFE") or TEFLON, or the like.

Silicone polymers are preferred, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying formation of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be formed and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in Duffy et al., "Rapid Prototyping of Microfluidic Systems and Polydimethylsiloxane," Anal. Chem., 70:474-480, 1998.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

Channels

The microfluidic substrates of the present invention include channels that form the boundary for a fluid. A "channel," as used herein, means a feature on or in a substrate that at least partially directs the flow of a fluid. In some cases, the channel may be formed, at least in part, by a single component, e.g., an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

The channels of the invention can be formed, for example by etching a silicon chip using conventional photolithography techniques, or using a micromachining technology called "soft lithography" as described by Whitesides and Xia, Angewandte Chemie International Edition 37, 550 (1998).

An open channel generally will include characteristics that facilitate control over fluid transport, e.g., structural characteristics (an elongated indentation) and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases.

A "main channel" is a channel of the device of the invention which permits the flow of molecules, cells, small molecules or particles past a coalescence module for coalescing one or more droplets, and, if present, a detection module for detection (identification) or measurement of a droplet and a sorting module for sorting a droplet based on the detection in the detection module. The main channel is typically in fluid communication with the coalescence, detection and/or sorting modules, as well as, an inlet channel of the inlet module. The main channel is also typically in fluid communication with an outlet module and optionally with branch channels, each of which may have a collection module or waste module. These channels permit the flow of molecules, cells, small molecules or particles out of the main channel. An "inlet channel" permits the flow of molecules, cells, small molecules or particles into the main channel. One or more inlet channels communicate with one or more means for introducing a sample into the device of the present invention. The inlet channel communicates with the main channel at an inlet module.

The microfluidic substrate can also comprise one or more fluid channels to inject or remove fluid in between droplets in a droplet stream for the purpose of changing the spacing between droplets.

The channels of the device of the present invention can be of any geometry as described. However, the channels of the device can comprise a specific geometry such that the contents of the channel are manipulated, e.g., sorted, mixed, prevent clogging, etc.

A microfluidic substrate can also include a specific geometry designed in such a manner as to prevent the aggregation of biological/chemical material and keep the biological/chemical material separated from each other prior to encapsulation in droplets. The geometry of channel dimension can be changed to disturb the aggregates and break them apart by various methods, that can include, but is not limited to, geometric pinching (to force cells through a (or a series of) narrow region(s), whose dimension is smaller or comparable to the dimension of a single cell) or a barricade (place a series of barricades on the way of the moving cells to disturb the movement and break up the aggregates of cells).

To prevent material (e.g., cells and other particles or molecules) from adhering to the sides of the channels, the channels (and coverslip, if used) may have a coating which minimizes adhesion. The surface of the channels of the microfluidic device can be coated with any anti-wetting or blocking agent for the dispersed phase. The channel can be coated with any protein to prevent adhesion of the biological/chemical sample. Channels can be coated by any means known in the art. For example, the channels are coated with TEFLON, BSA, PEG-silane and/or fluorosilane in an amount sufficient to prevent attachment and prevent clogging. In another example, the channels can be coated with a cyclized transparent optical polymer obtained by copolymerization of perfluoro (alkenyl vinyl ethers), such as the type sold by Asahi Glass Co. under the trademark Cytop. In such an example, the coating is applied from a 0.1-0.5 wt % solution of Cytop CTL-809M in CT-Solv 180. This solution can be injected into the channels of a microfluidic device via a plastic syringe. The device can then be heated to about 90° C. for 2 hours, followed by heating at 200° C. for an additional 2 hours. In another embodiment, the channels can be coated with a hydrophobic coating of the type sold by PPG Industries, Inc. under the trademark Aquapel (e.g., perfluoroalkylalkylsilane surface treatment of plastic and coated plastic substrate surfaces in conjunction with the use of a silica primer layer) and disclosed in U.S. Pat. No.

5,523,162. By fluorinating the surfaces of the channels, the continuous phase preferentially wets the channels and allows for the stable generation and movement of droplets through the device. The low surface tension of the channel walls thereby minimizes the accumulation of channel clogging particulates.

The surface of the channels in the microfluidic device can be also fluorinated by any means known in the art to prevent undesired wetting behaviors. For example, a microfluidic device can be placed in a polycarbonate dessicator with an open bottle of (tridecafluoro-1,1,2,2-tetrahydrooctyl)trichlorosilane. The dessicator is evacuated for 5 minutes, and then sealed for 20-40 minutes. The dessicator is then backfilled with air and removed. This approach uses a simple diffusion mechanism to enable facile infiltration of channels of the microfluidic device with the fluorosilane and can be readily scaled up for simultaneous device fluorination.

Fluids

The fluids described herein are related to the fluids within the droplet libraries and to the fluids within a microfluidic device.

The microfluidic device of the present invention is capable of controlling the direction and flow of fluids and entities within the device. The term "flow" means any movement of liquid or solid through a device or in a method of the invention, and encompasses without limitation any fluid stream, and any material moving with, within or against the stream, whether or not the material is carried by the stream. For example, the movement of molecules, beads, cells or virions through a device or in a method of the invention, e.g. through channels of a microfluidic chip of the invention, comprises a flow. This is so, according to the invention, whether or not the molecules, beads, cells or virions are carried by a stream of fluid also comprising a flow, or whether the molecules, cells or virions are caused to move by some other direct or indirect force or motivation, and whether or not the nature of any motivating force is known or understood. The application of any force may be used to provide a flow, including without limitation, pressure, capillary action, electro-osmosis, electrophoresis, dielectrophoresis, optical tweezers, and combinations thereof, without regard for any particular theory or mechanism of action, so long as molecules, cells or virions are directed for detection, measurement or sorting according to the invention. Specific flow forces are described in further detail herein.

The flow stream in the main channel is typically, but not necessarily, continuous and may be stopped and started, reversed or changed in speed. A liquid that does not contain sample molecules, cells or particles can be introduced into a sample inlet well or channel and directed through the inlet module, e.g., by capillary action, to hydrate and prepare the device for use. Likewise, buffer or oil can also be introduced into a main inlet region that communicates directly with the main channel to purge the device (e.g., or "dead" air) and prepare it for use. If desired, the pressure can be adjusted or equalized, for example, by adding buffer or oil to an outlet module.

As used herein, the term "fluid stream" or "fluidic stream" refers to the flow of a fluid, typically generally in a specific direction. The fluidic stream may be continuous and/or discontinuous. A "continuous" fluidic stream is a fluidic stream that is produced as a single entity, e. g., if a continuous fluidic stream is produced from a channel, the fluidic stream, after production, appears to be contiguous with the channel outlet. The continuous fluidic stream is also referred to as a continuous phase fluid or carrier fluid. The continuous fluidic stream may be laminar, or turbulent in some cases.

Similarly, a "discontinuous" fluidic stream is a fluidic stream that is not produced as a single entity. The discontinuous fluidic stream is also referred to as the dispersed phase fluid or sample fluid. A discontinuous fluidic stream may have the appearance of individual droplets, optionally surrounded by a second fluid. The dispersed phase fluid can include a biological/chemical material. The biological/chemical material can be tissues, cells, particles, proteins, antibodies, amino acids, nucleotides, small molecules, and pharmaceuticals. The biological/chemical material can include one or more labels known in the art. The label can be an optical label, an enzymatic label or a radioactive label. The label can be any detectable label, e.g., a protein, a DNA tag, a dye, a quantum dot or a radio frequency identification tag, or combinations thereof. Preferably the label is an optical label. The label can be detected by any means known in the art. Preferably, the label is detected by fluorescence polarization, fluorescence intensity, fluorescence lifetime, fluorescence energy transfer, pH, ionic content, temperature or combinations thereof. Various labels and means for detection are described in greater detail herein.

The term "emulsion" refers to a preparation of one liquid distributed in small globules (also referred to herein as drops, droplets or NanoReactors) in the body of a second liquid. The first and second fluids are immiscible with each other. For example, the discontinuous phase can be an aqueous solution and the continuous phase can a hydrophobic fluid such as an oil. This is termed a water in oil emulsion. Alternatively, the emulsion may be a oil in water emulsion. In that example, the first liquid, which is dispersed in globules, is referred to as the discontinuous phase, whereas the second liquid is referred to as the continuous phase or the dispersion medium. The continuous phase can be an aqueous solution and the discontinuous phase is a hydrophobic fluid, such as an oil (e.g., decane, tetradecane, or hexadecane). The droplets or globules of oil in an oil in water emulsion are also referred to herein as "micelles", whereas globules of water in a water in oil emulsion may be referred to as "reverse micelles".

The fluidic droplets may each be substantially the same shape and/or size. The droplets may be uniform in size. The shape and/or size can be determined, for example, by measuring the average diameter or other characteristic dimension of the droplets. The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, is the mathematically-defined average diameter of the droplet, integrated across the entire surface. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

As used herein, the term "NanoReactor" and its plural encompass the terms "droplet", "nanodrop", "nanodroplet", "microdrop" or "microdroplet" as defined herein, as well as an integrated system for the manipulation and probing of droplets, as described in detail herein. Nanoreactors as described herein can be 0.1-1000 μm (e.g., 0.1, 0.2 ... 5, 10, 15, 20, 25, 30, 35, 40, 45, 50 ... 1000), or any size within this range. Droplets at these dimensions tend to conform to the size and shape of the channels, while maintaining their respective volumes. Thus, as droplets move from a wider channel to a narrower channel they become longer and thinner, and vice versa.

The microfluidic substrate of this invention most preferably generate round, highly uniform, monodisperse droplets (<1.5% polydispersity). Droplets and methods of forming monodisperse droplets in microfluidic channels is described in WO 2006/040551; WO 2006/040554; WO 2004/002627; WO 2004/091763; WO 2005/021151; WO 2006/096571; WO 2007/089541; WO 2007/081385 and WO 2008/063227.

The droplet forming liquid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with the population of molecules, cells or particles to be analyzed and/or sorted can be used. The fluid passing through the main channel and in which the droplets are formed is one that is immiscible with the droplet forming fluid. The fluid passing through the main channel can be a non-polar solvent, decane (e.g., tetradecane or hexadecane), fluorocarbon oil, silicone oil or another oil (for example, mineral oil).

The droplet may also contain biological/chemical material (e.g., molecules, cells, or other particles) for combination, analysis and/or sorting in the device. The droplets of the dispersed phase fluid can contain more than one particle or can contain no more than one particle.

Droplets of a sample fluid can be formed within the inlet module on the microfluidic device or droplets (or droplet libraries) can be formed before the sample fluid is introduced to the microfluidic device ("off chip" droplet formation). To permit effective interdigitation, coalescence and detection, the droplets comprising each sample to be analyzed must be monodisperse. As described in more detail herein, in many applications, different samples to be analyzed are contained within droplets of different sizes. Droplet size must be highly controlled to ensure that droplets containing the correct contents for analysis and coalesced properly. As such, the present invention provides devices and methods for forming droplets and droplet libraries.

Surfactants

The fluids used in the invention may contain one or more additives, such as agents which reduce surface tensions (surfactants). Surfactants can include Tween, Span, fluorosurfactants, and other agents that are soluble in oil relative to water. In some applications, performance is improved by adding a second surfactant to the aqueous phase. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing. The present invention provides compositions and methods to stabilize aqueous droplets in a fluorinated oil and minimize the transport of positively charged reagents (particularly, fluorescent dyes) from the aqueous phase to the oil phase.

The droplets may be coated with a surfactant. Preferred surfactants that may be added to the continuous phase fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In addition, ionic surfactants such as sodium dodecyl sulfate (SDS) may also be used. However, such surfactants are generally less preferably for many embodiments of the invention. For instance, in those embodiments where aqueous droplets are used as nanoreactors for chemical reactions (including biochemical reactions) or are used to analyze and/or sort biomaterials, a water soluble surfactant such as SDS may denature or inactivate the contents of the droplet.

The carrier fluid can be an oil (e.g., decane, tetradecane or hexadecane) or fluorocarbon oil that contains a surfactant (e.g., a non-ionic surfactant such as a Span surfactant) as an additive (preferably between about 0.2 and 5% by volume, more preferably about 2%). A user can preferably cause the carrier fluid to flow through channels of the microfluidic device so that the surfactant in the carrier fluid coats the channel walls.

Fluorocarbon oil continuous phases are well-suited as the continuous phase for aqueous droplet libraries for a number of reasons. Fluorous oils are both hydrophobic and lipophobic. Therefore, they have low solubility for components of the aqueous phase and they limit molecular diffusion between droplets. Also, fluorous oils present an inert interface for chemistry and biology within droplets. In contrast to hydrocarbon or silicone oils, fluorous oils do not swell PDMS materials, which is a convenient material for constructing microfluidic channels. Finally, fluorocarbon oils have good solubility for gases, which is necessary for the viability of encapsulated cells.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the fluorous oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A very large body of fundamental research and commercial application development exists for non-fluorous surfactants and emulsions ranging from sub-micron droplets to very large, macroscopic emulsions. In contrast, fundamental knowledge and commercial practice with fluorinated oils and surfactants is much less common. More specifically, testing and development of fluorosurfactants and fluorous oil formulations for the application of creating large libraries of micron-scale droplets with unique composition is limited to only a few groups throughout the world. Only a few commercially-available fluorosurfactants that stabilize water-in-fluorocarbon oil emulsions exist. For instance, surfactants with short fluorotelomer-tails (typically perfluorinated $C_6$ to $C_{10}$) are available, but they do not provide sufficient long-term emulsion stability. Fluorosurfactants with longer fluorocarbon tails, such as perfluoropolyether (PFPE), are limited to molecules with ionic headgroups.

Classes of oils are available from wide variety of fluorinated oils and are available from commercial sources. The requirements for the oil are (1) immiscibility with the aqueous phase, (2) solubility of emulsion stabilizing surfactants in the oil, and (3) compatibility and/or insolubility of reagents from the droplet phase. Oils include hydrofluoroethers, which are fluorinated alkyl chains coupled with hydrocarbon chemistry through and ether bond. One supplier of this type of oil is 3M. The products are marketed as Novec Engineered Fluids or HFE-series oils. This oils include but are not limited to, HFE-7500, which is a preferred embodiment as it provides superior droplet stability seems to be higher. Other oils include HFE-7100, -7200, -7600, which are examples of other HFEs available from 3M. These can be used as stand-alone oils or components of oil mixtures to optimize emulsion properties and performance. Other hydrofluoroethers are also available from other producers, distributors, or resellers may offer hydrofluoroethers.

Another class of oil is perfluoroalkylamines, which are perfluorinated oils based on perfluoroalkyl amine structures. 3M produces these oils as Fluorinert Electronic Liquids (FC-oils). Fluorinert products differ by variations in alkyl chain length, branch structure, and combinations of different structures or pure oils. Many of them offer the potential for stand-alone oils or components of oil mixtures to optimize emulsion properties and performance. Specific examples are Fluorinert FC-3283, Fluorinert FC-40, which are a preferred embodiments. Higher viscosity and boiling point useful for applications requiring elevated temperature (e.g., thermocyling for PCR). Other Fluorinert series can be used for stand-alone oils or components of oil mixtures to optimize emulsion properties and performance. Again, other perfluoroalkylamines are available from other producers, distributors, or resellers may offer perfluoroalkylamines.

Fluorinated organics/solvents offer a number of perfluorinated or partially fluorinated solvents are available from a variety of producers, distributors, and/or resellers. Many of them offer the potential for stand-alone oils or components of oil mixtures to optimize emulsion properties and performance. Examples of fluorinated organic reagents utilized, included (but not limited to) trifluoroacetic acid and hexafluoroisopropanol, to improve droplet stability in other fluorinated oil systems. Additionally, fluoropolymers may also be used within a microfluidic system. Examples of fluoropolymers include, Krytox GPL oils, Solvay Galden oils, and other liquid fluoropolymers. Other fluorinated materials find widespread use in a variety of industries, but they are generally not well-known in the disciplines of interfacial, colloidal, physical, or synthetic organic chemistry. Therefore, a number of other candidates for oils exist in specialty and niche market applications. As such, new oils have been targeted partially that are per-fluorinated materials, which are not widely recognized.

The properties of oils selected are based upon their chemical properties, such as, among others molecular structure, fluorine content and solvating strength. Physical properties of oils examined include viscosity, boiling point, thermal expansion coefficient, oil-in-water solubility, water-in-oil solubility, dielectric constant, polarity, and oil-in-water surface tension.

Classes of surfactants include fluorosurfactants that can be categorized by the type of fluorophilic portion of the molecule, the type of hydrophilic, or polar, portion, and the chemistry used to link the different parts of the molecule. Materials developed are capable of stabilizing an emulsion or droplet library. The preferred embodiment is the EA surfactant. Specifically, the EA surfactant is a Krytox-PEG-Krytox. The EA surfactant is a nonionic tri-block copolymer surfactant was developed to avoid issues that the ionic surfactants (e.g., RR, see below) which result from the use of some other ionic surfactant. Specifically, ionic surfactants interact with charged species in the droplets and can sequester ions (e.g., magnesium required for the PCR reaction) or other reagents to the oil phase. The structure of the EA surfactant comprises a PEG—approximately 600 Da with amine end functionality, PFPE—Mn is ~5000-8000 from a Krytox FSH starting material and the linker is an amide coupling. Another surfactant includes the RR surfactant, which is a Krytox ammonium carboxylate.

Alternative materials are alternative fluorophilic portion, i.e., PFPE (Solvay or Demnum), Poly(fluoroalkylacrylate) and other non-polymeric and partially fluorinated materials. Alternative head-group chemistry for the hydrophilic portion includes, non-ionic head groups like PEG (Mw, Mw/Mn (PDI)) and functionality (i.e., diblock, triblock and dendritic). Others include morpholino. Ionic head groups for the hydrophilic portion include anionic, such as elemental and amine salts and further cationic head portions. Other head group chemistries include zwitterionic, hybrid (e.g., PEG-ionic and zonyl FSO/FSN), lipophilic (e.g, lipophilic to promote bilayer and lipophilic spacer to hydrophile). Another alternative is alternative coupling chemistry such as, phosphoryl/Friedel-Crafts, spacer to organic handle and others.

Characteristics of surfactants are their molecular structure, determined by NMR, chromatography (e.g., HPLC, GPC/SEC), FTIR, mass spectrometry, and titrations. Purity of surfactants is another characteristic examined in addition to the fluorophile-hydrophile balance.

A preferred embodiment includes oil-surfactant formulation for the application of library emulsions is R-oil (HFE-7500) mixed with 2 wt % EA surfactant ("REA20"). Concentrations of EA or RR surfactant at 0.1 wt % or lower to 5% or greater. Other formulations of oils and surfactants and other components added to the aqueous phase are used to improved and optimized the performance of the droplets performance. Those properties of the oil-surfactant mixture include simple mixtures (i.e., one oil and one surfactant, with varied surface concentration), co-surfactants, oil mixtures and additives, such as zonyl and TFA.

Oil and surfactant mixture properties include surfactant solubility, critical micelle concentration (CMC), surfactant diffusivity, and interfacial tension, i.e., dynamic and equilibrium. Emulsion properties are also accounted for, those properties include size (absolute and size distribution), stability, transport, and biocompatibility. Stability relates directly to the coalesced droplets and their deformability/breaking and shredding ability. More particularly, the stability of the droplets in their generation, storage and shipping.

In general, production of surfactant and oils begins with the synthesis of surfactants and starting materials, such as PEG-diamine, EA and RR and also accounts for the purification processes, characterization, quality control, mixing and packaging.

In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the continuous phase of the emulsion.

In another embodiment, a quaternary ammonium salt at the terminus of a hydrophilic oligomer is linked to a perfluoropolyether tail as shown in the following formula:

PFPE-C(O)NH—$CH_2CH_2CH_2$—(O$CH_2CH_2$)$_3$O—$CH_2CH_2CH_2$—N(CH$_3$)$_3$+I-Some specific molecular features of the present invention include, but are not limited to, PFPE is from Krytox 157 FSH (Mn-6500), amide bond linking PFPE to hydrophile, propyl group immediately adjacent to the amide, propyl group immediately adjacent to the trimethylamino terminus. Specific structural formations can alter performance relationships, for example, PFPE chain is sufficiently long for molecule to be soluble in perfluorinated oils, amide linker provides hydrolytic stability and hydrogen bonding site, and a combination of PEG and quaternary ammonium cation provide high anchoring strength to the aqueous phase as well as electrostatic repulsion and steric hindrance to minimize reagent transport.

Variables in the molecular structure include, but are not limited to, PFPE molecular weight and polydispersity, PFPE structure, alternative perfluorinated tail chemistries, PEG molecular weight and polydispersity, shorter hydrocarbon linkers (ethyl or methyl versus propyl), longer hydrocarbon spacers (C4 or higher), alternative counterions, such as monovalent anions, monovalent, polyatomic anions and di- or tri-valent counterions (to produce two or more tail fluorosurfactants). Further variables in the molecule structure include alternative linker chemistries (e.g., ether, ester, etc), alternative hydrophilic oligomers (e.g., polyalcohol, polyacrylamide, etc.), alternative quaternary ammonium cations, and alternative ionic groups (e.g., anionic terminus—carboxylate etc.; alternative cations).

The present invention is also directed to the coupling of PEG-diamines with carboxylic acid-terminated perfluoropolyether (Krytox 157) to form surfactants. Specifically, the present invention is directed to a fluorosurfactant molecule made by the ionic coupling of amine-terminated polyethyleneglycol (PEG-amine) with the carboxylic acid of DuPont Krytox perfluoropolyether (PFPE). The resulting structure conveys good performance in the stabilization of aqueous droplets in fluorinated oil in a microfluidic system. Examples of specific surfactants are shown in Examples 1 and 2. Preferred surfactants are also described in WO 2008/021123.

The present invention provides droplets with a fluorosurfactant interface separating the aqueous droplet and its contents from the surrounding immiscible fluorocarbon oil. In one example, DNA amplification reactions occurring inside these droplets generate material that does not interact with the channel walls, and collection of the DNA-containing droplets for subsequent manipulation and sequencing is straightforward. This technology provides a solution for amplification of DNA from single cells, allowing for both genotyping and whole genome amplification. In addition, use within a microfluidic device or platform as described herein achieves very high throughput, with droplets processed at rates in excess of 5000 droplets per second, enabling greater than $1 \times 10^6$ single-cell droplets to be formed and manipulated per hour.

Other examples of materials related to this invention include the formation of salts made by combination of various primary, secondary, or tertiary amines with PFPE carboxylic acid. The resulting amphiphilic structure could be useful as a stand-alone surfactant or a cosurfactant. Similarly, fluorinated materials with carboxylic acids other than Krytox PFPE could be used to form ionic fluorosurfactants with various amine containing compounds.

Alternative amine-containing compounds for use with the present invention include, but are not limited to, PEG-monoamine (molecular weights range from 200 to 1,000,000 or more), PEG-diamine (molecular weights range from 200 to 1,000,000 or more), Multifunctional PEG amines (e.g., branched or dendritic structures), other hydrophilic polymers terminated with amines. Sugars include, but are not limited to, Sugars, Peptides, Biomolecules, Ethanolamine or Alkyl amines—primary, secondary, or tertiary (e.g., triethylamine, trimethylamine, methylamine, ethylamine, butylamine)

Alternative fluorinated groups for use with the present invention include, but are not limited to, Krytox FSL and FSM (alternative molecular weights), Demnum PFPE materials, Fluolink PFPE materials or Fluorinated small molecules with carboxylic acids.

The data described herein show that the fluorosurfactants comprised of PEG amine salts provide better performance (compared to other fluorosurfactants) for stabilization of aqueous droplets in fluorinated oils in droplet-based microfluidics applications. These novel surfactants are useful either in combination with other surfactants or as a stand-alone surfactant system.

Driving Forces

The invention can use pressure drive flow control, e.g., utilizing valves and pumps, to manipulate the flow of cells, particles, molecules, enzymes or reagents in one or more directions and/or into one or more channels of a microfluidic device. However, other methods may also be used, alone or in combination with pumps and valves, such as electro-osmotic flow control, electrophoresis and dielectrophoresis as described in Fulwyer, Science 156, 910 (1974); Li and Harrison, Analytical Chemistry 69, 1564 (1997); Fiedler, et al. Analytical Chemistry 70, 1909-1915 (1998) and U.S. Pat. No. 5,656,155. Application of these techniques according to the invention provides more rapid and accurate devices and methods for analysis or sorting, for example, because the sorting occurs at or in a sorting module that can be placed at or immediately after a detection module. This provides a shorter distance for molecules or cells to travel, they can move more rapidly and with less turbulence, and can more readily be moved, examined, and sorted in single file, i.e., one at a time.

Positive displacement pressure driven flow is a preferred way of controlling fluid flow and dielectrophoresis is a preferred way of manipulating droplets within that flow. The pressure at the inlet module can also be regulated by adjusting the pressure on the main and sample inlet channels, for example, with pressurized syringes feeding into those inlet channels. By controlling the pressure difference between the oil and water sources at the inlet module, the size and periodicity of the droplets generated may be regulated. Alternatively, a valve may be placed at or coincident to either the inlet module or the sample inlet channel connected thereto to control the flow of solution into the inlet module, thereby controlling the size and periodicity of the droplets. Periodicity and droplet volume may also depend on channel diameter, the viscosity of the fluids, and shear pressure. Examples of driving pressures and methods of modulating flow are as described in WO 2006/040551; WO 2006/040554; WO 2004/002627; WO 2004/091763; WO 2005/021151; WO 2006/096571; WO 2007/089541; WO 2007/081385 and WO 2008/063227; U.S. Pat. No. 6,540,895 and U.S. Patent Application Publication Nos. 20010029983 and 20050226742

Inlet Module

The microfluidic device of the present invention includes one or more inlet modules. An "inlet module" is an area of a microfluidic substrate device that receives molecules, cells, small molecules or particles for additional coalescence, detection and/or sorting. The inlet module can contain one or more inlet channels, wells or reservoirs, openings, and other features which facilitate the entry of molecules, cells, small molecules or particles into the substrate. A substrate may contain more than one inlet module if desired. Different sample inlet channels can communicate with the main channel at different inlet modules. Alternately, different sample inlet channels can communication with the main channel at the same inlet module. The inlet module is in fluid communication with the main channel. The inlet module generally comprises a junction between the sample inlet channel and the main channel such that a solution of a sample (i.e., a fluid containing a sample such as molecules, cells, small molecules (organic or inorganic) or particles) is introduced to the main channel and forms a plurality of droplets. The sample solution can be pressurized. The sample inlet channel can intersect the main channel such that the sample solution is introduced into the main channel at an angle perpendicular to a stream of fluid passing through the main channel. For example, the sample inlet channel and main channel intercept at a T-shaped junction; i.e., such that the sample inlet channel is perpendicular (90 degrees) to the main channel. However, the sample inlet channel can intercept the main channel at any angle, and need not introduce the sample fluid to the main channel at an angle that is perpendicular to that flow. The angle between intersecting channels is in the range of from about 60 to about 120 degrees. Particular exemplary angles are 45, 60, 90, and 120 degrees. Embodiments of the invention are also provided in which there are two or more inlet modules introducing droplets of samples into the main channel. For example, a first inlet module may introduce droplets of a first sample into a flow of fluid in the main channel and a second inlet module may introduce droplets of a second sample into the flow of fluid in main channel, and so forth. The second inlet module is preferably downstream from the first inlet module (e.g., about 30 µm). The fluids introduced into the two or more different inlet modules can comprise the same fluid or the same type of fluid (e.g., different aqueous solutions). For example, droplets of an aqueous solution containing an enzyme are introduced into the main channel at the first inlet module and droplets of aqueous solution containing a substrate for the enzyme are introduced into the main channel at the second inlet module. Alternatively, the droplets introduced at the different inlet modules may be droplets of different fluids which may be compatible or incompatible. For example, the different droplets may be different aqueous solutions, or droplets introduced at a first inlet module may be droplets of one fluid (e.g., an aqueous solution) whereas droplets introduced at a second inlet module may be another fluid (e.g., alcohol or oil).

Filters

An important element in making libraries utilizing the microfluidic device of the present invention is to include features in the channels of the device to remove particles that may effect the microfluidic system. When emulsions are injected or re-injected onto a microfluidic device, they carry contaminants that collect at the nozzle and either clog the nozzle and/or induce uncontrolled coalescence up to the complete shredding of the emulsion. Debris/contaminants include small debris, such as dust or TCS, fibers, goop (glue and/or surfactant) and large debris such as PDMS skins/shavings. In one example, the present invention provides a post trap for large debris, a pocket trap for small debris, a serpentine trap for fibers and a step trap for large droplets/debris. EAP filters work well to filter out the contaminants.

The filter system filters out these contaminants and most importantly traps the contaminants out of the main pathway and allow the droplets to pass by so the contaminants cannot induce uncontrolled coalescence. The present invention comprises two distinct parts that specifically address two different scales. The first filters contaminants that are larger than the droplet size. The second filters contaminants that are smaller than the droplet and nozzle sizes. The large contaminants are easily trapped but are responsible for inducing uncontrolled coalescence, the small contaminants tend to stick to the nozzle and most probably induce wetting that results in the shredding of the emulsion.

To address the issue of large contaminants, a triangular shape filter is used that contains an internal-collection channel and smaller lateral channels connected to the internal-collection channel with a specific angle. On each side of the triangle are pockets to collect the contaminants that have been deflected by the triangle and directed there by the flow of the droplets due to the specific angle of the filter. In addition, the collection pockets are connected to a channel of high hydrodynamic resistance so that some of the flow will still go through and maintain the contaminants in the collection pockets. The lateral collection channels are located at a stepwise transition between a shallow layer and a deep layer. In one example, the droplets are collected in the Droplet Collection Channel through the lateral angled channels. The contaminants are deflected toward the Contaminant Collection Pocket because of the triangular shape and the droplet flow. Because of the use of high resistance channel for the Contaminants Collection Pockets, the droplets go through them only marginally, but enough to force the trapped contaminants to stay there.

To address the issue of the small contaminants, a series of posts are used, each one being offset by a half-period to the adjacent ones. This geometry intends to create a region of null-recirculation flow at the tip of each post due to the symmetry and contaminants are trapped in that region. In addition, the posts have an indentation to both increase the effect of the flow pattern described above and to trap the contaminants so that they are out of the way of the droplets. The posts can be designed just with an indentation or with a flow-through restriction of high hydrodynamic resistance so that the contaminants will be directed and trapped deep in the structure. The symmetrical design creates a region where there is almost no flow, in this region creates the conditions to trap the contaminants that are smaller than the droplets. The droplets follow the main flow because of the high hydrodynamic resistance conditions. The posts on one side of the channel have a flow-through to ensure that the contaminants stay trapped there; on the other side the posts have only an indentation. Several series of these posts, offset by half of a period are used to increase both the filter capacity and the odds of trapping any given contaminant.

Droplet Interdigitation

Particular design embodiments of the microfluidic device described herein allow for a more reproducible and controllable interdigitation of droplets of specific liquids followed by pair-wise coalescence of these droplets, described in further detail herein. The droplet pairs can contain liquids of different compositions and/or volumes, which would then combine to allow for a specific reaction to be investigated. The pair of droplets can come from any of the following: (i) two continuous aqueous streams and an oil stream; (ii) a continuous aqueous stream, an emulsion stream, and an oil stream, or (iii) two emulsion streams and an oil stream. The term "interdigitation" as used herein means pairing of droplets from separate aqueous streams, or from two separate inlet nozzles, for eventual coalescence.

Various nozzle designs enhance the interdigitation of droplets and further improves coalescence of droplets due to the better control of the interdigitation and smaller distance between pairs of droplets. The greater control over interdigitation allows for a perfect control over the frequency of either of the droplets. To obtain the optimum operation, the spacing between droplets and coupling of the droplets can be adjusted by adjusting flow of any of the streams, viscosity of the streams, nozzle design (including orifice diameter, the channel angle, and post-orifice neck of the nozzle). Examples of preferred nozzle designs are as described in WO 2007/081385 and WO 2008/063227.

Reservoir/Well

A device of the invention can include a sample solution reservoir or well or other apparatus for introducing a sample to the device, at the inlet module, which is typically in fluid communication with an inlet channel. Reservoirs and wells used for loading one or more samples onto the microfluidic device of the present invention, include but are not limited to, syringes, cartridges, vials, eppendorf tubes and cell culture materials (e.g., 96 well plates). A reservoir may facilitate introduction of molecules or cells into the device and into the sample inlet channel of each analysis unit.

Coalescence Module

The microfluidic device of the present invention also includes one or more coalescence modules. A "coalescence module" is within or coincident with at least a portion of the main channel at or downstream of the inlet module where molecules, cells, small molecules or particles comprised within droplets are brought within proximity of other droplets comprising molecules, cells, small molecules or particles and where the droplets in proximity fuse, coalesce or combine their contents. The coalescence module can also include an apparatus, for generating an electric force.

The electric force exerted on the fluidic droplet may be large enough to cause the droplet to move within the liquid. In some cases, the electric force exerted on the fluidic droplet may be used to direct a desired motion of the droplet within the liquid, for example, to or within a channel or a microfluidic channel (e.g., as further described herein), etc.

The electric field can be generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments. As used herein, "integral" means that portions of the components integral to each other are joined in such a way that the components cannot be in manually separated from each other without cutting or breaking at least one of the components.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof.

Preferred electrodes and patterned electrically conductive layers are described in WO 2007/081385 and WO 2008/063227 and can be associated with any module of the device (inlet module, coalescence module, mixing module, delay module, detection module and sorting module) to generate dielectric or electric forces to manipulate and control the droplets and their contents.

Effective control of uncharged droplets within microfluidic devices can require the generation of extremely strong dielectric field gradients. The fringe fields from the edges of a parallel plate capacitor can provide an excellent topology to form these gradients. The microfluidic device according to the present invention can include placing a fluidic channel between two parallel electrodes, which can result in a steep electric field gradient at the entrance to the electrodes due to edge effects at the ends of the electrode pair. Placing these pairs of electrodes at a symmetric channel split can allow precise bi-directional control of droplet within a device. Using the same principle, only with asymmetric splits, can allow single ended control of the droplet direction in the same manner. Alternatively, a variation on this geometry will allow precise control of the droplet phase by shifting.

Dielectrophoresis is believed to produce movement of dielectric objects, which have no net charge, but have regions that are positively or negatively charged in relation to each other. Alternating, non-homogeneous electric fields in the presence of droplets and/or particles, such as cells or molecules, cause the droplets and/or particles to become electrically polarized and thus to experience dielectrophoretic forces. Depending on the dielectric polarizability of the particles and the suspending medium, dielectric particles will move either toward the regions of high field strength or low field strength. For example, the polarizability of living cells depends on their composition, morphology, and phenotype and is highly dependent on the frequency of the applied electrical field. Thus, cells of different types and in different physiological states generally possess distinctly different dielectric properties, which may provide a basis for cell separation, e.g., by differential dielectrophoretic forces. Likewise, the polarizability of droplets also depends upon their size, shape and composition. For example, droplets that contain salts can be polarized. According to formulas provided in Fiedler, et al. Analytical Chemistry 70, 1909-1915 (1998), individual manipulation of single droplets requires field differences (inhomogeneities) with dimensions close to the droplets.

The term "dielectrophoretic force gradient" means a dielectrophoretic force is exerted on an object in an electric field provided that the object has a different dielectric constant than the surrounding media. This force can either pull the object into the region of larger field or push it out of the region of larger field. The force is attractive or repulsive depending respectively on whether the object or the surrounding media has the larger dielectric constant.

Manipulation is also dependent on permittivity (a dielectric property) of the droplets and/or particles with the suspending medium. Thus, polymer particles, living cells show negative dielectrophoresis at high-field frequencies in water. For example, dielectrophoretic forces experienced by a latex sphere in a 0.5 MV/m field (10 V for a 20 micron electrode gap) in water are predicted to be about 0.2 piconewtons (pN) for a 3.4 micron latex sphere to 15 pN for a 15 micron latex sphere (Fiedler, et al. Analytical Chemistry, 70, 1909-1915 (1998)). These values are mostly greater than the hydrodynamic forces experienced by the sphere in a stream (about 0.3 pN for a 3.4 micron sphere and 1.5 pN for a 15 micron sphere). Therefore, manipulation of individual cells or particles can be accomplished in a streaming fluid, such as in a cell sorter device, using dielectrophoresis. Using conventional semiconductor technologies, electrodes can be microfabricated onto a substrate to control the force fields in a microfabricated sorting device of the invention. Dielectrophoresis is particularly suitable for moving objects that are electrical conductors. The use of AC current is preferred, to prevent permanent alignment of ions. Megahertz frequencies are suitable to provide a net alignment, attractive force, and motion over relatively long distances. See U.S. Pat. No. 5,454,472.

The electric field generator can be constructed and arranged (e.g., positioned) to create an electric field applicable to the fluid of at least about 0.01 V/micrometer, and, in some cases, at least about 0.03 V/micrometer, at least about 0.05 V/micrometer, at least about 0.08 V/micrometer, at least about 0.1 V/micrometer, at least about 0.3 V/micrometer, at least about 0.5 V/micrometer, at least about 0.7 V/micrometer, at least about 1 V/micrometer, at least about 1.2 V/micrometer, at least about 1.4 V/micrometer, at least about 1.6 V/micrometer, or at least about 2 V/micrometer. In some embodiments, even higher electric field intensities may be used, for example, at least about 2 V/micrometer, at least about 3 V/micrometer, at least about 5 V/micrometer, at least about 7 V/micrometer, or at least about 10 V/micrometer or more.

As described, an electric field may be applied to fluidic droplets to cause the droplets to experience an electric force. The electric force exerted on the fluidic droplets may be, in some cases, at least about $10^{-16}$ N/micrometer$^3$. In certain cases, the electric force exerted on the fluidic droplets may be greater, e.g., at least about $10^{-15}$ N/micrometer$^3$, at least about $10^{-14}$ N/micrometer$^3$, at least about $10^{-13}$ N/micrometer$^3$, at least about $10^{-12}$ N/micrometer$^3$, at least about $10^{-11}$ N/micrometer$^3$, at least about $10^{-10}$ N/micrometer$^3$, at least about $10^{-9}$ N/micrometer$^3$, at least about $10^{-8}$ N/micrometer$^3$, or at least about $10^{-7}$ N/micrometer or more. The electric force exerted on the fluidic droplets, relative to the surface area of the fluid, may be at least about $10^{-15}$ N/micrometer$^2$, and in some cases, at least about $10^{-14}$ N/micrometer$^2$, at least about $10^{-13}$ N/micrometer$^2$, at least about $10^{-12}$ N/micrometer$^2$, at least about $10^{-11}$ N/micrometer$^2$, at least about $10^{-10}$ N/micrometer$^2$, at least about $10^{-9}$ N/micrometer$^2$, at least about $10^{-8}$ N/micrometer$^2$, at least about $10^{-7}$ N/micrometer$^2$, or at least about $10^{-6}$ N/micrometer$^2$ or more. In yet other embodiments, the electric force exerted on the fluidic droplets may be at least about $10^{-9}$ N, at least about $10^{-8}$ N, at least about $10^{-7}$ N, at least about $10^{-6}$ N, at least about $10^{-5}$ N, or at least about $10^{-4}$ N or more in some cases.

Channel Expansion Geometries

In preferred embodiments described herein, droplet coalescence is presently carried out by having two droplet forming nozzles emitting droplets into the same main channel. The size of the nozzles allow for one nozzle to form a large drop that fills the exhaust line while the other nozzle forms a drop that is smaller than the first. The smaller droplet is formed at a rate that is less than the larger droplet rate, which insures that at most one small droplet is between big droplets. Normally, the small droplet will catch up to the larger one over a relatively short distance, but sometimes the recirculation zone behind the large drop causes the small drop to separate from the large drop cyclically. In addition, the small drop occasionally does not catch up with the large one over the distance between the nozzles and the coalescing electrodes. Thus, in some situations is a need for a more robust coalescence scheme.

Geometric alterations in the coalescence module can create a more robust, reliable coalescence or fusing of droplets over a wider range of sizes and flows. The solution to improve the performance is to place an expansion in the main channel between the electrodes. Optionally, a small constriction (neckdown) just before this expansion can be used to better align the droplets on their way into the coalescence point. This optional neckdown can help center the small droplet in the channel stream lines, reducing the chance that it will flow around the larger droplet prior to coalescing in the expansion. The electrode pair may be placed on either one side of the channel or on both sides.

The expansion in the coalescing region allows for a dramatic catching up of the small drop to the large drop, as shown through micrographs taken on an operating device. The volume of the expansion is big enough to slow the large droplet down so that the small drop always catches up to the large drop, but doesn't allow the next large drop to catch up and make contact with the pair to be coalesced. The electrodes allow for coalescence to take place when the drops are in contact with each other and passing through the field gradient.

Detection Module

The microfluidic device of the present invention can also include one or more detection modules. A "detection module" is a location within the device, typically within the main channel where molecules, cells, small molecules or particles are to be detected, identified, measured or interrogated on the basis of at least one predetermined characteristic. The molecules, cells, small molecules or particles can be examined one at a time, and the characteristic is detected or measured optically, for example, by testing for the presence or amount of a reporter. For example, the detection module is in communication with one or more detection apparatuses. The detection apparatuses can be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at the sorting module. However, other detection techniques can also be employed The terms "detecting" or "determining," as used herein, generally refers to the analysis or measurement of a species, for example, quantitatively or qualitatively, and/or the detection of the presence or absence of the species. "Detecting or "determining" may also refer to the analysis or measurement of an interaction between two or more species, for example, quantitatively or qualitatively, or by detecting the presence or absence of the interaction. Examples of suitable techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasielectric light scattering; polarimetry; refractometry; or turbidity measurements as described further herein.

A detection module is within, communicating or coincident with a portion of the main channel at or downstream of the inlet module and, in sorting embodiments, at, proximate to, or upstream of, the sorting module or branch point. The sorting module may be located immediately downstream of the detection module or it may be separated by a suitable distance consistent with the size of the molecules, the channel dimensions and the detection system. Precise boundaries for the detection module are not required, but are preferred.

Sensors

One or more detections sensors and/or processors may be positioned to be in sensing communication with the fluidic droplet. "Sensing communication," as used herein, means that the sensor may be positioned anywhere such that the fluidic droplet within the fluidic system (e.g., within a channel), and/or a portion of the fluidic system containing the fluidic droplet may be sensed and/or determined in some fashion. For example, the sensor may be in sensing communication with the fluidic droplet and/or the portion of the fluidic system containing the fluidic droplet fluidly, optically or visually, thermally, pneumatically, electronically, or the like. The sensor can be positioned proximate the fluidic system, for example, embedded within or integrally connected to a wall of a channel, or positioned separately from the fluidic system but with physical, electrical, and/or optical communication with the fluidic system so as to be able to sense and/or determine the fluidic droplet and/or a portion of the fluidic system containing the fluidic droplet (e.g., a channel or a microchannel, a liquid containing the fluidic droplet, etc.). For example, a sensor may be free of any physical connection with a channel containing a droplet, but may be positioned so as to detect electromagnetic radiation arising from the droplet or the fluidic system, such as infrared, ultraviolet, or visible light. The electromagnetic radiation may be produced by the droplet, and/or may arise from other portions of the fluidic system (or externally of the fluidic system) and interact with the fluidic droplet and/or the portion of the fluidic system containing the fluidic droplet in such as a manner as to indicate one or more characteristics of the fluidic droplet, for example, through absorption, reflection, diffraction, refraction, fluorescence, phosphorescence, changes in polarity, phase changes, changes with respect to time, etc. As an example, a laser may be directed towards the fluidic droplet and/or the liquid surrounding the fluidic droplet, and the fluorescence of the fluidic droplet and/or the surrounding liquid may be determined. "Sensing communication," as used herein may also be direct or indirect. As an example, light from the fluidic droplet may be directed to a sensor, or directed first through a fiber optic system, a waveguide, etc., before being directed to a sensor.

Non-limiting examples of detection sensors useful in the invention include optical or electromagnetically-based systems. For example, the sensor may be a fluorescence sensor (e.g., stimulated by a laser), a microscopy system (which may include a camera or other recording device), or the like. As another example, the sensor may be an electronic sensor, e.g., a sensor able to determine an electric field or other electrical characteristic. For example, the sensor may detect capacitance, inductance, etc., of a fluidic droplet and/or the portion of the fluidic system containing the fluidic droplet. In some cases, the sensor may be connected to a processor, which in turn, cause an operation to be performed on the fluidic droplet, for example, by sorting the droplet.

Characteristics

Characteristics determinable with respect to the droplet and usable in the invention can be identified by those of ordinary skill in the art. Non-limiting examples of such characteristics include fluorescence, spectroscopy (e.g., optical, infrared, ultraviolet, etc.), radioactivity, mass, volume, density, temperature, viscosity, pH, concentration of a substance, such as a biological substance (e.g., a protein, a nucleic acid, etc.), or the like.

A corresponding signal is then produced, for example indicating that "yes" the characteristic is present, or "no" it is not. The signal may correspond to a characteristic qualitatively or quantitatively. That is, the amount of the signal can be measured and can correspond to the degree to which a characteristic is present. For example, the strength of the signal may indicate the size of a molecule, or the potency or amount of an enzyme expressed by a cell, or a positive or negative reaction such as binding or hybridization of one molecule to another, or a chemical reaction of a substrate catalyzed by an enzyme. In response to the signal, data can be collected and/or a control system in the sorting module, if present, can be activated to divert a droplet into one branch channel or another for delivery to the collection module or waste module. Thus, in sorting embodiments, molecules or cells within a droplet at a sorting module can be sorted into an appropriate branch channel according to a signal produced by the corresponding examination at a detection module. The means of changing the flow path can be accomplished through mechanical, electrical, optical, or some other technique as described herein.

A preferred detector is an optical detector, such as a microscope, which may be coupled with a computer and/or other image processing or enhancement devices to process images or information produced by the microscope using known techniques. For example, molecules can be analyzed and/or sorted by size or molecular weight. Enzymes can be analyzed and/or sorted by the extent to which they catalyze chemical reaction of a substrate (conversely, substrate can be analyzed and/or sorted by the level of chemical reactivity catalyzed by an enzyme). Cells can be sorted according to whether they contain or produce a particular protein, by using an optical detector to examine each cell for an optical indication of the presence or amount of that protein. The protein may itself be detectable, for example by a characteristic fluorescence, or it may be labeled or associated with a reporter that produces a detectable signal when the desired protein is present, or is present in at least a threshold amount. There is no limit to the kind or number of characteristics that can be identified or measured using the techniques of the invention, which include without limitation surface characteristics of the cell and intracellular characteristics, provided only that the characteristic or characteristics of interest for sorting can be sufficiently identified and detected or measured to distinguish cells having the desired characteristic(s) from those which do not. For example, any label or reporter as described herein can be used as the basis for analyzing and/or sorting molecules or cells, i.e. detecting molecules or cells to be collected.

Fluorescence Polarization/Fluorescence Lifetime

As described herein, the biological/chemical entity to be analyzed may itself be detectable, for example by a characteristic fluorescence, or it may be labeled or associated with a reporter that produces a detectable signal when the desired protein is present, or is present in at least a threshold amount.

Luminescent colloidal semiconductor nanocrystals called quantum dots or q-dots (QD) are inorganic fluorophores that have the potential to circumvent some of the functional limitations encountered by organic dyes. In particular, CdSe—ZnS core-shell QDs exhibit size-dependent tunable photoluminescence (PL) with narrow emission bandwidths (FWHM ~30 to 45 nm) that span the visible spectrum and broad absorption bands. These allow simultaneous excitation of several particle sizes (colors) at a common wavelength. This, in turn, allows simultaneous resolution of several colors using standard instrumentation. CdSe—ZnS QDs also have high quantum yields, are resistant to photodegradation, and can be detected optically at concentrations comparable to organic dyes.

Quantum dots are nano-scale semiconductors typically consisting of materials such as crystalline cadmium selenide. The term 'q-dot' emphasizes the quantum confinement effect of these materials, and typically refers to fluorescent nanocrystals in the quantum confined size range. Quantum confinement refers to the light emission from bulk (macroscopic) semiconductors such as LEDs which results from exciting the semiconductor either electrically or by shining light on it, creating electron-hole pairs which, when they recombine, emit light. The energy, and therefore the wavelength, of the emitted light is governed by the composition of the semiconductor material. If, however, the physical size of the semiconductor is considerably reduced to be much smaller than the natural radius of the electron-hole pair (Bohr radius), additional energy is required to "confine" this excitation within the nanoscopic semiconductor structure leading to a shift in the emission to shorter wavelengths. Three different q-dots in several concentrations each can be placed in a microdroplet, and can then be used with a microfluidic device to decode what is in the drop. The Q-dot readout extension to the fluorescence station can be incorporated into the design of the microfluidic device. A series of dichroic beamsplitters, emission filters, and detectors can be stacked onto the system, allowing measurement of the required five emission channels (two fluorescence polarization signals and three q-dot bands).

Fluorescence Polarization (FP) detection technology enables homogeneous assays suitable for high throughput screening assays in the Drug Discovery field. The most common label in the assays is fluorescein. In FP-assay the fluorophore is excited with polarized light. Only fluorophores parallel to the light absorb and are excited. The excited state has a lifetime before the light emission occurs. During this time the labeled fluorophore molecule rotates and the polarization of the light emitted differs from the excitation plane. To evaluate the polarization two measurements are needed: the first using a polarized emission filter parallel to the excitation filter (S-plane) and the second with a polarized emission filter perpendicular to the excitation filter (P-plane). The Fluorescence Polarization response is given as mP (milli-Polarization level) and is obtained from the equation:

$$\text{Polarization (mP)} = 1000 * (S - G*P)/(S + G*P)$$

Where S and P are background subtracted fluorescence count rates and G (grating) is an instrument and assay dependent factor.

The rotational speed of a molecule is dependent on the size of the molecule, temperature and viscosity of the solution. Fluorescein has a fluorescence lifetime suitable for the rotation speeds of molecules in bio-affinity assays like receptor-ligand binding assays or immunoassays of haptens. The basic principle is that the labeled compound is small and rotates rapidly (low polarization). When the labeled compound binds to the larger molecule, its rotation slows down considerably (polarization changes from low to high polarization). Thus, FP provides a direct readout of the extent of tracer binding to protein, nucleic acids, and other biopolymers.

Fluorescence polarization technology has been used in basic research and commercial diagnostic assays for many decades, but has begun to be widely used in drug discovery only in the past six years. Originally, FP assays for drug discovery were developed for single-tube analytical instruments, but the technology was rapidly converted to high-throughput screening assays when commercial plate readers with equivalent sensitivity became available. These assays include such well-known pharmaceutical targets such as kinases, phosphatases, proteases, G-protein coupled receptors, and nuclear receptors. Other homogeneous technologies based on fluorescence intensity have been developed. These include energy transfer, quenching, and enhancement assays. FP offers several advantages over these. The assays are usually easier to construct, since the tracers do not have to respond to binding by intensity changes. In addition, only one tracer is required and crude receptor preparations may be utilized. Furthermore, since FP is independent of intensity, it is relatively immune to colored solutions and cloudy suspensions. FP offers several advantages in the area of instrumentation. Because FP is a fundamental property of the molecule, and the reagents are stable, little or no standardization is required. FP is relatively insensitive to drift in detector gain settings and laser power.

The dyes chosen for FP are commonly used in most cell- and enzyme-based assays and are designed not to overlap significantly with the q-dots. The dyes are evaluated both independently and together with the q-dots (at first off-instrument) to assess the cross-talk. Preferably, the liquid q-dot labels are read outside a spectral wavelength band currently used in FACS analysis and sorting (i.e., the dyes flourescein, Cy3, Cy5, etc). This permits the use of currently-available assays (dependent on these dyes). Using specific q-dots, crosstalk is minimized.

Accordingly, the present invention provides methods to label droplets and/or nanoreactors formed on a microfluidic device by using only a single dye code to avoid cross-talk with other dyes during FP. Additionally, the present invention provides methods to create FP dye codes to label compounds contained within liquids (including droplets and/or nanoreactors) where the compound is designed to be differentiated by FP on a microfluidic device. In this manner, dye codes having the same color, absorption, and emission could be used to label compounds within liquids.

In one aspect, the present invention is directed to the use of fluorescence polarization to label liquids. Droplets can be labeled using several means. These labeling means include, but are not limited to, the use of different dyes, quantum dots, capacitance, opacity, light scattering, fluorescence intensity (FI), fluorescence lifetime (FL), fluorescence polarization (FP), circular dichroism (CD), fluorescence correlation and combinations of all of these previous labeling means. The following disclosure describes the use of FP and FI as a means to label droplets on a microfluidic device. In addition, the use of FL as a means to adjust the overall FP of a solution, and by varying the concentration of the total FI, to create a 2-dimensional encoding scheme is demonstrated.

In general, molecules that take up more volume will tumble slower than a smaller molecule coupled to the same fluorophore. FP is independent of the concentration of the dye; liquids can have vastly different concentrations of FITC in them yet still have identical FP measurements.

In a preferred embodiment, a FP dye is an organic dye that does not interfere with the assay dye is used. Furthermore, since the total intensity of the FP dye can be quantified, a second dimension in which to label the droplet is provided. Thus, one can exploit the differences in FP to create an encoding scheme of dye within a liquid solution, including droplets. Examples of ways to exploit the differences in FP are described in WO 2007/081385 and WO 2008/063227. In a single dimension, FP can be used to create an encoding scheme. However, the present invention can also use Fluorescence Intensity (FI) of the overall solution to create even more labels in a second dimension. Interestingly, the differences of the fluorescence lifetime (FL) of two dyes with spectral overlap in the detected emission wavelength to change the overall FP of the combined solution can also be exploited.

Although the use of multiple compounds to which a dye molecule is attached to span a range of FP can be utilized, it is also possible to span the range using a high and low molecular weight compound set. For example, a dye can be attached to a large compound (for example streptavidin) and kept at a fixed concentration, to which a smaller compound (for example, a free dye molecule) would be titrated into the same solution. The FP of the solution can be adjusted to be in discernable increments from the value of the large molecule to somewhere slightly greater than the FP of the smaller molecule. The [total] dye intensity can be varied by varying the concentration of the mixture of the two dye-attached compounds. By varying total dye concentration and the FP, two dimensions can be used to generate the FP dye codes (FPcodes). Accordingly, many FPcodes can be generated using only two compounds.

This could also include use of large fluorescent proteins such as GFP and the phycobiliproteins combined with a smaller molecule.

Examples of dyes commonly used in biological dyes are listed in Table 2 below.

TABLE 2

| Excitation Wavelength | Emission Wavelength | Examples of Compatible Dyes |
| --- | --- | --- |
| 450 | 500 | Cyan 500 |
| 483 | 533 | SYBR Green, FAM |
| 523 | 568 | HEX, VIC |
| 558 | 610 | RED 610 |
| 615 | 640 | RED 640 |
| 650 | 670 | CY5 |

In another aspect, the present invention is directed labeling solids using properties other than dye emission and dye concentration. In one embodiment the solid can include, for example, a bead or location on a solid support or chip. As demonstrated above for liquids, FI and FL can be two of many dimensions of characteristics used as labels. By way of non-limiting example, it is possible to use two dyes with different FL to change the overall FP for a solid such as a bead or other mobile solid support.

In another embodiment, a linker can be used to couple the dye to the bead. The linker can be varied so as to allow the dye to have differing degrees of freedom in which to rotate (i.e., tumble). Varying the linker in this manner can change the FP of the attached dye, which in unique combinations can be used as a label. In some embodiments, the beads can be swollen in organic solvent and the dyes held in place by hydrophobic forces. In this case, the FP, FI, FL methods described above for liquid labeling can also be used as a means for labeling the beads. A quenching molecule can also be used to change the characteristics of a dye. Such quenching can be continuous or brought about through the interaction of a molecule, such as a peptide or nucleic acid linker, with differing means of bringing molecules together depending on the strength of linker-internal interaction (e.g., a nucleotide stem loop structure of varying lengths).

The reactions analyzed on the virtual, random and non-random arrays (discussed briefly below) can be also increased beyond the two (cy3 and cy5 intensities) commonly used for multiplexing. For example, different FP, FI, etc can be used as a read-out.

Random array decoding: Beads of the prior art use one or more pre-attached oligonucleotide-coupled beads that are held in place in a fiber-optic faceplate (for example, those used by Illumina). The oligos on the beads are decoded using sequential hybridization of a labeled complementary oligo. The assay of the prior art uses a separate oligonucleotide complementary zipcode ('Illumacode') attached to each type of bead.

The invention described herein is superior to the methods of the prior art in that the FP, FI, FL-labeled bead or mobile solid support can be placed into a random array (e.g., a chip as manufactured by Illumina) and the FP, FI, FL used to decode the bead. The FP, FI, FL of the bead can be decoded before using the chip and the different beads 'mapped' as to their specific locations. Alternatively, the bead can be decoded during attachment of the assay read-out. Significantly, the methods described by the present invention can be used to pre-determine the location of each bead-type either before, or during analysis.

Virtual array decoding: Methods of the prior art use 2 lasers and 3 detectors to differentiate a set of 100 bead-types. The beads-types are differentiated by the FI of two different dyes present in 1 of 10 concentrations (per dye) contained within the bead, and the assay detector is used to measure fluorescein concentration on the bead. The dyes, which are added to organic-solvent swollen beads, are not directly attached to the beads, but remain held within the bead by hydrophobic forces.

Using the methods of the present invention as described herein, a second detector to the machines of the prior art used to measure FP can be added, thereby adding a third dimension and extending the encoding scheme beyond the 100 available in the prior art.

Non-random array decoding: In chips of the prior art (such as those used by Affymetrix) oligonucleotides are synthesized directly on the chip. Decoding is simply a matter of knowing the location of the assay on the chip.

The methods as described herein can be advantageously used in conjunction with such chips to increase the number of things that can be simultaneously analyzed (i.e., multiplexed) on the chip. By way of non-limiting example, Cy3, Cy5, FL and FP can be used as analysis markers for hybridization reactions.

The present invention also provides methods for labeling micro or nano-sized droplets using Radio Frequency Identification (RFID). RFID tags can improve the identification of the contents within the droplets. Preferably, the droplets are utilized within a microfluidic device.

RFID is an automatic identification method, relying on storing and remotely retrieving data using devices called RFID tags or transponders. An RFID tag is an object that can be attached to or incorporated into a product, animal, or person for the purpose of identification using radio waves. Chip-based RFID tags contain silicon chips and antennae. Passive tags require no internal power source, whereas active tags require a power source. Hitachi has "powder" 0.05 mm×0.05 mm RFID chips. The new chips are 64 times smaller than the previous record holder, the 0.4 mm×0.4 mm mu-chips, and nine times smaller than Hitachi's last year prototype, and have room for a 128-bit ROM that can store a unique 38-digit ID number.

In one embodiment, a solution containing RFID tags are emulsified into droplets and are used as a label for the identification of the material within the droplet solution. Applications include, but are not limited to; genetics, genomics, proteomics, chemical synthesis, biofuels, and others.

In some embodiments, fluorescent polarization is used for digital assays. In this method, positive (enzyme-containing) droplets are identified and counted using changes in the fluorescence polarization of fluorescent molecules in the droplets. Fluorescence polarization (FP) detection technology can use a label such as fluorescein. In an FP-assay the fluorophore is excited with polarized light. Only fluorophores parallel to the light absorb and are excited. The excited state has a lifetime before the light emission occurs. During this time the labeled fluorophore molecule rotates and the polarization of the light emitted differs from the excitation plane. In some embodiments, to evaluate the polarization two measurements are used: the first using a polarized emission filter parallel to the excitation filter (S-plane) and the second with a polarized emission filter perpendicular to the excitation filter (P-plane). Fluorescence Lifetime (FL) changes can be detected based on the chemical environment of the fluorophore such that bound and unbound antibodies can be distinguished by FL measurements well known to one skilled in the art.

The rotational speed of a molecule is dependent on the size of the molecule, temperature and viscosity of the solution. The principle here is that the labeled compound is small and rotates rapidly (low polarization). When the labeled compound binds to the larger molecule, its rotation slows down considerably (polarization changes from low to high polarization). In general, molecules that take up more volume will tumble slower than a smaller molecule coupled to the same fluorophore. FP is independent of the concentration of the dye; liquids can have vastly different concentrations of FITC in them yet still have identical FP measurements. Thus, FP provides a direct readout of the extent of binding to protein, nucleic acids, and other biopolymers or targets.

FP offers advantages in the context of multiplexing (discussed in more detail elsewhere herein). Since FP is independent of intensity, it is relatively immune to colored solutions and cloudy suspensions. FP offers several advantages in the area of instrumentation. Because FP is a fundamental property of the molecule, and the reagents are stable, little or no standardization is required.

The dyes chosen for FP include any suitable dye such as, for example, fluorescein, Cy3, Cy5, etc. Suitable dyes include (name followed by [excitation wavelength, emission wavelength]): Cyan 500 [450, 500]; SYBR Green, FAM [483, 533], HEX, VIC [523, 568]; RED 610 [558, 610]; RED 640 [615, 640]; and CY5 [650, 670].

In some embodiments, an FP dye is an organic dye that does not interfere with other labels or dyes in an assay. Furthermore, since the total intensity of the FP dye can be quantified, a second dimension in which to label the partition is provided. Thus, one can exploit the differences in FP to create an encoding scheme of dye within a liquid solution, including droplets. Examples of ways to exploit the differences in FP are described in WO 2007/081385 and WO 2008/063227. Fluorescence polarization is discussed in U.S. Pub. 2010/0022414, the contents of which are hereby incorporated by reference in their entirety.

Figure 15A:
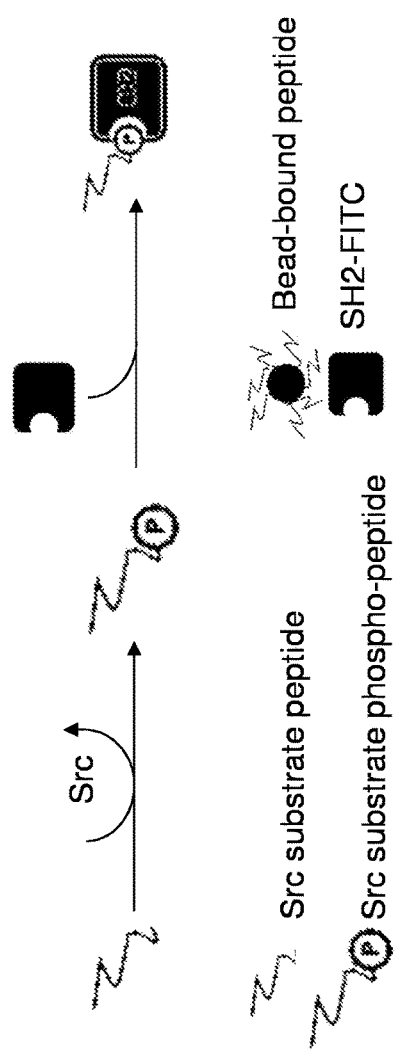
FIGS. 15A and 15B show fluorescent polarization as another mode for readout.
Figure 15B:
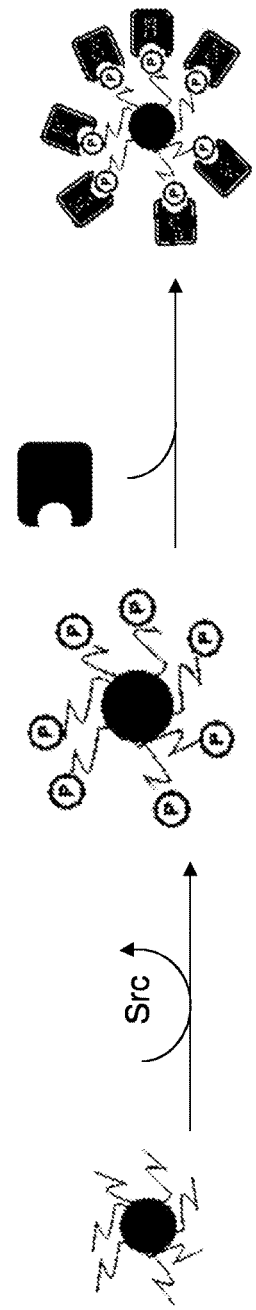

In the example shown in FIG. 15A, the enzyme Src kinase (Src) phosphorylates a Src substrate peptide and creates a binding surface for a fluorescent reporter. A reporter construct containing the Src homology 2 domain (SH2) and a fluorescein isothiocyanate (FITC) serves as a fluorescent reporter (SH2-FITC). When SH2-FITC is added, it will bind to the phosphorylated Src substrate peptide. FIG. 15B shows the same sequence of steps but in which Src substrate peptide is bound to a bead.

When the fluorescent reporter SH2-FITC is free in solution it has a low fluorescence polarization, whereas when bound to a phosphorylated peptide (e.g., the last step shown in each of FIGS. 15A and 15B) it has a measurably higher fluorescence polarization. Detection of fluorescent polarization indicates a reaction-positive fluid partition. Many other enzymes, binding motifs, and fluorescent reporters can be used.

Lasers

To detect a reporter or determine whether a molecule, cell or particle has a desired characteristic, the detection module may include an apparatus for stimulating a reporter for that characteristic to emit measurable light energy, e.g., a light source such as a laser, laser diode, light emitting diode (LED), high-intensity lamp, (e.g., mercury lamp), and the like. Where a lamp is used, the channels are preferably shielded from light in all regions except the detection module. Where a laser is used, the laser can be set to scan across a set of detection modules from different analysis units. In addition, laser diodes or LED's may be microfabricated into the same chip that contains the analysis units. Alternatively, laser diodes or LED's may be incorporated into a second chip (i.e., a laser diode chip) that is placed adjacent to the analysis or microchip such that the laser light from the diodes shines on the detection module(s).

An integrated semiconductor laser and/or an integrated photodiode detector can be included on the substrate in the vicinity of the detection module. This design provides the advantages of compactness and a shorter optical path for exciting and/or emitted radiation, thus minimizing distortion and losses.

Fluorescence produced by a reporter is excited using a laser beam focused on molecules (e.g., DNA, protein, enzyme or substrate) or cells passing through a detection region. Fluorescent reporters can include, but are not limited to, rhodamine, fluorescein, Texas red, Cy 3, Cy 5, phycobiliprotein (e.g., phycoerythrin), green fluorescent protein (GFP), YOYO-1 and PicoGreen. In molecular fingerprinting applications, the reporter labels can be fluorescently labeled single nucleotides, such as fluorescein-dNTP, rhodamine-dNTP, Cy3-dNTP, etc.; where dNTP represents dATP, dTTP, dUTP or dCTP. The reporter can also be chemically-modified single nucleotides, such as biotin-dNTP. The reporter can be fluorescently or chemically labeled amino acids or antibodies (which bind to a particular antigen, or fragment thereof, when expressed or displayed by a cell or virus).

The device can analyze and/or sort cells based on the level of expression of selected cell markers, such as cell surface markers, which have a detectable reporter bound thereto, in a manner similar to that currently employed using fluorescence-activated cell sorting (FACS) machines. Proteins or other characteristics within a cell, and which do not necessarily appear on the cell surface, can also be identified and used as a basis for sorting. The device can also determine the size or molecular weight of molecules such as polynucleotides or polypeptides (including enzymes and other proteins) or fragments thereof passing through the detection module. Alternatively, the device can determine the presence or degree of some other characteristic indicated by a reporter. If desired, the cells, particles or molecules can be sorted based on this analysis. The sorted cells, particles or molecules can be collected from the outlet channels in collection modules (or discarded in wasted modules) and used as needed. The collected cells, particles or molecules can be removed from the device or reintroduced to the device for additional coalescence, analysis and sorting.

Processors

As used herein, a "processor" or a "microprocessor" is any component or device able to receive a signal from one or more sensors, store the signal, and/or direct one or more responses (e.g., as described above), for example, by using a mathematical formula or an electronic or computational circuit. The signal may be any suitable signal indicative of the environmental factor determined by the sensor, for example a pneumatic signal, an electronic signal, an optical signal, a mechanical signal, etc.

The device of the present invention can comprise features, such as integrated metal alloy components and/or features patterned in an electrically conductive layer, for detecting droplets by broadcasting a signal around a droplet and picking up an electrical signal in proximity to the droplet.

Beads

The device of the present invention also comprises the use of beads and methods for analyzing and sorting beads (i.e., bead reader device). The device can read and either sort or not sort droplets containing one or more of a set of two or more beads. Each bead can be differentiated from each other bead within a set. Beads can be separated by several tags including, but not limited to, quantum dyes, fluorescent dyes, ratios of fluorescent dyes, radioactivity, radio-tags, etc. For example, a set of beads containing a ratio of two dyes in discrete amounts with an apparatus for detecting and differentiating beads containing one discrete ratio from the other beads in this set having a different ratio of the two dyes. The microfluidic device can include paramagnetic beads. The paramagnetic beads can introduce and remove chemical components from droplets using droplet coalescence and breakup events. The paramagnetic beads can also be used for sorting droplets.

The present invention provides methods of screening molecular libraries on beads through limited-dilution-loading and then chemical or optical release inside of droplets. Provided are methods for chemical synthesis on a bead and releasing said chemical attached to the bead using a releasing means (chemical, UV light, heat, etc) within a droplet, and then combining a second droplet to the first droplet for further manipulation. For example, tea-bag synthesis of chemicals on a bead simultaneously with a means for identifying said bead (using, for example, a mass spec tag). Using the resulting mixed-chemistry beads in a droplet within a fluid flow, and exposing the beads to UV light to release the chemical synthesized from the bead into the droplet environment. Combining the droplet containing the released chemical with a droplet containing a cell, and performing a cell-based assay. Sorting droplets having the desired characteristics (for example, turn on of a reporter gene), and then analyzing the sorted beads using mass spectroscopy.

The device of the present invention can comprise column separation prior to bead sorting. A device containing a channel loaded with a separating means for chromatographically sorting the sample prior to droplet formation. Such separating means could include size, charge, hydrophobicity, atomic mass, etc. The separating can be done isocratic or by use of a means for generating a gradient chemically, (for example using salt or hydrophobicity), electrically, by pressure, or etc. For example, a channel is preloaded with Sepharose size exclusion media. A sample is loaded at one end, and the droplets are formed at an opposing end. The sample separates by size prior to becoming incorporated within a droplet.

Sorting Module

The microfluidic device of the present invention can further include one or more sorting modules. A "sorting module" is a junction of a channel where the flow of molecules, cells, small molecules or particles can change direction to enter one or more other channels, e.g., a branch channel for delivery to an outlet module (i.e., collection or waste module), depending on a signal received in connection with an examination in the detection module. Typically, a sorting module is monitored and/or under the control of a detection module, and therefore a sorting module may "correspond" to such detection module. The sorting region is in communication with and is influenced by one or more sorting apparatuses. A sorting apparatus comprises techniques or control systems, e.g., dielectric, electric, electro-osmotic, (micro-) valve, etc. A control system can employ a variety of sorting techniques to change or direct the flow of molecules, cells, small molecules or particles into a predetermined branch channel. A "branch channel" is a channel which is in communication with a sorting region and a main channel. The main channel can communicate with two or more branch channels at the sorting module or "branch point", forming, for example, a T-shape or a Y-shape. Other shapes and channel geometries may be used as desired. Typically, a branch channel receives molecules, cells, small molecules or particles depending on the molecule, cells, small molecules or particles characteristic of interest as detected by the detection module and sorted at the sorting module. A branch channel can have an outlet module and/or terminate with a well or reservoir to allow collection or disposal (collection module or waste module, respectively) of the molecules, cells, small molecules or particles. Alternatively, a branch channel may be in communication with other channels to permit additional sorting.

The device of the present invention can further include one or more outlet modules. An "outlet module" is an area of the device that collects or dispenses molecules, cells, small molecules or particles after coalescence, detection and/or sorting. The outlet module can include a collection module and/or a waste module. The collection module can be connected to a means for storing a sample. The collection module can be a well or reservoir for collecting and containing droplets detected to have a specific predetermined characteristic in the detection module. The collection module can be temperature controlled. The waste module can be connected to a means for discarding a sample. The waste module can be a well or reservoir for collecting and containing droplets detected to not have a specific predetermined characteristic in the detection module. The outlet module is downstream from a sorting module, if present, or downstream from the detection module if a sorting module is not present. The outlet module may contain branch channels or outlet channels for connection to a collection module or waste module. A device can contain more than one outlet module.

A characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). A fluidic droplet is preferably sorted or steered by inducing a dipole in the uncharged fluidic droplet (which may be initially charged or uncharged), and sorting or steering the droplet using an applied electric field. The electric field may be an AC field, a DC field, etc. Methods of sorting or steering droplets in an electric field are as described in WO 2006/040551; WO 2006/040554; WO 2004/002627; WO 2004/091763; WO 2005/021151; WO 2006/096571; WO 2007/089541; WO 2007/081385 and WO 2008/063227. Improvements in the efficiency, accuracy, and reliability of the preferred dielectric droplet sorting technique described above are possibly by utilizing additional channel and electrode geometries, as described in WO 2007/081385 and WO 2008/063227.

Alternately, a fluidic droplet may be directed by creating an electric charge (e.g., as previously described) on the droplet, and steering the droplet using an applied electric field, which may be an AC field, a DC field, etc. As an example, an electric field maybe selectively applied and removed (or a different electric field may be applied) as needed to direct the fluidic droplet to a particular region. The electric field may be selectively applied and removed as needed, in some embodiments, without substantially altering the flow of the liquid containing the fluidic droplet. For example, a liquid may flow on a substantially steady-state basis (i.e., the average flowrate of the liquid containing the fluidic droplet deviates by less than 20% or less than 15% of the steady-state flow or the expected value of the flow of liquid with respect to time, and in some cases, the average flowrate may deviate less than 10% or less than 5%) or other predetermined basis through a fluidic system of the invention (e.g., through a channel or a microchannel), and fluidic droplets contained within the liquid may be directed to various regions, e.g., using an electric field, without substantially altering the flow of the liquid through the fluidic system.

In some embodiments, the fluidic droplets may be sorted into more than two channels. Alternately, a fluidic droplet may be sorted and/or split into two or more separate droplets, for example, depending on the particular application. Any of the above-described techniques may be used to spilt and/or sort droplets. As a non-limiting example, by applying (or removing) a first electric field to a device (or a portion thereof), a fluidic droplet may be directed to a first region or channel; by applying (or removing) a second electric field to the device (or a portion thereof), the droplet may be directed to a second region or channel; by applying a third electric field to the device (or a portion thereof), the droplet may be directed to a third region or channel; etc., where the electric fields may differ in some way, for example, in intensity, direction, frequency, duration, etc. In a series of droplets, each droplet may be independently sorted and/or split; for example, some droplets may be directed to one location or another, while other droplets may be split into multiple droplets directed to two or more locations.

In some cases, high sorting speeds may be achievable using certain systems and methods of the invention. For instance, at least about 1 droplet per second may be determined and/or sorted in some cases, and in other cases, at least about 10 droplets per second, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1000 droplets per second, at least about 1500 droplets per second, at least about 2000 droplets per second, at least about 3000 droplets per second, at least about 5000 droplets per second, at least about 7500 droplets per second, at least about 10,000 droplets per second, at least about 15,000 droplets per second, at least about 20,000 droplets per second, at least about 30,000 droplets per second, at least about 50,000 droplets per second, at least about 75,000 droplets per second, at least about 100,000 droplets per second, at least about 150,000 droplets per second, at least about 200,000 droplets per second, at least about 300,000 droplets per second, at least about 500,000 droplets per second, at least about 750,000 droplets per second, at least about 1,000,000 droplets per second may be determined and/or sorted in such a fashion.

Sample Recovery

The present invention proposes methods for recovering aqueous phase components from aqueous emulsions that have been collected on a microfluidic device in a minimum number of steps and in a gentle manner so as to minimize potential damage to cell viability.

In one aspect, a stable aqueous sample droplet emulsion containing aqueous phase components in a continuous phase carrier fluid is allowed to cream to the top of the continuous phase carrier oil. By way of nonlimiting example, the continuous phase carrier fluid can include a perfluorocarbon oil that can have one or more stabilizing surfactants. The aqueous emulsion rises to the top or separates from the continuous phase carrier fluid by virtue of the density of the continuous phase fluid being greater than that of the aqueous phase emulsion. For example, the perfluorocarbon oil used in one embodiment of the device is 1.8, compared to the density of the aqueous emulsion, which is 1.0.

The creamed emulsion is then placed onto a second continuous phase carrier fluid which contains a de-stabilizing surfactant, such as a perfluorinated alcohol (e.g., 1H,1H, 2H,2H-Perfluoro-1-octanol). The second continuous phase carrier fluid can also be a perfluorocarbon oil. Upon mixing, the aqueous emulsion begins to coalesce, and coalescence is completed by brief centrifugation at low speed (e.g., 1 minute at 2000 rpm in a microcentrifuge). The coalesced aqueous phase can now be removed (cells can be placed in an appropriate environment for further analysis).

Additional destabilizing surfactants and/or oil combinations can be identified or synthesized to be useful with this invention.

Additional Modules

The microfluidic devices of the present invention can further include one or more mixing modules, one or more delay modules, one or more acoustic actuators and/or UV-release modules, as described in WO 2007/081385 and WO 2008/063227.

Assays

The droplet generation rate, spacing and size of the water droplets made on a microfluidic device are tuned to the desired size, such as picoliter to nanoliter volumes. Additionally, droplet libraries of the present invention can be introduced back onto a medium for additional processing. Multicomponent droplets can easily be generated by bringing together streams of materials at the point where droplets are made (co-flow). Alternatively, one can combine different droplets, each containing individual reactants. This is achieved by selecting droplet sizes such that one droplet is roughly wider than the channel width and the other droplet is smaller so that the small droplets rapidly catch up to the larger droplets. An electric field is then used to induce dipoles in the droplet pairs, forcing them to combine into a single droplet and permitting them to intermix the contents.

Optics for fluorescence detection capable of measuring fluorophores within the aqueous droplets, while simultaneously permitting visual monitoring via a high speed video microscope. Specifically, three separate lasers provide excitation at 405 nm, 488 nm, and 561 nm wavelengths focused to a spot approximately 17 microns in diameter, illuminating each droplet as it enters the detection zone. The system is configured to detect emitted light using a series of photomultiplier tubes, and is able to detect less than 10,000 FITC molecule equivalents at a 5 kHz droplet rate.

A critical component for isolating sub-populations or rare cells from a heterogeneous cell mixture is a fluorescence-activated microfluidic droplet sorter as described in greater detail herein. Sorting in microfluidic devices can be done using a dielectrophoretic force on neutral droplets. Providing an alternate means that can be precisely controlled, can be switched at high frequencies, and requires no moving parts. After the contents of individual droplets are probed in the fluorescence detection zone, selected droplets can be sorted into discreet streams for recovery and further processing.

A key feature for improving genomic characterization of the heterogeneous mixture of cell types present in a typical tissue or biopsy would be the ability to fractionate the initial cell population into sub-populations, permitting analysis of rare cells and enabling molecular correlation studies. The microfluidic device provides the ability to sort cell-containing droplets based on fluorescent signals. A number of immediate uses for this capability include: 1) sorting cell-containing droplets away from empty droplets; 2) sorting sub-populations based on specific nucleic acid hybridization; 3) sorting sub-populations based on cell surface binding properties; 4) sorting sub-populations based on secreted activities or reporter enzyme products. A number of these approaches have already been tested in preliminary experiments, using either bacterial or mammalian cells.

For example, Sort-on-Generation is a combination of modules that generates single cell containing-droplets (along with approximately 10 times more empty droplets, from Poisson distribution as described herein and subsequently sorts the cell-containing droplets away from the empty droplets, based on fluorescent signals.

Also, it has been demonstrated the ability to sort-on-generation using DNA-intercalating dyes. This approach is enabled for any stained cell.

Determining the volume of an individual drop from a 2-D image in a microfluidic channel can be accomplished relatively easily with tools typically associated with microfluidics. The basic equipment needed are; simple optics with a camera, a fluorescent laser detector, a microfluidic device, and pumps.

A 10 pt calibration is done by plotting the average projected area vs. the average volume of a drop. The average projected area is determined by real-time image analysis of droplets during emulsion generation in a specific region of the chip. This region is clearly marked and called the calibration region. Calibration is accomplished by simultaneously logging the projected area of individual droplets for 60 s and calculating the average, and using a laser is to count the total number of droplets that pass through the channel at the calibration region. From this count, one can determine the average frequency and the average volume of a droplet. Where, $$f = \frac{\text{Drops}}{t}$$

$$V = \frac{F_{Buffer}\left[\frac{\text{uL}}{\text{hr}}\right] * 10^6\left[\frac{\text{pL}}{\text{uL}}\right]}{f\left[\frac{\text{Drops}}{\text{s}}\right] * 3600\left[\frac{\text{s}}{\text{hr}}\right]}$$

Plotting this data for all points yields a calibration curve.

During reinjection of an emulsion, using image analysis, one can log the projected area of each individual droplet and estimate the volume of each droplet by using the calibration curve. From this data, one can calculate the average volume and size distribution for a given population of droplets.

The microfluidic device of the present invention can be utilized to conduct numerous chemical and biological assays, including but not limited to, creating emulsion libraries, flow cytometry, gene amplification, isothermal gene amplification, DNA sequencing, SNP analysis, drug screening, RNAi analysis, karyotyping, creating microbial strains with improved biomass conversion, moving cells using optical tweezer/cell trapping, transformation of cells by electroporation, μTAS, and DNA hybridization.

PCR in Droplets

An emulsion library comprising at least a first aqueous droplet and at least a second aqueous droplet within a fluorocarbon oil comprising at least one fluorosurfactant, wherein the at least first and the at least second droplets are uniform in size and wherein at least first droplet comprises at least a first pair or oligonucleotides and the at least second droplet comprises at least a second pair or oligonucleotides, wherein the first and second pair of oligonucleotides is different.

In an embodiment, the oligonucleotide is DNA; in another embodiment, the oligonucleotide is RNA. In a further embodiment, the oligonucleotide has at least 5 nucleotides, e.g., 5 to 100, 10 to 90, 12 to 80, 14 to 70, 15 to 60, 15 to 50, 15 to 40, 15 to 35, 15 to 30, 15 to 28, 15 to 25, 15 to 23, and 15 to 20 nucleotides. In one embodiment, the two oligonucleotides in the pair of oligonucleotides have the same number of nucleotides; in another embodiment, the two oligonucleotides in the pair of oligonucleotides have different number of nucleotides.

The present invention provides a method for amplifying a genomic DNA, comprising (a) providing a first sample fluid wherein said first sample fluid comprises an emulsion library comprising at least a first aqueous droplet and at least a second aqueous droplet within a fluorocarbon oil comprising at least one fluorosurfactant, wherein the at least first and the at least second droplets are uniform in size and wherein at least first droplet comprises at least a first pair or oligonucleotides and the at least second droplet comprises at least a second pair or oligonucleotides, wherein the first and second pair of oligonucleotides is different; (b) providing a second sample fluid wherein said second sample fluid comprises a plurality of aqueous droplets comprising said genomic DNA within an immiscible fluorocarbon oil comprising at least one fluorosurfactant; (c) providing a microfluidic substrate comprising at least two inlet channels adapted to carry at least two dispersed phase sample fluids and at least one main channel adapted to carry at least one continuous phase fluid; (d) flowing the first sample fluid through a first inlet channel which is in fluid communication with said main channel at a junction, wherein said junction comprises a first fluidic nozzle designed for flow focusing such that said first sample fluid forms a plurality of droplets of a first uniform size in said continuous phase; (e) flowing the second sample fluid through a second inlet channel which is in fluid communication with said main channel at a junction, wherein said junction comprises a second fluidic nozzle designed for flow focusing such that said second sample fluid forms a plurality of droplets of a second uniform size in said continuous phase, wherein the size of the droplets of the second sample fluid are smaller than the size of the droplets of the first sample fluid; (f) providing a flow and droplet formation rate of the first and second sample fluids wherein the droplets are interdigitized such that a first sample fluid droplet is followed by and paired with a second sample fluid droplet; (g) providing channel dimensions such that the paired first sample fluid and the second sample fluid droplet are brought into proximity; (h) coalescing the paired first and second sample droplets as the paired droplets pass through an electric field, and (i) amplifying said genomic DNA comprised within the coalesced droplets.

A unique feature of the described droplet-based microfluidic approach for working with nucleic acids is that it uses immiscible oil-encapsulated aqueous droplets to shield the DNA from the inner surfaces of the microfluidic chip, with a surfactant interface separating the aqueous droplet and its contents from the surrounding immiscible fluorocarbon oil. Therefore, DNA amplification reactions occurring inside these droplets generate material that does not interact with the channel walls, and collection of the DNA-containing droplets for subsequent manipulation and sequencing is straightforward. This technology provides a solution for amplification of DNA from single cells, allowing for both genotyping and whole genome amplification.

Evidence shows that specific loci can be amplified by PCR in droplets generated on the microfluidic device, either by performing PCR on-chip (with droplets moving through a serpentine channel across several different temperatures under microfluidic control), or by placing the collected droplets into a standard thermocycler. Droplets generated containing DNA and reagents required for PCR-based amplification (thermostable polymerase, dNTPs, Mg, appropriate buffer) have been demonstrated to be extremely robust, showing high stability for both on-chip and off-chip (standard thermocycler) amplification. Each droplet remains intact and separate during cycling, including during the denaturation steps at 98° C. In one embodiment, a microfluidic device as described herein, fuses droplets with individual primer pairs for PCR amplification and preparation of many exons in parallel for high throughput re-sequencing.

Antibodies and ELISA

The present invention provides a method for performing an ELISA assay, comprising (a) providing a first sample fluid wherein said first sample fluid comprises an emulsion library comprising a plurality of aqueous droplets within an immiscible fluorocarbon oil comprising at least one fluorosurfactant, wherein each droplet is uniform in size and comprises at least a first antibody, and a single element linked to at least a second antibody, wherein said first and second antibodies are different; (b) providing a second sample fluid wherein said second sample fluid comprises a plurality of aqueous droplets within an immiscible fluorocarbon oil comprising at least one fluorosurfactant, said droplets comprising a test fluid; (c) providing a third sample fluid wherein said third sample fluid comprises a plurality of aqueous droplets within an immiscible fluorocarbon oil comprising at least one fluorosurfactant, said droplets comprising at least one enzyme; (d) providing a fourth sample fluid wherein said fourth sample fluid comprises a plurality of aqueous droplets within an immiscible fluorocarbon oil comprising at least one fluorosurfactant, said droplets comprising at least one substrate; (e) providing a microfluidic substrate comprising at least two inlet channels adapted to carry at least two dispersed phase sample fluids and at least one main channel adapted to carry at least one continuous phase fluid; (f) flowing the first sample fluid through a first inlet channel which is in fluid communication with said main channel at a junction, wherein said junction comprises a first fluidic nozzle designed for flow focusing such that said first sample fluid forms a plurality of droplets of a first uniform size in said continuous phase; (g) flowing the second sample fluid through a second inlet channel which is in fluid communication with said main channel at a junction, wherein said junction comprises a second fluidic nozzle designed for flow focusing such that said second sample fluid forms a plurality of droplets of a second uniform size in said continuous phase, wherein the size of the droplets of the second sample fluid are smaller than the size of the droplets of the first sample fluid; (h) providing a flow and droplet formation rate of the first and second sample fluids wherein the droplets are interdigitized such that a first sample fluid droplet is followed by and paired with a second sample fluid droplet; (i) providing channel dimensions such that the paired first sample fluid and the second sample fluid droplet are brought into proximity; (j) coalescing the paired first and second sample droplets as the paired droplets pass through an electric field, forming at least a first coalesced droplet; (k) flowing the third sample fluid through a third inlet channel which is in fluid communication with said main channel at a junction, wherein said junction comprises a third fluidic nozzle designed for flow focusing such that said third sample fluid forms a plurality of droplets of a third uniform size in said continuous phase, wherein the size of the droplets of the third sample fluid are smaller than the size of the droplets of at least first coalesced droplet; (l) providing a flow and droplet formation rate of the third sample fluid wherein the third sample fluid droplet and at least first coalesced droplet are interdigitized such that the at least first coalesced droplet is followed by and paired with the third sample fluid droplet; (m) providing channel dimensions such that the paired at least first coalesced droplet and the third sample fluid droplet are brought into proximity; (n) coalescing the paired at least first coalesced droplet and third sample droplets as the paired droplets pass through an electric field, forming at least a second coalesced droplet; (o) flowing the fourth sample fluid through a fourth inlet channel which is in fluid communication with said main channel at a junction, wherein said junction comprises a fourth fluidic nozzle designed for flow focusing such that said fourth sample fluid forms a plurality of droplets of a fourth uniform size in said continuous phase, wherein the size of the droplets of the fourth sample fluid are smaller than the size of the droplets of at least second coalesced droplet; (p) providing a flow and droplet formation rate of the fourth sample fluid wherein the fourth sample fluid droplet and at least second coalesced droplet are interdigitized such that the at least second coalesced droplet is followed by and paired with the fourth sample fluid droplet; (q) providing channel dimensions such that the paired at least second coalesced droplet and the fourth sample fluid droplet are brought into proximity; (r) coalescing the paired at least second coalesced droplet and fourth sample droplets as the paired droplets pass through an electric field, forming at least a third coalesced droplet, and (s) detecting the conversion of said substrate to a product by said enzyme within the at least a third coalesced droplet.

The present invention also provides a method for performing an ELISA assay, comprising (a) providing a first sample fluid wherein said first sample fluid comprises an emulsion library comprising a plurality of aqueous droplets within an immiscible fluorocarbon oil comprising at least one fluorosurfactant, wherein each droplet is uniform in size and comprises at least a first element linked to at least a first antibody, and at least a second element linked to at least a second antibody, wherein said first and second antibodies are different; (b) providing a second sample fluid wherein said second sample fluid comprises a plurality of aqueous droplets within an immiscible fluorocarbon oil comprising at least one fluorosurfactant, said droplets comprising a test fluid (c) providing a third sample fluid wherein said third sample fluid comprises a plurality of aqueous droplets within an immiscible fluorocarbon oil comprising at least one fluorosurfactant, said droplets comprising at least one substrate; (d) providing a microfluidic substrate comprising at least two inlet channels adapted to carry at least two dispersed phase sample fluids and at least one main channel adapted to carry at least one continuous phase fluid; (e) flowing the first sample fluid through a first inlet channel which is in fluid communication with said main channel at a junction, wherein said junction comprises a first fluidic nozzle designed for flow focusing such that said first sample fluid forms a plurality of droplets of a first uniform size in said continuous phase; (f) flowing the second sample fluid through a second inlet channel which is in fluid communication with said main channel at a junction, wherein said junction comprises a second fluidic nozzle designed for flow focusing such that said second sample fluid forms a plurality of droplets of a second uniform size in said continuous phase, wherein the size of the droplets of the second sample fluid are smaller than the size of the droplets of the first sample fluid; (g) providing a flow and droplet formation rate of the first and second sample fluids wherein the droplets are interdigitized such that a first sample fluid droplet is followed by and paired with a second sample fluid droplet; (h) providing channel dimensions such that the paired first sample fluid and the second sample fluid droplet are brought into proximity; (i) coalescing the paired first and second sample droplets as the paired droplets pass through an electric field, forming at least a first coalesced droplet, wherein if the two antibodies bind an antigen in the test sample the at least first and at least second elements interact to form a functional enzyme; (j) flowing the third sample fluid through a third inlet channel which is in fluid communication with said main channel at a junction, wherein said junction comprises a third fluidic nozzle designed for flow focusing such that said third sample fluid forms a plurality of droplets of a third uniform size in said continuous phase, wherein the size of the droplets of the third sample fluid are smaller than the size of the droplets of at least first coalesced droplet; (k) providing a flow and droplet formation rate of the third sample fluid wherein the third sample fluid droplet and at least first coalesced droplet are interdigitized such that the at least first coalesced droplet is followed by and paired with the third sample fluid droplet; (l) providing channel dimensions such that the paired at least first coalesced droplet and the third sample fluid droplet are brought into proximity; (m) coalescing the paired at least first coalesced droplet and third sample droplets as the paired droplets pass through an electric field, forming at least a second coalesced droplet, and (n) detecting the conversion of said substrate to a product by said enzyme within the at least a second coalesced droplet.

Small sample volumes are needed in performing immunoassays. Non-limiting examples include cases where the sample is precious or limited, i.e., serum archives, tissue banks, and tumor biopsies. Immunoassays would ideally be run in droplets where only 10 to 100 pL of sample were consumed for each assay. Specifically, the lack of a robust convenient wash step has prevented the development of ELISA assays in droplets. The present invention provides for methods in which beads can be used to perform ELISA assays in aqueous droplets within channels on a microfluidic device. The advantage of utilizing microfluidic devices is it greatly reduces the size of the sample volume needed. Moreover, a benefit of droplet based microfluidic methods is the ability to run numerous assays in parallel and in separate micro-compartments.

In the examples shown herein, there are several non-limiting read-outs that can be applied to signal amplification in a microfluidic device. The amplification methods include enzyme amplification and rolling circle amplification of signal that uses a nucleic-acid intermediate. In addition, a non-enzymatic means for signal amplification can also be used.

Cell Libraries

The present invention provides a method for generating an enzyme library, comprising (a) providing a first sample fluid wherein said first sample fluid comprises an emulsion library comprising a plurality of aqueous droplets within an immiscible fluorocarbon oil comprising at least one fluorosurfactant, said droplets comprising at least one cell transformed with at least one nucleic acid molecule encoding for an enzyme, wherein said cells replicate within said droplets thereby secreting produced enzymes within the droplets; (b) providing a second sample fluid wherein said second sample fluid comprises a plurality of aqueous droplets within an immiscible fluorocarbon oil comprising at least one fluorosurfactant, said droplets comprising at least one substrate; (c) providing a microfluidic substrate comprising at least two inlet channels adapted to carry at least two dispersed phase sample fluids and at least one main channel adapted to carry at least one continuous phase fluid; (d) flowing the first sample fluid through a first inlet channel which is in fluid communication with said main channel at a junction, wherein said junction comprises a first fluidic nozzle designed for flow focusing such that said first sample fluid forms a plurality of droplets of a first uniform size in said continuous phase; (e) flowing the second sample fluid through a second inlet channel which is in fluid communication with said main channel at a junction, wherein said junction comprises a second fluidic nozzle designed for flow focusing such that said second sample fluid forms a plurality of droplets of a second uniform size in said continuous phase, wherein the size of the droplets of the second sample fluid are smaller than the size of the droplets of the first sample fluid; (f) providing a flow and droplet formation rate of the first and second sample fluids wherein the droplets are interdigitized such that a first sample fluid droplet is followed by and paired with a second sample fluid droplet; (g) providing channel dimensions such that the paired first sample fluid and the second sample fluid droplet are brought into proximity; (h) coalescing the paired first and second sample droplets as the paired droplets pass through an electric field, and (i) detecting enzyme activity within the coalesced droplets, wherein the conversion of substrate to product indicates the presence of an enzyme library.

In a small library, the use of microfluidic system to emulsify a library of 3-5 bacteria strains that encode a single protease with a known range of activity against a designated substrate in microdroplets, and sort via a fluorescence assay to demonstrate the ability to identify and sort one of the cell strains that expresses a protease that is more active against a specified substrate than the other strains.

Further in a full library screen, the use of a microfluidic system to emulsify a library of mutagenized bacteria cells in microdroplets, identify and sort via a fluorescence assay a subpopulation of cells to produce a $10^4$ fold enrichment of cells expressing a designated enzyme variant, and recover viable cells and enriched library.

The present invention provides a method for sorting a plurality of cells, comprising (a) providing a first sample fluid wherein said first sample fluid comprises an emulsion library comprising a plurality of aqueous droplets within an immiscible fluorocarbon oil comprising at least one fluorosurfactant, said droplets comprising at least one cell labeled with an enzyme; (b) providing a second sample fluid wherein said second sample fluid comprises a plurality of aqueous droplets within an immiscible fluorocarbon oil comprising at least one fluorosurfactant, said droplets comprising at least one substrate; (c) providing a microfluidic substrate comprising at least two inlet channels adapted to carry at least two dispersed phase sample fluids and at least one main channel adapted to carry at least one continuous phase fluid; (d) flowing the first sample fluid through a first inlet channel which is in fluid communication with said main channel at a junction, wherein said junction comprises a first fluidic nozzle designed for flow focusing such that said first sample fluid forms a plurality of droplets of a first uniform size in said continuous phase; (e) flowing the second sample fluid through a second inlet channel which is in fluid communication with said main channel at a junction, wherein said junction comprises a second fluidic nozzle designed for flow focusing such that said second sample fluid forms a plurality of droplets of a second uniform size in said continuous phase, wherein the size of the droplets of the second sample fluid are smaller than the size of the droplets of the first sample fluid; (f) providing a flow and droplet formation rate of the first and second sample fluids wherein the droplets are interdigitized such that a first sample fluid droplet is followed by and paired with a second sample fluid droplet; (g) providing channel dimensions such that the paired first sample fluid and the second sample fluid droplet are brought into proximity; (h) coalescing the paired first and second sample droplets as the paired droplets pass through an electric field; (i) detecting enzyme activity within the coalesced droplets, and (j) selecting cells where the enzyme has converted substrate to product.

Whole Genome Amplification

Whole Genome Amplification (WGA) is a method that amplifies genomic material from minute samples, even from a single cell, enabling genome sequencing. A number of commercially available WGA methodologies have been developed, including PCR-based methods like degenerate oligonucleotide primed PCR (DOP-PCR) and primer extension pre-amplification (PEP-PCR), and multiple displacement amplification (MDA) which uses random hexamers and using high fidelity D29 or Bst DNA polymerases to provide isothermal amplification. Several analyses have shown that MDA products generate the least amplification bias and produce a higher yield of amplified DNA. This method has been used recently to amplify genomic DNA for sequencing from single cells, with partial genome sequencing demonstrated. MDA-based WGA has also been performed on cell populations selected using flow-FISH.

Non-specific DNA synthesis due to contaminating DNA and non-template amplification (NTA) are characteristic problems associated with WGA. Recent evidence demonstrates that NTA and also amplification bias are reduced when using very small reaction volumes, with one group using 60 nanoliter microfluidic chambers for single cell WGA reactions. Based on these findings, the use of picoliter-volume droplets in a microfluidic system reduces NTA even further. In addition, amplification from contaminating DNA templates will be constrained to individual compartments (droplets), minimizing the overwhelming effects of contamination in bulk WGA reactions.

Next Generation Sequencing

Next generation sequencing instruments offer two distinct advantages in the pursuit of microbiome characterization. First, they do not require conventional clone-based approaches to DNA sequencing, and thus ensure that the commonly experienced biasing against specific sequences in the *E. coli* host system does not impact the representation of genomes being sequenced. Second, they offer a streamlined and robust workflow for preparing DNA for sequencing that has far fewer steps than conventional workflows. Hence, a library can be prepared for sequencing in about 2 days. The Roche/454 FLX pyrosequencer was the first "next generation", massively parallel sequencer to achieve commercial introduction (in 2004) and uses a sequencing reaction type known as "pyrosequencing" to read out nucleotide sequences. In pyrosequencing, each incorporation of a nucleotide by DNA polymerase results in the release of pyrophosphate, which initiates a series of downstream reactions that ultimately produce light by the firefly enzyme luciferase. The light amount produced is proportional to the number of nucleotides incorporated (up to the point of detector saturation). In the Roche/454 instrument, the DNA fragments to be sequenced first have specific A and B adapter oligos ligated to their ends, and then are mixed with a population of agarose beads whose surfaces carry oligonucleotides complementary to 454-specific adapter sequences on the DNA fragments, such that each bead is associated with a single DNA fragment. By isolating each of these fragment:bead complexes into individual oil:water micelles that also contain PCR reactants, thermal cycling ("emulsion PCR") of the micelles produces approximately one million copies of each DNA fragment on the surface of each bead. These amplified single molecules are then sequenced en masse by first arraying them into a PicoTiter Plate (PTP—a fused silica capillary structure), that holds a single bead in each of several hundred thousand single wells, providing a fixed location at which each sequencing reaction can be monitored. Enzyme-containing beads that catalyze the downstream pyrosequencing reaction steps then are added to the PTP, and centrifuged to surround the agarose beads. On instrument, the PTP acts as a flow cell, into which each pure nucleotide solution is introduced in a stepwise fashion, with an imaging step after each nucleotide incorporation step. Because the PTP is seated opposite a CCD camera, the light emitted at each bead that is being actively sequenced is recorded. In practice, the first four nucleotides (TCGA) on the adapter fragment adjacent to the sequencing primer added in library construction are first to be sequenced, and this sequence corresponds to the sequential flow of nucleotides into the flow cell. This strategy allows the 454 base calling software to calibrate the light emitted by a single nucleotide incorporation, which then enables the software to call novel bases downstream according to the light emission levels. However, the calibrated base calling cannot properly interpret long stretches (>6) of the same nucleotides occurring in a stretch ("homopolymer" run), due to detector saturation, so these stretches are prone to base insertion and deletion errors during base calling. By contrast, since each incorporation step is nucleotide specific, substitution errors are rarely encountered in Roche/454 sequence reads.

Enzyme Inhibitor Screening

The present invention provides a method for screening for an enzyme inhibitor, comprising (a) providing a first sample fluid wherein said first sample fluid comprises an emulsion library comprising a plurality of aqueous droplets within an immiscible fluorocarbon oil comprising at least one fluorosurfactant, said droplets comprising at least one compound; (b) providing a second sample fluid wherein said second sample fluid comprises a plurality of aqueous droplets within an immiscible fluorocarbon oil comprising at least one fluorosurfactant, said droplets comprising at least one enzyme and substrate; (c) providing a microfluidic substrate comprising at least two inlet channels adapted to carry at least two dispersed phase sample fluids and at least one main channel adapted to carry at least one continuous phase fluid; (d) flowing the first sample fluid through a first inlet channel which is in fluid communication with said main channel at a junction, wherein said junction comprises a first fluidic nozzle designed for flow focusing such that said first sample fluid forms a plurality of droplets of a first uniform size in said continuous phase; (e) flowing the second sample fluid through a second inlet channel which is in fluid communication with said main channel at a junction, wherein said junction comprises a second fluidic nozzle designed for flow focusing such that said second sample fluid forms a plurality of droplets of a second uniform size in said continuous phase, wherein the size of the droplets of the second sample fluid are smaller than the size of the droplets of the first sample fluid; (f) providing a flow and droplet formation rate of the first and second sample fluids wherein the droplets are interdigitized such that a first sample fluid droplet is followed by and paired with a second sample fluid droplet; (g) providing channel dimensions such that the paired first sample fluid and the second sample fluid droplet are brought into proximity; (h) coalescing the paired first and second sample droplets as the paired droplets pass through an electric field, and (i) detecting enzyme activity within the coalesced droplets, wherein the failure of the enzyme to convert the substrate to product indicates the compound is an enzyme inhibitor.

The present invention provides compositions and methods for generating, manipulating, and analyzing aqueous droplets of precisely defined size and composition. These microfluidic device-generated droplets can encapsulate a wide variety of components, including those that are used in enzymatic assays. Kinases are a therapeutically important class of enzymes, and this collaboration examines the feasibility of performing analysis and interrogation of kinases with potentially inhibitory compounds using the described microfluidic platform and systems.

High-Throughput Droplet Live-Dead Assay Screening

The present invention provides a method for screening for a live cell, comprising (a) providing a first sample fluid wherein said first sample fluid comprises an emulsion library comprising a plurality of aqueous droplets within an immiscible fluorocarbon oil comprising at least one fluorosurfactant, said droplets comprising at least one cell; (b) providing a second sample fluid wherein said second sample fluid comprises a plurality of aqueous droplets within an immiscible fluorocarbon oil comprising at least one fluorosurfactant, said droplets comprising at least one cell-membrane-permeable fluorescent dye and at least one cell-membrane-impermeable fluorescent dye; (c) providing a microfluidic substrate comprising at least two inlet channels adapted to carry at least two dispersed phase sample fluids and at least one main channel adapted to carry at least one continuous phase fluid; (d) flowing the first sample fluid through a first inlet channel which is in fluid communication with said main channel at a junction, wherein said junction comprises a first fluidic nozzle designed for flow focusing such that said first sample fluid forms a plurality of droplets of a first uniform size in said continuous phase; (e) flowing the second sample fluid through a second inlet channel which is in fluid communication with said main channel at a junction, wherein said junction comprises a second fluidic nozzle designed for flow focusing such that said second sample fluid forms a plurality of droplets of a second uniform size in said continuous phase, wherein the size of the droplets of the second sample fluid are smaller than the size of the droplets of the first sample fluid; (f) providing a flow and droplet formation rate of the first and second sample fluids wherein the droplets are interdigitized such that a first sample fluid droplet is followed by and paired with a second sample fluid droplet; (g) providing channel dimensions such that the paired first sample fluid and the second sample fluid droplet are brought into proximity; (h) coalescing the paired first and second sample droplets as the paired droplets pass through an electric field, and (i) detecting fluorescence within the coalesced droplets, wherein the detection of fluorescence of cell-membrane-permeable dye indicates a droplet comprising a dead cell and the detection of fluorescence of cell-membrane-impermeable dye indicates a droplet comprising a live cell.

Single-cell analysis in the context of cell populations avoids the loss of information on cellular systems that is inherent with averaged analysis. In recent years, this type of analysis has been aided by the development of sophisticated instrumentation. Microfluidic technologies have the potential to enhance the precision and throughput of these single-cell assays by integrating and automating the cell handling, processing, and analysis steps. However, major limitations in microfluidic systems hinder the development of high-throughput screening platforms. One challenge is to achieve sufficiently short mixing times. Mixing under the laminar flow conditions typically found in microfluidic devices occurs by diffusion, a relatively slow process for biological material and biochemical reactants. Most importantly, as the scale of these reactors shrinks, contamination effects due to surface adsorption and diffusion limit both the smallest sample size and the repeated use of channels for screening different conditions. These limitations are major hurdles when this technology is to be applied for screening libraries containing thousands of different compounds each corresponding to different experimental conditions.

The confinement of reagents in droplets in an immiscible carrier fluid overcomes these limitations. The droplet technology is an essential enabling technology for a high-throughput microfluidic screening platform. Droplet isolation allows the cells to be exposed to discrete concentrations of chemicals or factors. Most importantly, the droplet format ensures that the sample materials never touch the walls of the microfluidic channels and thus eliminates the risk of contamination. The reagents can be mixed within a droplet and sample dispersion is simultaneously minimized. The advantages of this technique include the physical and chemical isolation of droplets from one another and the ability to digitally manipulate these droplets at very high-throughput. Finally, the absence of any moving parts and in particular valves brings the degree of robustness required for screening applications.

Possible cell applications include screen for combinatorial cell assays, cloning, FACS-like assays, and polymer encapsulation for cell-based therapies. As a small number of cells are consumed per sample, this technology is particularly suitable for working with cells of limited availability, like primary cells. In addition, for rare cell sorting, the dilution factor in the collection droplets can be orders of magnitude smaller than for a standard bench-scale flow cytometer. Finally, the use of fluorocarbons that can dissolve large amount of oxygen as carrier fluids is regarded as a key feature for long-term survival of encapsulated cells.

Numerous modules have been developed for performing a variety of key tasks on droplets. They include the generation of monodisperse aqueous droplets and its use for cell encapsulation. Droplets can be fused or coalesced, their content mixed, incubated on-chip, and their incubation time tuned with an oil-extractor, their fluorescent content can be interrogated, and finally they can be sorted. The assembly of such modules into complete systems provides a convenient and robust way to construct droplet microfluidic devices that would fulfill the promises of the droplet technology as a screening platform.

Example 9 illustrates some examples of live-dead assays. The device has been designed to sequentially accomplish six different functions: (i) separated cell and dye encapsulations, (ii) fusion of droplets containing cells and droplets containing dyes, (iii) mixing of cell with dyes in each fused droplet, (iv) oil-extraction to modulate on-chip incubation of droplets, (v) droplet incubation on-chip and (vi) interrogation of the fluorescent signal of each droplet. Furthermore, encapsulated cells can be collected into a syringe and re-inject the emulsion for on-chip scoring.

Kits

As a matter of convenience, predetermined amounts of the reagents, compound libraries, and/or emulsions described herein and employed in the present invention can be optionally provided in a kit in packaged combination to facilitate the application of the various assays and methods described herein. Such kits also typically include instructions for carrying out the subject assay, and may optionally include the fluid receptacle, e.g., the cuvette, multiwell plate, microfluidic device, etc. in which the reaction is to be carried out.

Typically, reagents included within the kit are uniquely labeled emulsions containing tissues, cells, particles, proteins, antibodies, amino acids, nucleotides, small molecules, substrates, and/or pharmaceuticals. These reagents may be provided in pre-measured container (e.g., vials or ampoules) which are co-packaged in a single box, pouch or the like that is ready for use. The container holding the reagents can be configured so as to readily attach to the fluid receptacle of the device in which the reaction is to be carried out (e.g., the inlet module of the microfluidic device as described herein). In one embodiment, the kit can include an RNAi kit. In another embodiment, the kit can include a chemical synthesis kit. It will be appreciated by persons of ordinary skill in the art that these embodiments are merely illustrative and that other kits are also within the scope of the present invention.

Enzyme Quantification

Described herein are methods for counting enzyme molecules in fluid partitions such as, for example, microdroplets. A number of readout modes and multiplexing formats are illustrated, and examples of assays coupled to the digital readout are shown.

In some embodiments, methods of the invention include a sandwich immunoassay, allowing for absolute counting of protein molecules in a sample (digital droplet ELISA). Any upfront assay that uses a chemical reaction at least one component of which includes a detectable label (e.g., a reporter enzyme system) can be used. Any suitable detectable label may be included (e.g., a fluorescent product, or other optical or detectable non-optical product) can be used with methods of the invention.

In certain embodiments, the invention provides methods for the direct detection and quantification of enzymatically active molecules potentially contained in samples (e.g., "bio-prospecting"). Reporter substrates specific for the target enzyme or enzyme class are used to assay for enzyme-containing samples (or coupled enzyme and substrates report to report on another enzyme molecule). For example, a sample can be obtained that is suspected to contain a target molecule of interest or a target molecule member of a class of interest. The sample can be distributed into a plurality of fluid partitions. Further, where a specific activity or moiety is of interest or if enzymes having a range or threshold of specific activity are of interest, a large number of targets can be assayed using methods and systems of the invention. The targets can be distributed among a plurality of fluid partitions, and each partition can be provided with reagents for a certain enzyme-catalyzed reaction. The occurrence of the reaction in certain partitions can be detected. Optionally, using sorting methods, enzyme-positive partitions can be isolated for further analysis. Thus, a single (or very low amount of) target, even an unknown target, can be identified and isolated according to activity. Further discussion can be found in Miller, et al., PNAS 109(2):378-383 (2012); Kiss, et al., Anal. Chem. 80(23):8975-8981 (2008); and Brouzes, et al., Droplet microfluidic technology for single-cell high-throughput screening, 10.1073/PNAS.0903542106 (Jul. 15, 2009), the contents of which are hereby incorporated by reference in their entirety.

Methods of the invention allow for the detection of two or more enzyme molecules or other molecules in a complex that can be assayed using an enzymatic reporter or other activatable and readable reporter (e.g. protein aggregation assay for mis-folded or disease associated molecules). Methods include providing separately detectable substrates for each enzyme species or where complexes/aggregates are detected by different product concentrations using the same enzyme type. A complex can be detected as both product signals are detected in the same fluid partition even when the fractional occupancy is low. For example, at very low fractional occupancies, there is a vanishing probability of the two enzymes being found in some number of the same fluid partitions if not in a complex together (modeled according to Poisson statistics). Thus, the detection of both product signals reveals a protein-protein interaction between the two enzymes.

A number of examples are shown utilizing 'endpoint' type digital counting, where the enzymatic reaction has reached a plateau. More than one endpoint can also be used for detection of multiple species. The invention further includes measurements at earlier time points during the reaction ('kinetic' measurements vs. 'endpoint' measurements) such that different signal intensities from single enzyme molecules reflect differences in enzymatic specific activity, the presence of inhibitory or activating molecules, or the presence of more than one enzyme molecule per droplet. Kinetic mode measurements can be made following droplet incubation at the appropriate temperature either off chip or on chip. For on-chip measurements, a 'timing module', such as a delay line, can be used to keep droplets on-chip for an appropriate length of time, and one or multiple measurement points along the length of the microfluidic channel can enable very precise kinetic measurements. A delay line can include, for example, a channel in a chip through which droplets flow. A delay line may include locations for stopping droplets, or locations for moving droplets out of the may stream of flow, or locations for droplets to separate from the oil by buoyancy differences between the oil and the droplets. A delay line may include a means of adding or removing oil to speed up or slow down the rate of travel of droplets through the delay line. A delay line may include neck-downs or other features to homogenize the average velocity of the droplets and minimize dispersion effects as droplets travel through the channel. A droplet trap may be utilized to trap droplets for a fixed period of time before releasing the droplets. Such a trap may include a valve, or require the reversal of the direction of flow through the trap region to release the trapped droplets or it may require that the chip be flipped over to reverse the direction that the droplets move in the gravitational field. One skilled in the art will recognize a number of ways to control the timing of the reaction. A portion of the channel may have a much broader cross-sectional area that upstream or downstream portions. Thus, for a certain volume per time flow rate, the distance per time flow rate in the broad portion will be much slower. Working with fluidic chips and known droplet behaviors, a channel can be designed with a delay line that delays the flow for a predetermined amount of time. This can allow reactions to incubate or progress for the appropriate amount of time. Temperature control of specific regions may be included in chip designs and interfaces with the chips.

Analyte or reporter molecule may also include non-enzyme species, provided the molecule or complex participates in generation of a readable signal (e.g. an enzymatic activator or inhibitor).

In general, the invention provides methods and systems for measuring a molecular target. A plurality of fluid partitions are formed. Fluid partitions can be any known in the art such as, for example, wells on a plate or water-in-oil droplets. A detectable reaction, such as an enzyme-catalyzed reaction, is performed in some subset of the fluid partitions. For example, where a sample suspected of containing the molecular target is separated into the fluid partitions (including via an optional dilution or serial dilution step), the subset of partitions that contain the target will include a certain number of partitions. That number can be associated with the amount of target in the sample.

A detectable reaction occurs in the subset of partitions that contain the molecular target. In some embodiments, the molecular target is an enzyme, and all of the partitions are provided with a fluorescently labeled substrate. The enzyme-catalyzed reaction can release the fluorescent label from the substrate such that the fluor becomes un-quenched or can be quantified by its location in the partition. In certain embodiments, the target is a substrate, and all of the partitions are provided with an enzyme and optionally an additional substrate or a co-factor. One of the reaction ingredients contains a molecular label that is released when the reaction occurs.

Because a productive reaction only takes place within the subset of partitions that contain the target, determining the number of partitions within which the reaction takes place (i.e., determining the number of the subset) allows one to determine the amount of target in the original sample. Since each partition is counted as reaction-positive or reaction-negative (e.g., in the subset or not), this detection is said to be digital. This includes cases where the positives can be further quantified as containing quantized numbers of targets.

In certain embodiments, digital detection operates through a reaction that includes a number of stages including, in various embodiments, enzymes that are themselves substrates for other enzyme-catalyzed reactions and substrates and/or enzymes or targets that are dark (i.e., not reporting) when participating in reactions and that are detectable when not. To illustrate, in certain embodiments, a partition includes an enzyme and a substrate which together will report the presence and number of target molecules. The substrate is labeled such that it gives a dark state as long as the enzyme is present. A target molecule that inhibits the enzyme can be assayed for according to the steps described herein. Since the target inhibits the reporting enzyme, then presence of the target will cause the reporter to generate a readable signal.

In certain embodiments, a substrate is included in a reaction mixture along with an enzyme that catalyzes a readable reaction of the substrate, but the included enzyme is in an inactive form and exposure of the included enzyme to the target molecule will catalyze its conversion to an active form. In this fashion, the presence or absence of target initiates an enzyme cascade that results in a readable assay (the cascade can include multiple steps) and quantified. In one embodiment, an apoenzyme is used to detect the presence of a protease. The apoenzyme is provided in a fluid partition with a substrate of the active form of the enzyme. The apoenzyme will only be cleaved to form the active form if the protease is present in the target sample.

The invention further provides methods and systems for detecting or quantifying the presence of an enzyme inhibitor or activator. For example, fluid partitions can be provided with an enzyme and its substrate. A sample suspected to contain an inhibitor or activator is separated into the partitions (with optional dilution). Release of a reporter via an enzyme catalyzed activity indicates the presence of an activator or absence of an inhibitor. Further, enzyme kinetics as well as inhibition or activation can be studied with methods described herein.

Methods of the invention can be used with any suitable enzyme(s) or substrate(s). For example, beyond the variety of examples given herein, the invention can further be used to detect cleavage of a peptide by a protease. Where a sample is suspected to contain a protease, a fluorescently labeled peptide substrate can be provided in the fluid partitions.

As another example, methods of the invention can include use of a polymerase enzyme and fluorescently labeled nucleotides to detect activity of a ligase. Given the appropriate conditions, the polymerase will only act on a product of a reaction catalyzed by the ligase (e.g., a polynucleotide). When the polymerase catalyzes a reaction it releases the fluorescent reporter as a readable signal.

In one other illustrative example, the presence, type, and number of restriction enzyme(s) can be quantified by providing a construct that includes an oligonucleotide with a fluor and a quencher close enough to each other that the quencher quenches the fluor but is separated by a restriction site. The presence of the restriction enzyme in the target sample will light up what is otherwise a dark fluid partition. The presence, type, and number of a set of analytes can be assayed using restriction enzymes that are specific for different readable substrates, or can be configured into a 'one-of-many' type of assay where all the analytes have the same restriction enzyme and substrate, or can be grouped into different classes using enzyme/substrate classes.

In certain embodiments, the invention provides systems and methods for detecting and quantifying classes of enzymes or substrates. Any class of target can be the subject of an assay including, for example, all enzymes exhibiting a certain activity or all enzymes in a certain taxonomic group.

Another embodiment includes a downstream reporter that is split (e.g., split green fluorescent protein or a split enzyme reporter) into multiple parts that do not interact productively in the absence of the upstream reporter (e.g. cleavage of the modified downstream reporter by the upstream reporter enzyme-oligo-modified reporter activated by the action of a restriction enzyme or a peptide-modified reporter activated by protease reporter), or that require being brought into close proximity for activity (e.g. following cleavage of the inhibiting modification, two halves of a split enzyme are brought into proximity for folding and activation). Two subsections of the reporter can be separated by an oligo containing a restriction site such that if the restriction enzyme (or, remembering that an enzyme can in turn be a substrate for another enzyme, an enzyme that activates the restriction enzyme) is present, the oligo is cleaved and the two subsections can come together to form the active reporter. Alternatively, cleavage of linked moieties can release inhibition of an activity that produces a readable signal.

One of skill in the art will recognize that any number of the examples given herein can be combined to create multi-step assays. Thus, for example, a restriction enzyme can cleave an oligo that is separating two halves of a protease. The active protease can cleave an apoenzyme to release an active phosphorylase that phosphorylates and de-activates a downstream enzyme. If the downstream enzyme is an inhibitor of a final enzyme, then deactivation of a downstream enzyme can result in activity of the final enzyme. One of skill in the art will recognize the wide variety of combinations of the scenarios given herein that can be used.

Figure 8B:
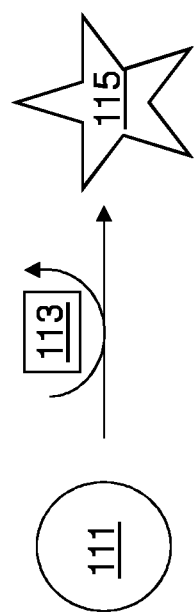
FIGS. 8A-8G show droplet formation and detection of reaction positive droplets.
Figure 8A:
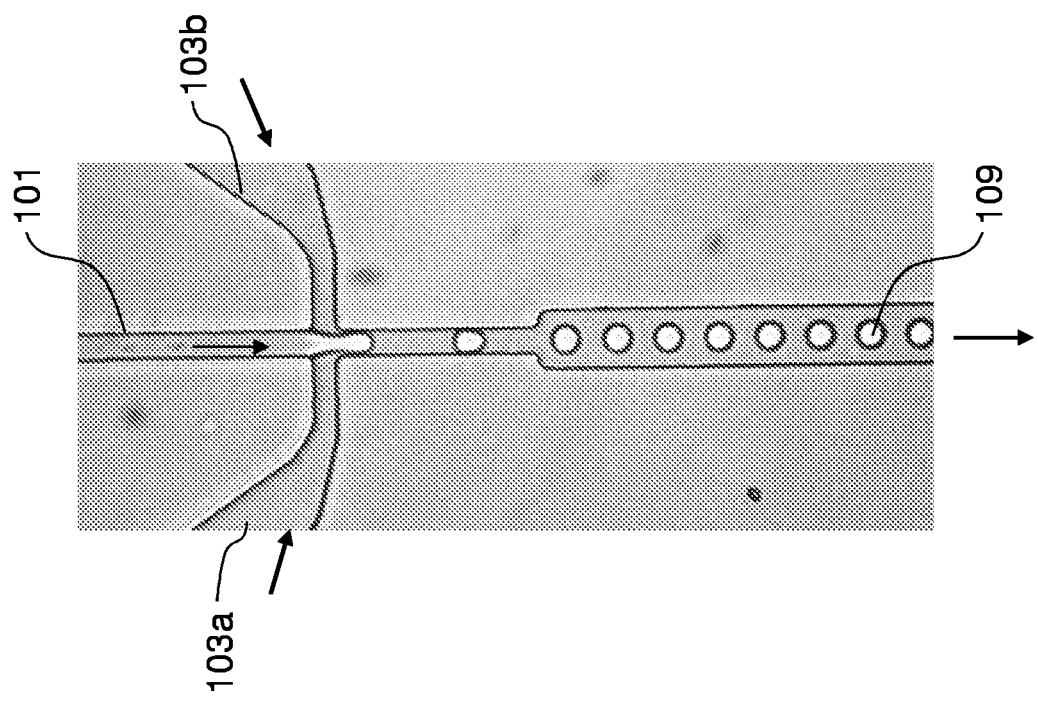

FIGS. 8A-8G show a workflow example for a digital droplet reporter enzyme assay. In FIG. 8A, the enzyme molecules to be counted are mixed with a fluorogenic substrate and loaded into droplets via introduction into a microfluidic nozzle. The aqueous mixture of enzyme and substrate flows down inlet channel 101 and forms an emulsion when merged with oil from carrier fluid channels 103$a$ and 103$b$. In FIG. 8A, arrows indicate the direction of flow. The co-infusion of an immiscible oil segments the aqueous stream into a number of uniformly sized droplet 109.

The droplet emulsion is collected into a suitable container for off-chip incubation at an appropriate temperature for enzymatic function.

FIG. 8B illustrates a schematic overview of a reaction according to certain embodiments of the invention. In general, as shown in FIG. 8B, an enzyme 113 catalyzes the conversion of a fluorogenic substrate 111 to a fluorescent product 115.

In one exemplary embodiment, enzyme 113 was streptavidin-conjugated beta galactosidase (β-gal) (Calbiochem product #569404 from Merck KGaA (Darmstadt, Germany)) and fluorogenic substrate 111 was fluorescein di-β-D-galactopyranoside (FDG) sold under the trademark MOLECULAR PROBES as product number F1179 by Life Technologies (Carlsbad, Calif.), with active enzyme able to cleave the substrate to release, as fluorescent product 115, fluorescein isothiocyanate (FITC) and two galactose.

Figure 8E:
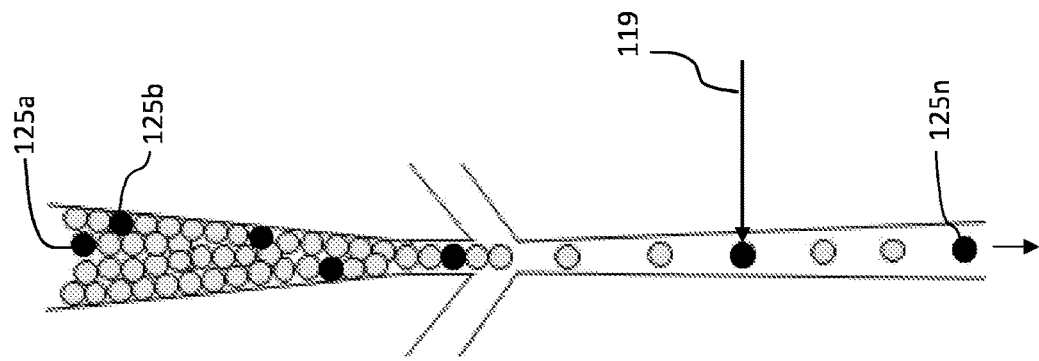
Figure 8D:
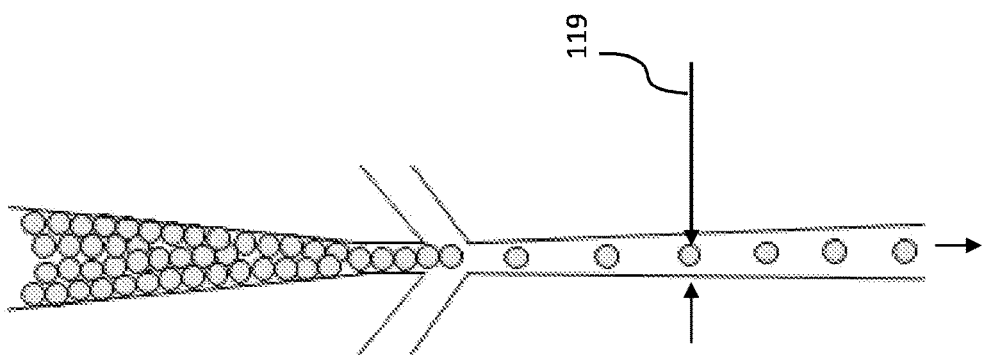
Figure 8C:
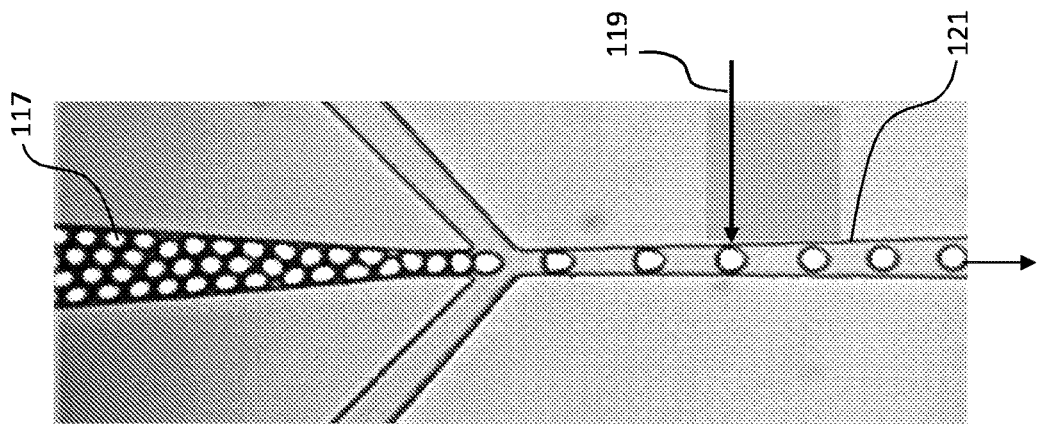
Figure 8F:
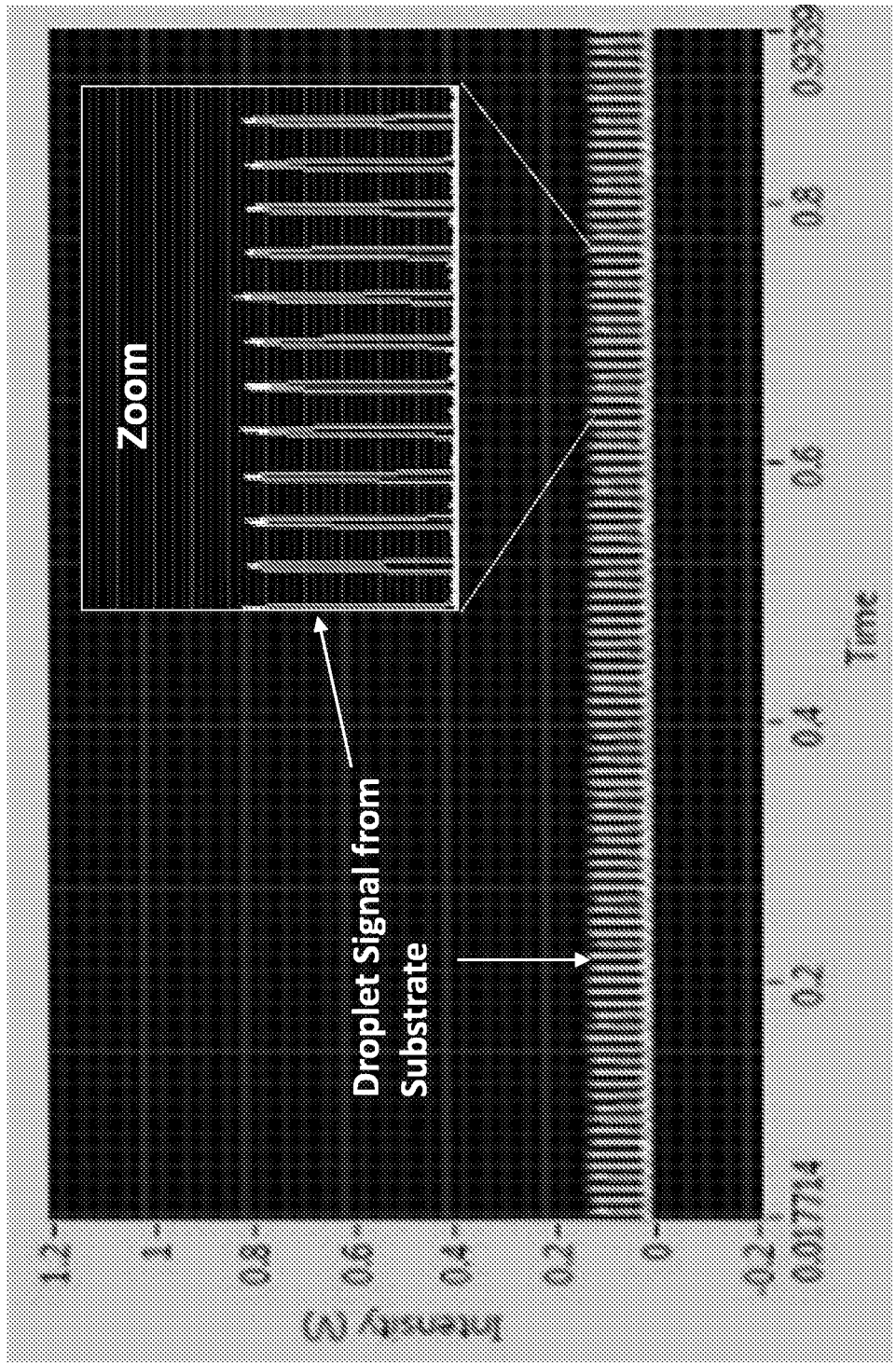

As shown in FIG. 8C, after incubation of the droplet emulsion at 37° C. for a determined time, the droplet temperature can be changed such that the enzyme is no longer affecting the readable signal, and the droplets can be infused into a second microfluidic nozzle 117, spaced into a train of individual droplets using an immiscible oil, and run past laser spot 119 focused in microfluidic channel 121. FIG. 8D is an illustration depicting the detection step when no enzyme is present (or after enzyme is loaded but before incubation). The droplets in FIG. 8D all exhibit uniformly low fluorescence intensity, indicating a lack of conversion of substrate 111 to product 115.

As discussed with reference to FIGS. 8C-8E, detection can include droplets flowing past a detector. However, any suitable method of detecting an enzymatic reaction in a fluid partition can be used including, for example, optical or non-optical detection such as pH change or change in impedance or conductivity within a fluid partition, or any other suitable detection method. In some embodiments, non-optical detection includes nuclear magnetic resonance (NMR) analysis of materials from fluid partitions. Detection after release of the digitally generated reporter moieties from the partitions may also be used (e.g. array, electrode, magnet, sequencer, mass spectrometer, other methods).

FIG. 8E is an illustration depicting the detection step when a low concentration of enzyme is present, after incubation. Laser spot 119 is used to detect a number n of positive droplets 125$a$, 125$b$, . . . , 125$n$. By counting the results of laser detection, the number of partitions (here, droplets) in the subset of partitions in which an enzyme-catalyzed reaction occurred is determined.

Figure 8G:
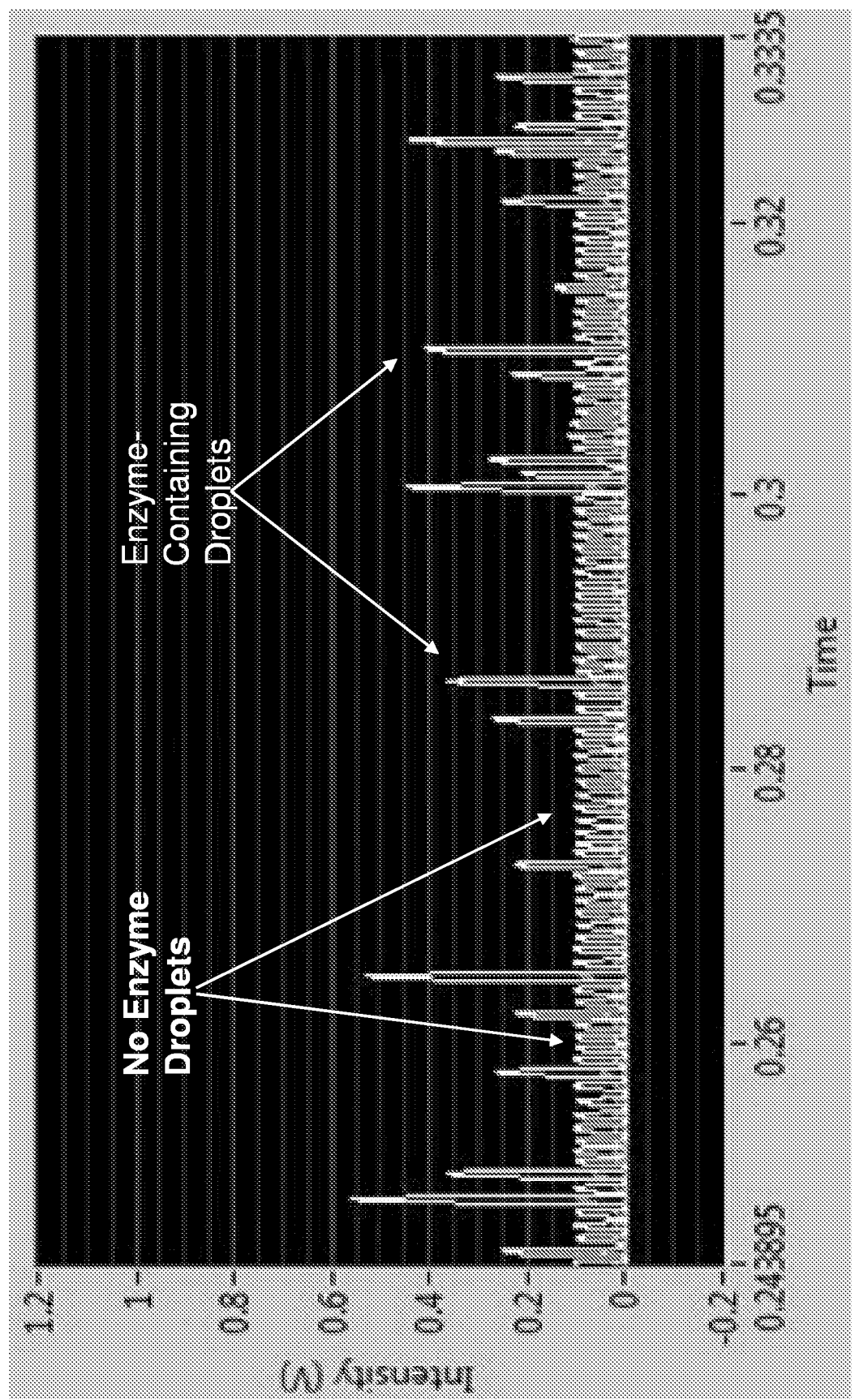
Figure 9A:
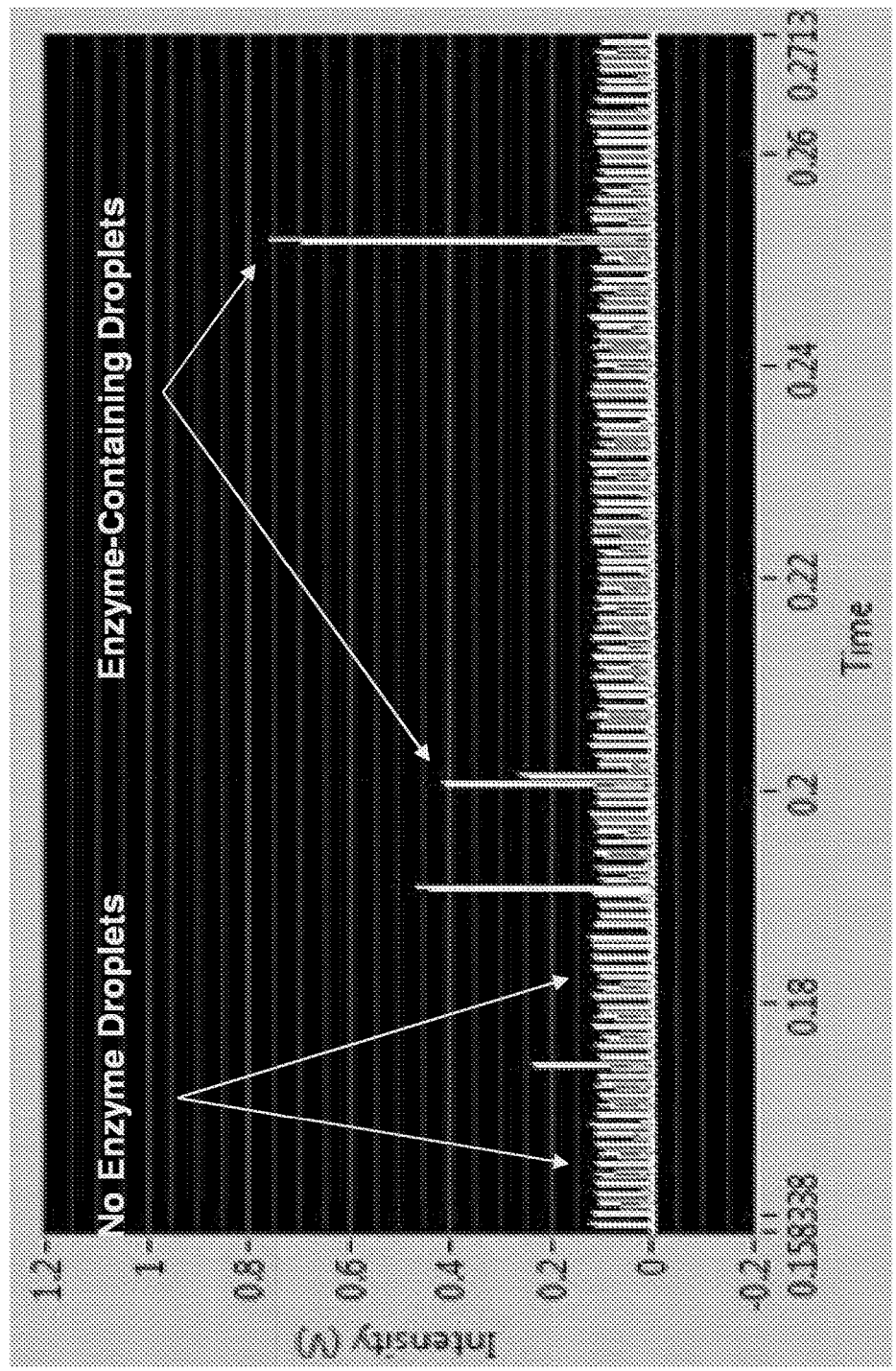
FIGS. 9A-9D show readouts of time traces at different enzyme concentrations. Time traces show digital reactions in droplets at low enzyme concentrations.
Figure 9B:
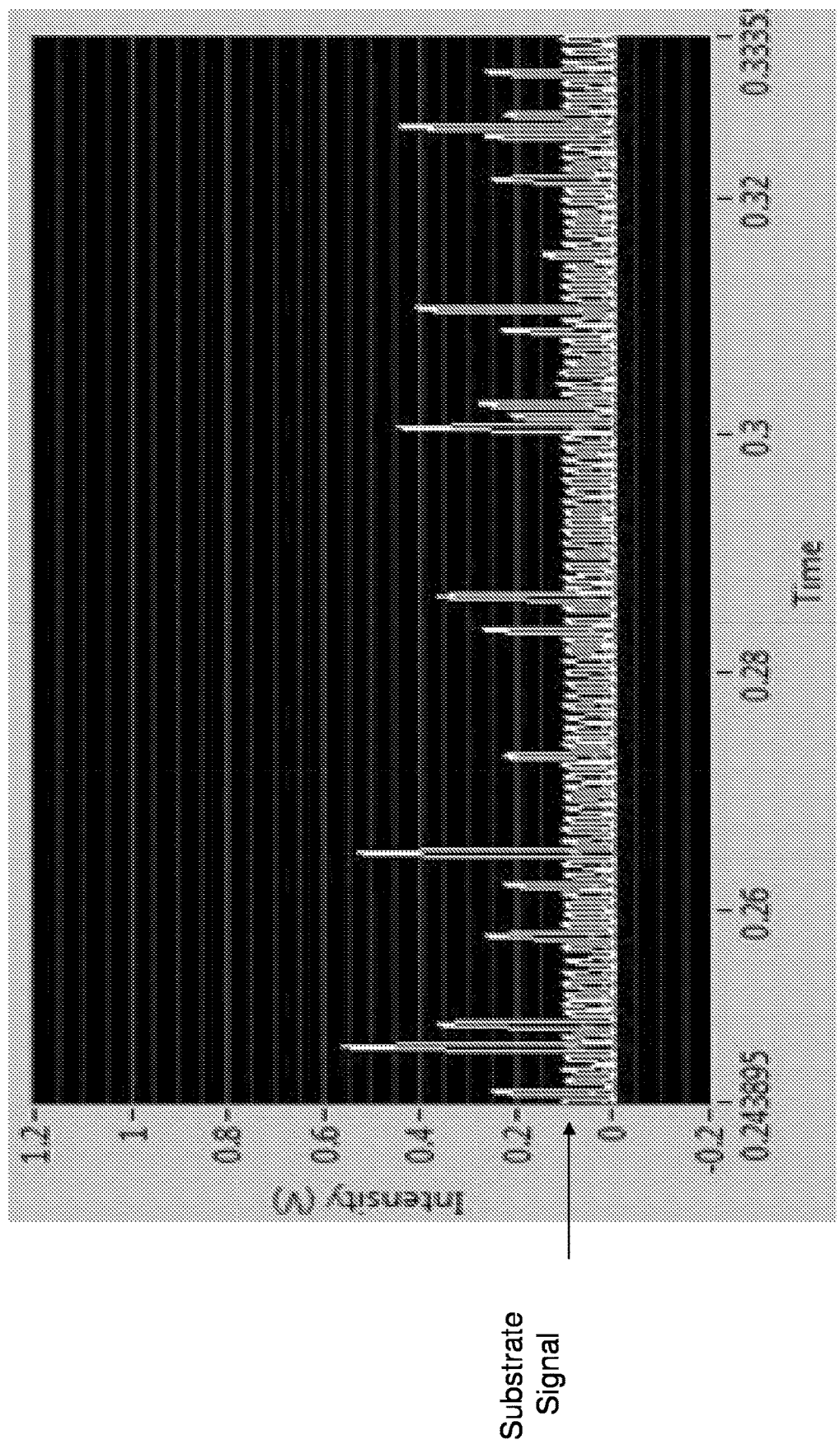
Figure 9C:
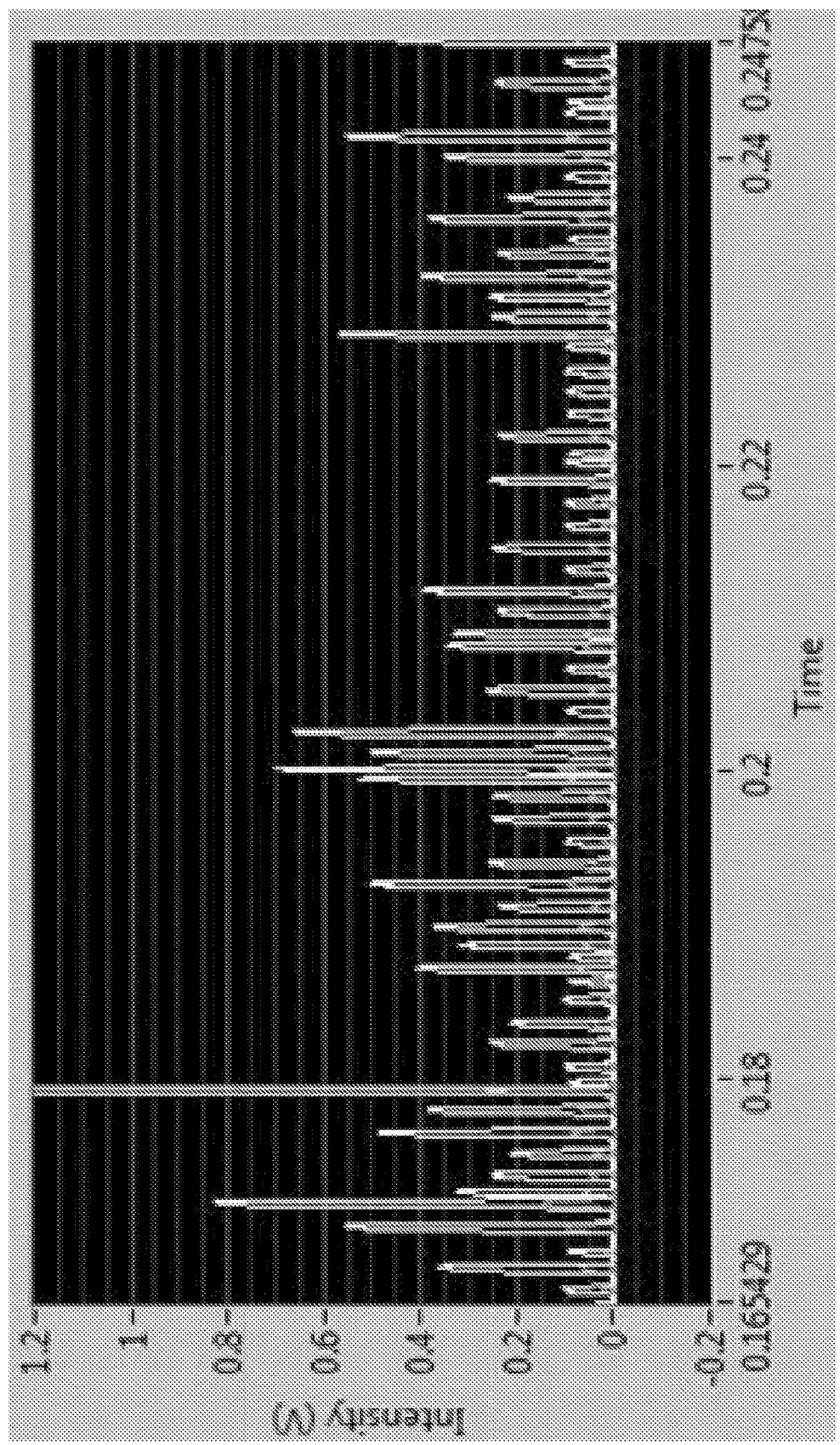
Figure 9D:
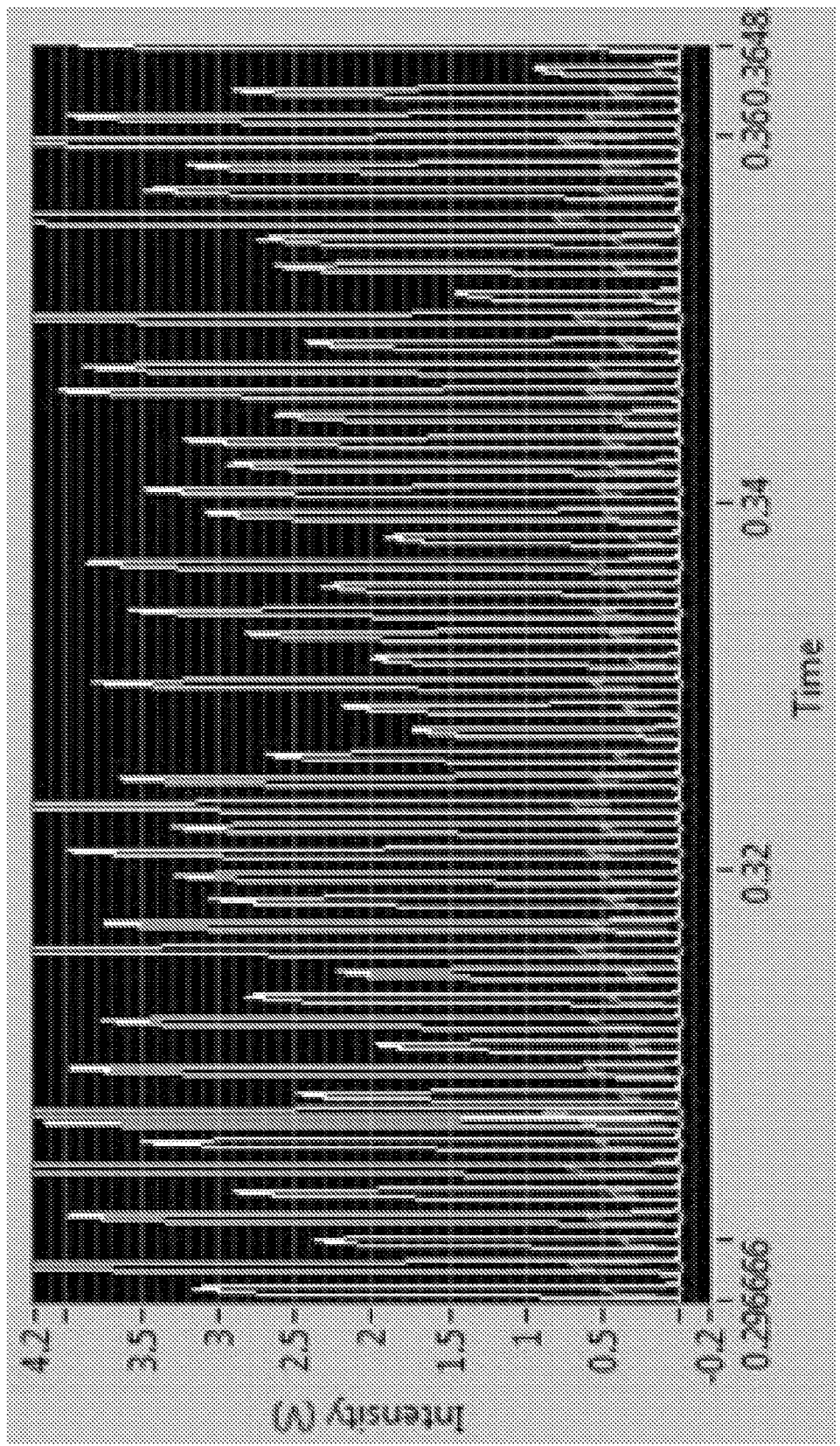

The resulting signal time traces from detection photomultiplier tubes show examples for when either there were no enzyme molecules loaded or after loading enzyme molecules but before incubation (shown in FIG. 8F with an insert showing a zoomed image of 10 individual droplet traces), and droplets generated with a low concentration of enzyme after incubation (FIG. 8G). The droplets that have no enzyme molecules (or have enzyme molecules that were not incubated to allow for enzymatic activity) show uniformly low fluorescent signal intensity, coming from the unconverted fluorogenic substrate. For the case where a low concentration of enzyme was used (see FIG. 8G) loading of enzyme molecules into droplets occurs in a quantized manner, with the signal time trace showing droplets that have no enzyme molecules (with similar signal intensity to that seen at generation) and droplets with enzyme molecules (showing quantized levels of signal intensity that correspond to different numbers of enzyme molecules per droplet).

The distribution of the number of enzyme molecules per droplet (i.e. 0, 1, 2, 3, etc. molecules per droplet) is dependent on the starting concentration of enzyme loaded into the droplets and the whether the enzyme molecules are in un-dissociated complexes. FIGS. 9A-9D and FIGS. 10A-10D illustrate this phenomenon, showing the time traces (FIGS. 9A-9D) and histogram distributions (FIGS. 10A-10D) for increasing concentrations of β-gal, as shown by fluorescent intensity of FITC (lowest concentration shown in FIGS. 9A and 10A, highest concentration shown in FIGS. 9D and 10D). These measurements were made on droplets that had been incubated for about an hour. As the starting enzyme concentration is increased, the time traces show the number of 'negative' (no enzyme) droplets decrease, the number of 'positive' droplets increase, and the number of enzyme molecules in any positive droplet increases (seen as a higher signal intensity).

Figure 10A:
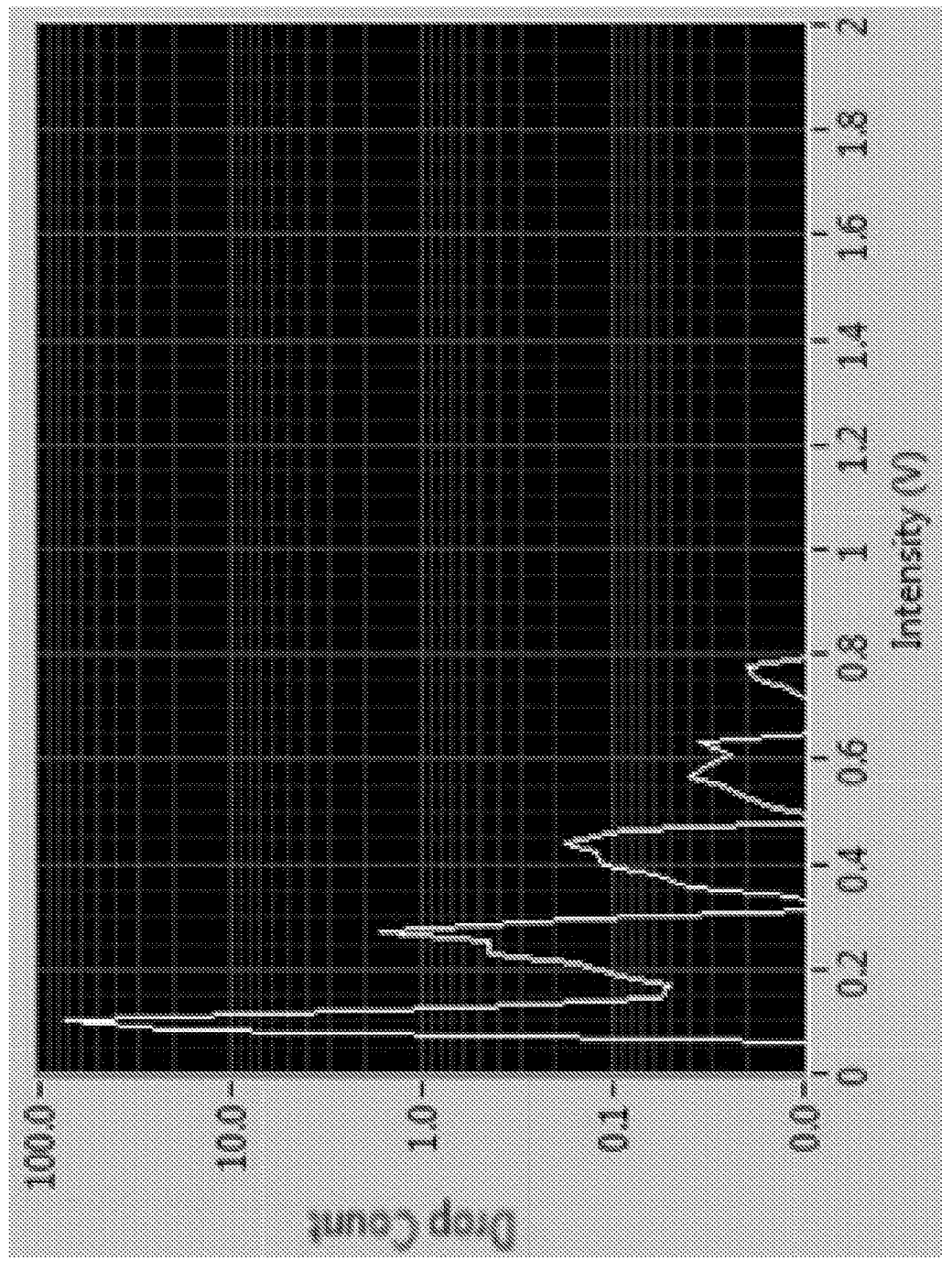
FIGS. 10A-10D show readouts of histograms. Increasing enzyme concentrations shifts the distribution from quantized to average regime.
Figure 10B:
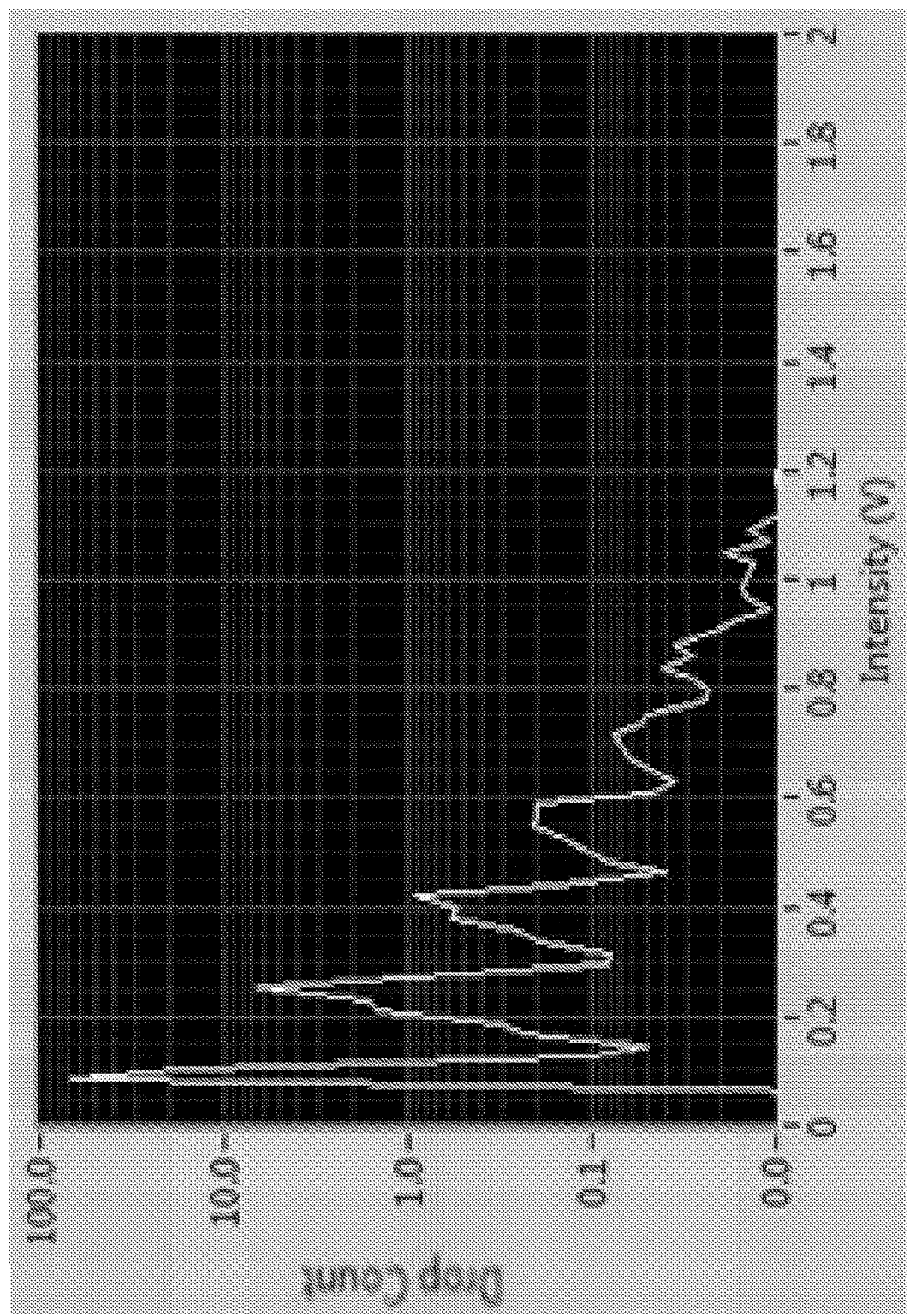
Figure 10C:
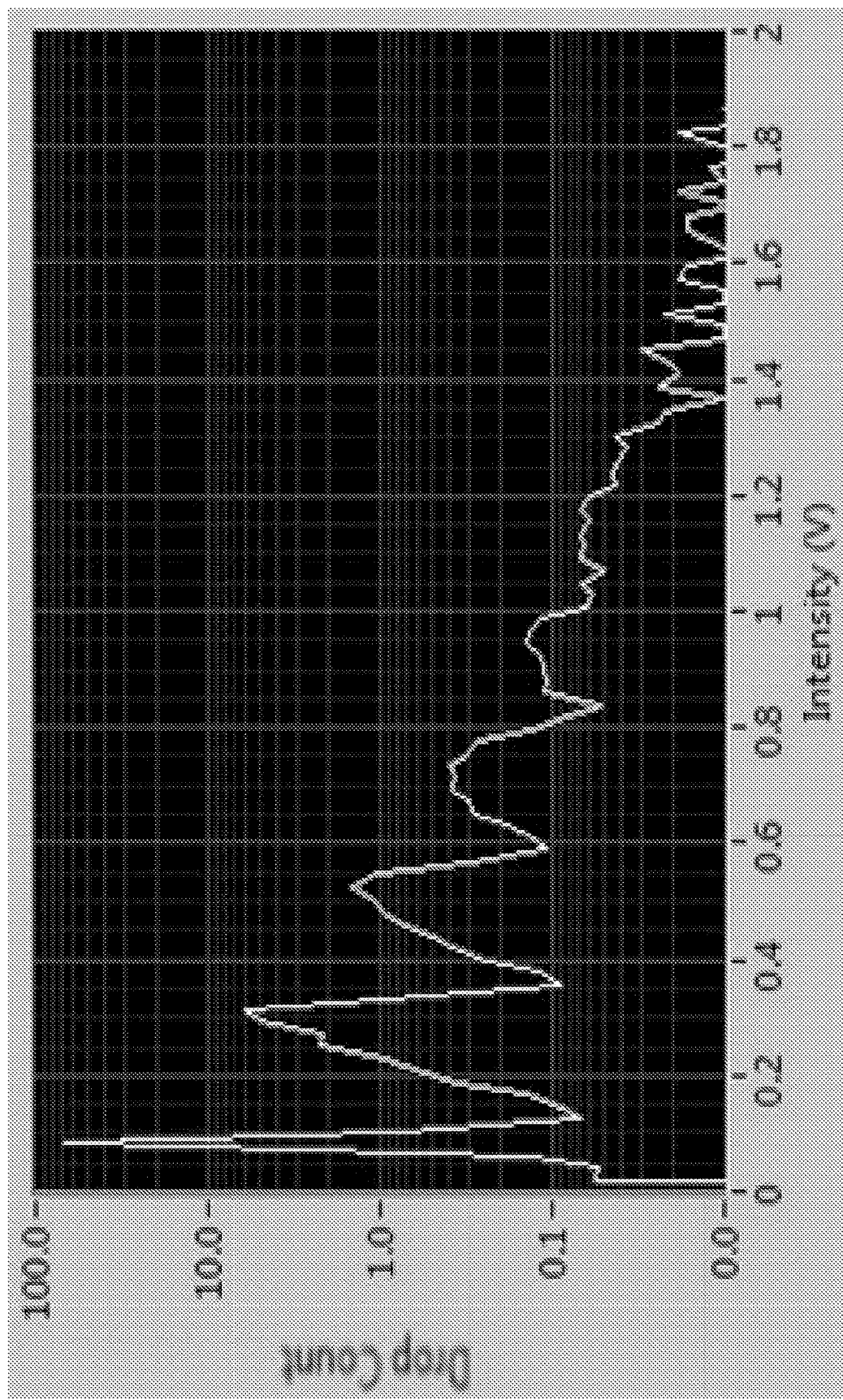
Figure 10D:
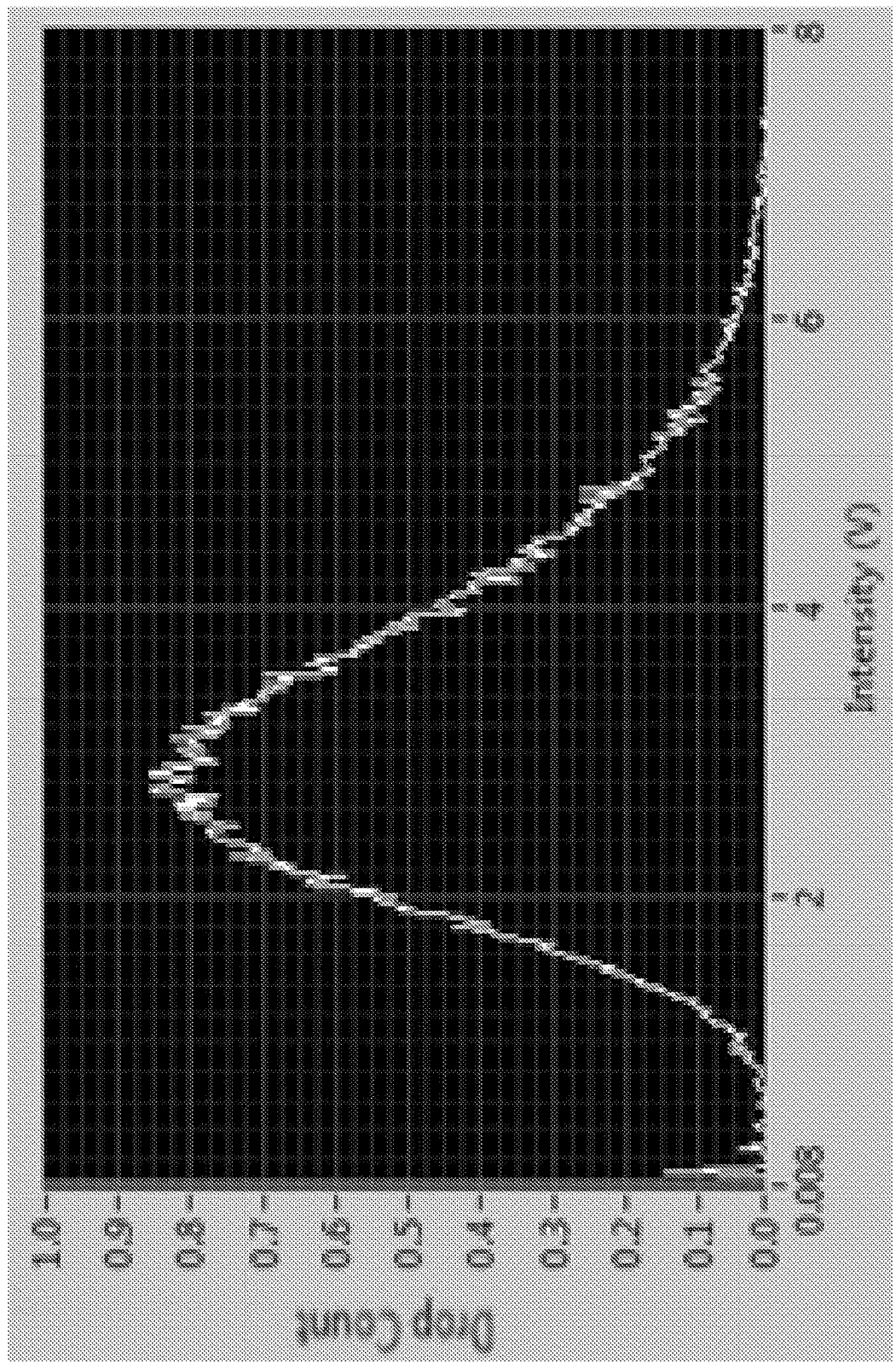

The distribution of enzyme molecules into droplets can occur according to a Poisson Distribution, or can occur in a non-Poisson fashion. FIG. 10A shows a non-Poisson distribution. In some cases the degree to which the distribution varies from a Poisson distribution will be indicative of a degree of aggregation of the component. In some cases the interpretation of the variation from a Poisson distribution will be diagnostic. In FIG. 10A, the x-axis is given in volts indicting reporter intensity as measured through a photomultiplier. An appropriate scaling factor can be used (e.g., determined separately) to convert V to number of molecules per droplet. As shown in FIG. 10A, the first peak at about 0.1 V can indicate a number of the droplets (i.e., Drop Count) that had no s-gal activity in them. The second peak about 0.23 V can indicate a number of droplets that each had one active unit of enzyme. The third peak about 0.42 V can indicate a number of droplets that each contained two active units of enzyme. The fourth peak, at about 0.58 V, can indicate a number of droplets that contained three units of active enzyme. The fifth peak, at about 0.76 V, can indicate a number of droplets that contained four active units of enzyme. FIGS. 10B-10C show greater concentration of enzyme (i.e., less dilution). In certain embodiments, for an enzyme that exhibits no aggregation or covalent or non-covalent complex formation, a plot at the concentration illustrated in FIG. 10A would show a Poisson distribution. FIG. 10A can indicate that a substantial and statistically significant number of droplets contain more than 1 enzyme unit than is predicted by Poisson. Thus, FIG. 10A can show that β-gal exhibits aggregation. When the starting enzyme concentration is 1.6 pM (FIGS. 9D and 10D, there are no negative droplets, and the histogram shows most droplet signals centered around a single mean value, with a much smaller number showing a quantized distribution like that seen at lower concentrations (several small peaks close to the origin).

Figure 11A:
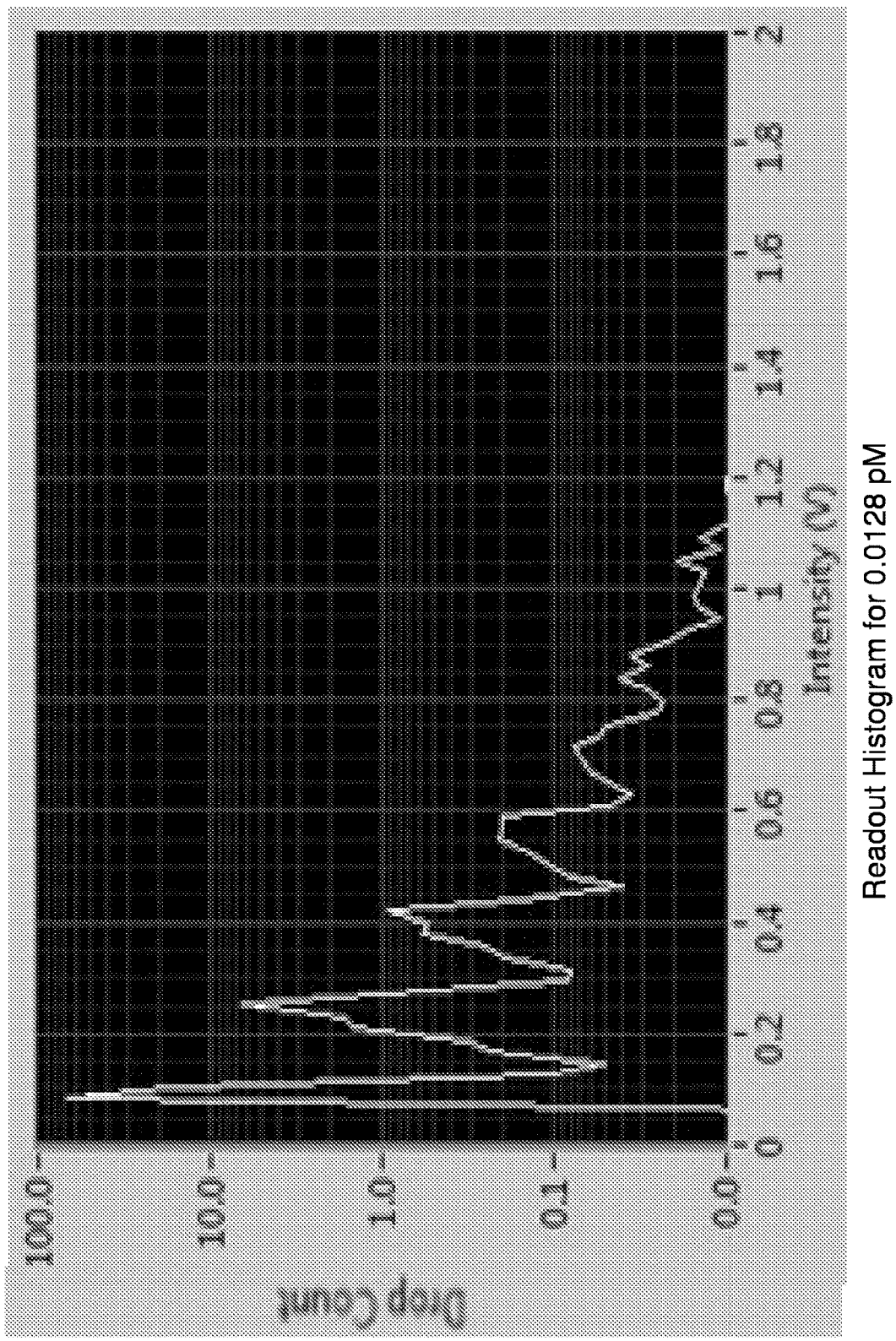
FIGS. 11A and 11B illustrate concentration determination using digital droplet data. Digital counting measurement of enzyme concentration matches known starting amount.
Figure 11B:
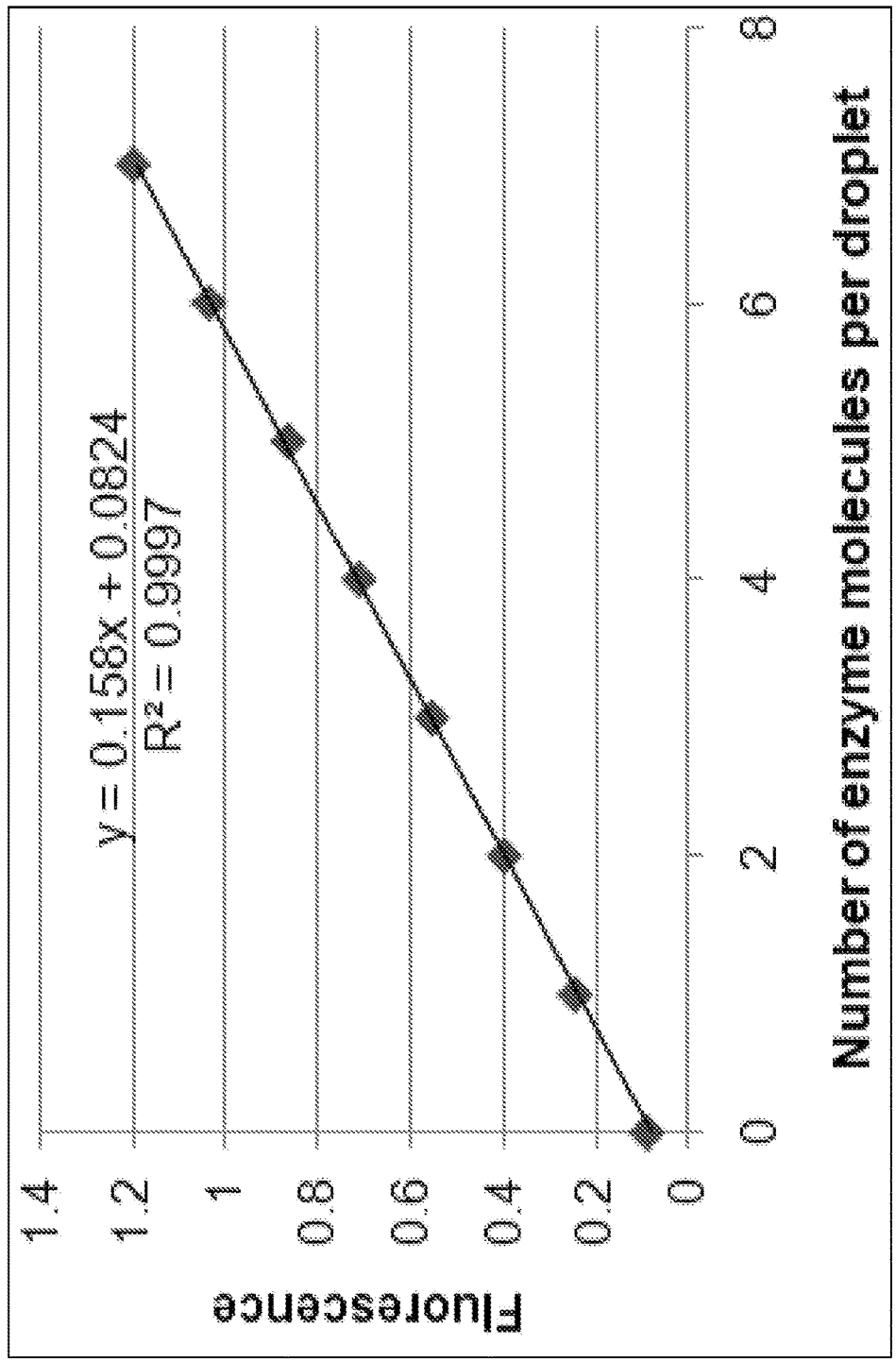

FIGS. 11A and 11B show an example of how this data can be used to quantify the concentration of active enzyme molecules loaded into droplets. FIG. 4A shows a readout histogram from an enzyme concentration that was calculated to be 0.0128 pM. Using the histogram from an enzyme concentration calculated to be 0.0128 pM, based on multiplying the starting concentration and the dilution factor (FIG. 11A), each peak's mean is determined and plotted as a function of integer enzyme molecules to show linearity (FIG. 11B). The number of droplets within each peak and the number of active enzyme molecules within each peak are counted and tabulated. The results are listed in Table 1.

TABLE 1

Distribution of #Droplets with #Molecules

| Enzyme/droplet | Droplets | #enzymes |
| --- | --- | --- |
| 0 | 113458 | 0 |
| 1 | 15249 | 15249 |
| 2 | 3637 | 7274 |
| 3 | 1356 | 4068 |
| 4 | 536 | 2144 |
| 5 | 280 | 1400 |
| 6 | 139 | 834 |
| 7 | 73 | 511 |
| >7 | 138 | 1405 |
| Total: | 137866 | 32885 |

By dividing the totals from Table (number of active enzyme molecules over total number of droplets counted) a number of molecules per droplet can be calculated as shown in Equation 1.

$$(\#molecules/droplet) = (32885/134866) = 0.24 \quad (1)$$

By multiplying by the appropriate scaling factors, the measured concentration (MC) can be calculated using Equation 2:

$$MC(pM) = \frac{\# \text{ molecules}}{\text{droplet}} \times \frac{\text{droplet}}{\text{volume } (pL)} \times \frac{1.0 \text{ pM}}{\frac{0.6023 \text{ molecules}}{pL}} \quad (2)$$

Using the value given by Equation 1 in Equation 2, gives the result shown in Equation 3.

$$MC(pM) = \frac{0.24 \text{ molecules}}{\text{droplet}} \times \frac{\text{droplet}}{30 \text{ pL}} \times \frac{1.0 \text{ pM}}{\frac{0.6023 \text{ molecules}}{pL}} = 0.01275 \text{ pM} \quad (3)$$

For this example, the measured concentration was 0.01275 pM, with the expected concentration based on dilution factor being 0.0128 pM.

The dynamic range of the assay can span regimes where the number of enzyme molecules is discretely quantized in all droplets or where the majority of droplets (or all droplets) contain a mean (with a distribution around the mean) number of enzyme molecules. For the specific format described in the example (i.e. droplet size, enzyme and substrate used) typically enzyme concentrations greater than ~pM can be analyzed using the mean distribution (and also the small quantized tail seen near the origin of the graph shown in FIG. 10D) and enzyme concentrations lower than ~pM can be analyzed using digital counting of the total number of droplets, the number of enzyme-containing droplets, and using the quantized signals from enzyme-containing droplets to count the number of enzyme molecules per droplet. Thus, the dynamic range of the assay is extremely wide, with the lower limit of detection determined by the number of detectable molecules present in the sample and the length of time required to run a sufficient number of droplets through the detector (e.g. if the droplet system runs at $10^6$ droplets per hour, the limit of detection is 1 in $10^6$ in an hour, and the limit of detection is 1 in $10^7$ in 10 hours), and the upper limit determined by the amount of substrate converted to product (as enzyme concentrations get higher, the substrate concentration will have to increase in order for the product fluorescence to remain linearly (or correlatively) related to enzyme mean concentration). Additional parameters that can be adjusted include the time and temperature of incubation, as well as the droplet volume used, and additional reaction components. In certain embodiments, fluid partitions are droplets and assays are performed in systems in which droplets are run past a detector at 3,000 s. In some embodiments, droplets are run at 10,000/s or at about 100,000 per second. In some embodiments, a lower limit of detection is 1 in $10^9$ and a flow rate is $10^9$ per hour.

Figure 12:
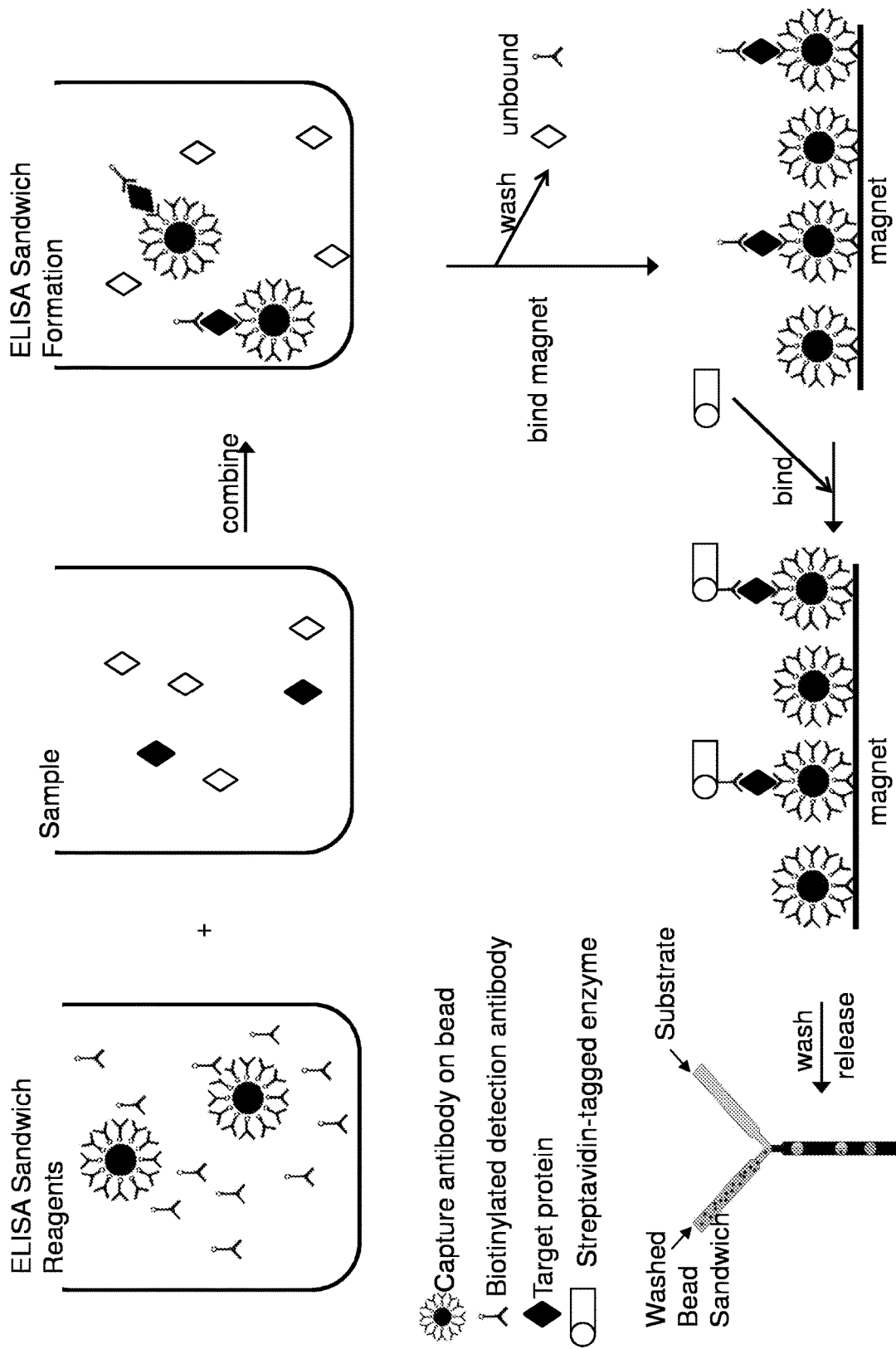
FIG. 12 is a schematic showing sandwich formation for digital droplet ELISA.

FIG. 12 shows an illustration of the concept and workflow for a digital droplet ELISA assay, one example of an upfront assay that can be coupled to the digital reporter enzyme assay readout. When protein concentrations are too low for standard detection methods (typically low-sub-picomolar), this invention enables protein quantification by counting individual protein molecules with a fluorescent readout. Droplets containing a single molecule (e.g. in an ELISA sandwich) will be fluorescent, and the number of fluorescent droplets in a population of total droplets will yield a digital count of molecules per volume (i.e. concentration) down to a limit of detection dependent only on the number of droplets examined.

FIG. 12 shows one example ELISA assay format and should not be considered the only or preferred format (e.g. magnetic beads could be added following antibody binding in solution). The protein-containing sample (three proteins shown as diamonds with the rare target protein to be counted shown as solid diamonds) is combined with the binding reagents and incubated for a sufficient time to bind into productive complexes.

In the "ELISA Sandwich Formation" step, each target protein molecule is bound to two affinity reagents (each binding separate epitopes of the same target molecule), generating an immunoaffinity "sandwich" complex. In the example shown, one of the affinity reagents (e.g. antibody) is immobilized onto a magnetic bead while the other biotinylated antibody is free in solution. In certain embodiments, the number of magnetic beads (with immobilized antibody) is significantly greater than the number of target proteins in solution, so that single target proteins are bound by single beads. If the second antibody is used at the same time, its concentration should be greater than the number of target molecules, but less than the number of immobilized antibodies. Alternatively, the second antibody can be added following the first binding step (ensuring that all target molecules are bound to the immobilized antibody first).

After the target proteins are bound into sandwich complexes, the magnetic beads are retained by a magnetic field to allow removal of unbound non-target proteins and free antibodies, and washed to remove non-specific binders. Addition of the reporter enzyme (e.g. streptavidin-beta galactosidase) results in binding to the second biotinylated antibody and assembly of the final ELISA sandwich, which is again washed to remove unbound reporter enzyme. The final material (see, e.g., FIG. 13A) is re-suspended in a small volume, along with a fluorogenic substrate, for processing in the digital droplet readout.

Figures 13A, 13B:
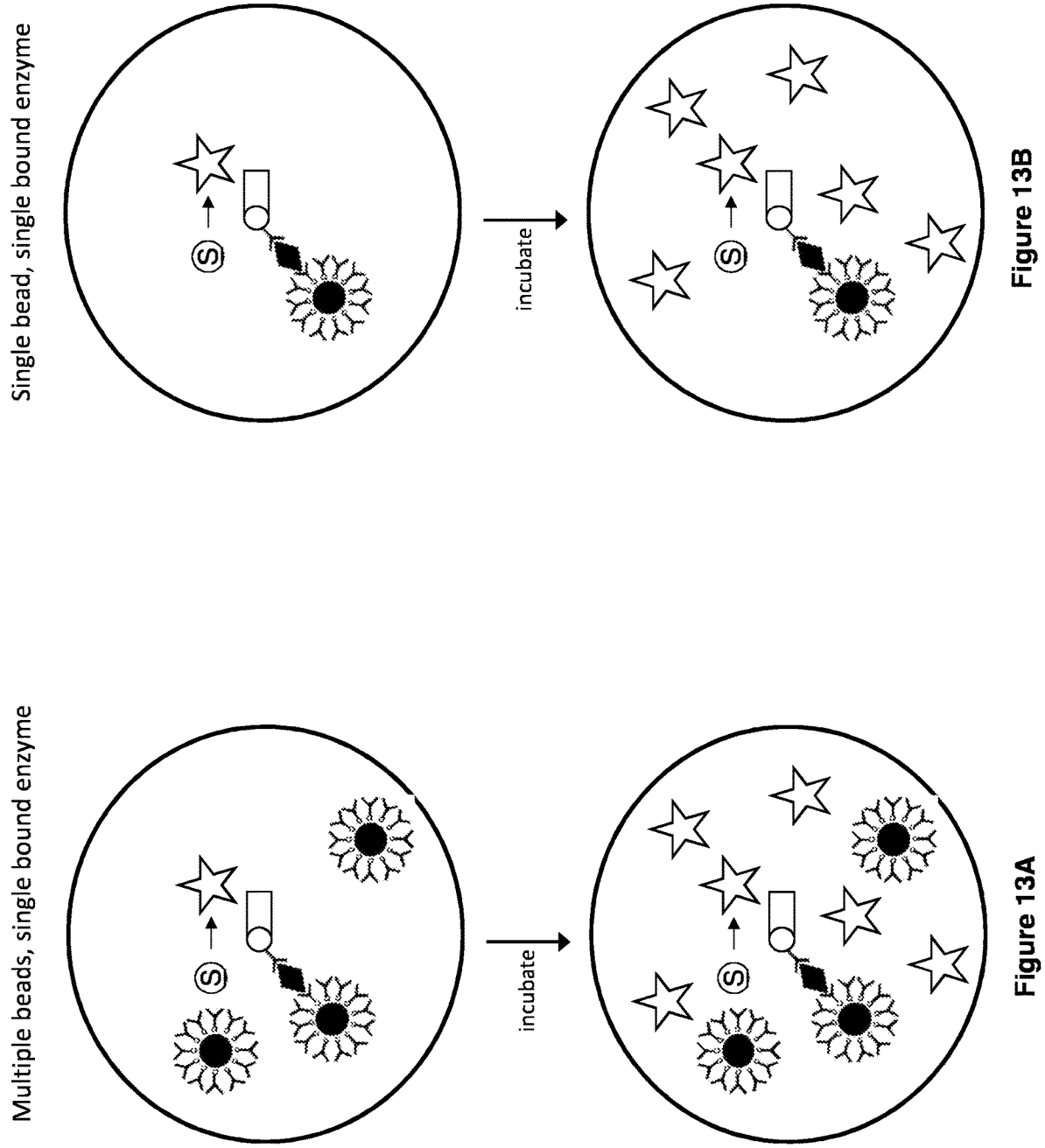
FIGS. 13A-13D illustrates different digital droplet ELISA readout counting modes.

FIGS. 13A-13D show a number of different readout 'modes' for running the digital droplet readout, following the ELISA sandwich complex construction. In FIG. 13A, more than one magnetic bead is in each generated droplet, but only a single ELISA sandwich is in any single droplet (e.g. in this case sub-micron magnetic beads are used).

FIG. 13B shows a mode where at most a single bead is in each droplet, with at most one ELISA sandwich.

Figure 13D:
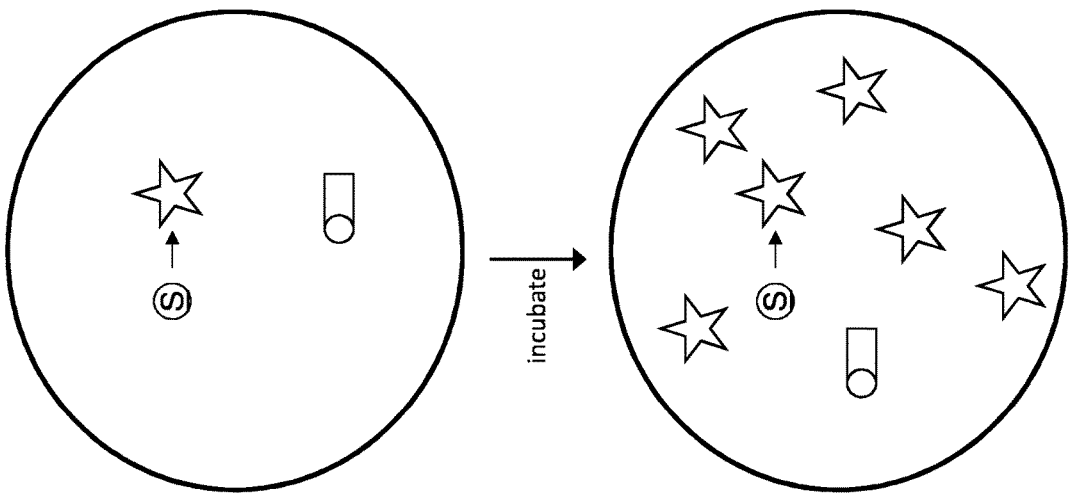
Figure 13C:
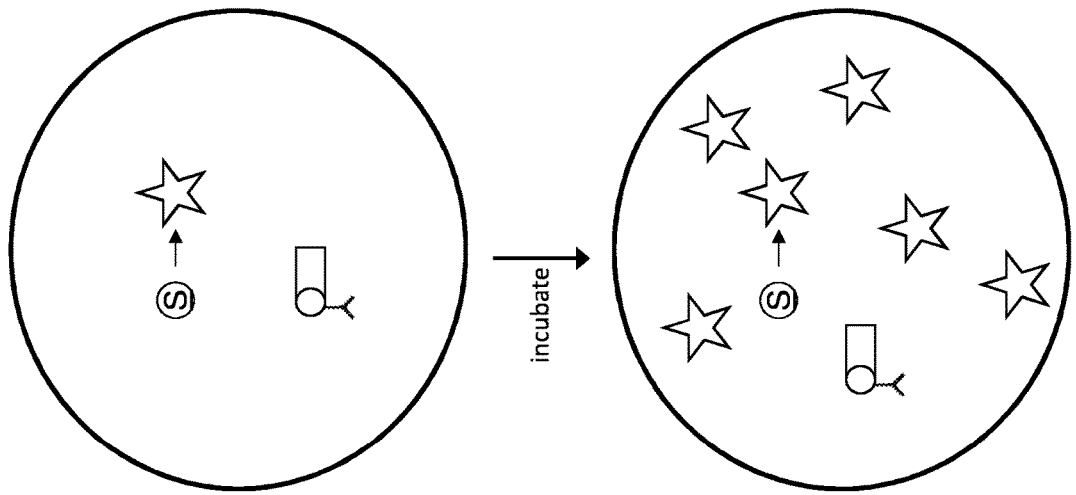

FIG. 13C shows a mode where the second antibody complexed to the reporter enzyme has been eluted off of the magnetic bead, and the droplets are loaded such that at most one antibody-reporter complex is present in any droplet.

In FIG. 13D, the reporter enzyme itself is released off of the magnetic bead, with droplets loaded such that at most one enzyme molecule is present in any droplet.

Any suitable method can be used for releasing the enzyme from the ELISA sandwich. Exemplary methods include: 1) competition of a desthiobiotin-streptavidin interaction using biotin; 2) reduction of a linker that contains a disulfide bond; 3) enzymatic cleavage of a linker group. Other variations can be considered, and Poisson and non-Poisson models can be used to enable high occupancy loading while still providing quantitative counting.

Figure 14A:
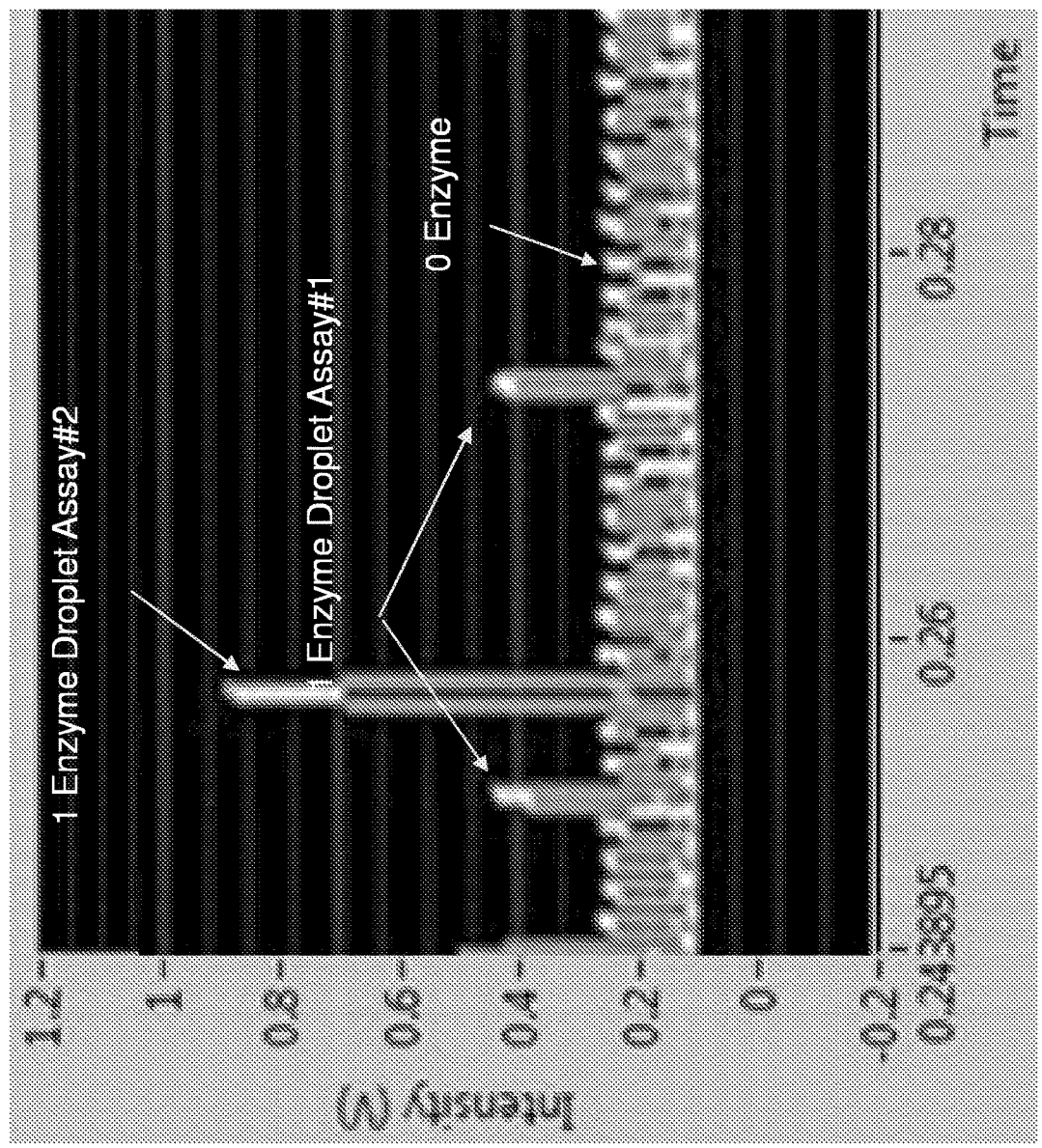
FIGS. 14A and 14B show embodiments for multiplexing digital assay.
Figure 14B:
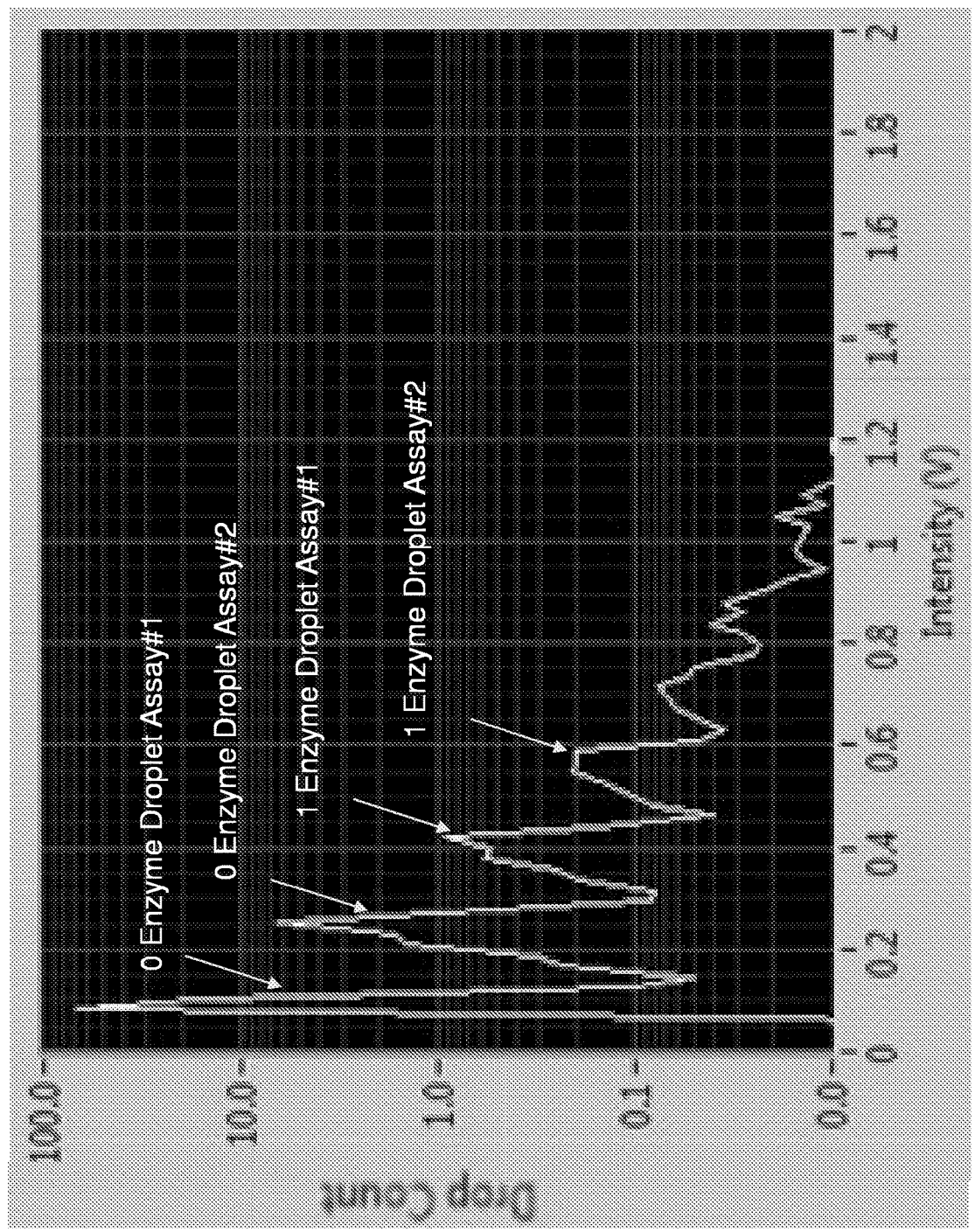

With reference to FIGS. 14A and 14B, the invention provides methods for multiplexing digital droplet reporter enzyme readout. Several modes for multiplexing a digital assay are provided.

In certain embodiments, methods including generating droplets that contain different fluorogenic substrates and enzymes that produce different fluorescent products. For example, beta galactosidase and FDG produce FITC, whereas horseradish peroxidase and Amplex Red produce resorufin. The first method uses completely separate enzyme and fluorogenic substrate pairs loaded into droplets at the same time. For example, beta galactosidase and FDG (FITC is the fluorescent product, with a peak emission wavelength of 518 nm) can be used to count one set of target molecules, while horseradish peroxidase and Amplex Red (Resorufin is the fluorescent product, with a peak emission wavelength of 582 nm) can be used to simultaneously report on a second set of target molecules, as the detection wavelengths can be easily distinguished with standard laser/filter setups.

Some combinations of different reporter enzymes and different substrates producing the same fluorescent product can be used. For example, beta galactosidase catalyzes reactions of FDG while alkaline phosphatase catalyzes reactions of FDP, with each of these combinations producing the same fluorescent product (FITC). Nonetheless, the endpoint product concentration for each single enzyme can be discriminated when multiplexing.

FIG. 14A illustrates discrimination by signal strength at endpoint. While different enzymes and substrates are used, the substrates generate the same fluorescent product (e.g. FITC). Careful titration of the endpoint product concentrations can enable separate counting of each target (e.g., traces with distinct intensities in FIG. 14A).

FIG. 14B illustrates discrimination by running at different time points. In these embodiments, a kinetic assay can be used rather than an endpoint assay (e.g. alkaline phosphatase and fluorescein diphosphate yield FITC as a product with much faster kinetics than beta galactosidase and FDG). One assay (assay #1) runs for a period of time and produces a detectable product. After an amount of time, the detectable product hits a plateau in intensity. Assay #1 is multiplexed with (i.e., run simultaneously with) assay #2. Assay #2 proceeds more slowly than assay #1. By the time that assay #2 begins any substantially uptick in activity, the product of assay #1 has plateaued. Thus, the level of detectable product from the plateau of assay #1 provides a baseline for the level of product of assay #2. Such a pattern can be further multiplexed to any suitable level of plexity.

In certain embodiments, all droplets within an assay have a substantially identical size (e.g., even where optical labeling is used). The same nozzle 105 can be used to generate droplets of identical size (discussed in greater detail below). Further, since all droplets are labeled separately for multiplexing, the droplets can be incubated identically, due to the fact that they can be handled in the same chamber or apparatus. Similarly, all droplets can be read with the same optical mechanism (e.g., they all flow through the same channel past the same detection point on-chip). Thus, optical sample indexing allows for higher throughput and better data comparisons.

While some descriptions herein illustrate digital enzyme quantification in droplets, systems and methods of the invention are applicable to any suitable fluid partition. Fluid volumes for partitions can be provided by chambers made from closing valves, SLIP-chips, wells, spontaneous breakup to form droplets on a structured surface, droplets formed using electrowetting methods, etc.

Allele-Specific Assay

Figure 17:
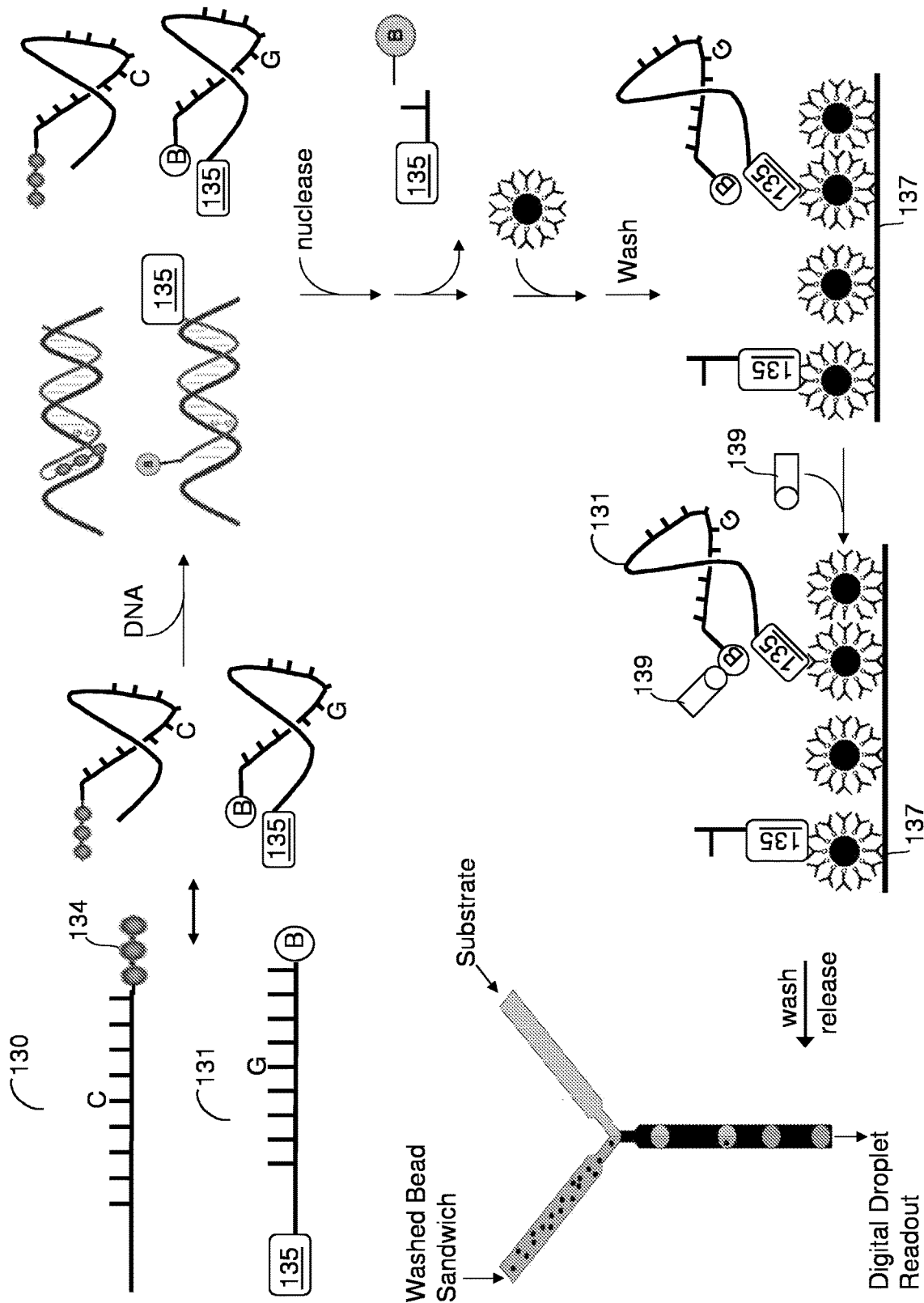
FIG. 17 is illustrates a digital competitive allele specific enzyme (CASE) assay.

FIG. 17 shows an illustration of the concept and workflow for a digital droplet competitive allele specific enzyme hybridization (CASE) assay, another example of an upfront assay that can be coupled to the digital reporter assay readout. The CASE hybridization assay uses allele-specific oligonucleotide probe hybridization to select rare genomic targets for binding to the reporter enzyme and subsequent digital counting.

Two probe types are used. Wild-type probe 130 is complimentary to the abundant wild-type allele. Wild type probe 130 includes a minor groove binding motif 134 (either 5' or 3' to the targeting oligonucleotide).

Mutant probe 131 is complimentary to the rare mutant allele. Mutant probe 131 includes an immunoaffinity tag 135 (e.g., TAG) on one end and a biotin on the other end. Other binding motifs can be used, but in this example a DIG TAG (which can be bound by an anti-DIG antibody) and biotin (which can be bound by streptavidin) are used.

Wild-type probe 130 with minor groove binder 134 outcompetes any non-specific binding of mutant probe 131 to the wild-type sample DNA, thus limiting hybridization and duplex formation such that only two duplex species form: wild-type DNA hybridized to wild-type probe 130, and mutant DNA hybridized to mutant probe 131. An excess of the two probes over sample DNA is used, ensuring that each single strand of mutant sample DNA is in a duplex with one mutant allele probe.

Following duplex formation, a single-strand nuclease is added such as Si nuclease. The nuclease digests any unbound mutant probe 131 such that tag 135 is dissociated from the biotin.

Magnetic beads coupled to anti-TAG antibodies are next added in excess, such that each bead will bind at most one complex of probe 131 and tag 135. The beads are immobilized using magnet 137 and washed to remove non-specifically bound material (digested biotinylated probe and the single strand nuclease).

Streptavidin-coupled reporter enzyme 139 is next added. After washing, the only enzyme remaining immobilized on the magnet is present in a one-to-one stoichiometry with the original rare mutant allele present in the sample DNA. Finally, the reporter enzyme is counted using the digital droplet reporter enzyme assay, as above.

While shown in FIG. 17 in a certain embodiment, a CASE assay can include any suitable probes for a particular assay. The anti-TAG antibodies can be provided on any suitable solid substrate. Reporter enzyme 139 can be any suitable enzyme, such as any of those discussed herein.

Optical Labeling

Figure 18A:
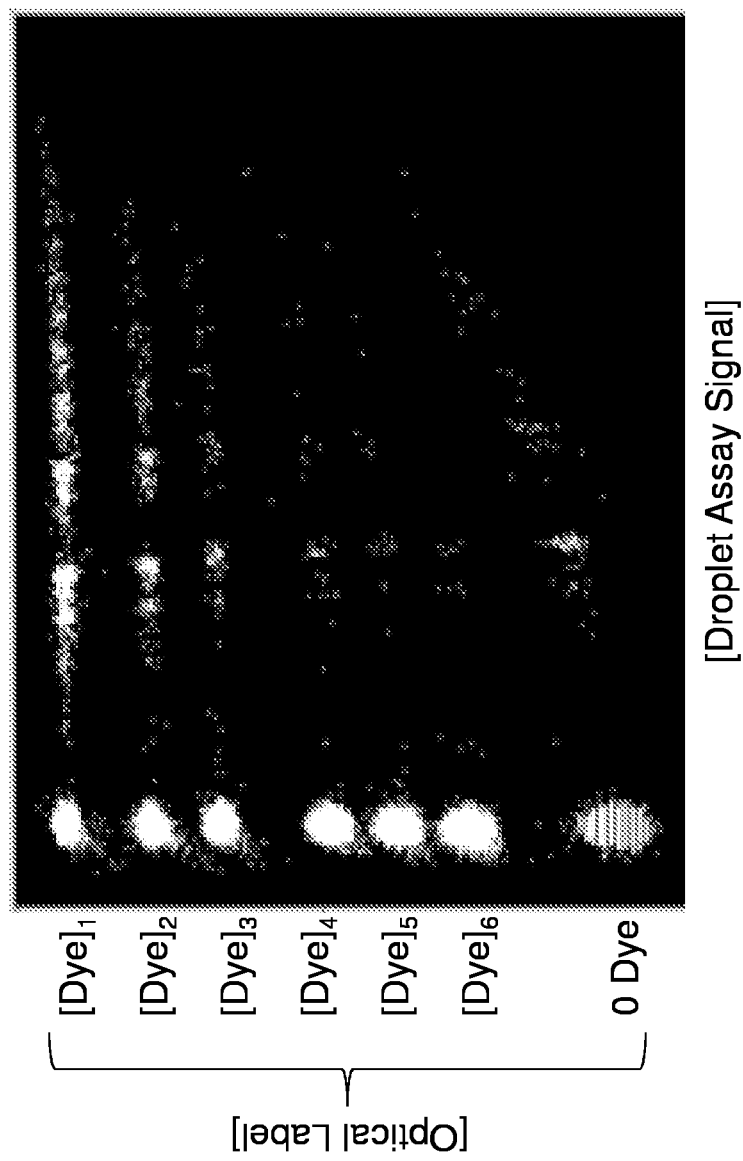
FIGS. 18A-18C show multiplexing embodiments.

In certain aspects, the invention provides methods and devices for optical labeling of samples or assays. Methods of optical labeling include adding a dye to a sample or assay before droplet formation. Different samples or assays can be multiplexed by adding one dye at different concentrations. FIG. 18A shows a plot in which the x-axis corresponds to the droplet assay signal and the y-axis corresponds to different concentrations of dye. As can be seen from FIG. 18A, fluid partitions can include dye in six different concentrations and still be clearly optically resolvable from one another. More than six different concentrations can be used such as, for example, seven, ten, fifty, or more.

Figure 18B:
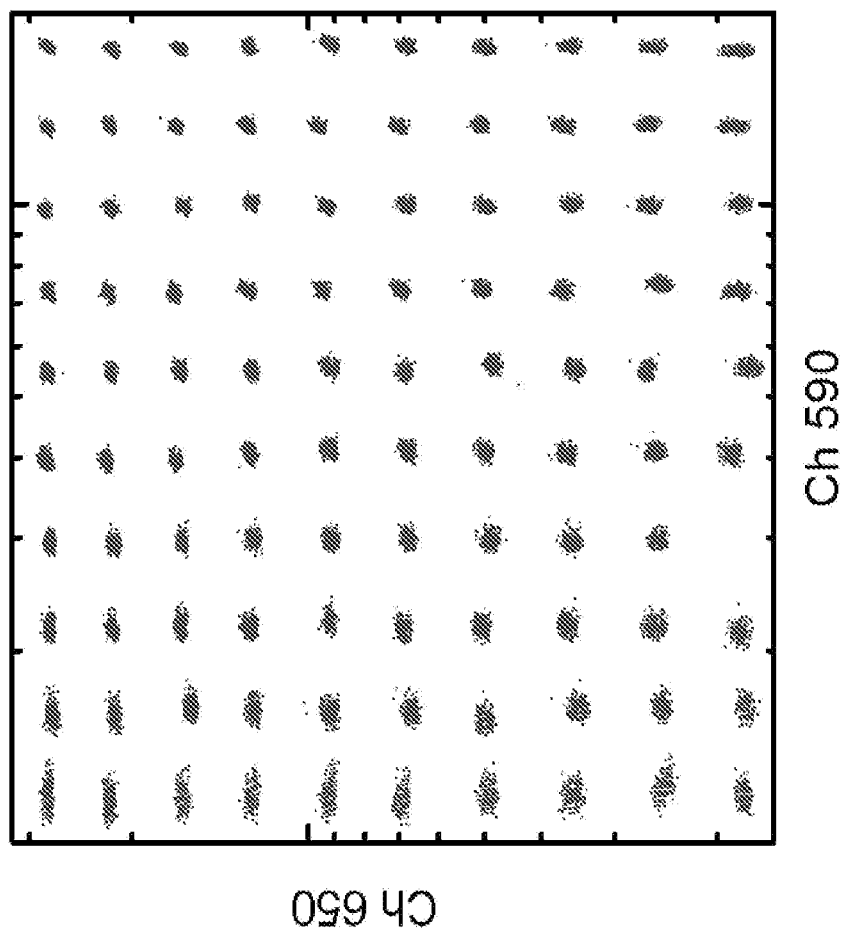

Optical labeling can include further multiplexing by using additional dyes. For example, FIG. 18B shows a plot in which the x-axis shows 10 different concentrations of a dye that emits at 590 nm, while the y-axis shows 10 different concentrations of day that emits at 650 nm. By including two dyes at 10 concentrations each, 100 samples can be separately labeled and run through a single assay (99 samples are shown in FIG. 18B).

Multiplexing by these methods provides a high throughput readout. In certain embodiments, a single dye laser set allows for 6-7 or more (e.g., 10, 25, more) index levels per run. An additional laser then allows greater numbers (e.g., >30). By multiplexing at these levels, positive and negative controls can be run in an assay.

Figure 18C:
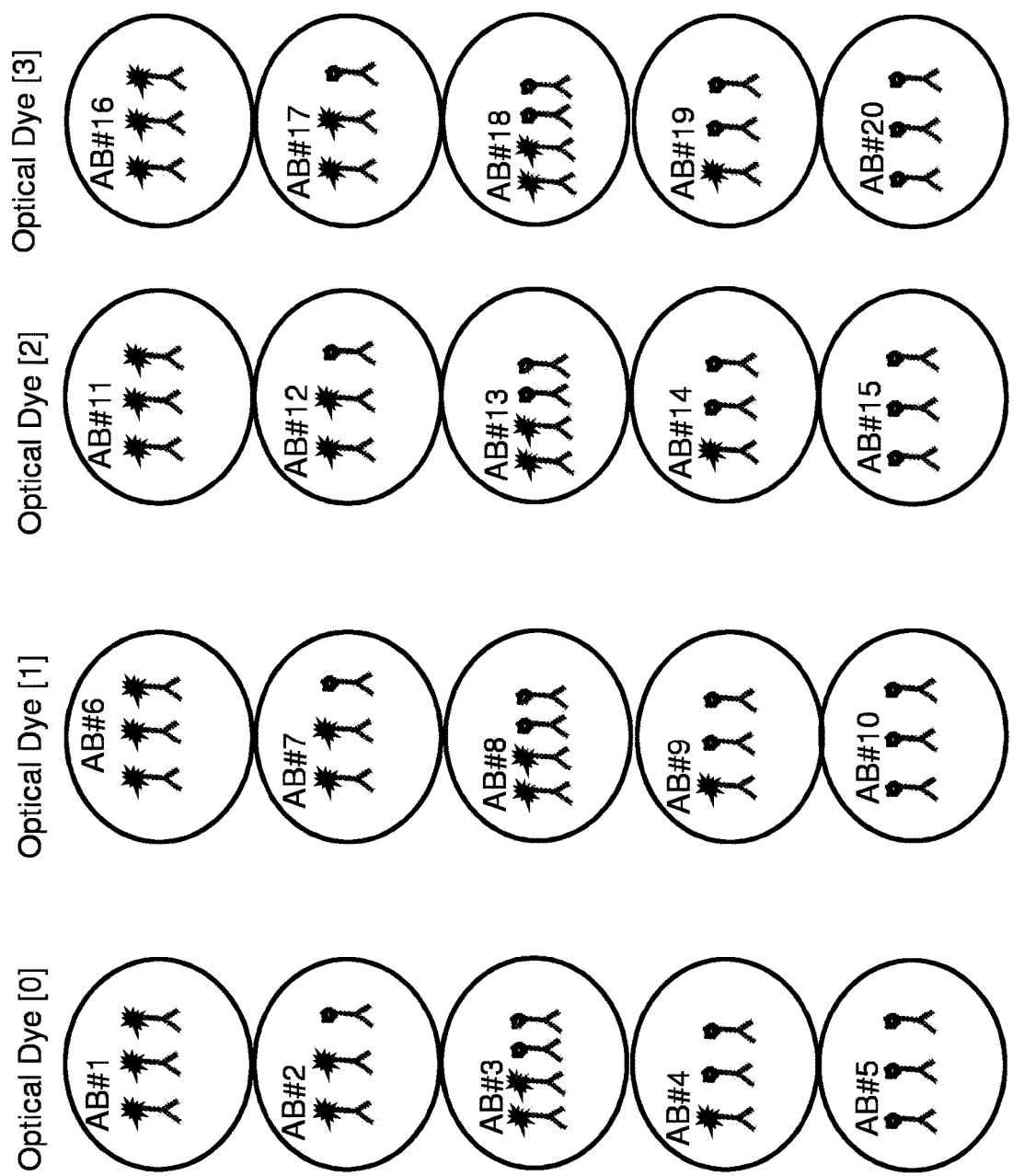

FIG. 18C shows the high levels of "plexity" for multiplexed reactions using different concentrations of an optical dye and different combinations of fluorescently labeled antibodies. As shown in FIG. 18C, each circle represents a fluid partition. Each inverted "Y" member represents an antibody. The labels "AB #1", "AB #2", . . . , "AB #20" refer to twenty different antibodies, and indicate that in any given fluid partition, all of the antibodies are the same. The antibodies are shown with two different fluorescent markers at their heads. A spiky marker indicates a first color (e.g., green), while a globular marker indicates a second color (e.g., red). "Optical Dye [1]" indicates a first dye concentration; "Optical Dye [2]" indicates a second dye concentration; "Optical Dye [3]" indicates a third dye concentration; and "Optical Dye [0]" indicates no dye.

Noting that in any given fluid partition in FIG. 18C all of the antibodies are the same, it can be seen that each fluid partition is nonetheless distinctly labeled by a combination of colored fluorescent markers and dye concentration. That is, no two partitions in one column contain the same combination of colors of fluorescent labels. Further, two different optical dyes can be included in each fluid partition, each separately detectable and each separately able to be provided at different concentrations. Imaging an idealized axis extending normal to the surface of FIG. 18C, it can be appreciated that a second optical dye provided in 3 distinct concentrations will allow the assay to be multiplexed with a "plexity" of 48—i.e., 48 different antibodies can be separately and distinctly labeled.

Localized Fluorescence

FIGS. 16A and 16B relate to methods of reaction detection in fluid partitions that employ a localized fluorescence method of detection. In these methods, positive (enzyme-containing) partitions are identified and counted using changes in the localized fluorescence of fluorescent molecules in the partitions. In general, methods of the invention employ any detection method that detects a localized concentration of a target in a fluid partition. For example, in certain embodiments, enzyme activity creates a binding surface for fluorescent molecules that can be monitored by localized fluorescent readout.

In the example shown in FIG. 16A, the enzyme Src kinase (Src) phosphorylates a Src substrate peptide that is immobilized on a bead. Phosphorylation of the Src substrate peptide creates binding motifs for the fluorescent reporter SH2-FITC. Thus, SH2-FITC binds to the bead-bound Src substrate phospho-peptide as shown in the last step of FIG. 16A.

FIG. 16B illustrates a reaction-negative fluid partition on the left side and a reaction-positive fluid partition on the right. Localization of the fluorescent molecules onto the bead surface can be detected as an increased signal on the bead surface, a decreased signal in a portion of the fluid partition (e.g., throughout the partition volume), or both. Many other enzymes, binding motifs, and fluorescent reporters can be used.

Any suitable method can be used to detect the pattern of localized fluorescence within a fluid partition. For example, in certain embodiments, fluid droplets are flowed through a narrow channel that forces the droplets to exhibit an elongated shape (as shown in FIG. 16B). As the droplets pass a laser detector, reaction-negative droplets give a uniform low-level fluorescence intensity along their length, while reaction-positive droplets show a spike corresponding to when the bead-bound fluorescent reporter passes the laser detector. In addition, when fluors become localized onto particle(s) within the droplet (e.g. on a bead or a cell surface) there is a coordinate depletion of the initial fluorescence in the regions of the droplet that do not contain the particle(s). Various signal processing algorithms can be used to combine local signal increases and background signal decreases into a more robust detection method.

Figure 19B:
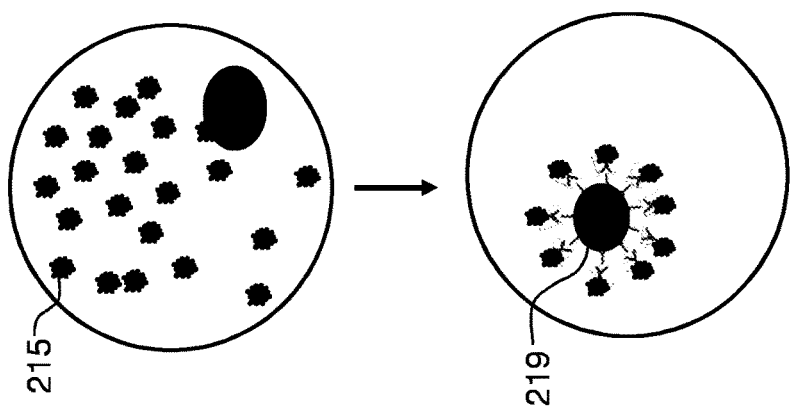
FIGS. 19A and 19B show a workflow for a localized fluorescence binding assay.
Figure 19A:
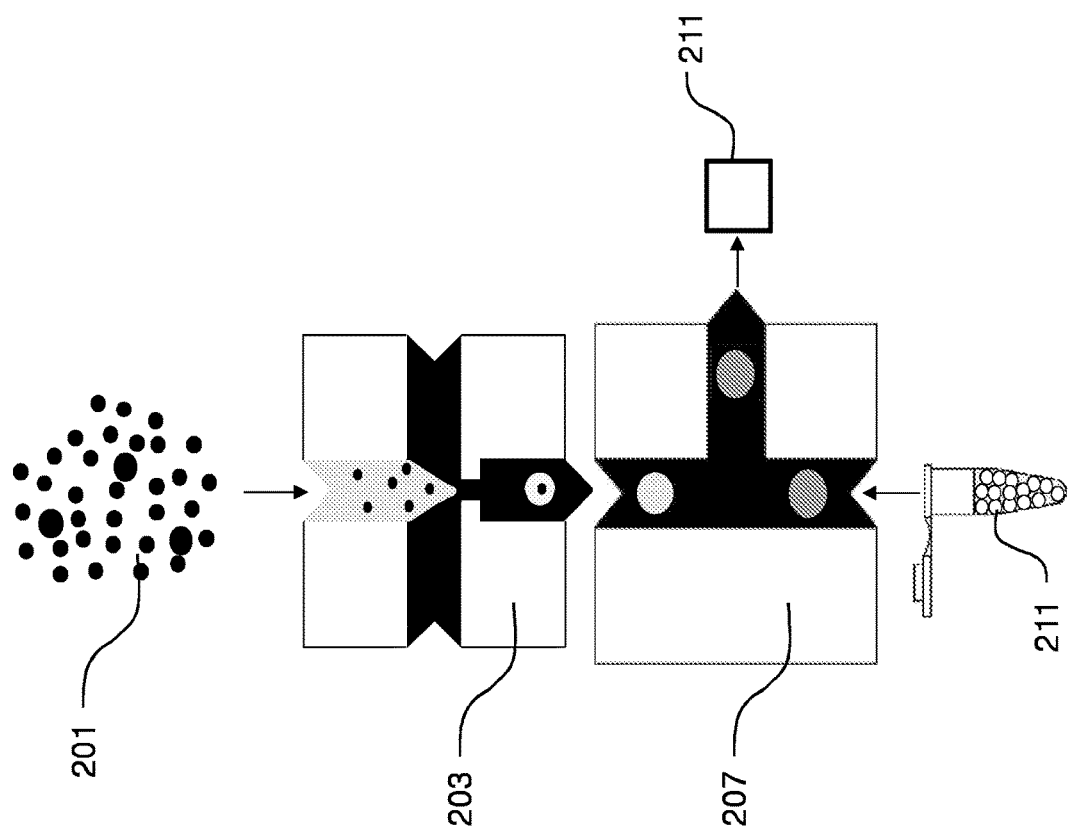

FIGS. 19A and 19B show a workflow for a localized fluorescence binding assay. Cell sample 201 provides cells that are flowed into droplet generator 203. An optically labeled library 211 (e.g., according to multiplexing embodiments discussed elsewhere herein) is flowed such that droplets from library 211 meet cell droplets from sample 201 in droplet merger 207. Droplets leave merger 207 having optical labels and reagents (e.g., fluorescent antibody to a biomarker of interest) and incubated (not shown) and then flow past detector 211. In certain embodiments, detector 211 includes a narrow channel portion 225 as discussed below in reference to FIG. 20. Libraries are discussed in U.S. Pub. 2010/0022414, the contents of which are hereby incorporated by reference in their entirety for all purposes.

FIG. 19B illustrates the principle of detection in detector 211. A fluid partition at the top of FIG. 19B includes a plurality of fluorescently labeled antibody 215 and a cell presenting an antigen of interest. After incubation, the fluid partition appears as at the bottom of FIG. 19B, where it is shown containing only one concentration of fluorescent marker 219, as all of the labeled antibody has bound to the cell.

FIG. 13 shows detection of CD45 on the surface of U937 monocytes with systems and methods of the invention. An optically labeled antibody library is flowed into the system from one input to merge with cells from the other (tracing the cell path across the figure from left to right). The streams merge and the droplets combine, after which the droplets are incubated "off chip", as indicated by the middle panel, in which the droplets can be seen without a surrounding microfluidic channel. After incubation, the droplets are flowed back onto a chip into a channel, after which they are flowed through narrow channel portion 225. Flowing through the narrow area causes the cells to elongate. A laser detector reads across the channel in the middle of narrow portion 225.

As the cells pass the laser, the detector detects fluorescence and creates a digital trace that can be stored and analyzed on a computer. The digital trace can be viewed on a display as a graph, in which the x-axis represents time (and corresponds to the length of the droplets as they pass the detector), and the y-axis corresponds to signal intensity (see example traces in FIGS. 21A-21C).

Throughput of the assay is adjustable and can be performed at, for example, about 1500 droplets per second (in the illustrated example, corresponding to about 150 cells/second). Incubation time (e.g., off chip, as shown in middle panel) can be adjusted. On chip, incubation can be adjusted by use of a delay line (i.e., wider portion of channel where flow slows). The interior diameter of narrow portion 225 can be adjusted to tune droplet elongation. For example, interior diameter can be about 10 micrometers or 15 micrometers.

In certain embodiments, localized fluorescence is used to screen for single-chain variable fragment (scFv) peptides in droplets. For example, a library of bacterially produced scFv's can be developed. Following a procedure as outlined in FIG. 19A, transformed bacteria cells 201 are encapsulated and incubated at 37° C. After incubation the droplets are combined with droplets that contain beads, antigens and a detection antibody from library 211.

The droplet based binding assays utilize localized fluorescence detection of scFv binding as shown in FIG. 19B. Specifically, the diffuse signal becomes bright and localized on the capture bead.

Figure 20:
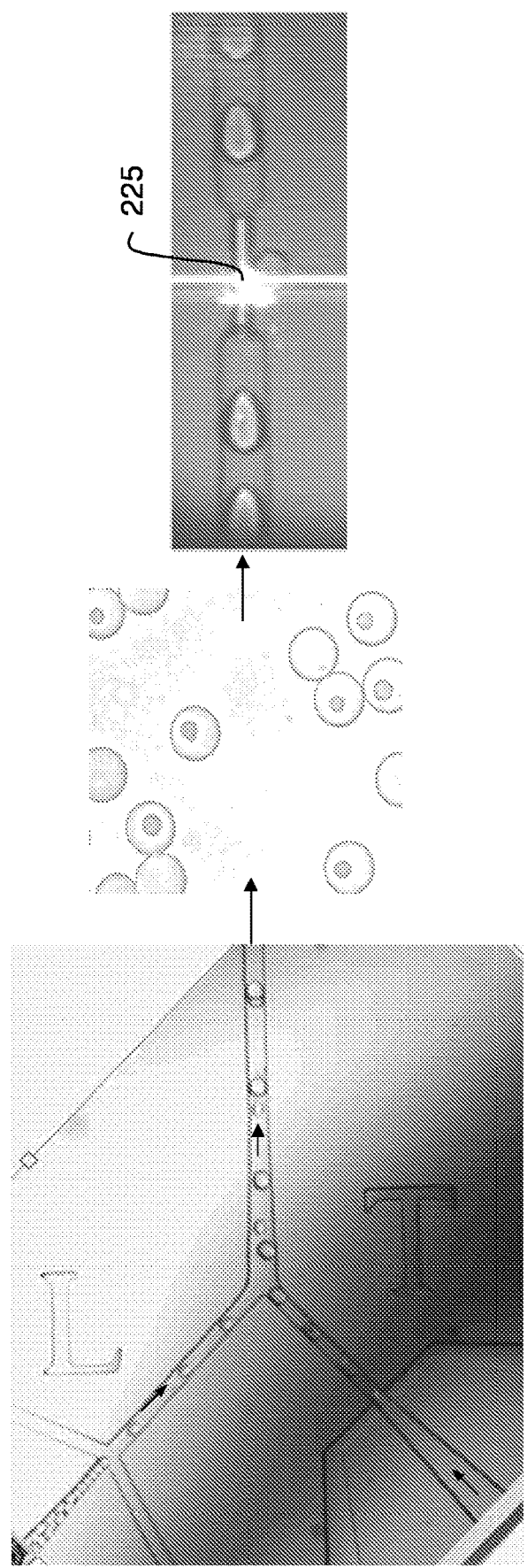
FIG. 20 shows monocyte detection according to certain embodiments.

Positive droplets are detected according to a localized fluorescence method such as the one illustrated in FIG. 20. In order to get a reading of the droplet and fluorescent level therein, the droplet is elongated for detection in narrow channel portion 225 as shown in FIG. 20.

The positive droplets can then be broken and the contents recovered and sequenced. The process is able to screen for scFv's in droplets at a rate of about $1 \times 10^6$ per hour. Localized fluorescence and scFv screening is discussed in U.S. Pub. 2010/0022414, the contents of which is hereby incorporated by reference in its entirety.

Figure 21A:
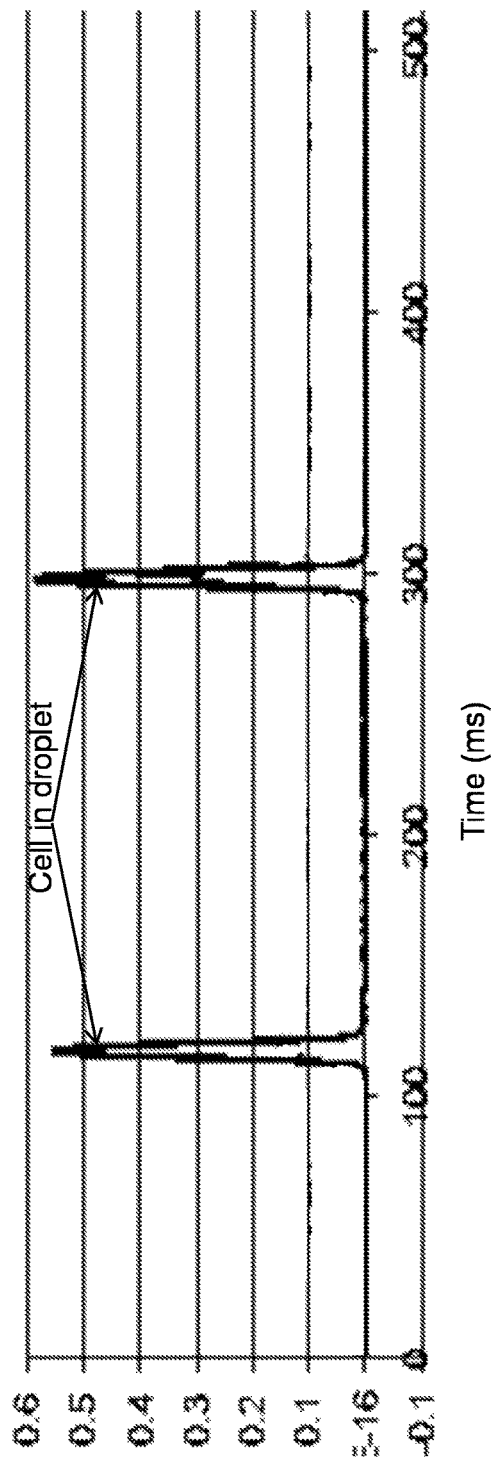
FIGS. 21A-21C illustrate single droplet traces including optical labels.
Figure 21B:
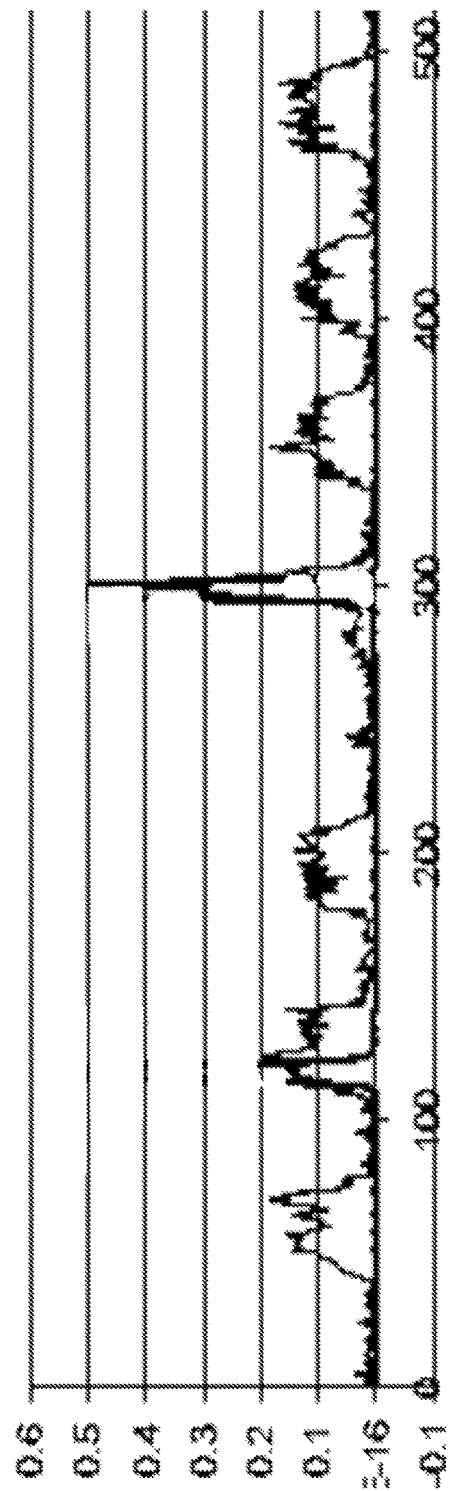
Figure 21C:
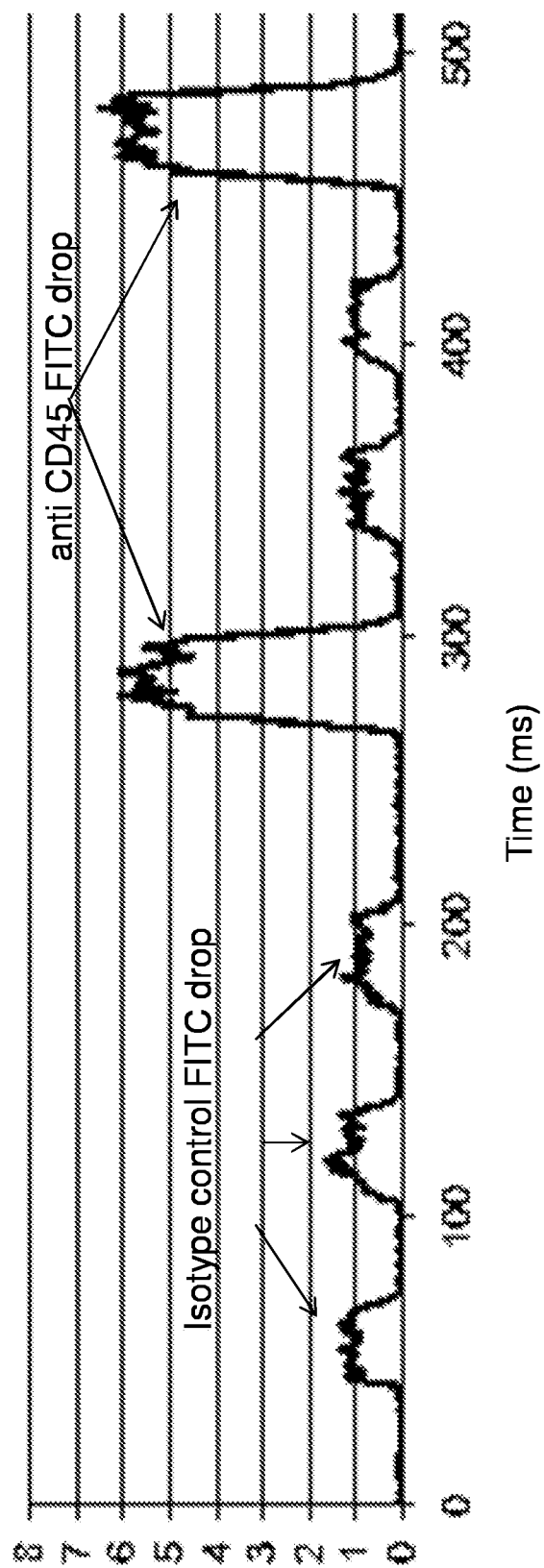

FIGS. 21A-21C illustrate single droplet traces including optical labels in a localized fluorescence assay. Note that the trace in each of FIGS. 14A-14C may be shown in a separate color for example on a single display. In each figure, the axes are the same and the traces can be obtained in a single run detecting three differently colored labels simultaneously. FIG. 21A shows a trace indicating measurement of cell viability stain. Here, calcein AM can be used, which gives a low intensity signal until it is cleaved by esterases located only inside a cell. The two spikes in FIG. 21A (at approximately 110 ms and approximately 300 ms) indicate the second and fourth droplets, respectively, to pass the fluorescent detector. These two spikes indicate that those droplets included a viable cell.

FIG. 21B shows a signal strength of FITC signal for droplets that include a labeled binder (e.g., anti-CD45-

FITC). A spike (e.g., at 30 ms) indicates binding (i.e., a localized increase in fluorescence) while "bulges" centered on about 60 ms, 125 ms, 190 ms, 355 ms, 420 ms, and 480 ms (corresponding to the second, third, fourth, sixth, seventh, and eight droplets to flow past the detector, respectively) indicate dispersed, low-level fluorescence and thus indicate no binding. In conjunction with to FIG. 21A, which indicate the presence of a viable cell in the fourth droplet, FIG. 21B indicates that the viable cell is binding anti-CD45.

It will appreciated in viewing FIG. 21B that the spike at about 300 ms is surrounded by a low-level "bulge" spanning about 275 ms to about 320 ms. A positive assay can be detected by the low level of the signal across this "bulge" as compared to the signal level in the reaction-negative bulges (e.g., consistently above about 0.1). Thus, localized fluorescence can be detected (and positive or negative reaction fluid partitions identified) by localized increases of fluorescence, partition-wide decreases in fluorescence, or both. For example, a ratio could be calculated between the localized increase and the partition-wide decrease, and this ratio would be a sensitive indicator and/or measurement of localization within the partition. Moreover, measurement of the total volume of the partition may also be taken into consideration to further scale or normalize the partition-wide decrease.

FIG. 21C illustrates optical labeling that was included with the droplets shown in FIG. 14B (shown here as a blue trace). Here, control droplets were labeled with a low concentration of dye, while test droplets (including the anti CD45-FITC) were labeled with a high concentration of the dye. Thus, the first three signals, the fifth signal, and the sixth signal indicate that the corresponding fluid partitions are negative controls. while the fourth and seventh droplets were test partitions. An independent (e.g., downstream or upstream) channel can be used to count cells, count droplets, sort cells, or perform other steps.

Figure 22A:
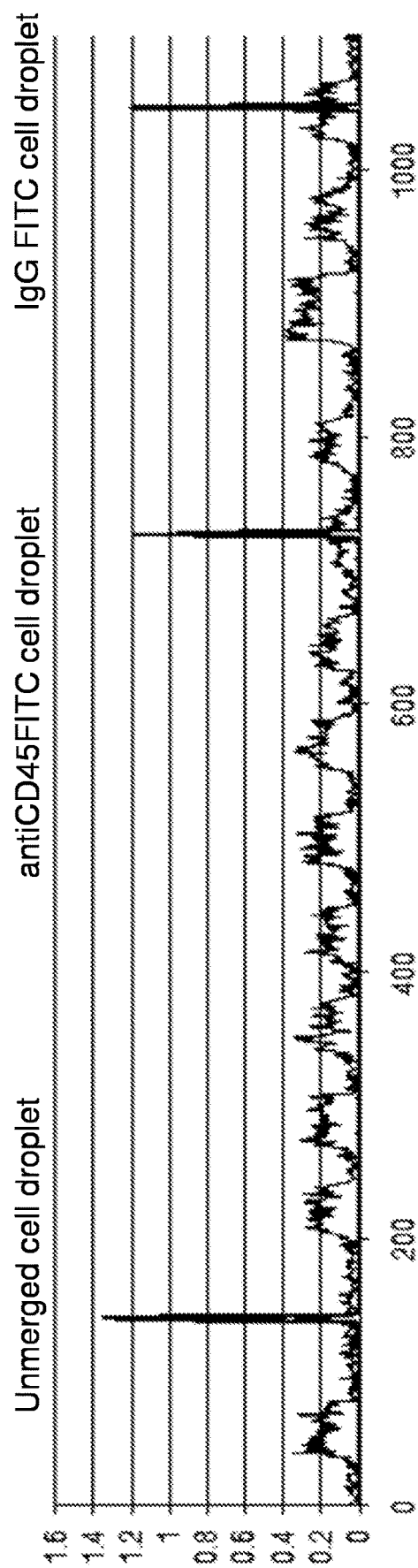
FIGS. 22A-22C give single droplet traces with a scatter plot and histogram.
Figure 22B:
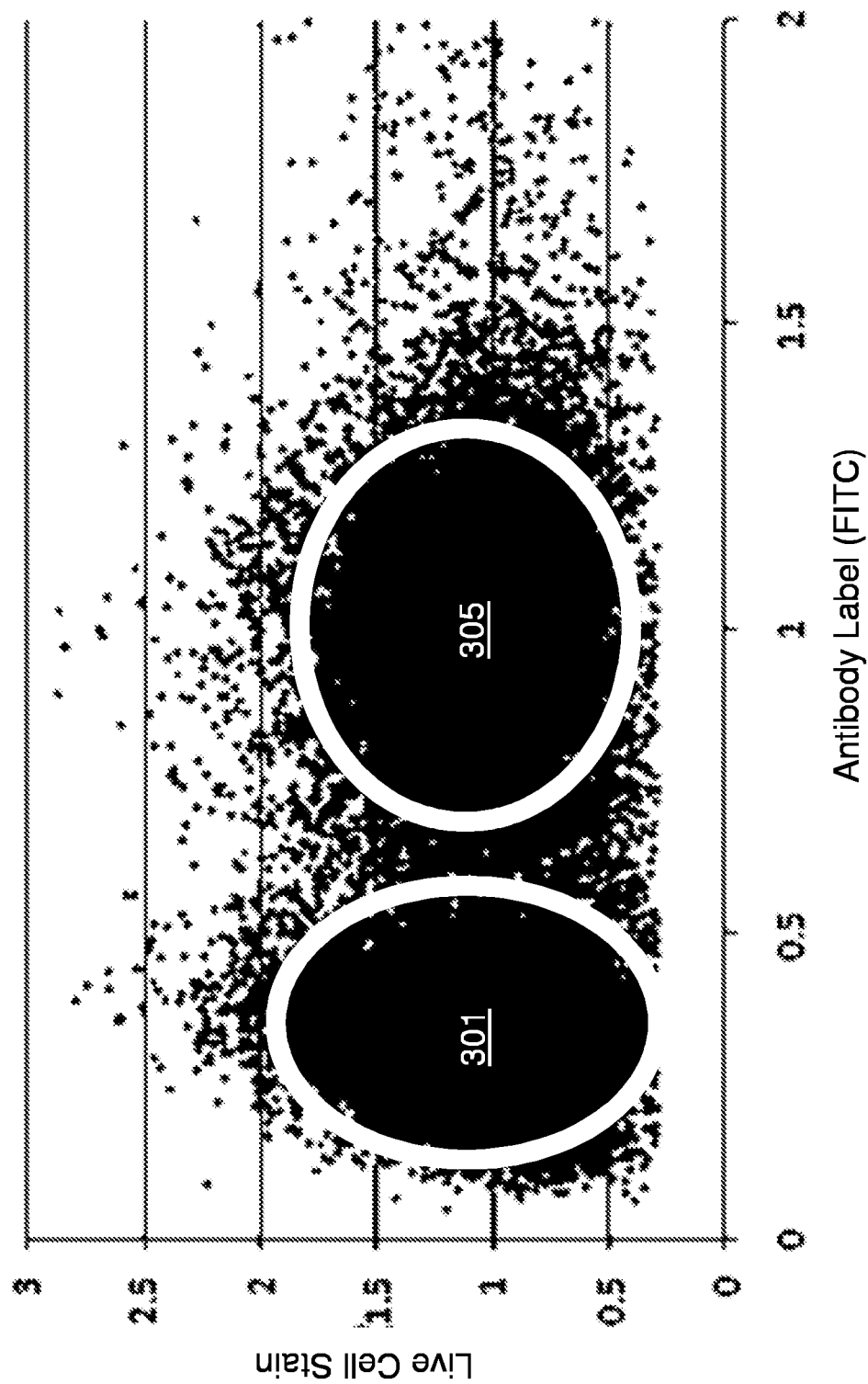
Figure 22C:
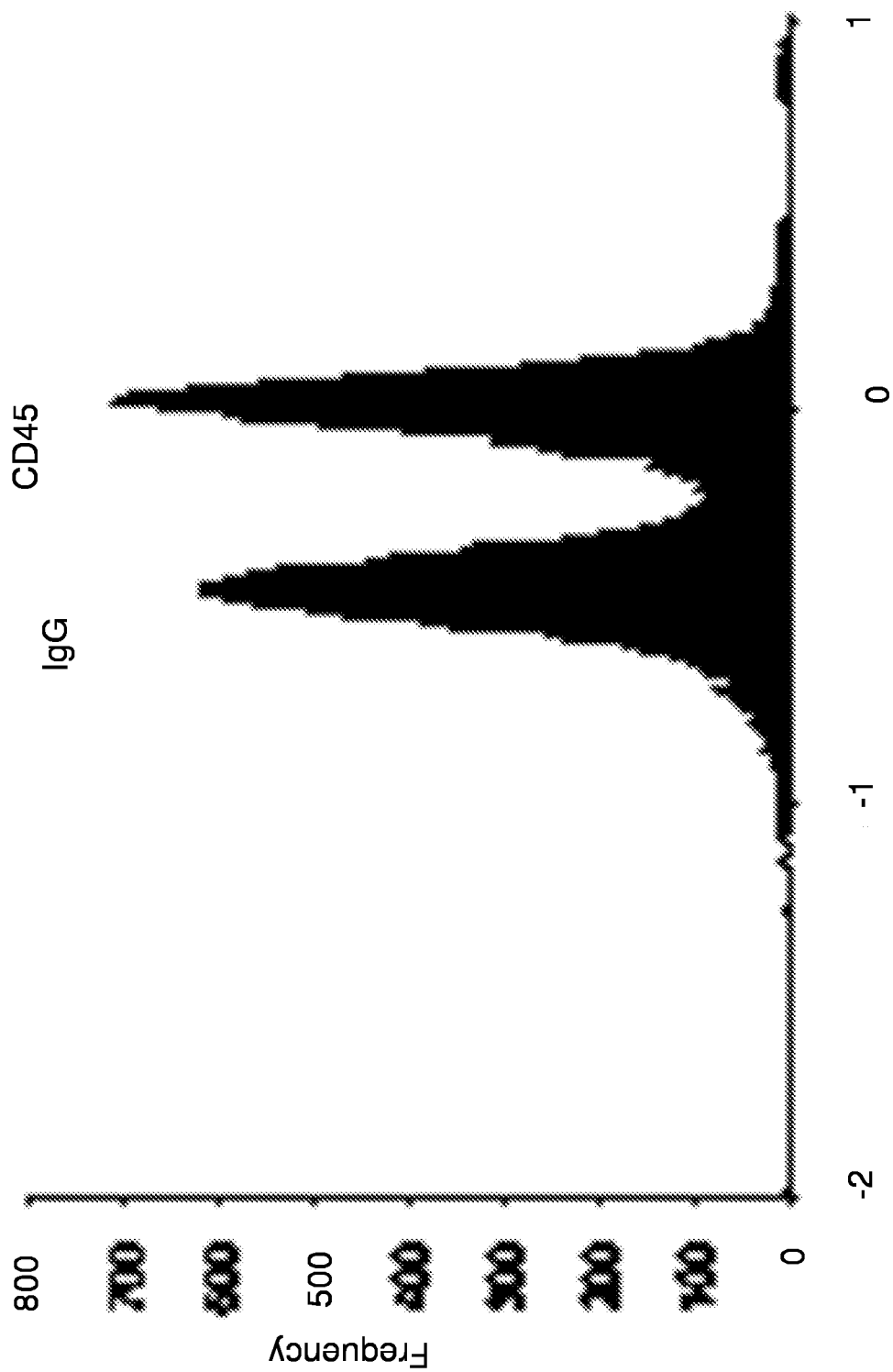

FIGS. 22A-22C give single droplet traces with a scatter plot and histogram. These figures illustrate the results of an assay for IgG and CD45. Here, two traces are superimposed. One trace indicates a level of fluorescence from FITC at locations within a fluid partition (similar to that shown in FIG. 21B). The other trace indicates a dye used in different concentrations to optically label the antiCD45 test partition distinctly from the IgG test partitions (i.e., the trace is similar to that in FIG. 21C). In FIG. 22A, the appearance of a signal at about 125 ms with no "shoulders" (i.e., lacking the trace that corresponds to FIG. 21B as discussed above) indicates a fluid partition that includes no FITC-labeled target. This indicates an unmerged cell droplet, i.e., a droplet that passed through merger 207 without receiving reaction reagents.

The signal at about 725 ms indicates an antiCD45-FITC positive droplet while the signal at about 1050 ms indicates an IgG-FITC positive droplet (the tenth and fourteenth droplets to pass the detector, respectively). Here, the tenth and fourteenth droplets are distinguished based on the concentration of the optical labeling dye (corresponding to the trace shown in FIG. 21C).

FIG. 22B gives a scatter-plot of results relating the traces shown in FIG. 22A. Along the x-axis is plotted an intensity of the antibody label and the y-axis corresponds to an intensity of a live cell stain. Population 305 corresponds to a CD45 positive population of fluid partitions and population 301 corresponds to an IgG positive population of fluid partitions. As unmerged droplets are also counted (e.g., second signal in FIG. 22A), the total number of droplets that is prepared can be accounted for. FIG. 22C shows a histogram corresponding to the plot shown in FIG. 22B. The x-axis is the unitless Bin and the y-axis is frequency. Such histograms are known in the art for display of flow cytometry results.

Figure 23A:
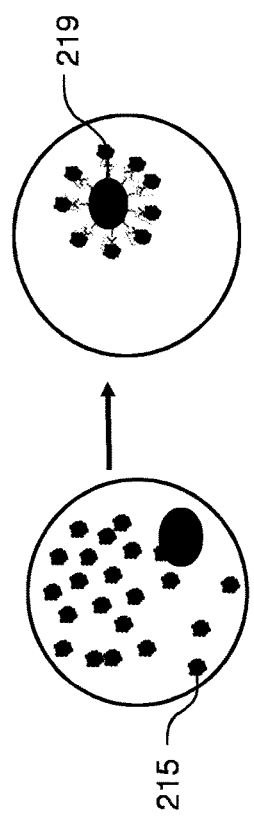
FIGS. 23A-23C diagram adjusting a dynamic range of a localized fluorescence assay.
Figure 23B:
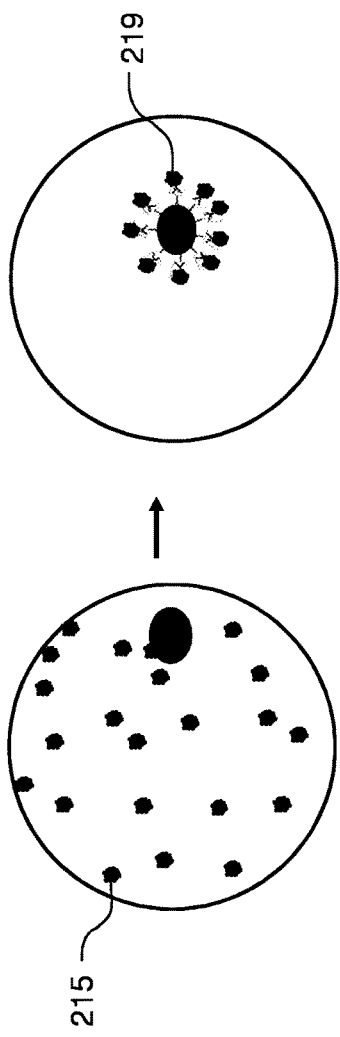
Figure 23C:
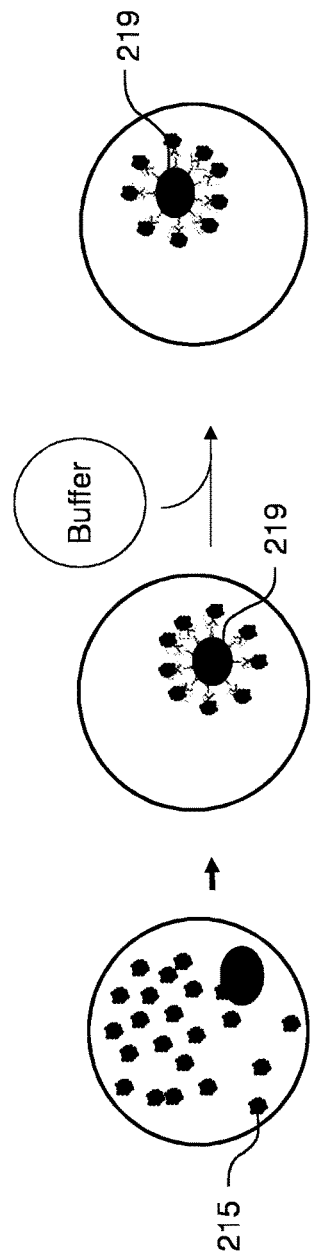

FIGS. 23A-23C show ways of controlling or adjusting the dynamic range of a localized fluorescence assay. As shown in FIG. 23A, an amount of fluorescently labeled antibody 215 can be provided in a determined relationship to a known or expected number of cell surface markers on cell 219. By controlling the concentration of antibody added (e.g., through a series of calibration runs), a desired signal of bound antibody can be established that is greater than the dispersed background signal.

FIG. 23B shows a method for lowering a strength of a background signal (shown to scale with the diagram shown in FIG. 23A). By making the fluid partitions larger, fluorescent antibody 215 will be more dispersed when in the unbound mode. However, when bound on cell 219, the bound signal will be substantially the same as between FIGS. 23A and 23B. Thus, by controlling a volume of a fluid partition, the signal gain can be modulated and the dynamic range of the assay adjusted.

FIG. 23C shows another way of adjusting the dynamic range by attenuating the background signal. Here, partitions included fluorescent antibody 215 are merged with partitions (only one is shown) that each contain at least one cell 219 (which may or may not be expressing the cell surface marker, i.e., positive and negative reaction partitions, where only positive is shown). A buffer is added to the fluid partitions. For example, droplets containing buffer are merged with assay droplets according to methods described herein. The buffer effectively dilutes the background signal. In certain embodiments, addition of the buffer does not substantially change the localized fluorescence signal (e.g., associated with reaction-positive instances of cell 219). The approach illustrated in FIG. 23C allows for a binding or incubation step to proceed at a substantially higher concentration (e.g., corresponding to concentration illustrated by left panel of FIG. 23A), while the detection step can employ a background (non-localized) fluorescence at a different concentration.

Localized fluorescence is applicable in combination with other assays and methods described herein including, for example, bead-capture based assays that involve rupturing or opening a partition to release the contents (as the signal may remain localized on the captured bead when it is, for example, but back into a fluid partition.

Digital Distribution Assays

In some aspects, the invention provides systems and methods for detecting distributions of molecules. For example, methods of the invention are useful to detect amounts of gene expression and proteins. In particular, methods of the invention are useful to detect protein aggregation or complexes. In one example, methods of the invention are used to detect anomalous or unexpected distributions of protein by conducting a chemical reaction that produces a detectable report indicative of the presence and amount of the protein (e.g., an ELISA or similar assay). The results of these assays are compared to expected results or control samples in order to determine whether there is an anomalous distribution or amount of a particular protein.

In certain embodiments, the invention is used to determine anomalous protein aggregation. In samples from the anomalous subset, peptide aggregation or complexes can be detected by the distribution of reactions in fluid partitions (e.g., digitally), as compared to the distribution from the non-anomolous rest of the population. Such a phenomenon may arise where a protein is known or suspected to exhibit alternative splicing, binding, or folding pathways or is in a stable complex. For example, one protein may be known to be differently processed (e.g., cleaved by hydrolysis or proteolysis; modified such as by phosphorylation; cross-linked; etc.) such that a complex or aggregate is formed when individuals have some disease propensity or state.

In Alzheimer's disease, for example, when amyloid precursor protein (APP) undergoes proteolysis, the resulting fragments can form aggregations such as fibrils. It is particularly hypothesized that a protein called tau becomes hyper-phosphorylated, causing the aggregation that results in neurofibrillary tangles and neuron disintegration. Thus, Alzheimer's disease may generally be associated with an aggregation of beta-amyloid protein. Accumulation of aggregated amyloid fibrils may induce apoptosis and may inhibit other critical enzyme functions.

This aggregation among proteins can result in there being an anomalous (e.g., non-Poisson) distribution of those proteins when assayed under dilution conditions which should produce Poisson-like statistic distributions, and this non-standard distribution can provide the basis for a digital detection assay.

Thus, digital assays are provided that relate to distributions of proteins and other cellular components. Assays according to methods of the invention involve determining an actual distribution and comparing that to an expected distribution.

Figure 26:
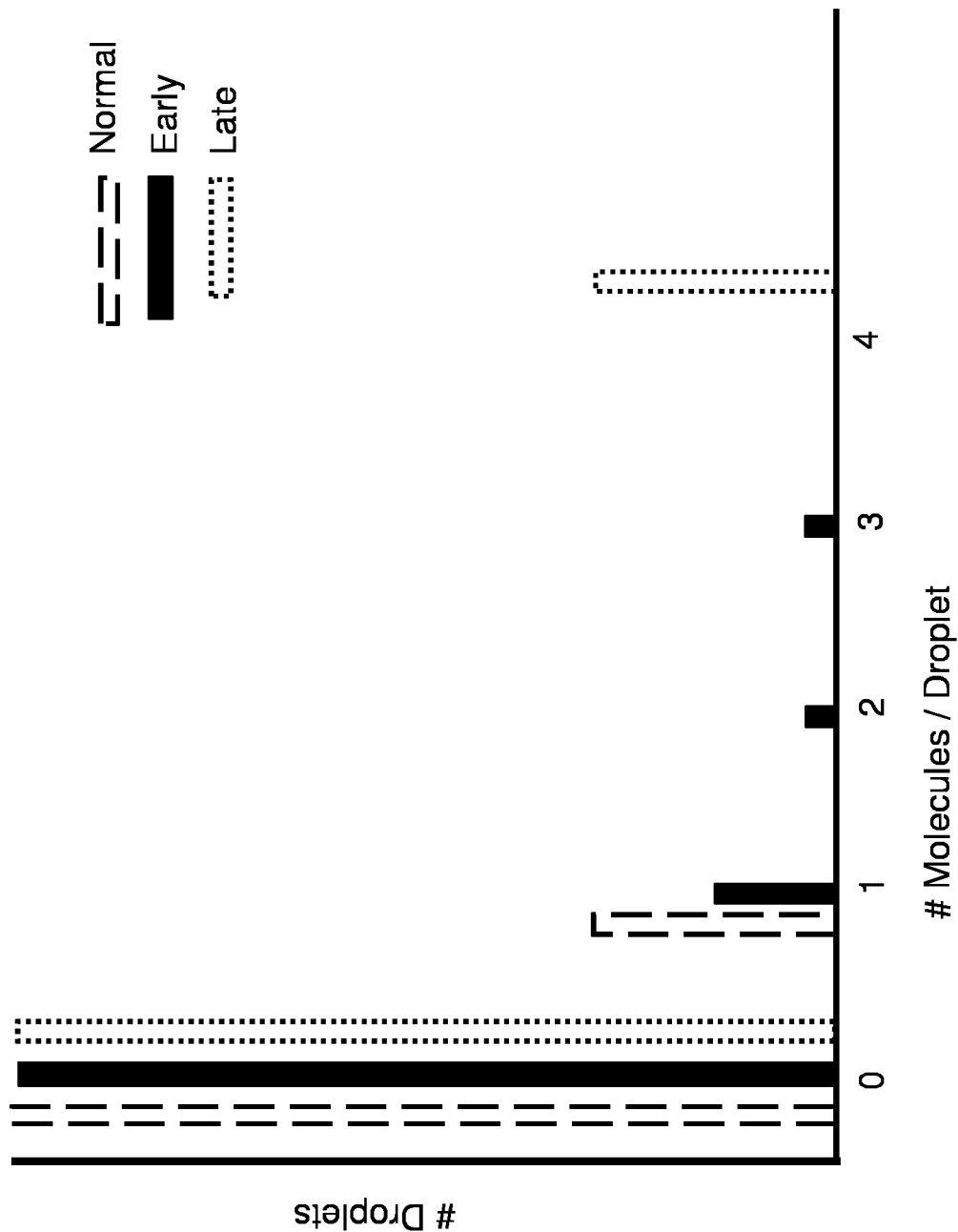
FIG. 26 is a diagram of results of a digital distribution assay.

FIG. 26 shows histograms corresponding to three different stages of protein aggregation. The histogram labeled "normal" indicates an expected distribution of proteins that are not aggregating. The histogram labeled "early" indicates a detected distribution in which proteins have started exhibiting aggregation. The histogram labeled "late" indicates a detected distribution of proteins that exhibit extensive aggregation.

Assays for digital distribution assays include any assay that can indicate a number of protein molecules per fluid partition. For example, where a protein has one epitope that is available while in either monomer or aggregated form, an assay can include antibodies bound to that epitope(s) coupled to reporters in each fluid partition. Each antibody can be linked (covalently or non, e.g., through biotin) to an enzyme. Each fluid partition is provided with fluorescently labeled substrate for the enzyme that fluoresces when the enzyme catalyzes a reaction on the substrate.

A sample is taken from a subject (e.g., a blood sample from a patient). Any desired concentration, isolation, or preparation steps are performed such that the target molecules become associated with a reporter for digital detection in partitions. The sample including the protein of interest and reporter is partitioned into fluid partition (this illustrative example is discussed in terms of a protein, but it will be appreciated that methods of the invention can detect a distribution of any target thus indicating aggregation or a complex).

Where the fluorescent reporter is the same for all antibodies, the number of proteins in each fluid is indicated by the fluorescent intensity of the signal. This can be run in "kinetic" mode, or "end point" mode. In end-point mode, each reaction is allowed to run to substantially completion, at which point the amount of product has substantially plateaued. The amount of product is then detected in each fluid partition and the number of proteins in each partition is correlated to the strength of the signal. The same correlation applies in kinetic mode. However, measurements are made at one or more time points before the amount of product plateaus. Where a whole series of time points is collect, that time series also gives information about enzyme kinetics.

In certain embodiments, where an assay is to be run in kinetic mode, a time point for measurement is first established in an independent calibration run. A series of droplets are made and incubated. The droplets are provided with a dilution of a protein that is known to aggregate and a reporter system (e.g., an enzyme-linked antibody that binds to an epitope of the protein). Fluorescence intensity is measured at multiple time points. For example, where measurement is on-chip and incubation is-off chip, all steps are performed at a temperature at which the enzyme exhibits no activity but incubation, which involves a temperature at which the enzyme exhibits activity. For example, R-gal exhibits no activity at 4° C., and is active at 37° C. For any given N-mer of aggregated protein, the fluid partitions that include one such N-mer will exhibit a characteristic sigmoidal time curve after a series of measurements of fluorescence are taken. To discriminate among some set of N-mers, a point along the time trace graph at which the corresponding sigmoidal time curves exhibit distinct heights is take for the measurement time.

In some embodiments, an expected distribution (i.e., from a healthy individual) is known, and an assay need only discriminate between a detected distribution and an expected distribution. Thus where, for example, an expected distribution has a known ratio of partitions that include 1 target to partitions that include more than one target, an assay can include detecting a ratio of partitions that include 1 target to partitions that include more than one target that is statistically significantly different than the known ratio. In some embodiments, a non-aggregating particle is expected to exhibit a Poisson or near-Poisson distribution, and an assay include detecting a number of droplets that contain greater than one target molecule, wherein the detected number does not agree with Poisson or near-Poisson distribution. In some embodiments, a Poisson distribution at a certain dilution is expected to yield a vanishingly small number of fluid partitions that include two target molecules and zero fluid partitions that include greater than two. Thus, an assay can detect a statistically significant number of partitions that includes more than one molecule to indicate the presence of protein aggregation and thus indicate the presence of a physiological condition. For reference, FIG. 10A shows a measurement result that may indicate protein aggregation (i.e., not match the expected distribution or Poisson).

In an alternative embodiment, each fluid partition is provided with enzyme linked antibodies in which all of the antibodies are the same, but a fraction (e.g., half) is linked to one enzyme that operates on one substrate to generate one reporter, and another portion of the antibodies are linked to another enzyme that catalyzes a reaction that produces a different reporter. In this example, assuming one reporter is blue and one is yellow, some number of fluid partitions that have more than one protein will produce both the blue and the yellow reporter. If the protein is not aggregating, at a certain dilution, it can be expected that blue and yellow will be found together in only some number of droplets (e.g., zero, or 0.00001% of them). In this example, detecting a blue with yellow in a greater number of droplets (e.g., 0.05%, 1%, etc.) indicates the protein is aggregating.

In distribution assays in which signal strength indicates a number of proteins in the droplet, for a given dilution of sample into droplets, assuming random distribution of a non-aggregating protein, there will be a characteristic expected distribution. Even for a protein that exhibits some aggregation in normal conditions, there will be a characteristic expected distribution. In certain embodiments, the expected distribution is predicted by Poisson or is Poisson-like. A substantially large number of droplets will contain zero proteins. A substantially majority of the droplets that contain any protein will contain 1 protein. Some small (maybe vanishingly small) number of protein-containing droplets will contain 2 or more.

In the case where the proteins aggregate, such an expected distribution will not obtain. For example, for a fully aggregated protein (e.g., "late" stage) that aggregates into 4-mers, a substantially large number of droplets will contain zero proteins and a substantial majority of the droplets that contain any protein will contain four proteins, as is illustrated in FIG. 26.

Furthermore, aggregation can be detected over time. That is, early stages of aggregation will exhibit an non-expected distribution. In some embodiments, protein folding into tertiary structures and/or quaternary assembly is studied over the course of, for example, minutes, hours, or days. In certain embodiments, a distribution of aggregation in a sample indicates a stage of progression of an aggregation-related condition that takes months, years, or decades to progress. For example, late stage distributions may only be expected after about 50 or 75 years. However, an assay run at an earlier time period (e.g., 15 or 25 years) may indicate an "early" stage aggregation distribution, as shown in FIG. 26.

In certain aspects, the invention provides a method for detecting a physiological condition in a human that includes forming fluid partitions that include components of a chemical reaction, in which at least one of the components has a detectable label that is acted on by the chemical reaction. The reaction proceeds in the partitions, and a number of reaction-positive partitions is identified and an amount of the component is determined. A statistically expected distribution or amount of the component is computed and compared to the actual distribution or amount. The results of the comparison can indicate the presence of an aggregation phenomenon.

In some embodiments, the invention provides a method for testing a response to a treatment for a condition or for monitoring a progression of a condition. A condition includes conditions that characterized by aggregation such as, for example, Alzheimer's disease. Determining a response to treatment is included in methods for development of treatments such as, for example, drug development. In some aspects, a candidate drug is tested (e.g., administered). A sample is taken and a distribution of molecules is determined. The molecules can be a protein such as beta-amyloid. Based on the determined distribution, an effectiveness of the drug is evaluated and a recommendation can be made. In some aspects, progress of a disease is monitored by methods that include taking a sample and determining a distribution of molecules within the sample according to methodologies described herein.

Digital distribution assays of the invention are highly sensitive and can proceed quickly with very small samples. For example, a 5 mL biological sample can be assayed in less than a day (e.g., about an hour), and a stage of aggregation can be determined.

In certain embodiments, the protein is beta-amyloid. A sample of human blood can be taken for the assay. An expected distribution can be calculated (e.g., statistically according to Poisson), derived empirically (e.g., sampling numerous members of a population for the majority pattern), or obtained from a reference such as a digital file or chart. Accordingly, in some embodiments, the invention offers a blood test for Alzheimer's disease. In certain embodiments, an assay of the invention can be performed on a patient at any life stage (e.g., childhood, teens, etc.). It will be appreciated that any aggregation pattern may be subject to detection by a digital distribution assay and aggregation generally includes the reverse phenomenon of fragmentation. As such, targets for a digital distribution assay may include peptides, nucleic acids, carbohydrates, lipids, or other molecules. A distribution assay can determine a stage of fragmentation as well as a stage of polymerization (e.g., esterification, poly peptide formation, carbohydrate cross-linking, synthetic polymerization, etc.).

Droplet Formation

Methods of the invention involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to Rain-Dance Technologies Inc. The content of each of which is incorporated by reference herein in its entirety. Droplets can be formed with various uniform sizes, a non-uniform size, or a range of sizes.

Figure 24:
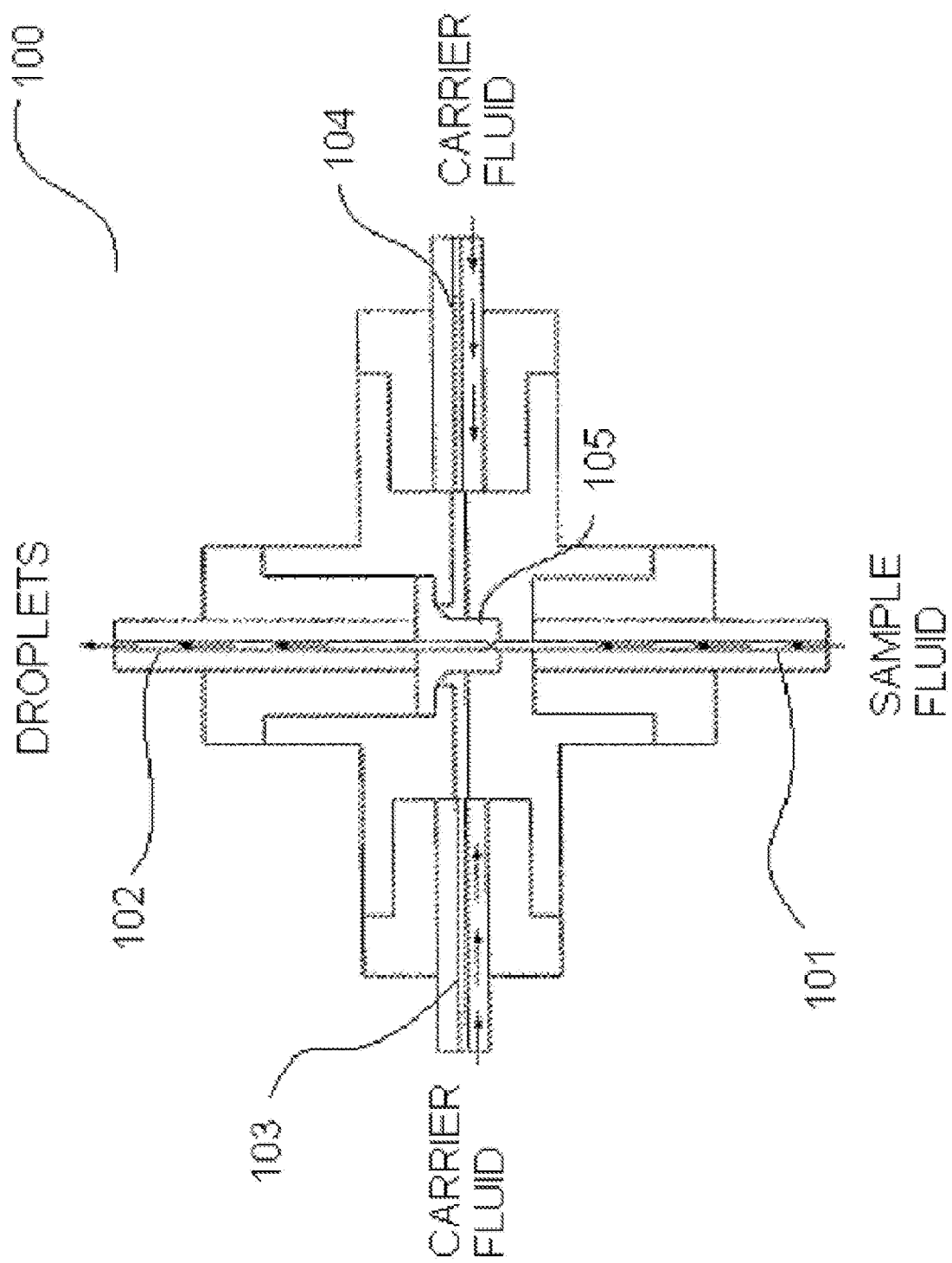
FIG. 24 is a drawing showing a device for droplet formation.
Figure 25:
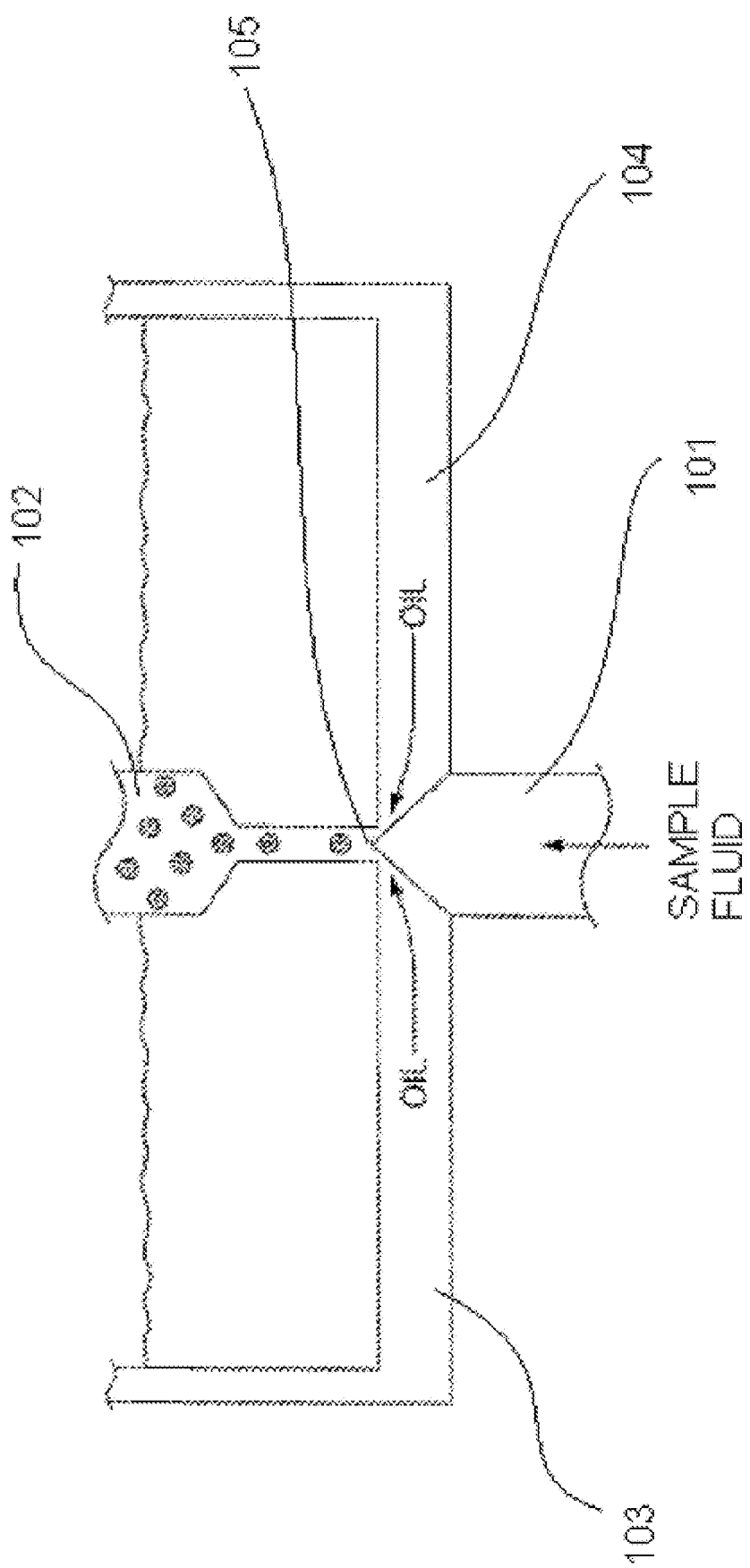
FIG. 25 is a drawing showing a device for droplet formation.

FIG. 24 shows an exemplary embodiment of a device 100 for droplet formation. Device 100 includes an inlet channel 101, and outlet channel 102, and two carrier fluid channels 103 and 104. Channels 101,102,103, and 104 meet at a junction 105. Inlet channel 101 flows sample fluid to the junction 105. Carrier fluid channels 103 and 104 flow a carrier fluid that is immiscible with the sample fluid to the junction 105. Inlet channel 101 narrows at its distal portion wherein it connects to junction 105 (See FIG. 25). Inlet channel 101 is oriented to be perpendicular to carrier fluid channels 103 and 104. Droplets are formed as sample fluid flows from inlet channel 101 to junction 105, where the sample fluid interacts with flowing carrier fluid provided to the junction 105 by carrier fluid channels 103 and 104. Outlet channel 102 receives the droplets of sample fluid surrounded by carrier fluid.

The sample fluid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with enzymes can be used. The carrier fluid is immiscible with the sample fluid. The carrier fluid can be a non-polar solvent, decane (e g., tetradecane or hexadecane), fluorocarbon oil, silicone oil or another oil (for example, mineral oil).

In certain embodiments, the carrier fluid contains one or more additives, such as agents which reduce surface tensions (surfactants). Surfactants can include Tween, Span, fluorosurfactants, and other agents that are soluble in oil relative to water. In some applications, performance is improved by adding a second surfactant. Surfactants can aid in controlling or optimizing droplet size, flow and uniformity, for example by reducing the shear force needed to extrude or inject droplets into a channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be coated with a surfactant. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, P-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt. %) in a fluorinated oil (e.g., Fluorinert (3M)), which then serves as the carrier fluid.

Unknown or known analytes or compounds over a very wide dynamic range of concentrations can be merged with droplets containing single or multiple enzyme molecules and reporters via the use of a Taylor dispersion that forms upstream of the droplet forming nozzle. Co-encapsulation of an optical dye that has similarly been dispersed via a Taylor flow profile can be used to track the analyte/compound concentration. (see, e.g., Miller, et al., PNAS 109(2):378-383 (2012); U.S. Pat. No. 7,039,527; and U.S. Pub. 2011/0063943, the contents of which are hereby incorporated by reference in their entirety).

In certain embodiments, an aliquot of a sample is aspirated into a PEEK tubing, such that a slug of the sample is in the PEEK tubing with a substantially uniform concentration. The tubing is inserted into a port into a microfluidic channel, and the sample enters the channel forming a concentration gradient in the aqueous phase, the gradient generally following Taylor-Aris dispersion mechanics. The sample fluid joins the carrier fluid first having a vanishingly small concentration and then increasing up a gradient asymptotically until a maximum (e.g., 10 micromolar) is reached, after which it decreases similarly. The fluid is flowed to a droplet nozzle, where a series of droplets are made. The sample can be pushed into the channel via a pump, a plunger, or be driven by pressure (e.g., from a gas tank).

In certain embodiments, the dispersion is created for each partition of a plurality (e.g., for numerous or all wells from a 96 well plate, in which every well has a target sample such as a small molecule). Systems and methods of the invention provide a series of microdroplets in which the contents have a controlled concentration gradient through a simple injection procedure. Further, the sample can be spiked with a dye having a known concentration, and the dye concentration can be measured downstream (e.g., during or after any other assay). The measured dye concentrations can be used to determine the sample concentration.

By methods and systems provided here, a controlled gradient of concentrations of one or more sample aliquots can be merged with droplets that include a single target such as a single enzyme molecule. Enzyme activity can be assayed and kinetics studied. For example, individual enzyme molecules can be tested against a concentration range of activators, inhibitors, etc.

Substrates or other reaction or reporter components may be co-encapsulated into droplets with the enzyme without mixing before droplet formation by 'co-flow' of the separate components. When co-flow is used, each separate component is flowed to the microfluidic channel upstream of the droplet-forming nozzle, and both components flow in a laminar fashion to the nozzle without mixing. In co-flow methods, components are flowed in parallel streams through a channel. Due to flow dynamics, the contents of the streams do not mix until they hit the lambda injector or droplet forming nozzle. Two separate streams can be co-flowed, or three, four, or more. Where hardware is configured for N streams, and N−1 streams containing reaction components are desired, a "dummy" stream of water or saline can be included.

Another technique for forming droplets including enzymes and substrates from different fluids or previously generated droplets involves droplet merging. The merging of droplets can be accomplished using, for example, one or more droplet merging techniques described for example in Link et al. (U.S. patent application numbers 2008/0014589, 2008/0003142, and 2010/0137163) and European publication number EP2047910 to Raindance Technologies Inc. In embodiments involving merging of droplets, two droplet formation modules are used. A first droplet formation module produces the droplets including enzymes. A second droplet formation module produces droplets that contain substrate. The droplet formation modules are arranged and controlled to produce an interdigitation of droplets flowing through a channel. Such an arrangement is described for example in Link et al. (U.S. patent application numbers 2008/0014589, 2008/0003142, and 2010/0137163) and European publication number EP2047910 to Raindance Technologies Inc.

Droplets are then caused to merge, producing a droplet that includes enzymes and substrates. Droplets may be merged for example by: producing dielectrophoretic forces on the droplets using electric field gradients and then controlling the forces to cause the droplets to merge; producing droplets of different sizes that thus travel at different velocities, which causes the droplets to merge; and producing droplets having different viscosities that thus travel at different velocities, which causes the droplets to merge with each other. Each of those techniques is further described in Link et al. (U.S. patent application numbers 2008/0014589, 2008/0003142, and 2010/0137163) and European publication number EP2047910 to Raindance Technologies Inc. Further description of producing and controlling dielectrophoretic forces on droplets to cause the droplets to merge is described in Link et al. (U.S. patent application number 2007/0003442) and European Patent Number EP2004316 to Raindance Technologies Inc. Additional methods may be used for controlled droplet merging, for example by altering the flow profiles of paired droplets via properly constrained microfluidic channel design. Merges can be performed in a successive fashion, enabling step-wise addition of substrates, reagents, or reaction step components.

Another approach to forming a droplet including enzymes and substrates involves forming a droplet including enzymes, and contacting the droplet with a fluid stream including substrate, in which a portion of the fluid stream integrates with the droplet to form a droplet including enzymes and substrates. In this approach, only one phase needs to reach a merge area in a form of a droplet. Further description of such method is shown in the co-owned and co-pending U.S. patent applications to Yurkovetsky, (U.S. patent application Ser. No. 61/441,985 and U.S. patent application Ser. No. 13/371,222), the content of which is incorporated by reference herein in its entirety.

A droplet is formed as described above. After formation of the droplet is contacted with a flow of a second sample fluid stream. Contact between the droplet and the fluid stream results in a portion of the fluid stream integrating with the droplet to form a droplet including nucleic acid from different samples.

The monodisperse droplets of the first sample fluid flow through a first channel separated from each other by immiscible carrier fluid and suspended in the immiscible carrier fluid. The droplets are delivered to the merge area, i.e., junction of the first channel with the second channel, by a pressure-driven flow generated by a positive displacement pump. While droplet arrives at the merge area, a bolus of a second sample fluid is protruding from an opening of the second channel into the first channel. Preferably, the channels are oriented perpendicular to each other. However, any angle that results in an intersection of the channels may be used.

The bolus of the second sample fluid stream continues to increase in size due to pumping action of a positive displacement pump connected to channel, which outputs a steady stream of the second sample fluid into the merge area. The flowing droplet containing the first sample fluid eventually contacts the bolus of the second sample fluid that is protruding into the first channel. Contact between the two sample fluids results in a portion of the second sample fluid being segmented from the second sample fluid stream and joining with the first sample fluid droplet to form a mixed droplet. In certain embodiments, each incoming droplet of first sample fluid is merged with the same amount of second sample fluid.

In certain embodiments, an electric charge is applied to the first and second sample fluids. Description of applying electric charge to sample fluids is provided in Link et al. (U.S. patent application number 2007/0003442) and European Patent Number EP2004316 to Raindance Technologies Inc. (Lexington, Mass.), the content of each of which is incorporated by reference herein in its entirety. Electric charge may be created in the first and second sample fluids within the carrier fluid using any suitable technique, for example, by placing the first and second sample fluids within an electric field (which may be AC, DC, etc.), and/or causing a reaction to occur that causes the first and second sample fluids to have an electric charge, for example, a chemical reaction, an ionic reaction, a photocatalyzed reaction, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used.

The electric field facilitates rupture of the interface separating the second sample fluid and the droplet. Rupturing the interface facilitates merging of bolus of the second sample fluid and the first sample fluid droplet. The forming mixed droplet continues to increase in size until it a portion of the second sample fluid breaks free or segments from the second sample fluid stream prior to arrival and merging of the next droplet containing the first sample fluid. The segmenting of the portion of the second sample fluid from the second sample fluid stream occurs as soon as the shear force exerted on the forming mixed droplet by the immiscible carrier fluid overcomes the surface tension whose action is to keep the segmenting portion of the second sample fluid connected with the second sample fluid stream. The now fully formed mixed droplet continues to flow through the first channel.

Droplet Sorting

Methods of the invention may further include sorting the droplets. A sorting module may be a junction of a channel where the flow of droplets can change direction to enter one or more other channels, e.g., a branch channel, depending on a signal received in connection with a droplet interrogation in the detection module. Typically, a sorting module is monitored and/or under the control of the detection module, and therefore a sorting module may correspond to the detection module. The sorting region is in communication with and is influenced by one or more sorting apparatuses.

A sorting apparatus includes techniques or control systems, e.g., dielectric, electric, electro-osmotic, (micro-) valve, etc. A control system can employ a variety of sorting techniques to change or direct the flow of molecules, cells, small molecules or particles into a predetermined branch channel. A branch channel is a channel that is in communication with a sorting region and a main channel. The main channel can communicate with two or more branch channels at the sorting module or branch point, forming, for example, a T-shape or a Y-shape. Other shapes and channel geometries may be used as desired. Typically, a branch channel receives droplets of interest as detected by the detection module and sorted at the sorting module. A branch channel can have an outlet module and/or terminate with a well or reservoir to allow collection or disposal (collection module or waste module, respectively) of the molecules, cells, small molecules or particles. Alternatively, a branch channel may be in communication with other channels to permit additional sorting.

A characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). In certain embodiments, a fluidic droplet is sorted or steered by inducing a dipole in the uncharged fluidic droplet (which may be initially charged or uncharged), and sorting or steering the droplet using an applied electric field. The electric field may be an AC field, a DC field, etc. For example, a channel containing fluidic droplets and carrier fluid, divides into first and second channels at a branch point. Generally, the fluidic droplet is uncharged. After the branch point, a first electrode is positioned near the first channel, and a second electrode is positioned near the second channel. A third electrode is positioned near the branch point of the first and second channels. A dipole is then induced in the fluidic droplet using a combination of the electrodes. The combination of electrodes used determines which channel will receive the flowing droplet. Thus, by applying the proper electric field, the droplets can be directed to either the first or second channel as desired. Further description of droplet sorting is shown for example in Link et al. (U.S. patent application numbers 2008/0014589, 2008/0003142, and 2010/0137163) and European publication number EP2047910 to Raindance Technologies Inc.

Droplet sorting relates to methods and systems described herein by allowing one to detect the effect of an enzymatic reaction in a fluid partition (or absence thereof) and to selectively examine that specific partition further. For example, where a specific class of molecule is being assayed for, an enzyme-positive droplet can be sorted and separated from the rest. That specific droplet can be "broken open" and its contents further examined. For example, a cDNA library can be prepared from all RNA (e.g., mRNA) in that droplet. Nucleic acids can then be sequenced.

Release from Droplets

Methods of the invention may further involve releasing the enzymes or products or other identifiable material from the droplets for further analysis. Methods of releasing contents from the droplets are shown for example in Link et al. (U.S. patent application numbers 2008/0014589, 2008/0003142, and 2010/0137163) and European publication number EP2047910 to Raindance Technologies Inc.

In certain embodiments, sample droplets are allowed to cream to the top of the carrier fluid. By way of non-limiting example, the carrier fluid can include a perfluorocarbon oil that can have one or more stabilizing surfactants. The droplet rises to the top or separates from the carrier fluid by virtue of the density of the carrier fluid being greater than that of the aqueous phase that makes up the droplet. For example, the perfluorocarbon oil used in one embodiment of the methods of the invention is 1.8, compared to the density of the aqueous phase of the droplet, which is 1.0.

The creamed liquids are then placed onto a second carrier fluid which contains a de-stabilizing surfactant, such as a perfluorinated alcohol (e.g. 1H,1H,2H,2H-Perfluoro-1-octanol). The second carrier fluid can also be a perfluorocarbon oil. Upon mixing, the aqueous droplets begins to coalesce, and coalescence is completed by brief centrifugation at low speed (e.g., 1 minute at 2000 rpm in a microcentrifuge). The coalesced aqueous phase can now be removed and further analyzed.

Definitions

The terms used in this specification generally have their ordinary meanings in the art, within the context of this invention and in the specific context where each term is used. Certain terms are discussed below, or elsewhere in the specification, to provide additional guidance to the practitioner in describing the devices and methods of the invention and how to make and use them. It will be appreciated that the same thing can typically be described in more than one way. Consequently, alternative language and synonyms may be used for any one or more of the terms discussed herein. Synonyms for certain terms are provided. However, a recital of one or more synonyms does not exclude the use of other synonyms, nor is any special significance to be placed upon whether or not a term is elaborated or discussed herein. All publications, patent applications, patents, and other references mentioned herein are incorporated by reference. In the case of conflict, the present specification, including definitions, will control. In addition, the materials, methods, and examples are illustrative only and are not intended to be limiting.

The invention is also described by means of particular examples. However, the use of such examples anywhere in the specification, including examples of any terms discussed herein, is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

As used herein, "about" or "approximately" shall generally mean within 20 percent, preferably within 10 percent, and more preferably within 5 percent of a given value or range.

The term "molecule" means any distinct or distinguishable structural unit of matter comprising one or more atoms, and includes for example polypeptides and polynucleotides.

The term "polymer" means any substance or compound that is composed of two or more building blocks ('mers') that are repetitively linked to each other. For example, a "dimer" is a compound in which two building blocks have been joined together.

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

Thus, a "polynucleotide" or "nucleotide sequence" is a series of nucleotide bases (also called "nucleotides") generally in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein).

This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The term "dielectrophoretic force gradient" means a dielectrophoretic force is exerted on an object in an electric field provided that the object has a different dielectric constant than the surrounding media. This force can either pull the object into the region of larger field or push it out of the region of larger field. The force is attractive or repulsive depending respectively on whether the object or the surrounding media has the larger dielectric constant.

"DNA" (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. "RNA" (ribonucleic acid) means any chain or sequence of the chemical building blocks adenine (A), guanine (G), cytosine (C) and uracil (U), called nucleotide bases, that are linked together on a ribose sugar backbone. RNA typically has one strand of nucleotide bases.

A "polypeptide" (one or more peptides) is a chain of chemical building blocks called amino acids that are linked together by chemical bonds called peptide bonds. A "protein" is a polypeptide produced by a living organism. A protein or polypeptide may be "native" or "wild-type", meaning that it occurs in nature; or it may be a "mutant", "variant" or "modified", meaning that it has been made, altered, derived, or is in some way different or changed from a native protein, or from another mutant.

An "enzyme" is a polypeptide molecule, usually a protein produced by a living organism, that catalyzes chemical reactions of other substances. The enzyme is not itself altered or destroyed upon completion of the reaction, and can therefore be used repeatedly to catalyze reactions. A "substrate" refers to any substance upon which an enzyme acts.

As used herein, "particles" means any substance that may be encapsulated within a droplet for analysis, reaction, sorting, or any operation according to the invention. Particles are not only objects such as microscopic beads (e.g., chromatographic and fluorescent beads), latex, glass, silica or paramagnetic beads, but also includes other encapsulating porous and/or biomaterials such as liposomes, vesicles and other emulsions. Beads ranging in size from 0.1 micron to 1 mm can be used in the devices and methods of the invention and are therefore encompassed with the term "particle" as used herein. The term particle also encompasses biological cells, as well as beads and other microscopic objects of similar size (e.g., from about 0.1 to 120 microns, and typically from about 1 to 50 microns) or smaller (e.g., from about 0.1 to 150 nm). The devices and methods of the invention are also directed to sorting and/or analyzing molecules of any kind, including polynucleotides, polypeptides and proteins (including enzymes) and their substrates and small molecules (organic or inorganic). Thus, the term particle further encompasses these materials.

The particles (including, e.g., cells and molecules) are sorted and/or analyzed by encapsulating the particles into individual droplets (e.g., droplets of aqueous solution in oil), and these droplets are then sorted, combined and/or analyzed in a microfabricated device. Accordingly, the term "droplet" generally includes anything that is or can be contained within a droplet.

A "small molecule" or "small molecule chemical compound" as used herein, is meant to refer to a composition that has a molecular weight of less than 500 Daltons. Small molecules are distinguished from polynucleotides, polypeptides, carbohydrates and lipids.

As used herein, "cell" means any cell or cells, as well as viruses or any other particles having a microscopic size, e.g. a size that is similar to or smaller than that of a biological cell, and includes any prokaryotic or eukaryotic cell, e.g., bacteria, fungi, plant and animal cells. Cells are typically spherical, but can also be elongated, flattened, deformable and asymmetrical, i.e., non-spherical. The size or diameter of a cell typically ranges from about 0.1 to 120 microns, and typically is from about 1 to 50 microns. A cell may be living or dead. Since the microfabricated device of the invention is directed to sorting materials having a size similar to a biological cell (e.g. about 0.1 to 120 microns) or smaller (e.g., about 0.1 to 150 nm) any material having a size similar to or smaller than a biological cell can be characterized and sorted using the microfabricated device of the invention. Thus, the term cell shall further include microscopic beads (such as chromatographic and fluorescent beads), liposomes, emulsions, or any other encapsulating biomaterials and porous materials. Non-limiting examples include latex, glass, orparamagnetic beads; and vesicles such as emulsions and liposomes, and other porous materials such as silica beads. Beads ranging in size from 0.1 micron to 1 mm can also be used, for example in sorting a library of compounds produced by combinatorial chemistry. As used herein, a cell may be charged or uncharged. For example, charged beads may be used to facilitate flow or detection, or as a reporter. Biological cells, living or dead, may be charged for example by using a surfactant, such as SDS (sodium dodecyl sulfate). The term cell further encompasses "virions", whether or not virions are expressly mentioned.

A "virion", "virus particle" is the complete particle of a virus. Viruses typically comprise a nucleic acid core (comprising DNA or RNA) and, in certain viruses, a protein coat or "capsid". Certain viruses may have an outer protein covering called an "envelope". A virion may be either living (i.e., "viable") or dead (i.e., "non-viable"). A living or "viable" virus is one capable of infecting a living cell. Viruses are generally smaller than biological cells and typically range in size from about 20-25 nm diameter or less (parvoviridae, picornoviridae) to approximately 200-450 nm (poxviridae). However, some filamentous viruses may reach lengths of 2000 nm (closterviruses) and are therefore larger than some bacterial cells. Since the microfabricated device of the invention is particularly suited for sorting materials having a size similar to a virus (i.e., about 0.1 to 150 nm), any material having a size similar to a virion can be characterized and sorted using the microfabricated device of the invention. Non-limiting examples include latex, glass or paramagnetic beads; vesicles such as emulsions and liposomes; and other porous materials such as silica beads. Beads ranging in size from 0.1 to 150 nm can also be used, for example, in sorting a library of compounds produced by combinatorial chemistry. As used herein, a virion may be charged or uncharged. For example, charged beads may be used to facilitate flow or detection, or as a reporter. Biological viruses, whether viable or non-viable, may be charged, for example, by using a surfactant, such as SDS.

A "reporter" is any molecule, or a portion thereof, that is detectable, or measurable, for example, by optical detection. In addition, the reporter associates with a molecule, cell or virion or with a particular marker or characteristic of the molecule, cell or virion, or is itself detectable to permit identification of the molecule, cell or virion's, or the presence or absence of a characteristic of the molecule, cell or virion. In the case of molecules such as polynucleotides such characteristics include size, molecular weight, the presence or absence of particular constituents or moieties (such as particular nucleotide sequences or restrictions sites). In the case of cells, characteristics which may be marked by a reporter includes antibodies, proteins and sugar moieties, receptors, polynucleotides, and fragments thereof. The term "label" can be used interchangeably with "reporter". The reporter is typically a dye, fluorescent, ultraviolet, or chemiluminescent agent, chromophore, or radio-label, any of which may be detected with or without some kind of stimulatory event, e.g., fluoresce with or without a reagent. In one embodiment, the reporter is a protein that is optically detectable without a device, e.g. a laser, to stimulate the reporter, such as horseradish peroxidase (HRP). A protein reporter can be expressed in the cell that is to be detected, and such expression may be indicative of the presence of the protein or it can indicate the presence of another protein that may or may not be coexpressed with the reporter. A reporter may also include any substance on or in a cell that causes a detectable reaction, for example by acting as a starting material, reactant or a catalyst for a reaction which produces a detectable product. Cells may be sorted, for example, based on the presence of the substance, or on the ability of the cell to produce the detectable product when the reporter substance is provided.

A "marker" is a characteristic of a molecule, cell or virion that is detectable or is made detectable by a reporter, or which may be coexpressed with a reporter. For molecules. a marker can be particular constituents or moieties, such as restrictions sites or particular nucleic acid sequences in the case of polynucleotides. For cells and virions, characteristics may include a protein, including enzyme, receptor and ligand proteins, saccharides, polynucleotides, and combinations thereof, or any biological material associated with a cell or virion. The product of an enzymatic reaction may also be used as a marker. The marker may be directly or indirectly associated with the reporter or can itself be a reporter. Thus, a marker is generally a distinguishing feature of a molecule, cell or virion, and a reporter is generally an agent which directly or indirectly identifies or permits measurement of a marker. These terms may, however, be used interchangeably.

The invention is further described below, by way of the following examples. The examples also illustrate useful methodology for practicing the invention. These examples do not limit the claimed invention.

EXAMPLES

Example 1

Example 1 shows methods of surfactant syntheses.

Below of the reaction scheme for creating the surfactants utilized in stabilizing the droplet libraries provided by the instant invention.

Reaction 1

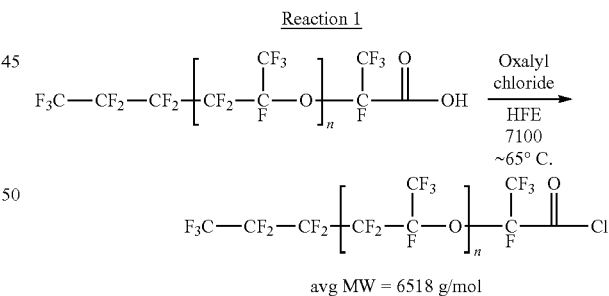

avg MW = 6518 g/mol

Reagent Table is as follows:

| Name | MW | Moles/Equiv. | Amount used | Other (density, purity, safety, misc.) |
| --- | --- | --- | --- | --- |
| Krytox FSH | 6500 | 1.54 mmol (1 eq) | 10.0 g | |
| Oxalyl Chloride | 126.93 | 15.4 mmol (10 eq) | 1.3 mL (1.95 g) | d = 1.5 g/mL; b.p. 62-65° C. |
| HFE 7100 | 250.06 | | 50 mL | b.p. 61° C. |

The procedure includes, adding 10.0 (1.54 mmol; eq) of Krytox acid FSH in 50 mL HIFE 7100 (not anhydrous) at right under Ar was added 1.95 g (15.4 mmol; 10 eq) of Oxalyl Chloride dropwise. Stirred 10 min, then the reaction was warmed to gentle reflux (note boiling points of solvent and reagent). Some bubbling was noted, even before reaction had reached reflux. Continued overnight.

The following day, the reaction was very slightly cloudy, and contained a very small amount of a yellow solid. Cooled, HFE and excess Oxalyl chloride evaporated. Residue dissolved in 40 mL fresh HFFE, then filtered to remove the solid. FE evaporated again, residue placed under hivac for 1 hr. Yield of a cloudy white oil 10.14 g. Used without further purification.

The procedure includes, drying the amine was by placing under hivac rotovap at a bath temp of 60° C. for 4 hrs. To a solution of 0.441 g (0.77 mmol; 1 eq) of PEG 600 diamine J and 0.325 mL (2.33 mmol; 3 eq) of $Et_3N$ in 20 ml anhydrous THF at rt under Ar was added a solution of 10.14 g (1.55 mmol; 2 eq) of crude JSJ 73-019 in 40 mL FC 3283. A white precipitate ($Et_3N.HCl$) was noted to form in the reaction and on the flask walls. The milky-white two-phase suspension was stirred well overnight.

The THF and most FC was evaporated. This left a solid residue dispersed in the FC solvent ($Et_3N.HCl$). Oil residue diluted with 50 mL FC3283, then filtered through Celite. Celite washed with 2×30 mL FC 3283. The solid left in the flask was found to be water soluble, suggesting that it was $Et_3N.HCl$. The filtrate was cloudy white. FC 3283 evaporated using hivac and 60° C. bath. Kept as such for ~1.5 hrs to evaporate all solvent.

Sample submitted for 19F NMR. Peak for the CF was in the correct position, indicating amide had formed

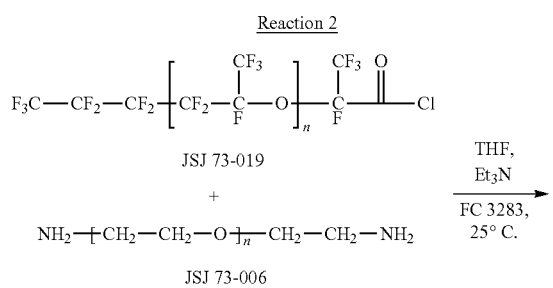

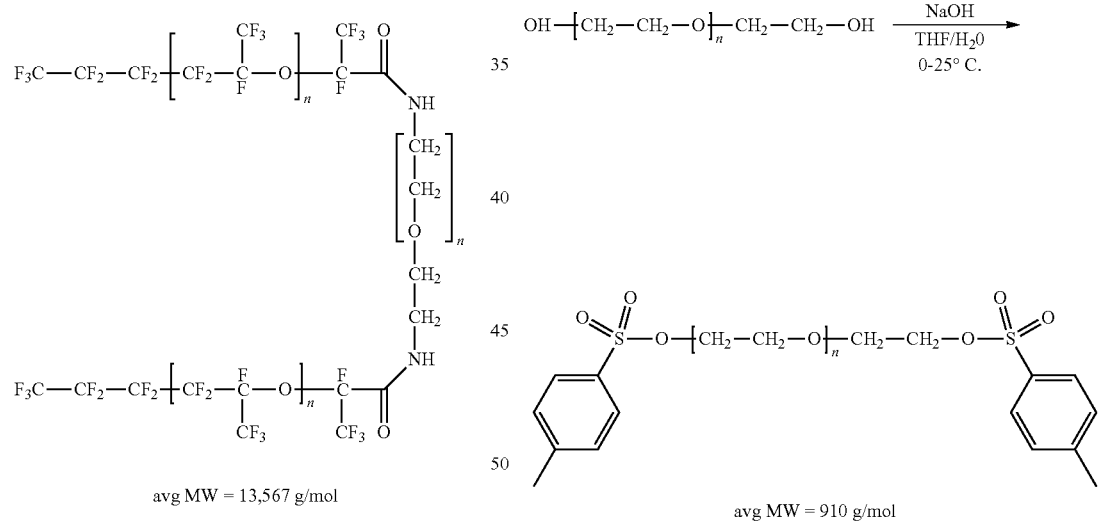

The reagent table is as follows:

| Name | MW | Moles/Equiv. | Amount used | Other (density, purity, safety, misc.) |
|---|---|---|---|---|
| JSJ 73-019 | 6518 | 1.55 mmol (2 eq) | 10.14 g | used crude |
| JSJ 73-006 | 568 | 0.77 mmol (1 eq) | 0.441 g | |
| Triethylamine | 101.19 | 2.33 mmol (3 eq) | 0.325 mL | d = 0.726; b.p. 88° C. |
| Tetrahydrofuran | | | 20 mL | b.p. 66° C. |
| FC 3283 | 521 | | 40 mL | b.p. 123-33° C.; dried over $CaSO_4$ |

The reagent table is as follows:

| Name | MW | Moles/Equiv. | Amount used | Other (density, purity, safety, misc.) |
|---|---|---|---|---|
| PEG 600 (Fluka) | 600 | 0.125 (1 eq) | 75.0 g | Avg. MW 600; CAS 25322-65-3; m.p. 17-22° C. |
| p-Toluene Sulfonyl chloride | 190.65 | 0.283 (2.3 eq) | 53.93 g | |
| Tetrahydrofuran | | | 525 mL | b.p. 66° C., not anhydrous |
| Sodium Hydroxide | 40.00 | 0.506 (4.05 eq) | 20.25 g | |
| Water | | | 156 mL | |

The procedure included adding to a solution of 20.25 g (0.506 mol; 4.05 eq) of NaOH in 156 mL water cooled in an ice-bath to ~0° C. (not under inert atmosphere) was added a solution of 75.0 g (0.125 mol; 1 eq, 2 eq of hydroxyl) of PEG 600 in 300 mL of TH dropwise via addition funnel. Internal temp was kept ~5° C. during the addition. After complete addition, the slightly cloudy reaction was stirred while warming to rt over 1 hr. Following this, the reaction was again cooled to ~0° C. and a solution of 53.93 g (0.283 mol; 2.3 eq) of Tosyl chloride in 225 mL THF was added dropwise via addition funnel, again keeping the internal temp ~10° C. during the addition. Reaction allowed to stir overnight while warming to rt.

Layers allowed to separate in an addition funnel, THF separated from aqueous layer and evaporated. Residue dissolved in 600 mL EtOAc and recombined w/aqueous from above. Shaken, separated. Organic washed 3×125 mL water, then with brine, dried over MgSO₄. Stirred over the weekend.

Filtered, solvent evaporated to give a colorless oil, which was dried under hivac rotovap 3 hrs at ~60° C. This gave 91.95 g of a colorless oil (81% yield). This was a typical yield for this reaction.

Reaction 4

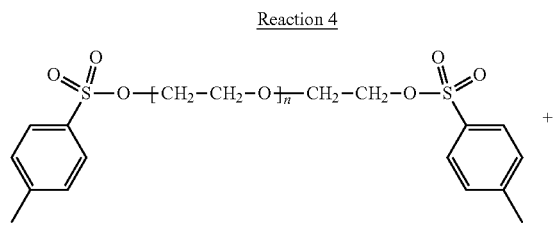

JSJ 73-078
avg MW = 910 g/mol

+

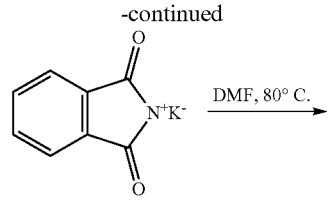

DMF, 80° C.

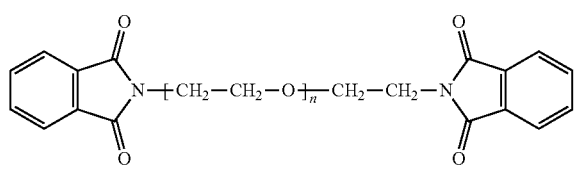

avg MW = 860 g/mol

The reagent table includes:

| Name | MW | Moles/Equiv. | Amount used | Other (density, purity, safety, misc.) |
|---|---|---|---|---|
| JSJ 73-078 | 910 | 102 mmol (1 eq) | 92.75 g | used crude |
| Potassium Phthalimide | 185.22 | 224 mmol (2.2 eq) | 41.5 g | |
| Dimethylformamide | 73.09 | | 600 mL | b.p. 153° C. |

The procedure includes adding to a solution of 92.75 g (102 mmol; 1 eq) of JSJ 73-078 in 600 mL anhydrous DMF at rt under Ar was added 41.5 g (224 mmol; 2.2 eq) of Potassium phthalimide as a solid in 2 portions. The heterogeneous solution was then warmed slowly to 85-90° C. (internal temp) and the rxn stirred overnight. The phthalimide slowly went into solution and the color became more yellow. A small amount of the phthalimide wasn't consumed, remaining a solid dispersed in the reaction.

While still warm, the reaction was poured into a separate flask and most of the DMF was evaporated (hivac at 80° C.). Any remaining solution was kept warm while the DMF was being evaporated. The resulting sludgy solid was diluted EtOAc (~1 L in total) and filtered. The sludge was triturated in a smaller portion of EtOAc (200 mL) and filtered again to ensure all product was recovered. Solid was triturated w/ another 200 mL EtOAc. Filtrate was then concentrated to give a yellow oil. Continued pumping on oil under hivac at 80° C. for several hours to remove residual DMF. This gave 57.93 g of orange-yellow oil. This was typical yield for this reaction.

Reaction 5

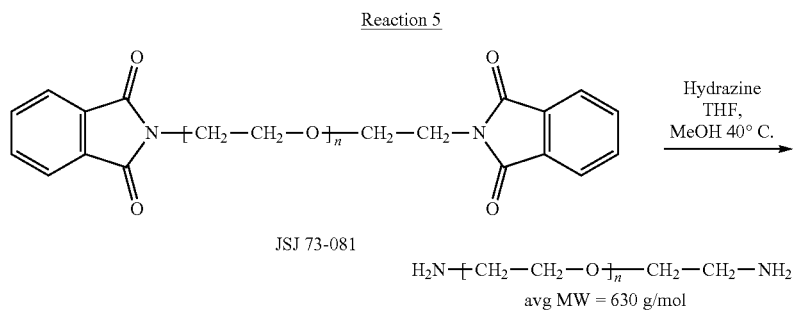

JSJ 73-081

$H_2N\text{—}\!\!+\!\!CH_2\text{—}CH_2\text{—}O\!\!+\!\!_n\text{—}CH_2\text{—}CH_2\text{—}NH_2$ avg MW = 630 g/mol The reagent table includes:

| Name | MW | Moles/ Equiv. | Amount used | Other (density, purity, safety, misc.) |
|---|---|---|---|---|
| JSJ 73-081 | 860 | 67 mmol (1 eq) | 57.93 g | used crude |
| Hydrazine, anhydrous | 32.05 | 471 mmol (7 eq) | 15 g (15 mL) | d = 1.021 g/mL, b.p. 113° C. |
| Tetrahydrofuran | | | 300 mL | b.p. 66° C. |
| Methanol | | | 300 mL | b.p. 65° C. |

The procedure includes adding to a solution of 57.93 g (67 mmol; 1 eq) of crude JSJ 73-081 in 300 mL anhydrous MeOH and 300 mL anhydrous THF at rt under Ar was added 15 mL (471 mmol; 7 eq) of Hydrazine and the reaction stirred (mechanical stirring used) at rt for 1.5 hrs. After ~45 min, white solid began to form from the homogeneous solution. This was thought to be the byproduct of the hydrazine-phthalimide reaction. The reaction was warmed to 40° C. and stirred overnight under Ar. The stirring became slightly more difficult as more solid formed, so the stirring was increased slightly.

The reaction appeared the same, very thick with the solid. Rxn cooled, THF and MeOH evaporated. The residue was diluted w/ EtOAc (300 mL) then filtered. Filtration was relatively easy, solid washed well w/ EtOAc (200 mL). Filtrate concentrated, upon which additional solid was noted. Residue diluted back in EtOAc (300 mL), giving a slightly cloudy solution (diamine may not be completely soluble in this volume of EtOAc). Filtered, solvent evaporated, giving a yellow oil.

This oil was placed under hivac rotovap at ~70° C. for several hours to remove residual solvents, Hydrazine, and also possibly any residual DMF brought from the SM in the previous step.

Example 2

Example 2 Shows PEG-Amine Derived Fluorosurfactant Syntheses

A PEG-amine derived fluorosurfactant can be made by the following process: 10.0 g of Krytox 157 FSH (PFPE, 6500 g/mol, 0.00154 mole) was dissolved in 25.0-mL of FC-3283 (521 g/mol, 45.5 g, 0.0873 mole). 0.567 g PEG 600 Diamine (566.7 g/mol, 0.001 mole, 0.65 mol eq.) was dissolved in 10.0-mL of THF (72.11 g/mol, 8.9 g, 0.1234 mole). The resulting solutions were then combined and emulsified. The resulting emulsion was spun on a BUCHI rota-yap, at ~75% for ~20 hours. The crude reaction mixture was then placed in centrifuge tubes with equal volumes of DI H2O, emulsified and centrifuged at 15,000 rpm for 15-minutes. Once the emulsion was broken, the oil layer was extracted, dried with anhydrous sodium sulfate and filtered over a 0.45-um disposable nylon filter. The filtered oil was then evaporated on a BUCHI rota-vap, model R-200 fitted with a B-490 water bath for ~2-hours at 70° C.

The procedure is depicted in Scheme 1:

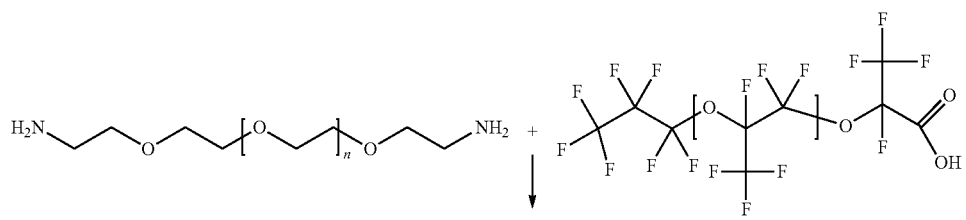

-continued

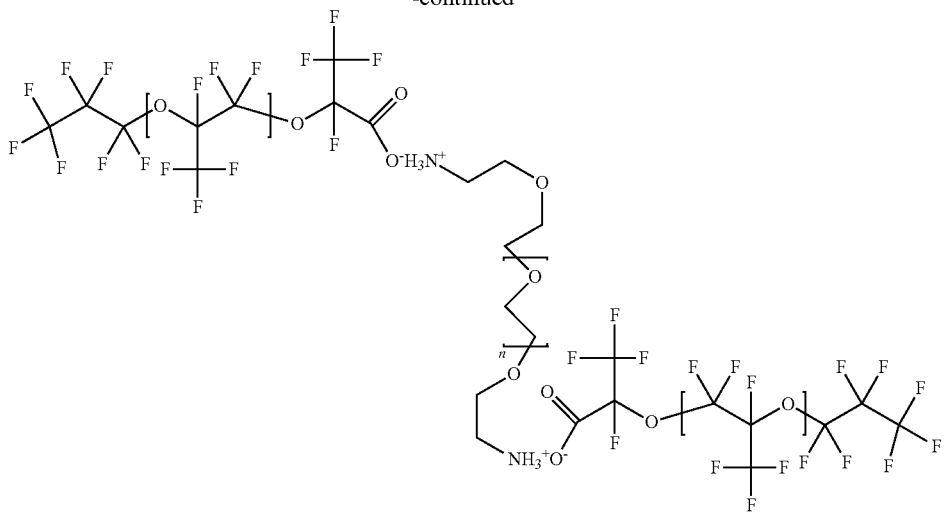

FIG. 5 shows Ammonium Carboxylate Salt of Krytox 157 FSH 2 Wt % FC 3283 without PEG amine salt (Panel A) and with PEG 600 Diammonium Carboxylate Salt of Krytox 157 FSH at 4.0% by volume (Panel B) (Flow Rates: 2000 ul/hr (FC oil), 500 ul/hr (aq). The difference in the number of coalesced drops in the right image indicates that the PEG amine salt is effective in stabilizing emulsions. Emulsions made with the Ammonium Carboxylate Salt of Krytox 157 FSH 2 Wt % FC 3283 with PEG 600 Diammonium Carboxylate Salt of Krytox 157 FSH co-surfactant added at 4.0% by volume were shown to remain stable when reinjected into a microfluidic channel.

Example 3

Primer Library Generation

Figure 6:
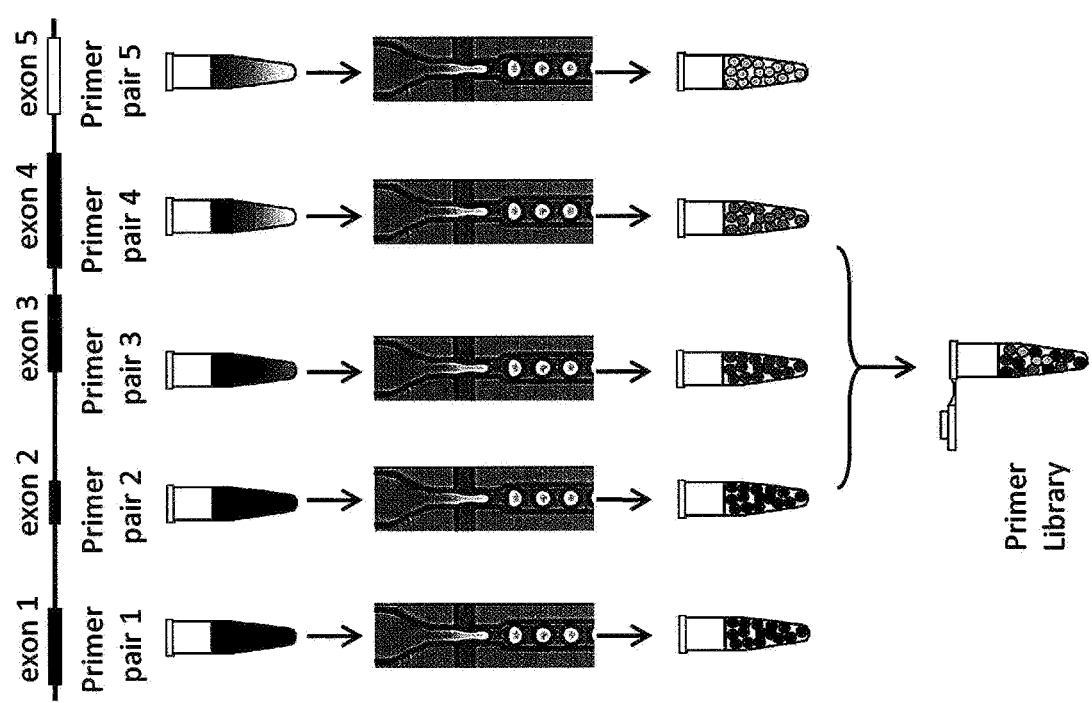
FIG. 6 is a schematic illustrating a primer library generation.

The primer droplet library generation is a Type IV library generation. FIG. 6 shows a schematic of the primer library generation. Step 1 of the library formation is to design primers for loci of interest. There are no constraints on primer design associated with traditional multiplex PCR. Step 2 requires synthesis of the primer pairs using standard oligo synthesis. After the library elements are created, the primer pairs are reformatted as droplets, where only one primer pair present in each droplet. Each droplet contains multiple copies of the single primer pair directed to a single target of interest. After the droplets for each type of primer pair is created, the emulsions are pooled as primer library. The droplet stability prevents cross-contamination of primer pairs.

Primer Library for Genome Selection

A pooled primer library can be placed onto a microfluidic device as provided by the instant invention. Each primer library droplet follows an inlet channel that intersects with another inlet channel, which has droplets containing gDNA, Taq, dNTPs and any other materials needed to perform PCR. At the intersection the two inlet channels merge into a single main channel where the two different types of droplets, i.e., the primer library droplet and the PCR component droplets travel singularly until they are coalesced. The droplets are coalesced within the main channel in which they are traveling, at a widened portion of the main channel. In addition to the widening in the channel, electrodes are used to coalesce the droplets containing the primer libraries and the droplets containing the PCR components. The coalesced droplets then continue along the same main channel and are collected onto well containing plates. The droplets in the plates are subjected to thermocycling to permit PCR amplification. The amplified DNA can then be sequenced by any means known in the art. The relative number of sequencing reads from each of 20 targeted exons can be plotted using primer libraries against human genomic DNA.

Primer Library for Digital qPCR Method

Disposable PDMS/glass microfluidic devices were designed with regions maintained at 95° C., and regions maintained at 67° C. and further including interrogation neckdowns. Aqueous fluid was infused into the microfluidic device perpendicularly to two channels flowing immiscible oil which generated 65 pL (50 um) droplets. The aqueous fluid contained the following reagents:

50 mM Tris/HCl (pH 8.3)
10 mM KCl
5 mM (NH4)2SO4
3.5 mM MgCl2
0.2 mM dNTP
0.5% Tetronics
0.1 mg/ml BSA
0.2 units per µL of FastStart Taq DNA polymerase
0.5 µM each of forward and reverse primers
0.25 µM FAM-labeled probe quenched with a 3' BHQ1
1 µM Alexa Fluor 594

Serial dilutions of the pAdeasy-1 vector (Stratagene, La Jolla, Calif.) were made from 60 to 0.0006 ng/uL or from 600 copies per/droplet to 0.006 copies per/droplet The concentrations of the diluted DNA were verified by qPCR using a traditional real-time thermocycler. PCR primers and probe were designed to detect a 245 bp region of the Adenovirus genome. Droplets were generated at a rate of 500 per second. The channels on the microfluidic device conveyed the droplets through of 2 thermal zones at a 95° C. and 67° C. for 34 passes which were the equivalent of 34 cycles of two step PCR with the following cycling parameters:

1 cycle-3 min hot start
34 cycles:
95° C. for 15 seconds
68° C. for 40 seconds

PCR droplets were interrogated at specific "neckdowns" which were 100 micron long regions of the microfluidic device where the channel width and depth decreased forcing droplets into a single file. A two wavelength laser excitation and detection system was used to interrogate the fluorescence at each of the neckdowns at cycles 4, 8, 11, 14, 17, 20, 23, 26, 29, 32, and 34. A fluorescent dye, Alexa Fluor 594, provided a constant signal in each droplet that was used for droplet detection without inhibiting PCR amplification efficiency or yield.

The distribution of fluorescence signal among droplets was determined as the droplets pass through the excitation lasers (488 nm and 561 nm) at the last interrogation neckdown (cycle 34). A bimodal distribution of FAM fluorescence was observed for droplets with starting template concentrations of less than one molecule per droplet, indicating the presence of two populations corresponding to empty droplets and droplets that supported amplification. A time trace of fluorescence signals from those droplets is readily plotted as those droplets pass one-by-one through the excitation lasers. For each of the Adenovirus dilutions examined, the percentage of PCR positive droplets was plotted versus cycle number.

Successful amplification was detected at Adenovirus concentrations as low as 0.006 copies per drop (0.003 pg/µl). Following amplification, the droplets collected from the microfluidic device were broken and analyzed by automated electrophoresis to confirm a product of the appropriate size. Consistent with the fluorescence data, gel analysis showed an increase in total product as the amount of starting material was increased. The observed titers were compared with the average percentage of positive reactions predicted for each starting template concentration by Poisson statistics and by MPN (most probable number) (see Table below).

cell or bead, follow a Poisson Distribution. Using the following, equation, the distributions were calculated based on theory using the following equation:

$$P(N) = ((CV)^N e^{-CV})/N!$$

where P is the probability of N particles per drop, C is the injection concentration, and V is the droplet volume.

Experimental results are based on beads that were injected at a concentration of 40 million/ml into 23 µm drops (6.37 pL); CV=0.2548. The results are shown in the following table:

| P(N) | Theoretical Poisson Distribution | Experimental Distribution | # of Drops Counted |
|---|---|---|---|
| P(0) | 77.5 | 79.8 | 1010 |
| P(1) | 19.7 | 17.3 | 219 |
| P(2) | 2.5 | 2.5 | 32 |
| P(3 and more) | 0.3 | 0.4 | 5 |
| Total | 100% | 100% | 1266 |

Example 5

Antibody-Bead Libraries—ELISA in Droplets

Figure 3:
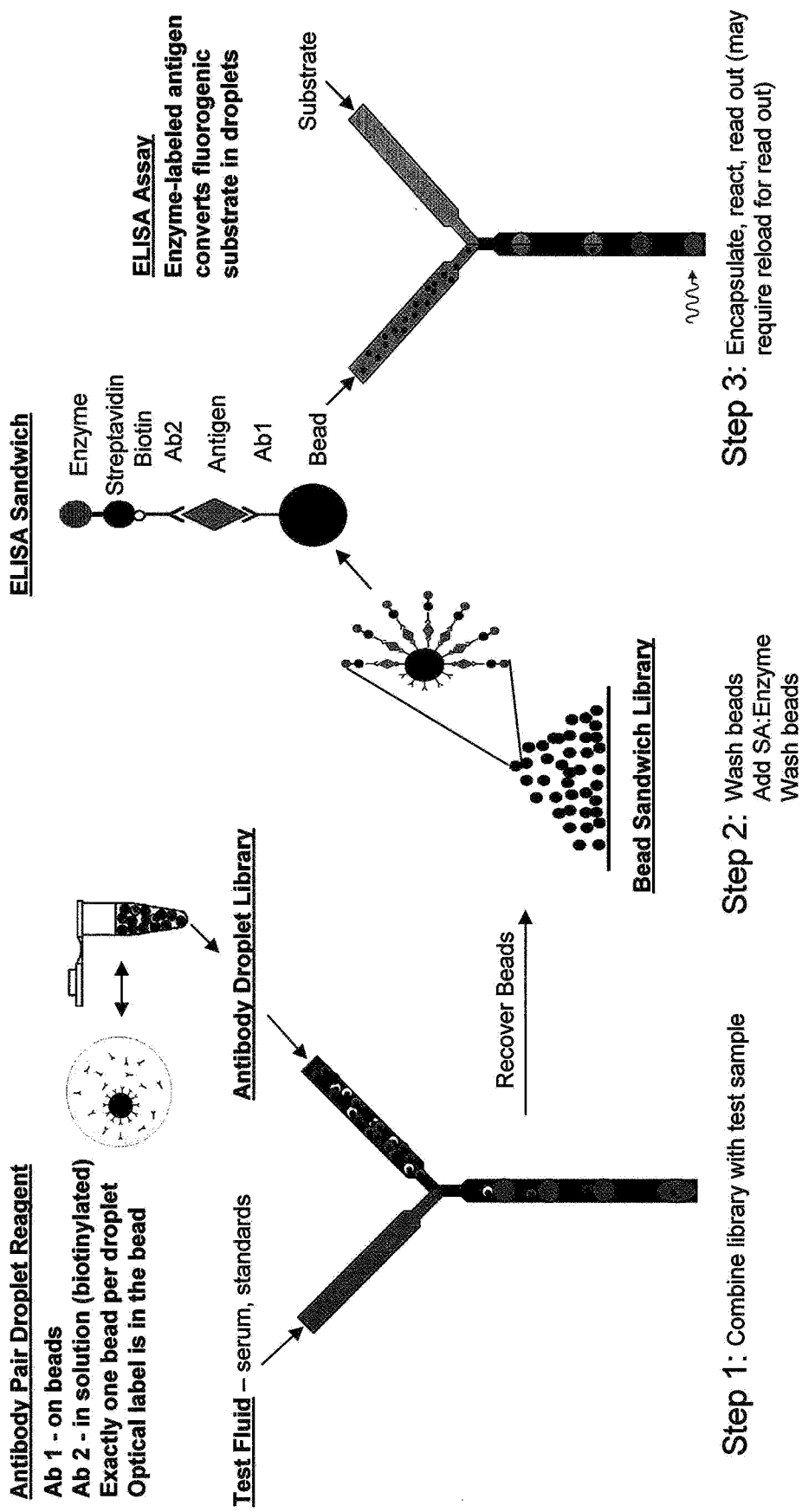
FIG. 3 is a schematic illustrating an antibody pair library for ELISA Application.

The primer droplet library generation is a Type II library generation. FIG. 3 shows a schematic of the antibody pair library generation. Reagent solutions 1 through n, where n is the number of parallel ELISA assays to be performed, are prepared in separate vials. Each solution contains two antibodies, one bound to beads and one free in solution. It is often desirable, but not essential, for the unbound antibody to be biotinylated or for it to be conjugated to an enzyme.

TABLE 3

Comparison of Observed Amplification Distribution to Poisson Statistics and MPN.

| Template Concentration | | PCR Positive Droplets | | |
|---|---|---|---|---|
| Copies per Droplet | Copies per Droplet (MPN adjusted)[a] | Observed | Expected (Poisson) | Expected (Poisson MPN adjusted)[a] |
| 0.006 | 0.0050 (± 0.000082) | 2.08% | 0.60% | 0.49-0.51% |
| 0.06 | 0.050 (± 0.00082) | 11.7% | 5.82% | 4.76-4.95% |
| 0.3 | 0.25 (± 0.0041) | 20.3% | 25.9% | 21.6-22.4% |
| 0.6 | 5.0 (± 0.0082) | 32.6% | 45.1% | 38.6-39.8% |
| 6 | 5.0 (± 0.082) | 89.0% | 99.8% | 99.2-99.4% |
| 60 | 50 (± 0.82) | 95.9% | 100% | 100% |
| 600 | 500 (± 8.2) | 98.2% | 100% | 100% |

[a]MPN calculation based on the 4 lowest dilutions was 0.83 ± 0.017. Adjusted values are within 95% confidence.

A percentage of droplets that supported amplification was plotted versus starting copy number compared to that predicted by Poisson. Very good agreement was seen between the percentage of droplets that supported amplification and the predicted Poisson distribution. Given the accuracy of the data for endpoint analysis this droplet-based strategy appears to be ideal for quantitative PCR applications that require single molecule detection.

Example 4

Generating Single Element Droplets

As described in detail herein, the formation of Type II library droplets, which encapsulate a library element, e.g., The beads are optically labeled using dyes, quantum dots or other distinguishing characteristics that make each of the n bead types uniquely identifiable, these characteristics can be also geometrical shape or features or fluorescence intensity or fluorescence polarization. For the emulsion library preparation: in separate locations, beads of each type are encapsulated in reagent droplets; the reagent contains an unbound second antibody matched for a specific immunoassay. It is often desirable, but not essential to have exactly one bead in a droplet. Droplets having exactly one bead are collected by sorting on droplet generation in a microfluidic device. The emulsion library consists of a pooled collection of the n different droplet types. The droplet stability prevents cross-contamination of antibody pairs.

FIG. 3 shows the test fluid is the sample fluid used to analyze one or more immunoassays. Example test fluids include serum, sputum, urine or tumor biopsies. In step 1 the test fluid is dispersed into droplets of uniform volume and combined with a single droplet from the library. There may be unpaired droplets of the library material. In step 2 the beads are recovered, washed in bulk, a readout enzyme is introduced. Non-limiting examples of readout enzymes could include a conjugate streptavidin-enzyme (typical enzymes are, for example but not limited to: β-Galactasidase, alkaline phosphatase, horseradish peroxidase), or conjugate antibody-enzyme (for example the same list of enzymes), followed by a final wash. In step 3 the beads are put back on microfluidic device at a low concentration so that limiting dilution conditions result. Most droplets will contain zero beads and most bead-containing droplets will have only one bead. Droplets containing exactly one bead will be used for the remainder of the assay. Droplets with no beads or more than one bead are sorted and discarded as discussed above. A fluorogenic substrate is added to the droplets under co-flow conditions at the time of droplet generation. The substrate is enzymatically turned-over to make a fluorescent product proportional to the concentration of analyte (and readout enzyme) in the sample fluid. An optical signal indicating the bead type and immunoassay number information is read on the beads simultaneously with the fluorescence signal from the product. This is done at one or more time points after the droplet is generated. Bead handling may benefit from using magnetic beads.

In some cases it may be advantageous to enhance step one with a sort procedure to remove the droplets containing excess beads that have not had the test fluid added to them. The sort can be triggered either by droplet size or through the introduction of a fluorescent dye to the test fluid.

In some cases it may be advantageous to collect all beads on-chip. This is achieved with a micro-fabricated bead filter. Beads can then be washed, introduced to additional reagents, and subsequently followed by a final wash. By performing all of the previous steps all on-chip, the need for bulk processing of beads is eliminated.

In some cases it is difficult to re-space beads after the final wash of step 1. In those cases it may be advantageous to capture beads in isolation on-chip. In the example, the substrate is added in bulk and the diffusion of the product around the bead is measured. There are several other non-limiting examples of methods that could also be applied in a microfluidic device. For example, one could use a tyramide amplification assay.

Auto-loading of sample fluids, injection loop and dispense techniques can be utilized to enhance efficiency. Test fluids can be run sequentially using conventional autoloaders and sample injection loops. Each sample would need to be separated by a rinse fluid and the off-chip processing of beads would require that the beads from each test fluid be collected separately.

Droplet ELISA Performance—Reported Enzyme

The activity of reporter enzyme bound to single positive beads (anti-m-biotin) or single negative beads in 30 um droplets can be assayed with HorseRadish Peroxidase (HRP) enzyme. Under the assay conditions, the beads were injected at a final concentration 10 million/ml, HRP readout at 10 minute time point—Amplex Ultra Red 100 uM, hydrogen peroxide 1 mM. HRP allows for adequate separation of bead containing droplets from empty droplets. Additionally, a linear response is seen down to 10 molecules in a 30 um drop (at 10 minutes).

Droplet ELISA Performance—Binding

Similar binding kinetics are seen when performing ELISA in a tube when compared to performance in droplets. Specifically, similar binding kinetics and a linear calibration curve is seen using droplets.

Droplet ELISA Performance—Full Assay

Serum concentration can be measured accurately and is able to be reproduced, generally within a CV of less that 6% as shown in the Table below that shows the results of serum sample replicates (~60,000 droplets/run)

| Antigen | t = 0 min | t = 10 min | |
|---|---|---|---|
| pg/ml | All drops | Empty drops | Bead drops |
| Human serum 1:1600 | 18.2 | 21.7 | 252 |
| Human serum 1:1600 | 19.7 | 25.8 | 264 |
| Human serum 1:1600 | 23.5 | 25.6 | 278 |
| Positive control beads | 20.5 | 56.2 | 4272 |

Example 6

Sorting Cells for Secreted Enzymatic Activity

Molecular biology methods allow for generation of large libraries of mutant enzymes, which can be cloned DNA, which can be developed into a mutagenized DNA library that is then put into a bacterial host. The droplet based screening is high-throughput, highly accurate and has low reagents costs. The droplets provide an accurate high-throughput screen versus a halo assay. Specifically, the DNA enzyme contained within the bacterial host is encapsulated within a droplet that also contains a fluorogenic substance, creating a droplet library of the bacteria, where only a single bacteria is contained with the droplets. All droplets, however, contain the fluorogenic substrate. After the droplet library is created the bacteria are allowed to replicate for a set time period, i.e., overnight. Using a green filter shows the discrete bacteria, within particular droplets, and using a red filter shows the secreted enzyme.

Droplet libraries can also be used in enzyme activity detection with single cell growth and enzyme secretion. A droplet library can include a number of droplets containing a single cell, where other droplets do not contain any cells. The cells remain in the droplets overnight and grow into clonal populations. Both the discrete bacteria and the secreted enzyme are detected with an overlay of assay and cell fluorescence. The droplet library is then sorted, such that the droplets all contain a clonal population of bacteria having secreted the desired enzyme. The droplet library enables a single cell generation to result in clonal populations within single droplets to be used in assays and or to be sorted.

Activity in droplets is similar to that seen in microtitre plates. Matching rank orders with microtiter plate assays and droplet assays show similar rank orders using either method.

Cell droplet libraries enable the sorting of the most active stain from a mixed cell library. In one example, droplets were generated with four individual strains and optical labeling using specific fluorescein concentrations (labeling plotted on y-axis). All of the droplets were collected into the same syringe and the mixed droplets were re-injected onto a microfluidic device after overnight growth at 30° C. A scatter plot shows the four labeled populations of droplets starting with no assay signal (on generation), and droplets having growing cells secreting protease showing assay activity moving to the right (after 16 hrs). The origin of each droplet is clearly identified, with the assay signal strength for each droplet type matching the appropriate strain ranking. Starting from a dilution of 1 positive in 100 Negatives viable bacteria can be recovered from sorted droplets to achieve sorted population.

In another example, a 5-member library sorting can be achieved. A starting ratio of one Pos #4-containing droplet to 30 cell-containing droplets was used. Pos #3 cells only are kanamycin resistant. After recovering and plating out the contents of the sorted droplets, there were 19 kanamycin-resistant colonies out of 1131 total colonies. This is equivalent to an apparent false positive rate of 1.7%.

Sorting the most active strain can also be done with large (i.e., 2 million members) mixed cell libraries. Further exemplified is a parent library of $2 \times 10^6$ discrete cell types (bacteria secreting mutagenized enzyme library) was placed into droplets for growth and screening. Two levels of sorting threshold stringency were used to recover either the top 100 cells or the top 10K cell. After re-growth, each population was placed in droplets for an enriched library analytical run. Three populations were optically labeled, and five minutes of data were collected after cell growth and assay development in droplets. Clear enrichment of the parent library is seen in the Top 10K-Enriched Library. Validation of Test Library #1 enrichment is seen. White and red filtered microscope images of the Parent Library (Test Library #1) in droplets after growth are observed. Similar images of the Top 10K-Enriched Library are seen. Clear enrichment for active clones are also observed.

Example 7

Sorting Cells for Biomarkers Using Enzyme Amplification—Flow Cytometry

Figure 7:
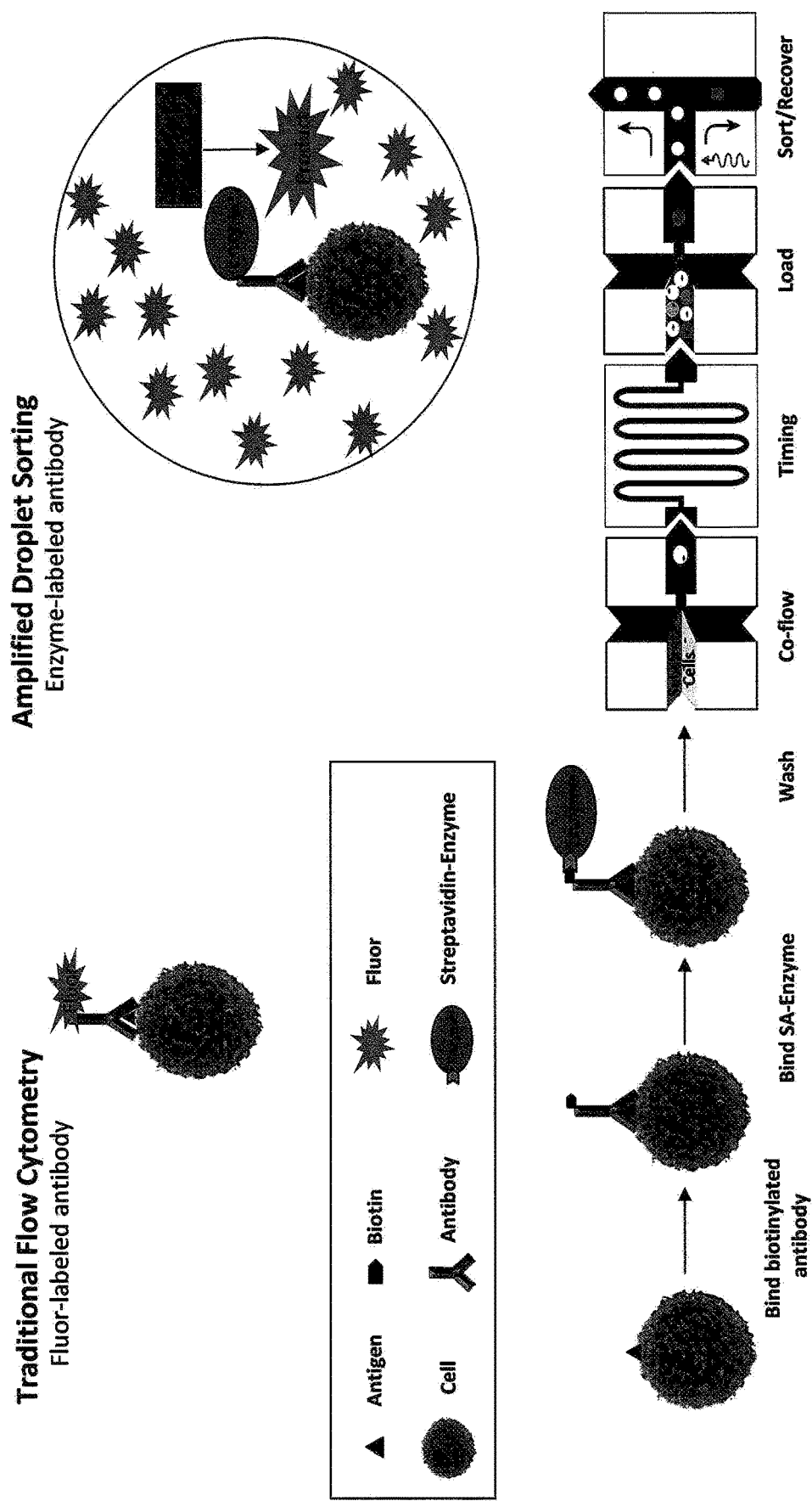
FIG. 7 is a schematic illustrating enzyme amplified flow cytometry.

FIG. 7 shows a schematic of the encapsulation of enzyme labeled individual cells in a substrate containing droplets. In contrast, traditional flow cytometry utilizes fluor-labeled antibodies. The contents of the droplets are then amplified, such that the contents of the droplet produce a labeled product. The contents are then put onto the microfluidic device in order to sort/recover the desired products.

A particular example is the U937 Monocyte Droplets, where cell library of an antibody, reporter enzyme and cell stain is prepared and co-flowed into droplets with the assay substrate. Depending on the contents of the droplet, a different signal is produced and the number of cells per droplet follows a Poisson distribution, where 8.4% of the droplets have a single cell, i.e., 25356 single cell droplets out of 300943 total droplets. Additionally, the enzyme amplified signal increases over time. The droplet libraries also enable multiplexed assays with optical labeling. Various labels can be utilized and overlayed. In a comparison of FACS and droplet sorting, droplet sorting provides improved cell population fractionation.

Example 8

Cell Libraries—Bacterial Libraries for Antibody Screening

Screen libraries of bacterially produced scFv's can also be developed. In one example, transformed bacteria are encapsulated and incubated at 37° C. After incubation the droplets are combined with droplets that contain beads, antigens and a detection antibody. After the two different droplets are combined they are collected and sorted. The positive droplets are then broken and the contents are recovered and sequenced. The process is able to screen for scFv's in droplets at a rate of about $1 \times 10^6$ per hour. The droplet based binding assays utilize localized fluorescence detection of scFV binding. Specifically, the diffuse signal becomes bright and localized on the capture bead.

Example 9

Compound Libraries—Screening for Inhibitor Enzymes

The present invention provides Immobilized Metal-Ion Affinity Partitioning (IMAP) FP detection of kinase reaction progress. Significant achievements allowing the instant method include:

Solving problems handling IMAP, such as precipitation and providing proper mixing.

Fast mixing/equilibrium in droplets allows direct on-chip analysis.

Initially, a significant precipitation of the IMAP particles in the syringe, particularly when present at high concentrations was observed. A mechanical mixing device and protocols was utilized to minimize this problem. Subsequently, this problem was fully solved by varying the ratio of buffers provided in Molecular Devices' Progressive Binding Buffer system, with a final concentration of 50% A:B buffer used for all assays. Buffer B contains a high salt concentration which prevented aggregation, and in addition allows a single buffer system to be used for many different kinases (using different substrates with a range of acidity).

There are several distinct steps in performing kinase assays within droplets. First the reaction components are encapsulated inside droplets generated by a microfluidic device and collected into a syringe. Next, the refrigerated syringe is brought up to the reaction temperature, and the 'emulsified' reaction mixture proceeds to react for a defined amount of time. Finally, the reaction emulsion is re-injected and each individual droplet is analyzed when it flows past a laser detector. In this scheme, detection of the phosphorylated reaction product is via measurement of its Fluorescence Polarization (FP) after binding to the commercially available Immobilized Metal-Ion Affinity Partitioning (IMAP) kit reagents (Molecular Probes). The scheme incorporates a formulation step allowing chemical compounds to be tested for their inhibitory properties towards kinases. The fluorescence polarization is measured for each droplet and changes upon binding. Specifically, the phosphorylated product binds to IMAP and increases its FP. Compound/DMSO dilution and encapsulation of the reaction reagents into droplets is formulated on the microfluidic device.

In one example, two sets of droplets are initially generated, one from an aqueous stream made of compound (provided in 70% DMSO) and ATP (nozzle 1), and the other from an aqueous stream containing the kinase and substrate in a reaction buffer (nozzle 2). These two droplet types are subsequently coalesced via the application of voltage from the electrode, generating the final reaction mixture droplets which is collected into a glass syringe.

When generating the compound/ATP droplets, fluid flow rates are set such that the compound that is initially in 70% DMSO is diluted to a concentration of 10% DMSO in the droplets generated by nozzle 1. The volume ratio of droplets generated at nozzle 1 vs. nozzle 2 is 1 to 3, therefore when droplets from nozzle 1 are coalesced with droplets from nozzle 2 (containing the kinase and substrate) there is another 4 fold dilution of DMSO is therefore 28-fold (the concentration of DMSO in the final reaction mix is 2.5%).

Coalescence of droplets with IMAP, IMAP binding, and timed readout of droplets are observed. Specifically, IMAP particles are encapsulated inside droplets which are subsequently coalesced with the emulsified reaction mixture droplets as they are being re-injected. The droplets enter a delay line which provides sufficient time for each droplet to be interrogated using an FP readout as it moves from left to right through the microfluidic channel shown.

A combined microfluidic device design was also developed in order to improve emulsion stability (by reducing microfluidic device connection manipulations) and to reduce the time required for switching microfluidic devices and re-equilibrating fluid pressures. In this design, the same channel is used for both emulsion collection and re-injection, allowing for emulsion generation, IMAP coalescence and FP readout all on one microfluidic device. This design provides for a higher degree of automation and reproducibility by reducing operator manipulations of the microfluidic devices and optics, reducing opportunities for contaminants to be introduced into the microfluidic system, and provides better control of the operation time.

In order to generate kinetic data on the kinase reaction progress, a collection of the reaction droplet emulsion at 4° C. was provided, to prevent the enzymatic reaction from proceeding until the temperature is raised. Once the emulsion has been generated, the syringe can be raised to any temperature desired (e.g. room temperature or 30° C.). All of the experiments shown in this report were performed at room temperature. Time course experiments were also performed by varying the time that the emulsion was kept at room temperature, before re-injection and coalescence with the IMAP detection reagent. Automated protocols were established allowing for time points to be collected every 10 minutes over a period up to 4 hours.

Optical components have been defined and developed to enable FP detection. Optical components were assembled, using a 25-milliwatt solid-state laser to generate a 10 micron focused laser spot in the microfluidic channel, allowing a fluorescence signal to be measured for each droplet. The prototype instrument used in this study is able to detect approximately 10,000 FITC molecules encapsulated in a 30 micron droplet passing through the detection point at a rate of up to 10,000 per second.

Binding of the IMAP particle to the phosphorylated peptide substrate can be directly observed using the microfluidic device. As each droplet moves at a defined flow rate through the circuitry, observation at different positions after IMAP coalescence defines specific times after binding. A delay line allows measurements over approximately 20 seconds after binding IMAP. Binding of the Akt positive control phospho-peptide to IMAP and the reaction of Abl-tide substrate with Abi kinase are seen. Binding of the IMAP reagent to both of these phospho-peptides reaches equilibrium within 10 seconds. Further, a comparison of on-chip and plate reader assays using 3 compounds where % inhibition time courses for Abl kinase and compounds E, A, and H show improved resolution for on-chip assays.

Example 10

Compound Libraries—Screening for Cytotoxic Drugs

In one example, one nozzle is used to encapsulate U937 mammalian cells that are cultivated in RPMI supplemented with fetal calf serum (10% v/v) under saturated $CO_2$ atmosphere (5%). Flow-focusing geometry to form the droplets was used. A water stream is infused from one channel through a narrow constriction; oil streams hydrodynamically focus the water stream and reduce its size as it passes through the constriction resulting in a "geometry-controlled" breakup of the droplet. The size of the water droplets is controlled in part by the relative flow rates of the oil and the water and in part by the nozzle section dimensions. The fluorinated oil contains a fluorocarbon surfactant (Ammonium Carboxylate Salt of Perfluoropolyether, 1% w/w) to stabilize the droplets. Cell density upon injection with discussion on Poisson's distribution and single cell analysis % drop size. Pluronic F-68 (0.1% final solution) a shear-protectant, is added to the cells just prior the injection to minimize the effect of shear-stress. The other nozzle generates droplets containing the Calcein-AM and Sytox Orange (Invitrogen) dyes that are used to respectively score live and dead cells. In brief, Calcein-AM is membrane permeant, non-fluorescent and diffuses into cells where the acetoxy groups are hydrolyzed by nonspecific esterases. The hydrolyzed dye (Calcein) is both cell membrane impermeant and fluorescent. Sytox Orange is impermeant and excluded from viable cells, but is able to enter cells with compromised membranes. In this case, it binds to DNA by intercalating between the bases with little sequence specificity and its fluorescence is greatly enhanced. Finally, a fluoro-surfactant (Zonyl-FSO, 1.3%, Dupont) was added in the dye solution to prevent the interaction of the dyes with the carboxylate group of the main surfactant. The droplet streams are interdigitated so that each cell droplet pairs with a dye droplet before entering the coalescence module. To this end, the fact that smaller droplets flow at higher velocities than larger droplets due to the parabolic flow velocity distribution in microfluidic channels was exploited. The small dye droplets catch up and come into contact with the larger cell droplets, but do not coalesce because they are stabilized with surfactant. In addition, in order to have each cell droplet paired with a dye droplet the formation rate of dye droplets is higher than the formation rate of cell droplets formation in a ratio close to 1:2. Coalescence is controllably induced when a pair of droplets passes through an alternative electric field (~300V·cm$^{-1}$, 100 kHz). The expansion in the coalescing region allows for a dramatic catching up of the small droplet to the large droplet and accounts for a very robust coalescence (fewer than 0.1% misses). The volume of the expansion is big enough to slow the large droplet down so that the small droplet always catches up to the large droplet, but doesn't allow the next droplet to catch up and make contact with the pair to be coalesced. After the droplet pairs are coalesced, their content, i.e. cells and dyes, is mixed by traveling through a passive serpentine mixer. Because the Calcein-AM dye has to be processed enzymatically by the cells to become fluorescent, the droplets need to be incubated on-chip for tens of minutes. To achieve this type of incubation on-chip the cross-section (600 μm×250 μm) and the length of the channel (1,550 mm) was increased so that the flow sweeps through a large volume. This design results in a significant residence time on the microfluidic device. In addition, to modulate with ease the incubation period without changing the flowrates used for generating the droplets oil from the flowing stream was extracted. The oil extractor consists of a series of T-junction whose sections are much smaller than the droplet size, which are used to specifically extract oil and reduce the overall flowrate and hence the droplet velocity. The combined use of the incubation line and the oil extractor results in a significant on-chip residency time of the droplets. Typically, the live-dead assay experiments are carried out with an incubation time of 70 minutes on the microfluidic device. For consistent fluorescent detection, all the cells are illuminated in the same conditions by confining them through a constriction and by using a slit geometry for the excitation spot. A confocal optical set-up is used and the signal is collected with a set of photomultipliers at a rate of 100 kHz.

A typical fluorescent readout is provided, over a timescale of 100 ms. The cell growth medium gives a dim fluorescent background which is much lower than the live-dead assay signals. To compensate for this low signal, some fluorescein (10 µM) (Invitrogen) was added into the dye solution to get a clear fluorescent signature of the droplets which is characterized by an approximately rectangular cross-section. Peak signals corresponding to cell staining are characterized by higher maximum signal and narrower Forward Half Maximum. They can be clearly distinguished on top of the homogeneous signal. Data processing software has been developed to extract different parameters (height, integrated area . . . ) after interpolation and curve fitting from each droplet signal. After scoring the cells retain a normal morphology without any apparent sign of shearing. Cell density upon injection with discussion on Poisson's distribution and single cell analysis % drop size.

To test the performances of the assay, a series of experiments were conducted to test its specificity and its sensitivity. First, the signal specificity was checked by injecting and scoring with the live-dead assay either only live or dead cells. Dead cells were prepared by incubating fresh cells with 70% Ethanol for 5 minutes. The experiment demonstrates that the assay is very specific as all the cells are scored properly. In addition, it shows that the injection does not kill the cells over a short-term period, in agreement with other's observations.

Second, the assay was test to see whether it was able to score all the injected cells disregarding their cell state (either alive or dead). To this purpose all the cells with a red dye (QDOT 655 wheat germ agglutinin, Invitrogen) were identified and checked that they were all scored. Again, live cells and dead cells were scored separately. It is noteworthy that these numbers are the result of the combined efficiencies of all the modules used for the live-dead assay, demonstrating the robustness of this assay and technology.

Third, to assess the usefulness of this assay for screening purpose a series of known ratios of live and dead cells were scored in the range of 0-10% dead cells. Indeed, the fraction of positive hits for a cytotoxicity large-scale screen is expected to be in the order of a few percent. For example, as little as 5% positive cells can be reproducibly detected in a sample population of 500-1,000 measured cells.

Finally, it was demonstrated that encapsulated cells can be collected into a syringe and the emulsions re-injected for on-chip scoring. This ability is an essential feature of the technology for conducting screens, as the cells will have to be incubated with compounds for a much longer time than achievable on-chip.

It was observed that the cell emulsion which is re-injected through the lower nozzle is still monodisperse. The stability depends critically on the use of the fluoro-surfactant and design of the microfluidic circuit to avoid uncontrolled coalescence. By the use of a scatter plot, it is determined that most of the cells are able to survive the collection-reinjection procedure.

The droplet microfluidic technology will facilitate an expansive list of microfluidic applications. In particular high-throughput cell screening and combinatorial screening at the single cell level will greatly benefit from this technology platform. The major advantages of this technology are the absence of contact between the sample and the channel walls eliminating contamination, and high-throughput manipulation.

The toxicity assay with droplets requires encapsulating cells determining the difference between live cells and dead cells. In order to get a reading of the droplet and fluorescent level therein, the droplet is elongated for detection. The cell viability does not significantly change over time (>3 days) in the droplets.

What is claimed is:

1. A method of performing a digital ELISA assay in droplets, the method comprising:
    providing reagent droplets comprising reporter antibodies and second antibodies bound to magnetic beads into a channel of a microfluidic device;
    introducing test droplets comprising a test fluid into the microfluidic device;
    combining the reagent droplets with the test droplets in the microfluidic device to form ELISA sandwiches, each ELISA sandwich comprising one bead-bound antibody, a target analyte from the test fluid, and one reporter antibody;
    adding, via the microfluidic device, a fluorogenic substrate into droplets that contain one of the ELISA sandwiches; and
    detecting fluorescence indicating presence of the target analyte, wherein the detecting step provides a digital count of a number of molecules of analyte per volume of the test fluid.

2. The method of claim 1, wherein the reporter antibodies are provided as biotinylated antibodies.

3. The method of claim 2, further comprising introducing a streptavidin-linked enzyme for use in forming the ELISA sandwiches.

4. The method of claim 3, wherein streptavidin-linked enzyme comprises streptavidin beta-galactosidase.

5. The method of claim 1, wherein the fluorogenic substrate comprises fluorescein di-beta-D-galactopyranoside (FDG).

6. The method of claim 1, wherein the target analyte comprises a protein, the detecting step yields a digital count of individual molecules of the protein per volume, and the method further comprises quantifying the protein in the test fluid from the digital count.

7. The method of claim 1, wherein the detecting step comprises reading a first optical signal indicating the bead type and the fluorescence signal indicating the presence of the target analyte.

8. The method of claim 1, wherein after the ELISA sandwiches are formed, the method includes retaining the magnetic beads by a magnetic field while removing unbound non-target proteins and free antibodies, prior to adding the fluorogenic substrate.

9. The method of claim 1 wherein the droplets containing the one ELISA sandwich are formed and—after the droplets containing the one ELISA sandwich are formed—the fluorogenic substrate is added.

10. The method of claim 1, further comprising—after forming the droplets—sorting droplets and discarding droplets with no beads or with more than one bead.

* * * * *